(12) United States Patent
Kim et al.

(10) Patent No.: US 10,991,889 B2
(45) Date of Patent: *Apr. 27, 2021

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Hyun Kim, Gyeonggi-do (KR); Doo-Hyeon Moon, Gyeonggi-do (KR); Sang-Hee Cho, Gyeonggi-do (KR); Sung-Wook Cho, Gyeonggi-do (KR)

(73) Assignee: Rohm and Haas Electronic Materials Korea Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/630,871

(22) PCT Filed: Jul. 19, 2018

(86) PCT No.: PCT/KR2018/008140
§ 371 (c)(1),
(2) Date: Jan. 14, 2020

(87) PCT Pub. No.: WO2019/017697
PCT Pub. Date: Jan. 24, 2019

(65) Prior Publication Data
US 2020/0152885 A1    May 14, 2020

(30) Foreign Application Priority Data

Jul. 21, 2017  (KR) .................. 10-2017-0092861
Jun. 12, 2018  (KR) .................. 10-2018-0067248

(51) Int. Cl.
*H01L 51/00*    (2006.01)
*H01L 51/50*    (2006.01)
*C07D 401/10*   (2006.01)
*C09K 11/06*    (2006.01)

(52) U.S. Cl.
CPC ........ *H01L 51/0067* (2013.01); *C07D 401/10* (2013.01); *C09K 11/06* (2013.01); *H01L 51/0072* (2013.01); *C09K 2211/1018* (2013.01); *H01L 51/50* (2013.01); *H01L 51/5012* (2013.01); *H01L 51/5072* (2013.01); *H01L 2251/558* (2013.01)

(58) Field of Classification Search
CPC ....... C07D 401/10; C09K 11/06; H01L 51/50; H01L 51/0067
USPC ............. 544/180; 257/40; 428/917; 313/501
See application file for complete search history.

(56) References Cited

U.S. PATENT DOCUMENTS

| | | | |
|---|---|---|---|
| 6,849,348 B2* | 2/2005 | Zheng | C08G 61/02 252/301.16 |
| 7,285,341 B2 | 10/2007 | Zheng et al. | |
| 8,993,128 B2 | 3/2015 | Lee et al. | |
| 2019/0207125 A1* | 7/2019 | Ahn | H01L 51/0061 |
| 2019/0214572 A1* | 7/2019 | Cho | C09K 11/06 |
| 2019/0221751 A1* | 7/2019 | Cho | H01L 51/0073 |

FOREIGN PATENT DOCUMENTS

| | | |
|---|---|---|
| CN | 105441066 A | 3/2016 |
| KR | 2012-0031684 A | 4/2012 |
| KR | 2016-0025777 A | 3/2016 |
| KR | 2016-0052399 A | 5/2016 |

OTHER PUBLICATIONS

Atzrodt et al. Angew. Chem. Int. Ed. 2007, 46, 7744-7765.*

* cited by examiner

*Primary Examiner* — Erich A Leeser
(74) *Attorney, Agent, or Firm* — S. Matthew Cairns

(57) ABSTRACT

The present disclosure relates to an organic electroluminescent compound and an organic electroluminescent device comprising the same. An organic electroluminescent device having a low driving voltage, a high luminous efficiency and/or excellent color coordinates can be provided by comprising the organic electroluminescent compound according to the present disclosure.

9 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent (EL) device is a self-light-emitting device with the advantages of providing a wider viewing angle, a greater contrast ratio, and a faster response time. The first organic EL device was developed by Eastman Kodak, by using small aromatic diamine molecules and aluminum complexes as materials for forming a light-emitting layer (see Appl. Phys. Lett. 51, 913, 1987).

An organic EL device (OLED) changes electric energy into light by the injection of a charge into an organic light-emitting material, and commonly comprises an anode, a cathode, and an organic layer formed between the two electrodes. The organic layer of the organic EL device may be composed of a hole injection layer, a hole transport layer, an electron blocking layer, a light-emitting layer (containing host and dopant materials), an electron buffer layer, a hole blocking layer, an electron transport layer, an electron injection layer, etc.; the materials used in the organic layer can be classified into a hole injection material, a hole transport material, an electron blocking material, a light-emitting material, an electron buffer material, a hole blocking material, an electron transport material, an electron injection material, etc., depending on functions. In the organic EL device, holes from an anode and electrons from a cathode are injected into a light-emitting layer by electric voltage, and an exciton having high energy is produced by the recombination of the holes and electrons. The organic light-emitting compound moves into an excited state by the energy and emits light from energy when the organic light-emitting compound returns to the ground state from the excited state.

Research is underway to improve the performance of an organic electroluminescent device by using a material suitable for each layer in the organic electroluminescent device.

For example, an electron transport material actively transports electrons from a cathode to a light-emitting layer and inhibits transport of holes which are not recombined in the light-emitting layer to increase recombination opportunity of holes and electrons in the light-emitting layer. Thus, electron-affinitive materials are used as an electron transport material. Organic metal complexes having light-emitting function such as $Alq_3$ have been conventionally used as an electron transport material. However, $Alq_3$ also has a limitation in providing an organic electroluminescent device having sufficiently satisfactory performance, thus, there is a demand for an electron transport material having improved performance capable of replacing $Alq_3$. Therefore, new electron transport materials have been required, which do not have the above problems, are highly electron-affinitive, and quickly transport electrons in organic EL devices to provide organic EL devices having high luminous efficiency.

Further, the electron buffer layer is a layer for solving the problem of a change in luminance caused by the change of a current characteristic of the device when exposed to a high temperature during a process of producing a panel. In order to obtain a similar current characteristic and a stability to high temperature compared to a device without an electron buffering layer, the characteristic of the compound comprised in the electron buffer layer is important.

U.S. Pat. No. 6,849,348 B2, U.S. Pat. No. 7,285,341 B2, U.S. Pat. No. 8,993,128 B2, and KR 2016-0052399 A disclose indenoquinoline derivatives as compounds for an organic electroluminescent device. However, the compounds disclosed in the above documents do not disclose the compounds of the present disclosure in view of specific compound structure including the kinds and position of the substituent.

DISCLOSURE OF THE INVENTION

Problems to be Solved

The objective of the present disclosure is to provide an organic electroluminescent compound which is effective for manufacturing an organic electroluminescent device having low driving voltage, high efficiency and/or excellent color coordinates.

Solution to Problems

Common compounds having a fluorene moiety can easily induce electron currents. However, the present inventors found that the compounds are stabilized against stress such as high temperature when the weak positions of quinoline, which are the second and the fourth carbon positions thereof, are protected. As a result of intensive studies, the present inventors found that the organic electroluminescent device comprising the indenoquinoline derivative which is substituted with e.g., aryl and/or heteroaryl at the second and the fourth carbon positions on the basis of quinoline has a higher luminous efficiency as well as a lower driving voltage than the indenoquinoline derivative having only one substituent in the quinoline moiety, and reached the present invention.

More specifically, the present inventors found the aforementioned objective can be achieved by the organic electroluminescent compound represented by the following formula 1, and completed the present invention.

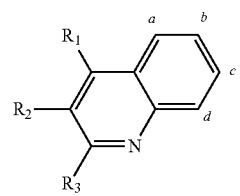
(1)

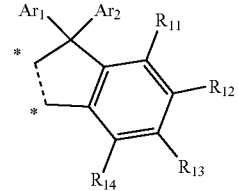
(2)

In formula 1

$R_1$ to $R_3$ each independently represent hydrogen, deuterium, halogen, cyano, a substituted or unsubstituted (C1-C30)alkyl, a substituted or unsubstituted (C6-C30)aryl, or a substituted or unsubstituted (5- to 30-membered)heteroaryl, provided that at least two of $R_1$ to $R_3$ each independently represent a substituted or unsubstituted (C1-C30)alkyl, a substituted or unsubstituted (C6-C30)aryl, or a substituted or unsubstituted (5- to 30-membered)heteroaryl;

a and b, or b and c, or c and d of formula 1 are combined with * of formula 2 to form a ring, wherein $B_1$ and $B_2$ are bonded at the positions not bonded to * of formula 2 among a to d, regardless of the sequence;

$B_1$ and $B_2$ each independently represent hydrogen, deuterium, halogen, cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

$Ar_1$ and $Ar_2$ each independently represent halogen, a substituted or unsubstituted (C1-C30)alkyl, a substituted or unsubstituted (C6-C30)aryl, or a substituted or unsubstituted (5- to 30-membered)heteroaryl; or may be linked to an adjacent substituent to form a substituted or unsubstituted (3- to 30-membered) mono- or polycyclic, alicyclic or aromatic ring, or a combination thereof;

$R_{11}$ to $R_{14}$ each independently represent hydrogen, deuterium, halogen, cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent to form a substituted or unsubstituted (3- to 30-membered) mono- or polycyclic, alicyclic or aromatic ring, or a combination thereof.

Effects of the Invention

According to the present disclosure, the organic electroluminescent device having a low driving voltage, a high luminous efficiency and/or excellent color coordinates is provided.

EMBODIMENTS OF THE INVENTION

Hereinafter, the present disclosure will be described in detail. However, the following description is intended to explain the invention, and is not meant in any way to restrict the scope of the invention.

The term "organic electroluminescent compound" in the present disclosure means a compound that may be used in an organic electroluminescent device, and may be comprised in any layer constituting an organic electroluminescent device, if necessary.

The term "organic electroluminescent material" in the present disclosure means a material that may be used in an organic electroluminescent device, and may comprise at least one compound. If necessary, the organic electroluminescent material may be comprised in any layer constituting an organic electroluminescent device. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material.

An organic electroluminescent material of the present disclosure comprises at least one compound represented by formula 1 above. The compound of formula 1 may be comprised in at least one layer, which consists of the organic electroluminescent device; and may be in the electron buffer layer and/or the electron transport layer, but not limited thereto; may be included as an electron buffer material when included in the electron buffer layer and may be included as an electron transport material when included in the electron transport layer.

The compound represented by formula 1 will be described in more detail as follows.

The compound represented by formula 1 may be represented by any one of the following formulae 3 to 8.

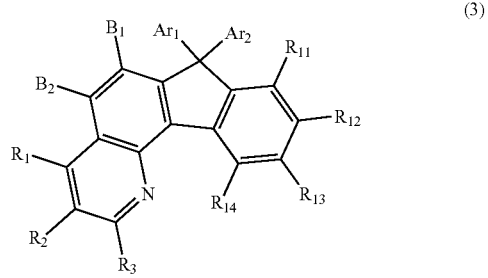

(3)

(4)

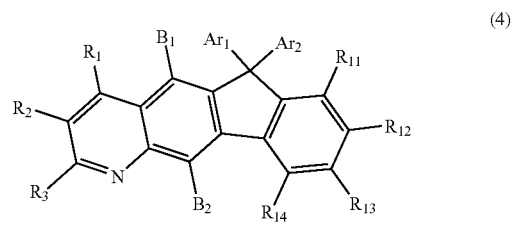

(5)

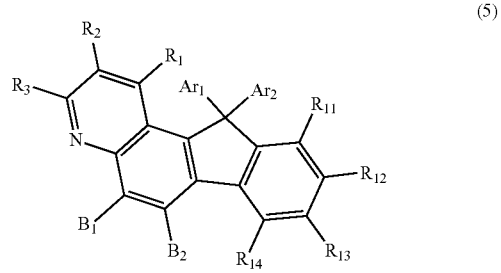

(6)

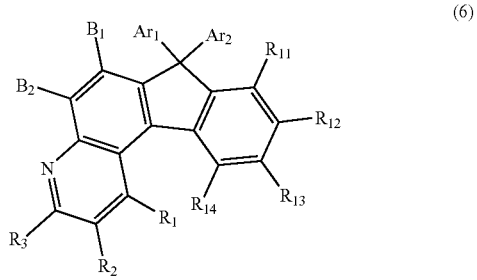

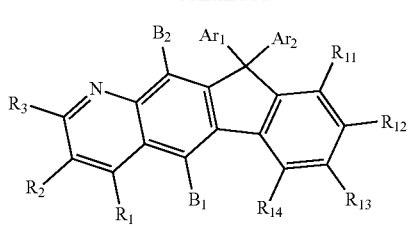

(7)

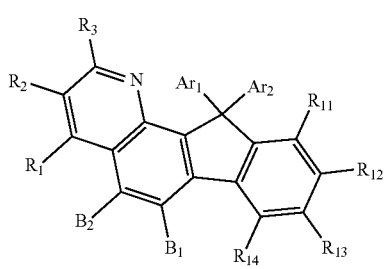

(8)

In formulae 3 to 8, $R_1$ to $R_3$, $B_1$, $B_2$, $Ar_1$, $Ar_2$, and $R_{11}$ to $R_{14}$ are as defined in formula 1.

In formula 1, $R_1$ to $R_3$ each independently represent hydrogen, deuterium, halogen, cyano, a substituted or unsubstituted (C1-C30)alkyl, a substituted or unsubstituted (C6-C30)aryl, or a substituted or unsubstituted (5- to 30-membered)heteroaryl, provided that at least two of $R_1$ to $R_3$ each independently represent a substituted or unsubstituted (C1-C30)alkyl, a substituted or unsubstituted (C6-C30)aryl, or a substituted or unsubstituted (5-to 30-membered)heteroaryl. In one embodiment of the present disclosure, $R_1$ and $R_3$ each independently represent a substituted or unsubstituted (C6-C20)aryl, or a substituted or unsubstituted (5- to 20-membered)heteroaryl, and $R_2$ represents hydrogen. In another embodiment of the present disclosure, $R_1$ and $R_3$ each independently represent a substituted or unsubstituted (C6-C20)aryl, or a substituted or unsubstituted (5- to 20-membered)heteroaryl, and wherein the substituents of the substituted aryl each independently represent (C6-C15)aryl-substituted or unsubstituted (5- to 25-membered)heteroaryl, wherein the substituents of the substituted heteroaryl each independently represent (C6-C15)aryl, and $R_2$ represents hydrogen. Specifically, $R_1$ and $R_3$ each independently may be phenyl; naphthyl; biphenyl; naphthylphenyl; carbazolyl; benzocarbazolyl; carbazolylphenyl; benzocarbazolylphenyl; dibenzocarbazolylphenyl; phenylindolocarbazolyl; triazinyl or pyrimidinyl substituted with one or more of phenyl and biphenyl; triazinyl substituted with one or more of phenyl, naphthyl, and biphenyl; or phenyl, naphthyl, biphenyl, phenylnaphthyl or naphthylphenyl substituted with pyrimidinyl.

a and b, or b and c, or c and d of formula 1 are combined with * of formula 2 to form a ring, wherein $B_1$ and $B_2$ are bonded at the positions not bonded to * of formula 2 among a to d, regardless of the sequence;

$B_1$ and $B_2$ each independently represent hydrogen, deuterium, halogen, cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino. In one embodiment of the present disclosure, $B_1$ and $B_2$ represent hydrogen.

$Ar_1$ and $Ar_2$ each independently represent halogen, a substituted or unsubstituted (C1-C30)alkyl, a substituted or unsubstituted (C6-C30)aryl, or a substituted or unsubstituted (5- to 30-membered)heteroaryl; or may be linked to each other to form a substituted or unsubstituted (3- to 30-membered) mono- or polycyclic, alicyclic or aromatic ring, or a combination thereof. In one embodiment of the present disclosure, $Ar_1$ and $Ar_2$ each independently represent a substituted or unsubstituted (C1-C6)alkyl, or a substituted or unsubstituted (C6-C12)aryl; or may be linked to each other to form a substituted or unsubstituted (5- to 15-membered) polycyclic, alicyclic or aromatic ring, or a combination thereof. In another embodiment of the present disclosure, $Ar_1$ and $Ar_2$ each independently represent an unsubstituted (C1-C6)alkyl or an unsubstituted (C6-C12)aryl; or may be linked to each other to form an unsubstituted (5- to 15-membered) polycyclic aromatic ring. Specifically, $Ar_1$ and $Ar_2$ may be each independently methyl or phenyl; or may be linked to each other to form a spirobifluorene ring.

$R_{11}$ to $R_{14}$ each independently represent hydrogen, deuterium, halogen, cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to each other to form a substituted or unsubstituted (3- to 30-membered) mono- or polycyclic, alicyclic or aromatic ring, or a combination thereof. In one embodiment of the present disclosure, $R_{11}$ to $R_{14}$ each independently represent hydrogen or a substituted or unsubstituted (C6-C12)aryl. In another embodiment of the present disclosure, $R_{11}$ to $R_{14}$ each independently represent hydrogen or an unsubstituted (C6-C12)aryl. According to another embodiment of the present disclosure, $R_{11}$, $R_{13}$ and $R_{14}$ are hydrogen, and $R_{12}$ is hydrogen or an unsubstituted (C6-C12) aryl. Specifically, $R_{11}$ to $R_{14}$ may be each independently hydrogen or phenyl.

In the formula of the present disclosure, when an adjacent substituent may be linked to form a substituted or unsubstituted (3- to 30-membered) mono- or polycyclic, alicyclic or aromatic ring, or a combination thereof, the formed alicyclic, aromatic ring, or a combination thereof may contain at least one heteroatom selected from nitrogen, oxygen, and sulfur.

In the formula of the present disclosure, the heteroaryl (ene) and the heterocycloalkyl each independently may contain at least one heteroatom selected from B, N, O, S, Si, and P.

In addition, the heteroatom may be combined with at least one of substituents selected from hydrogen, deuterium, halogen, cyano, a substituted or unsubstituted (C1-C30) alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

According to one embodiment of the present disclosure, in the formula 1, $R_1$ and $R_3$ each independently represent a substituted or unsubstituted (C6-C20)aryl or a substituted or unsubstituted (5- to 20-membered)heteroaryl; $R_2$ represents hydrogen; $B_1$ and $B_2$ represent hydrogen; $Ar_1$ and $Ar_2$ each independently represent a substituted or unsubstituted (C1-C6)alkyl or a substituted or unsubstituted (C6-C12)aryl, or may be linked to each other to form a substituted or unsubstituted (5- to 15-membered) polycyclic, alicyclic or aromatic ring, or a combination thereof; $R_{11}$ to $R_{14}$ each independently represent hydrogen or a substituted or unsubstituted (C6-C12)aryl.

According to another embodiment of the present disclosure, in formula 1, $R_1$ and $R_3$ each independently represent a substituted or unsubstituted (C6-C20)aryl or a substituted or unsubstituted (5- to 20-membered)heteroaryl, wherein the substituents of the substituted aryl each independently represent (C6-C15)aryl-substituted or unsubstituted (5- to 20-membered)heteroaryl, and the substituents of the substituted heteroaryl each independently represent (C6-C15)aryl; $R_2$ represents hydrogen; $B_1$ and $B_2$ represent hydrogen; $Ar_1$ and $Ar_2$ each independently represent an unsubstituted (C1-C6)alkyl or an unsubstituted (C6-C12)aryl; or may be linked to each other to form an unsubstituted (5- to 15-membered) polycyclic aromatic ring; $R_{11}$ to $R_{14}$ each independently represent hydrogen or an unsubstituted (C6-C12)aryl.

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, and tert-butyl, etc. "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "(3- to 7-membered)heterocycloalkyl" is a cycloalkyl having 3 to 7 ring backbone atoms, preferably 5 to 7 ring backbone atoms and at least one heteroatom selected from the group consisting of B, N, O, S, Si, and P, preferably O, S, and N, and includes tetrahydrofuran, pyrrolidine, thiolan, tetrahydropyran, etc. "(C6-C30)aryl(ene)" is a monocyclic or fused ring radical derived from an aromatic hydrocarbon having 6 to 30 ring backbone carbon atoms and may be partially saturated, in which the number of ring backbone carbon atoms is preferably 6 to 25, more preferably 6 to 18. The aryl includes those having a spiro structure, and includes phenyl, biphenyl, terphenyl, naphthyl, binaphthyl, phenylnaphthyl, naphthylphenyl, phenyl terphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. "(5- to 30-membered) heteroaryl(ene)" is an aryl group having at least one heteroatom selected from the group consisting of B, N, O, S, Si, and P, and 5 to 30 ring backbone atoms; having preferably 1 to 4 heteroatoms, and may be a monocyclic ring, or a fused ring condensed with at least one benzene ring; may be partially saturated. In addition, the heteroaryl(ene) in the present disclosure may be one formed by linking at least one heteroaryl or aryl group to a heteroaryl group via a single bond(s); may comprise those having a spiro structure; and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacridinyl, etc. "Halogen" includes F, Cl, Br, and I.

In addition, "substituted" in the expression "substituted or unsubstituted" means that a hydrogen atom in a certain functional group is replaced with another atom or functional group, i.e., a substituent. The substituents of the substituted alkyl, the substituted aryl, the substituted heteroaryl, the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, the substituted alkylarylamino, and the substituted mono- or polycyclic, alicyclic, aromatic ring, or the combination thereof, in $R_1$ to $R_3$, $B_1$, $B_2$, $Ar_1$, $Ar_2$, and $R_{11}$ to $R_{14}$ are each independently at least one selected from the group consisting of deuterium; halogen; cyano; carboxyl; nitro; hydroxy; (C1-C30)alkyl; halo(C1-C30)alkyl; (C2-C30)alkenyl; (C2-C30)alkynyl; (C1-C30)alkoxy; (C1-C30)alkylthio; (C3-C30)cycloalkyl; (C3-C30)cycloalkenyl; (3- to 7-membered)heterocycloalkyl; (C6-C30)aryloxy; (C6-C30)arylthio; (C6-C30)aryl-substituted or unsubstituted (5- to 30-membered)heteroaryl; (5- to 30-membered)heteroaryl-substituted or unsubstituted (C6-C30)aryl; tri(C1-C30)alkylsilyl; tri(C6-C30)arylsilyl; di(C1-C30)alkyl(C6-C30)arylsilyl; (C1-C30)alkyldi(C6-C30)arylsilyl; amino; a mono- or di-(C1-C30)alkylamino; (C1-C30)alkyl-substituted or unsubstituted mono- or di-(C6-C30)arylamino; (C1-C30)alkyl(C6-C30)arylamino; (C1-C30)alkylcarbonyl; (C1-C30)alkoxycarbonyl; (C6-C30)arylcarbonyl; di(C6-C30)arylboronyl; di(C1-C30)alkylboronyl; (C1-C30)alkyl(C6-C30)arylboronyl; (C6-C30)ar(C1-C30)alkyl; and (C1-C30)alkyl(C6-C30)aryl. In one embodiment of the present disclosure, the substituents are each independently (C6-C15)aryl or (C6-C15)aryl-substituted or unsubstituted (5- to 25-membered)heteroaryl. Specifically, the substituents may be each independently phenyl; biphenyl; carbazolyl; benzocarbazolyl; dibenzocarbazolyl; and triazinyl or pyrimidinyl, etc., substituted with at least one of phenyl, naphthyl and biphenyl.

The compound represented by formula 1 may be specifically illustrated by the following compounds, but is not limited thereto:
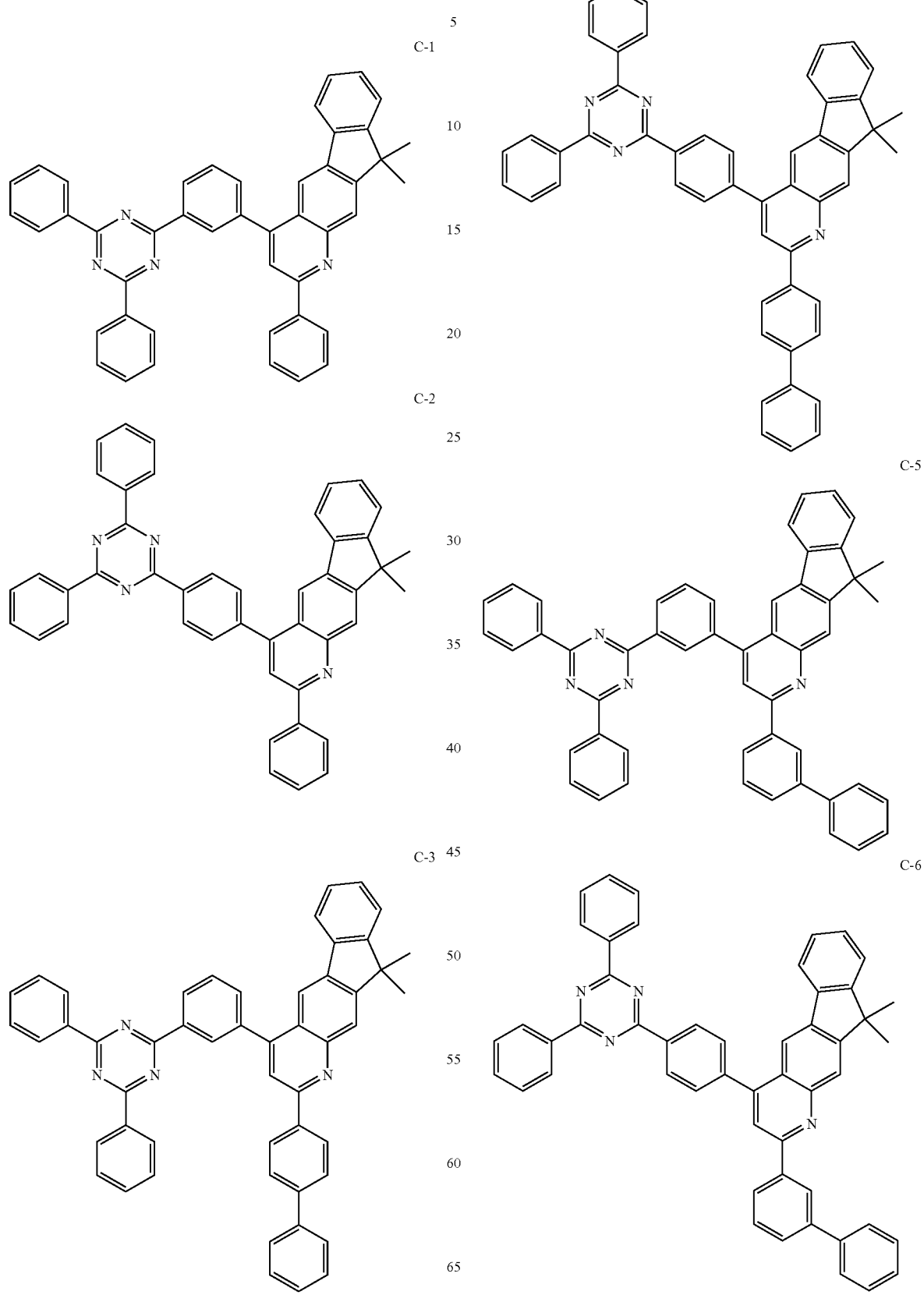

C-7
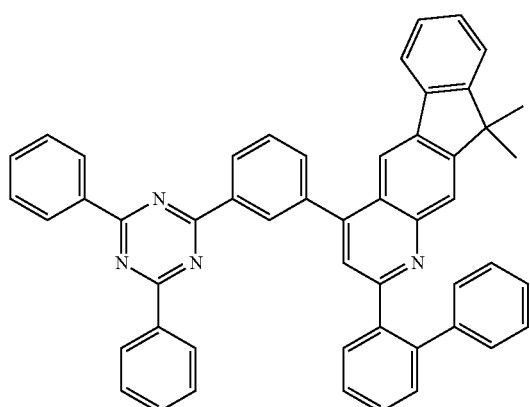
C-8
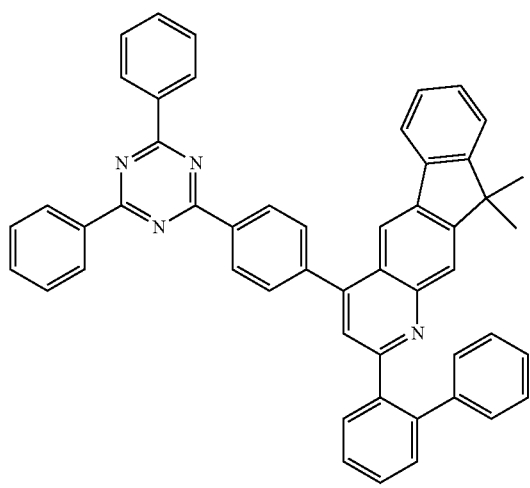
C-9
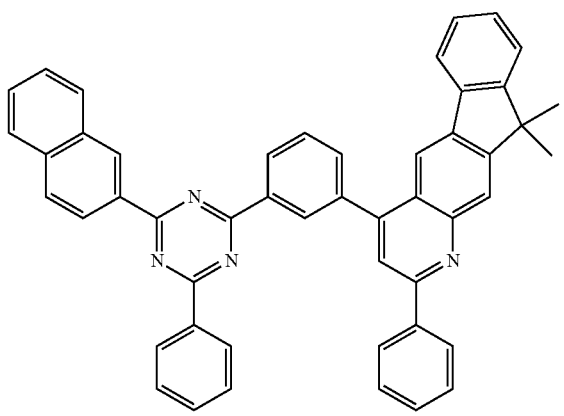
C-10
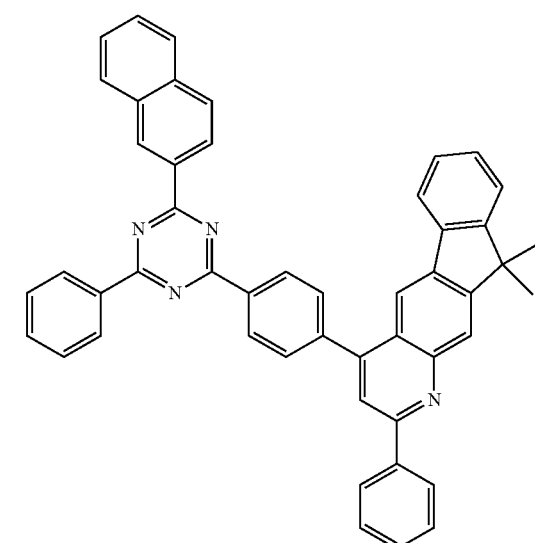
C-11
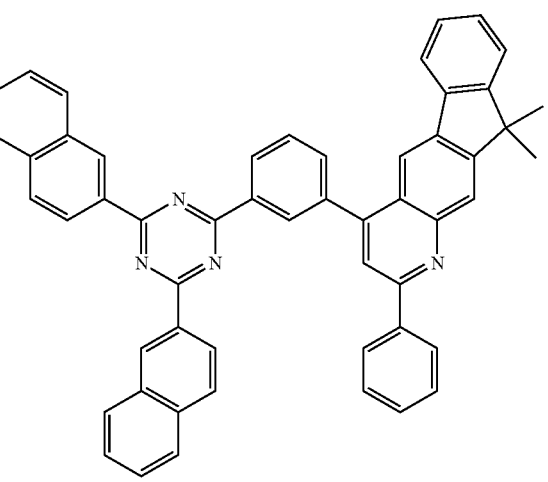
C-12
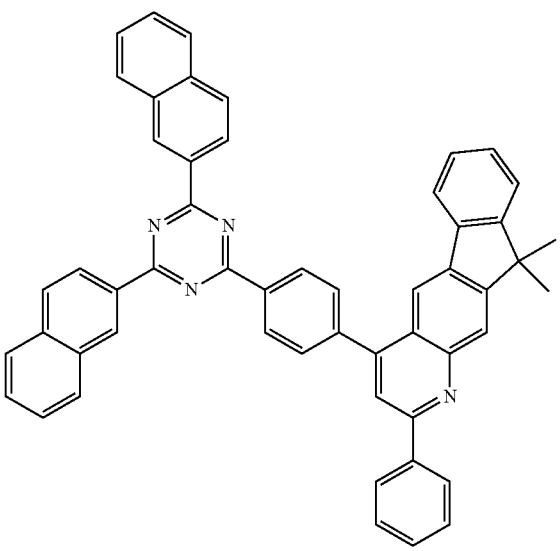

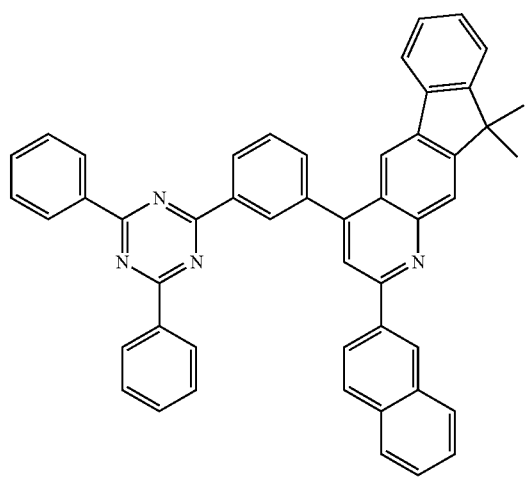
C-13
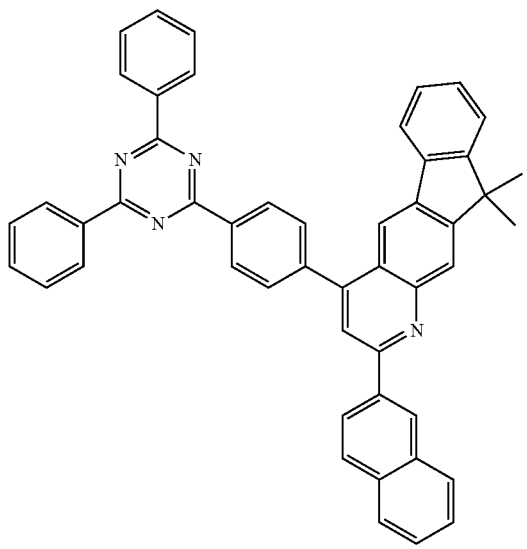
C-14
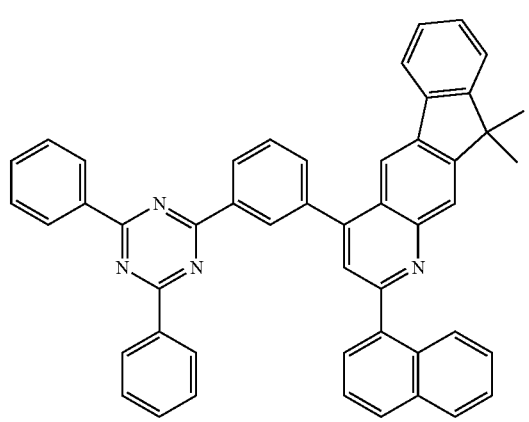
C-15
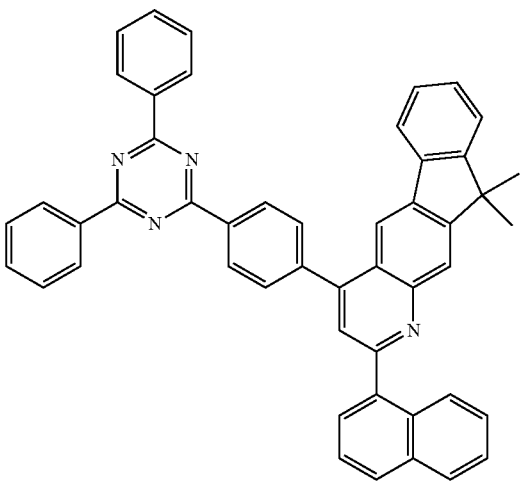
C-16
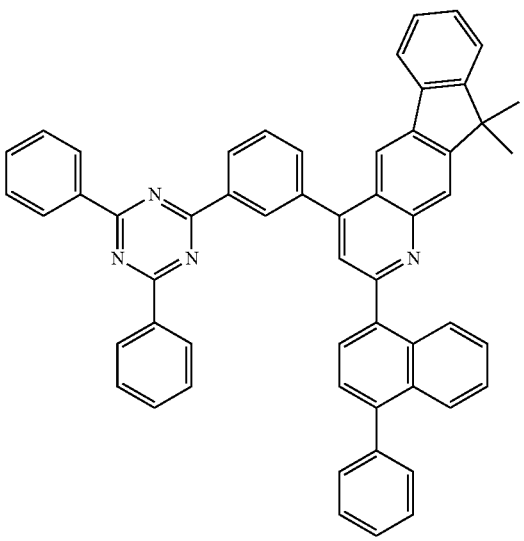
C-17

C-18
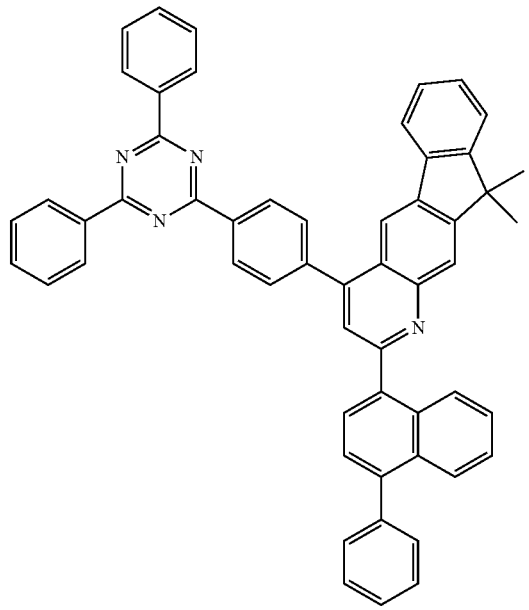
C-19
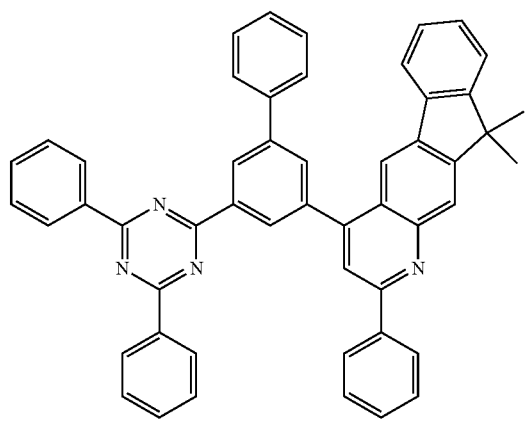
C-20
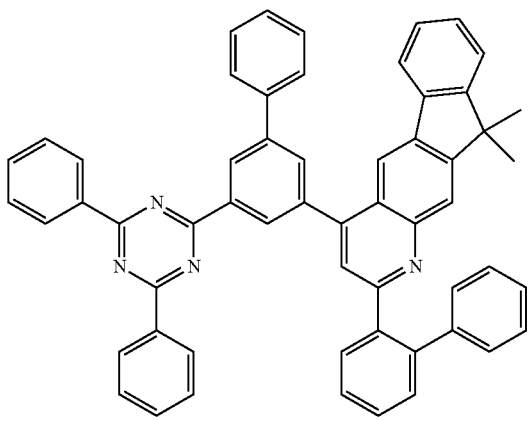
C-21
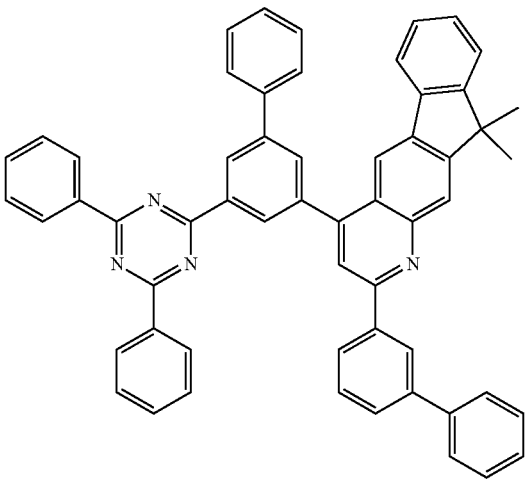
C-22
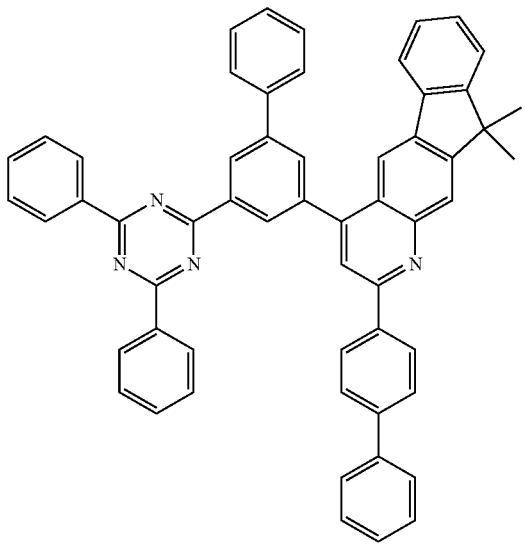
C-23
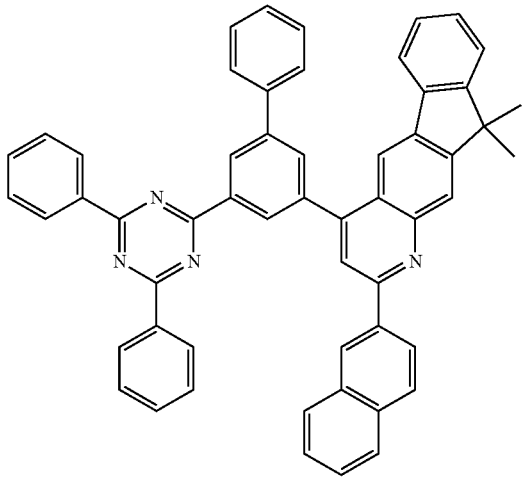

C-24
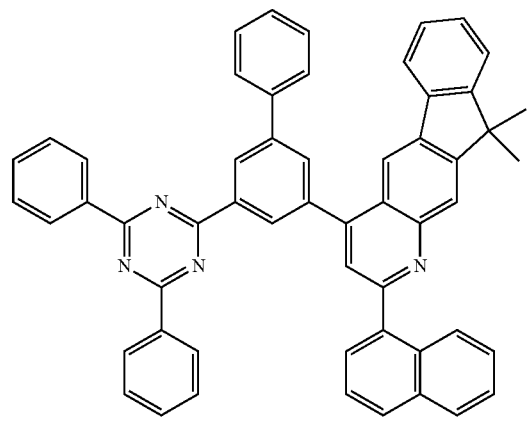
C-27
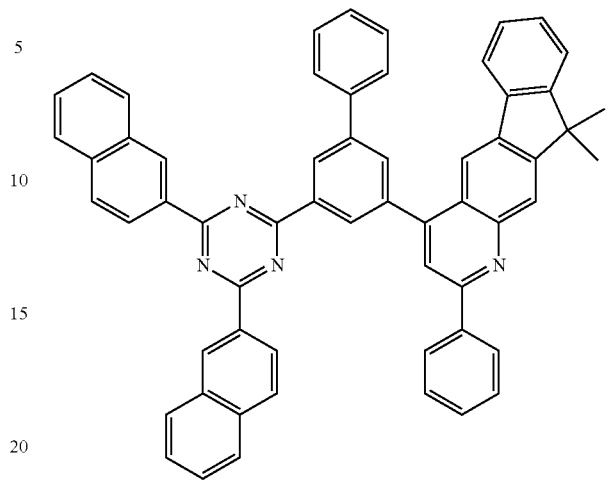
C-25
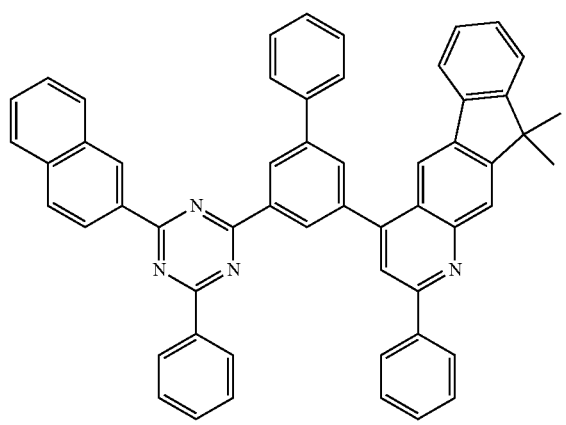
C-28
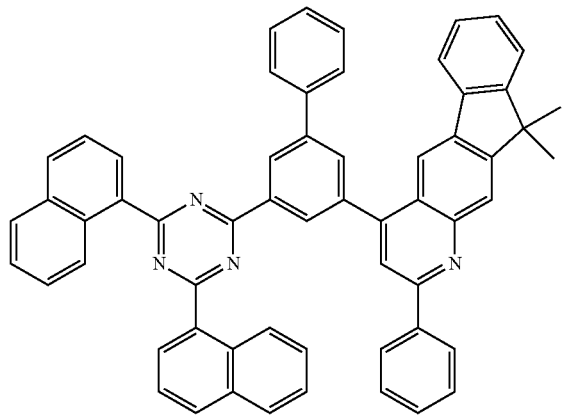
C-26
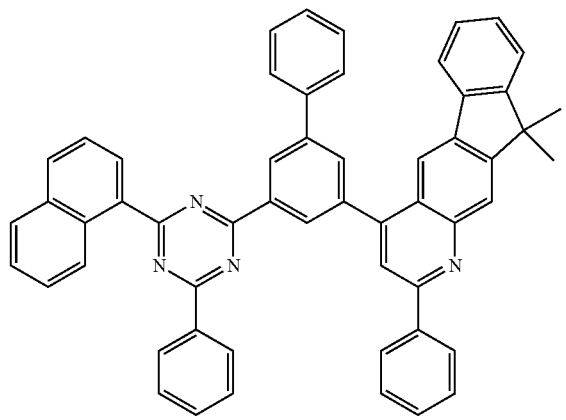
C-29
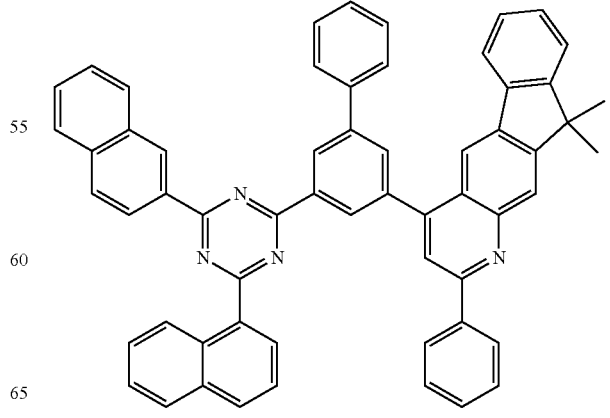

C-30
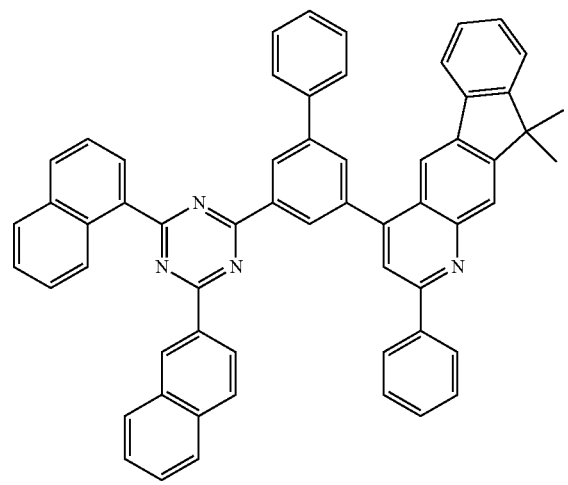
C-33
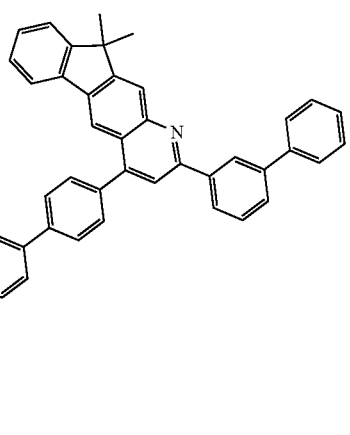
C-31
C-34
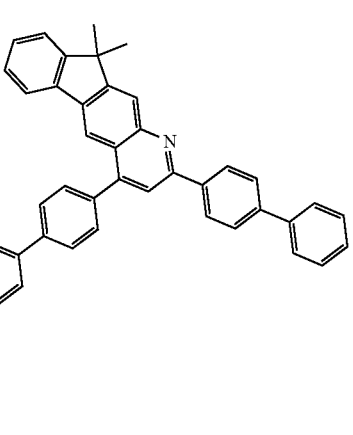
C-32
C-35
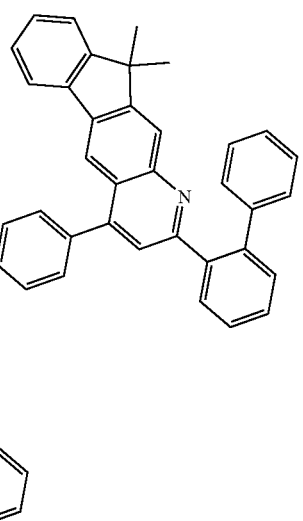

C-36
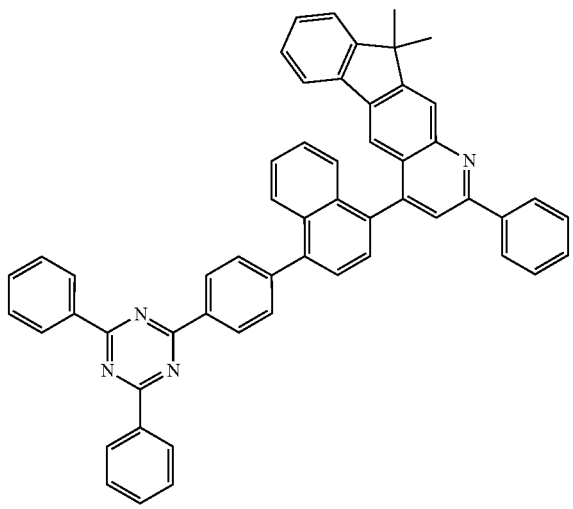
C-37
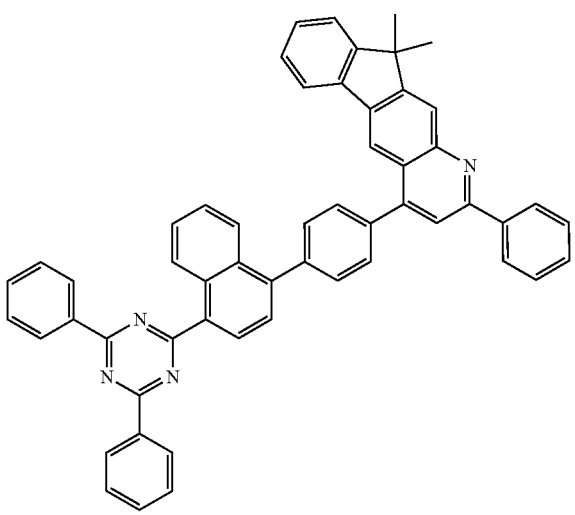
C-38
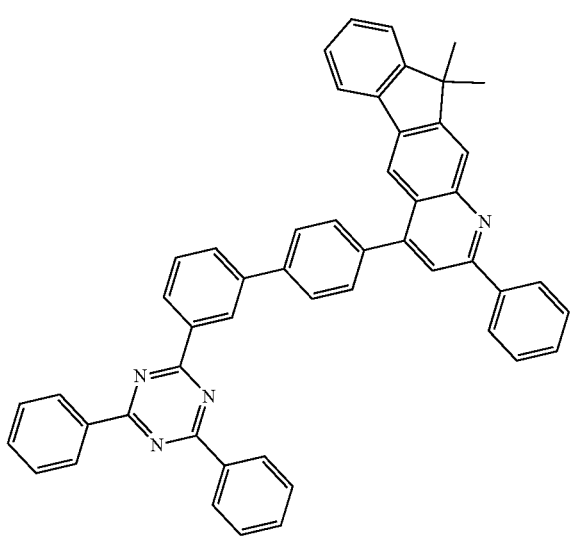
C-39
C-40
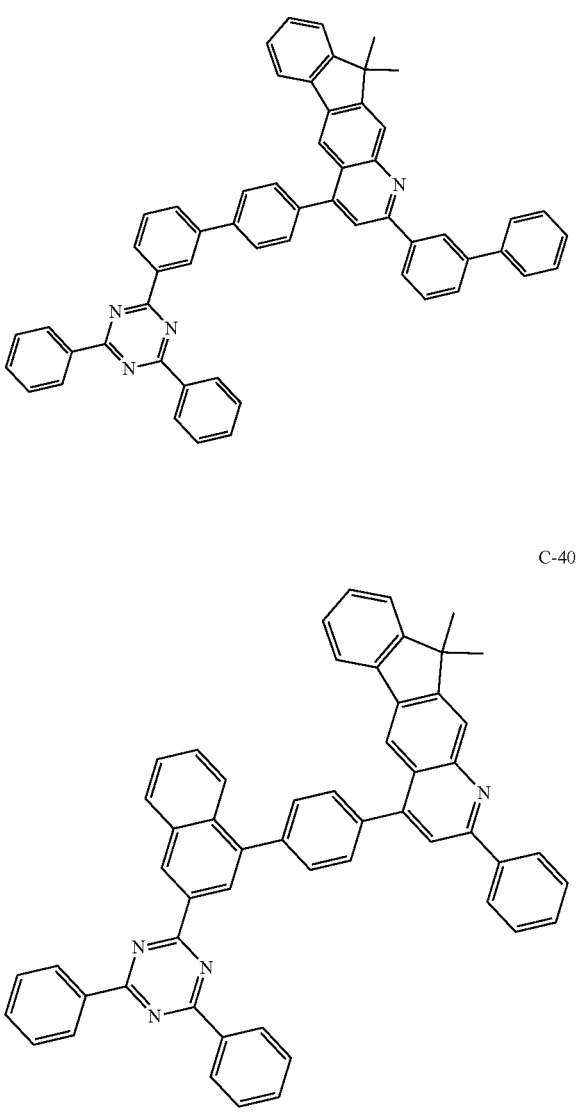
C-41
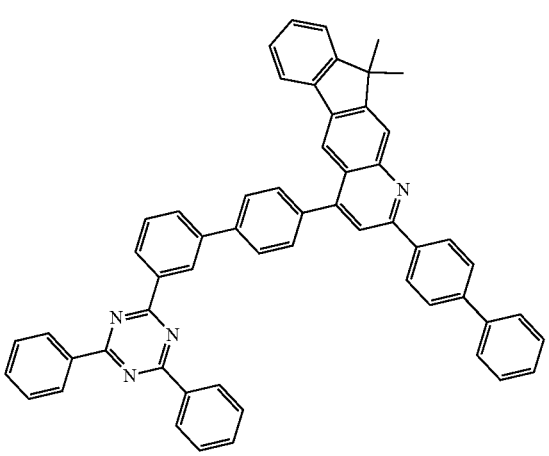

C-42
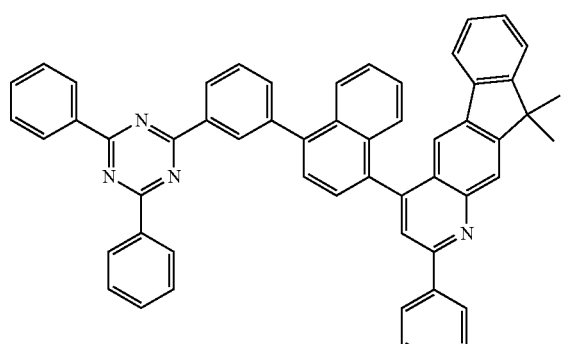
C-43
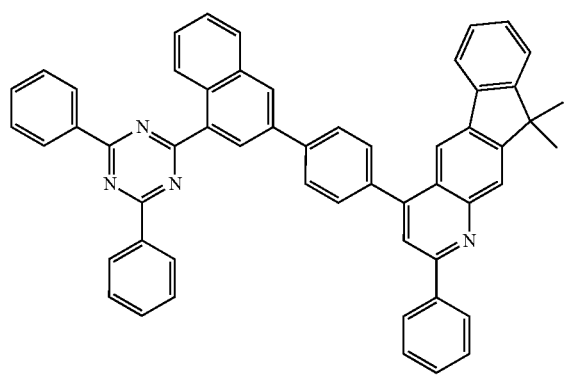
C-44
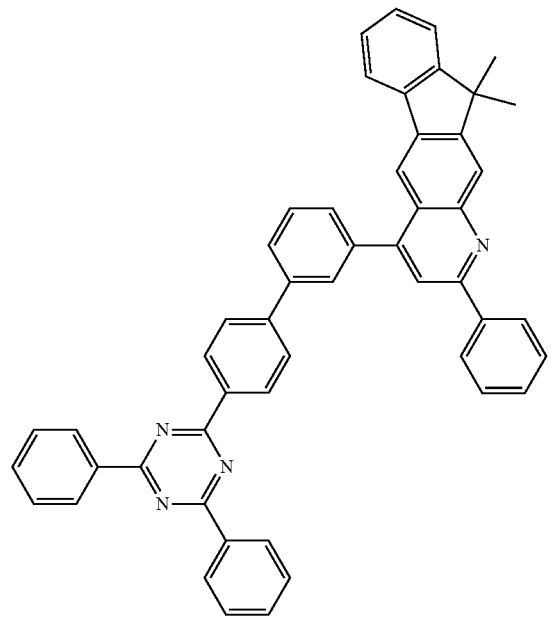
C-45
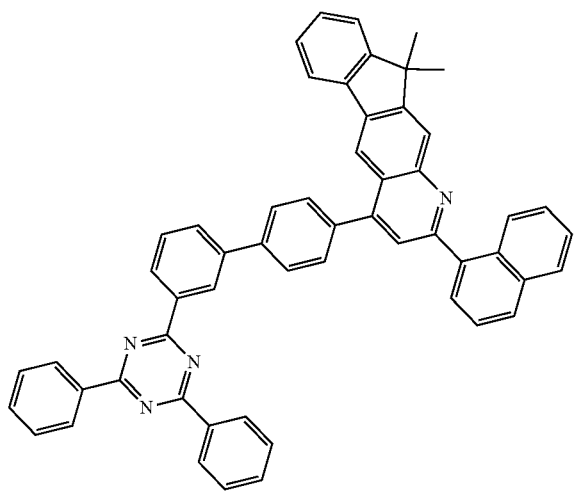
C-46
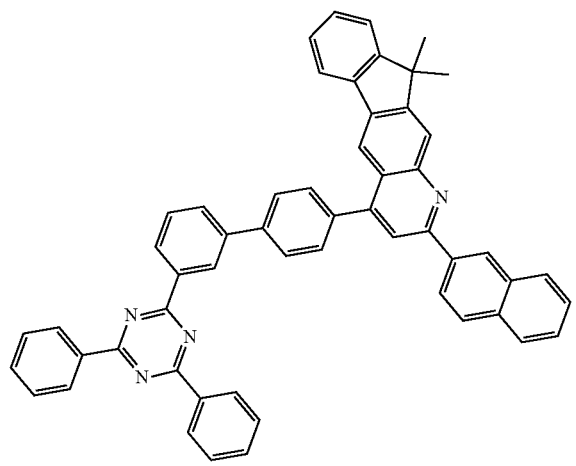
C-47
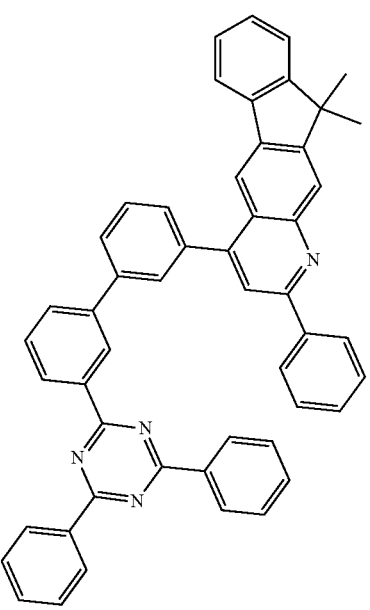

C-48
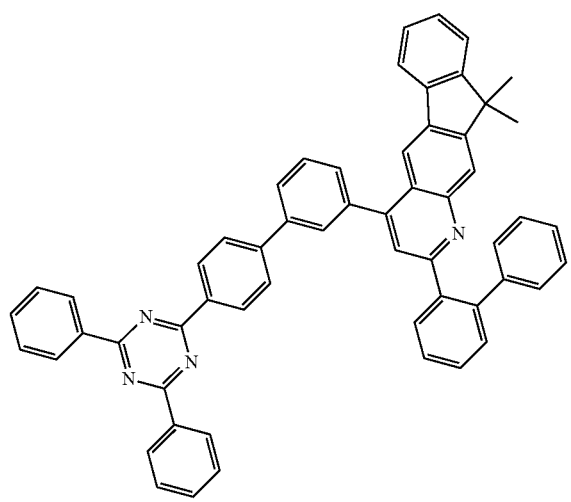
C-49
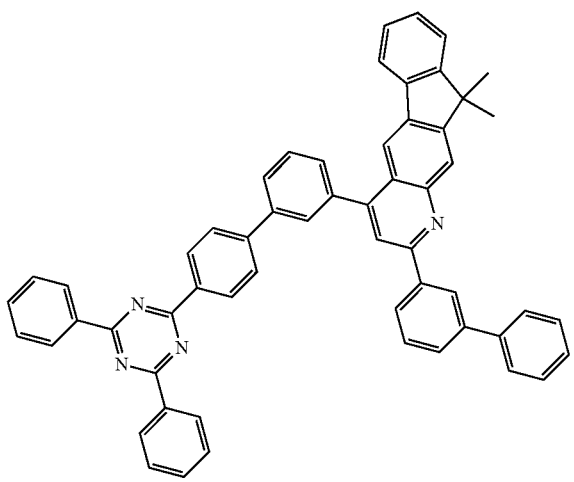
C-50
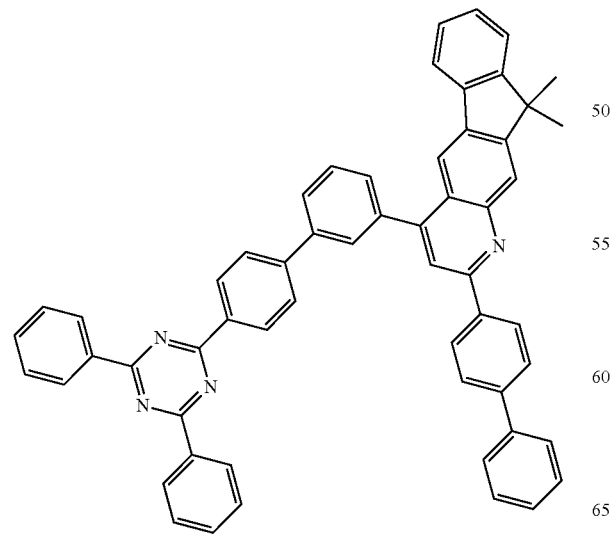
C-51
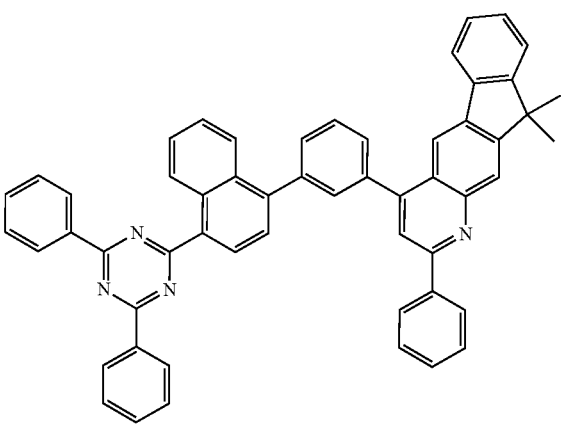
C-52
C-53
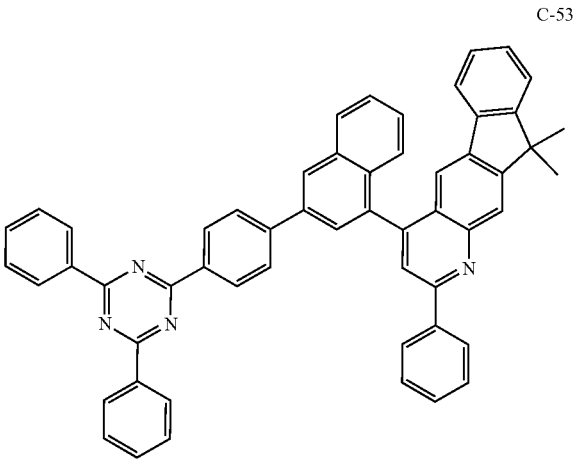

C-54
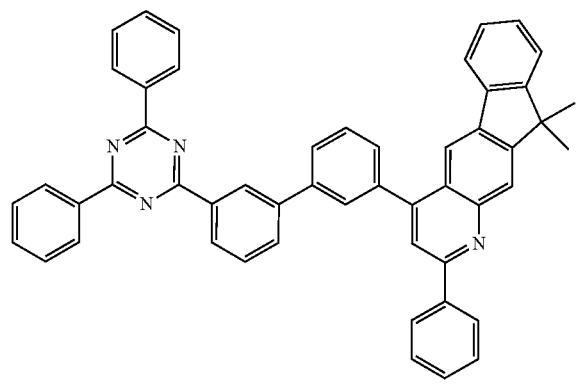
C-55
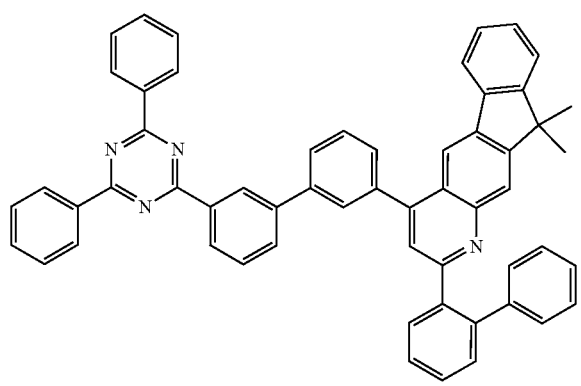
C-56
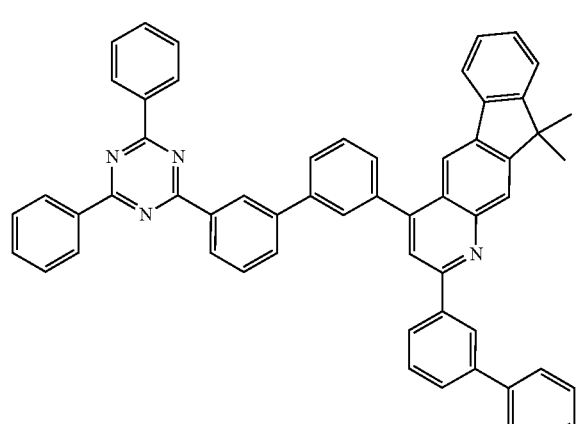
C-57
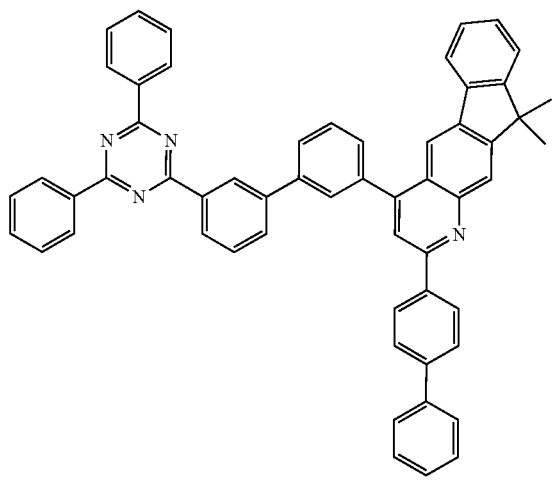
C-58
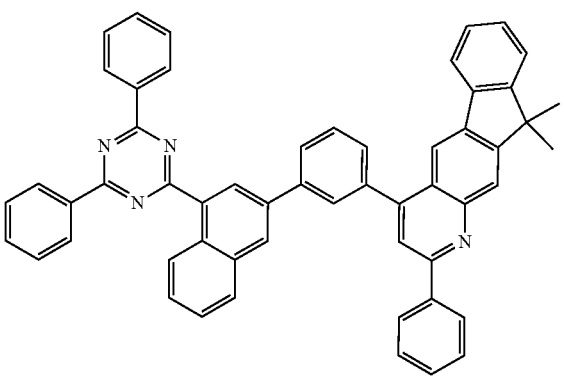
C-59
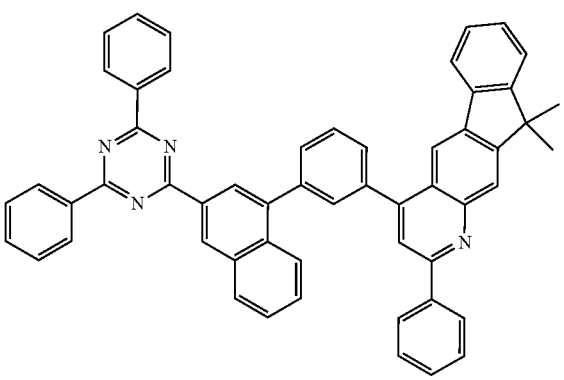
C-60
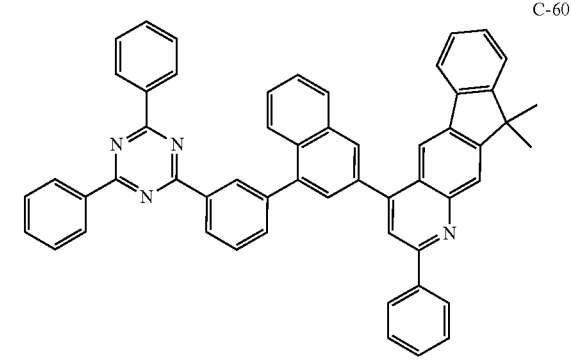

C-61
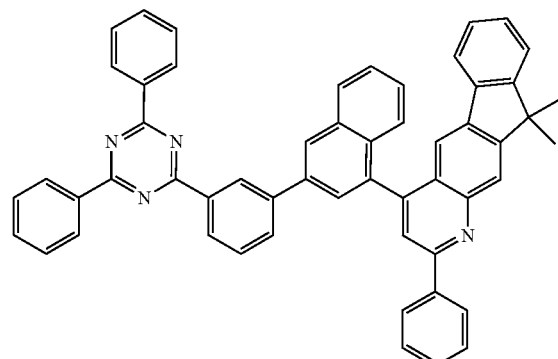
C-62
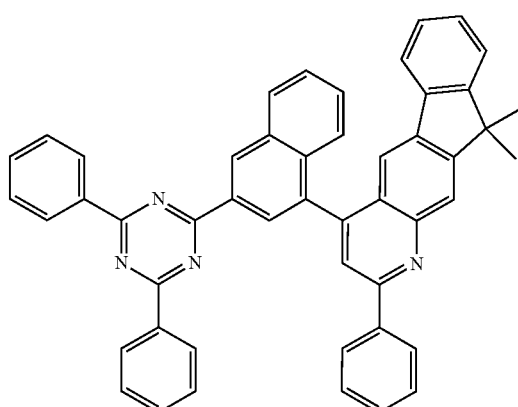
C-63
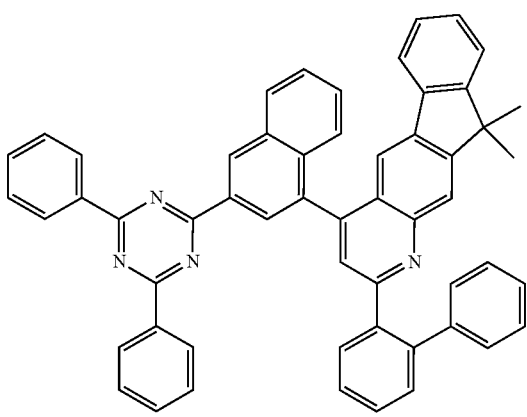
C-64
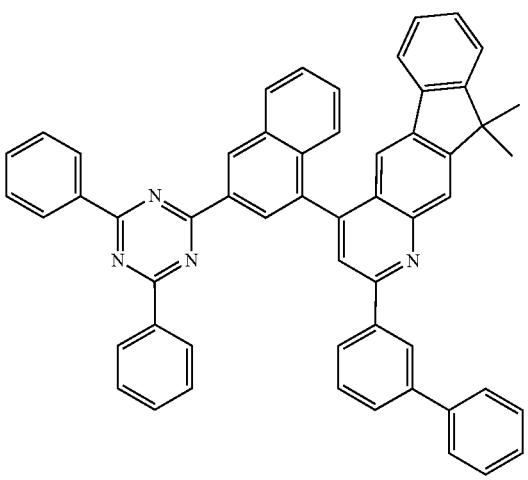
C-65
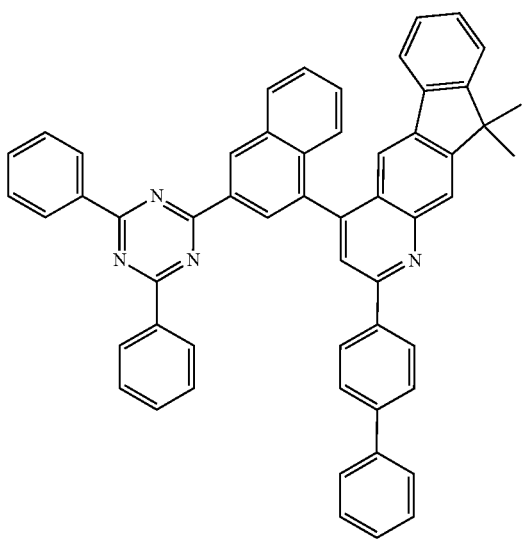
C-66
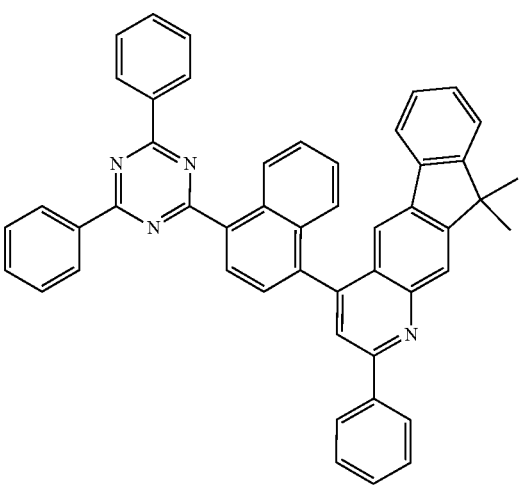

C-67
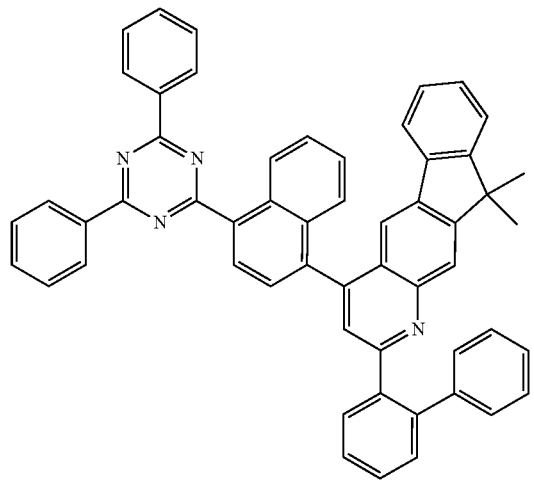
C-68
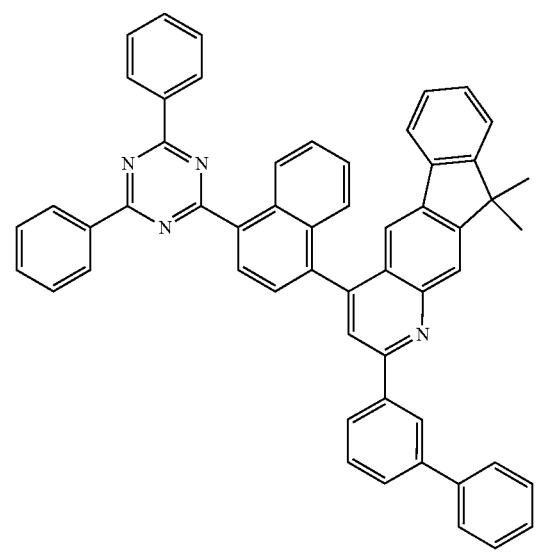
C-69
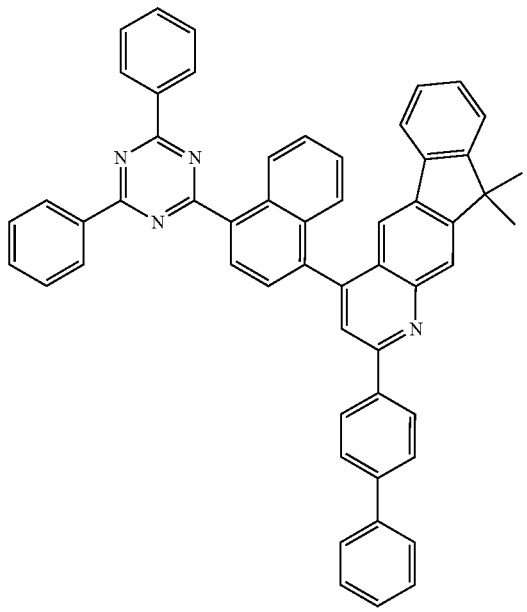
C-70
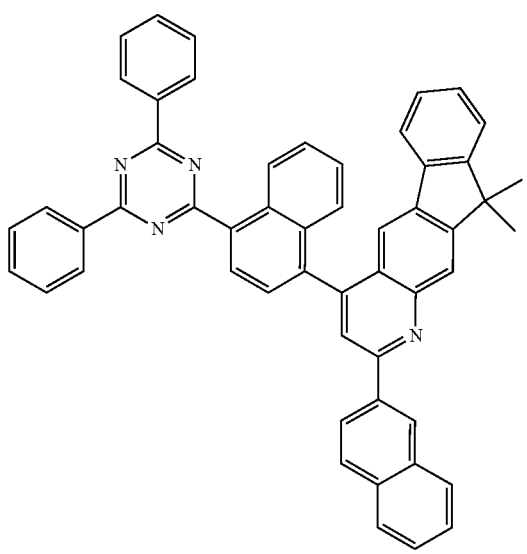
C-71
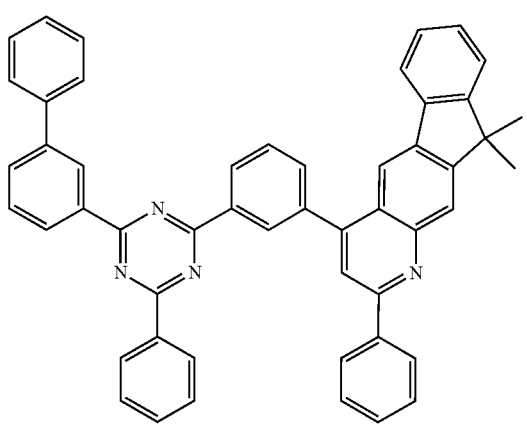

C-72
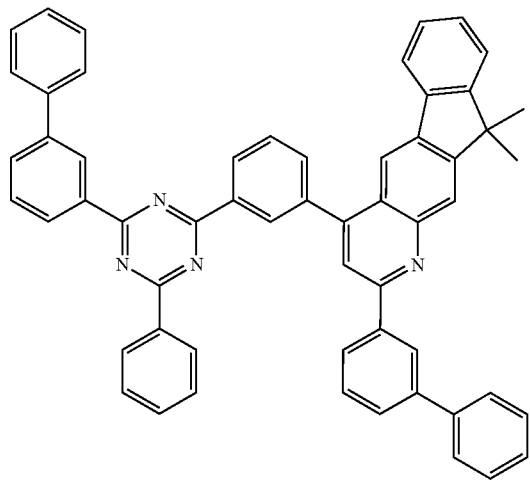
C-75
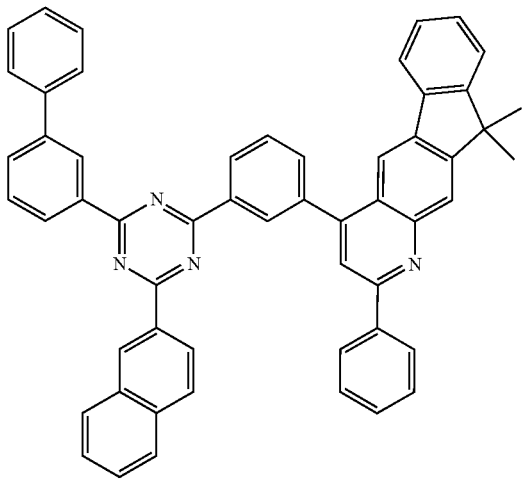
C-73
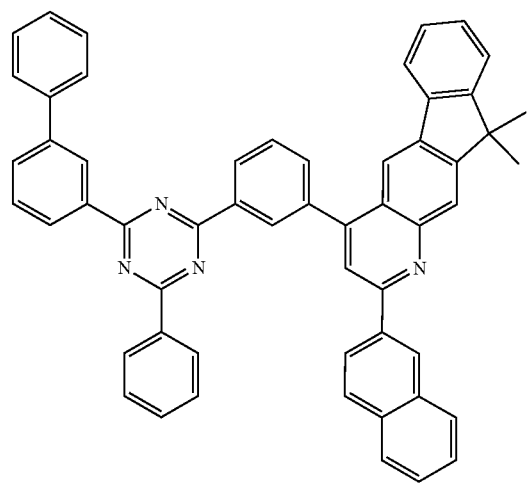
C-76
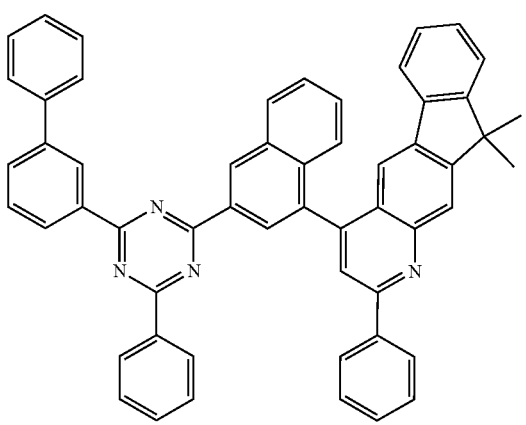
C-74
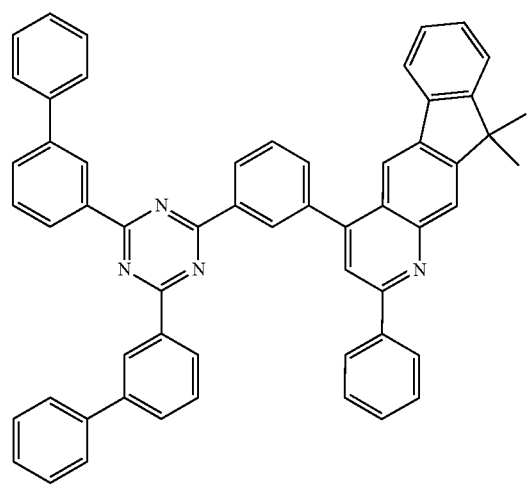
C-77
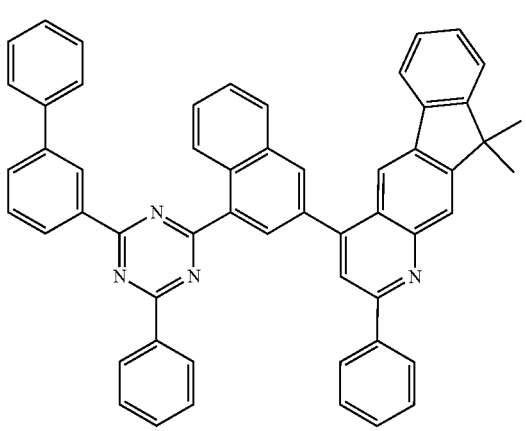

-continued
C-78
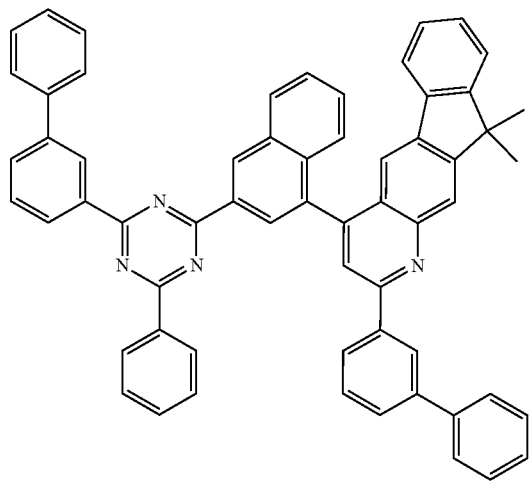
C-79
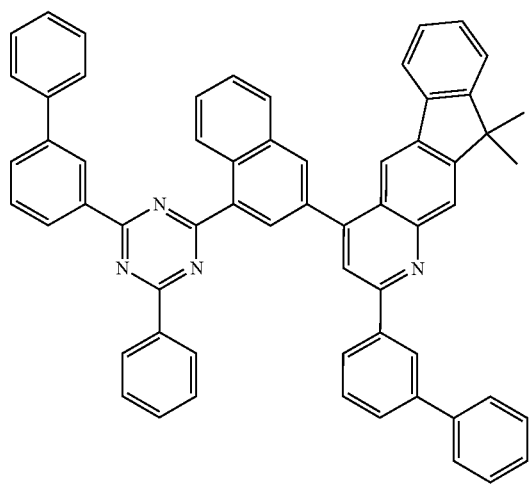
C-80
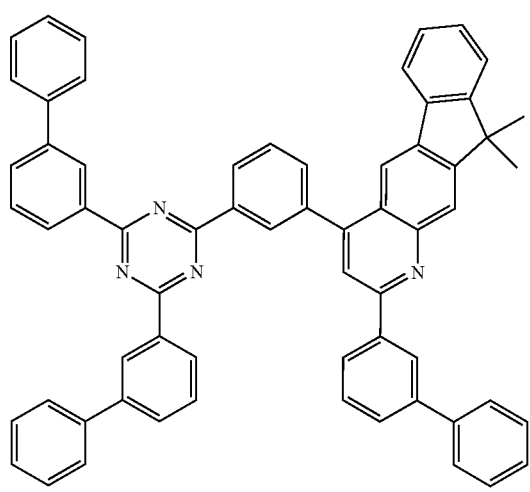
C-81
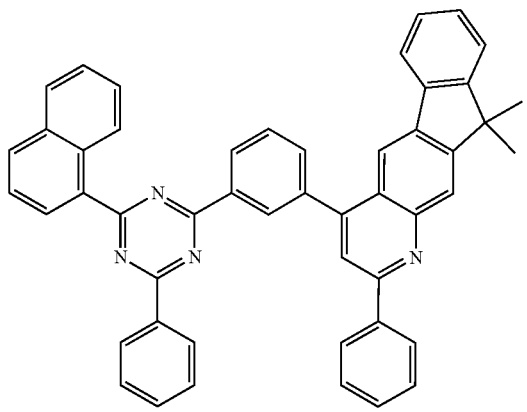
C-82
C-83
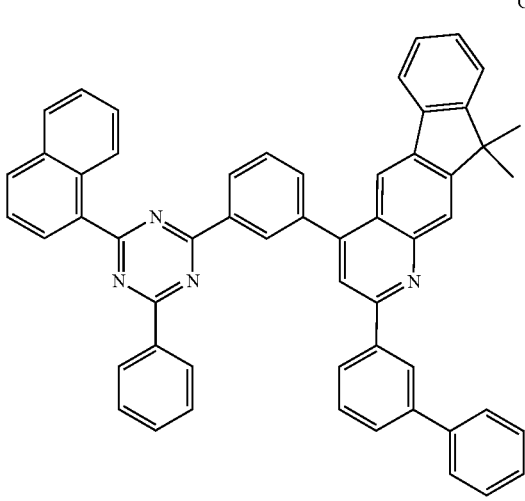

-continued
C-84
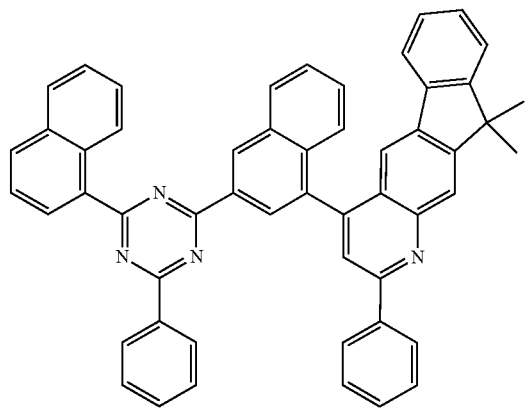
C-85
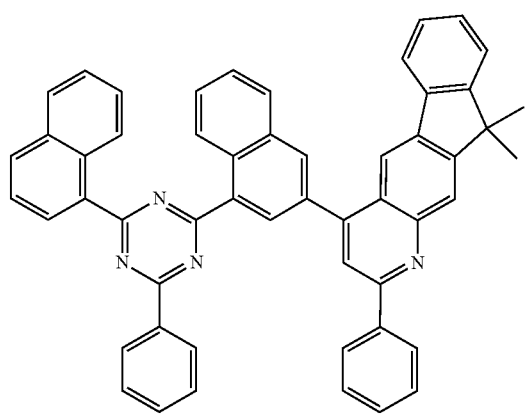
C-86
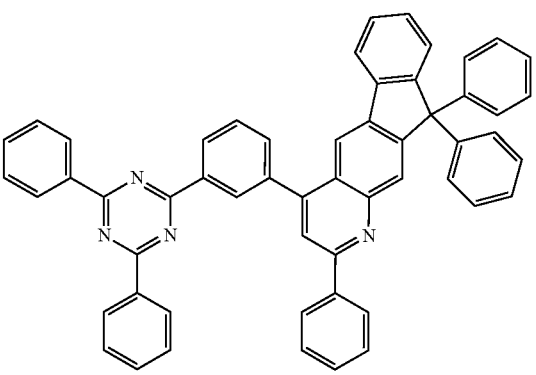
C-87
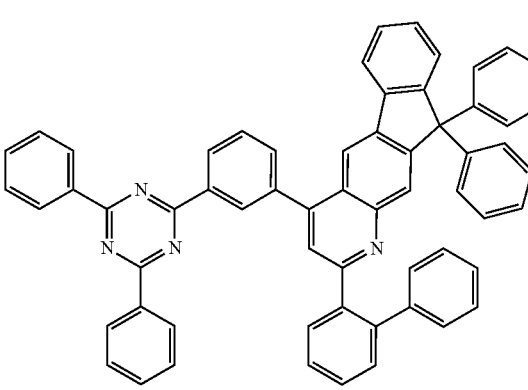
-continued
C-88
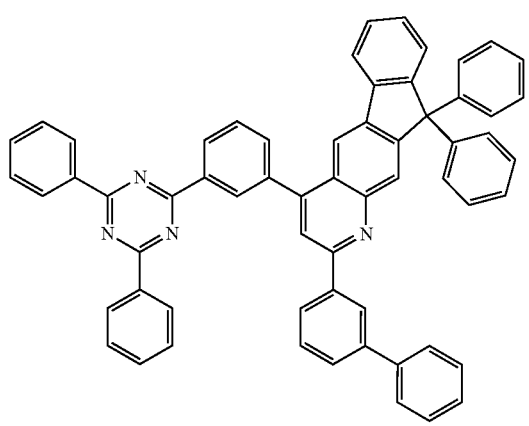
C-89
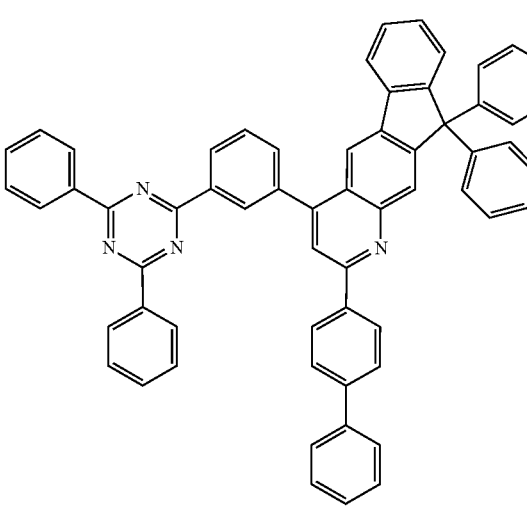
C-90
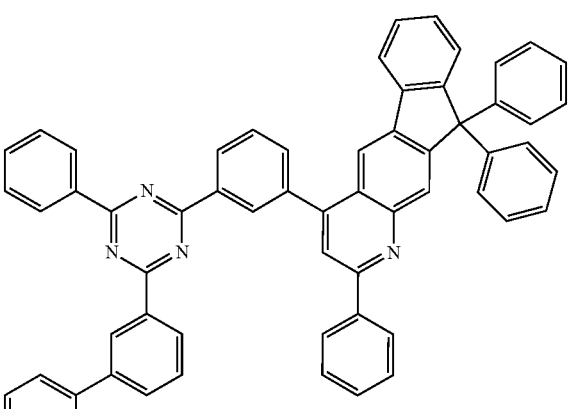

C-91
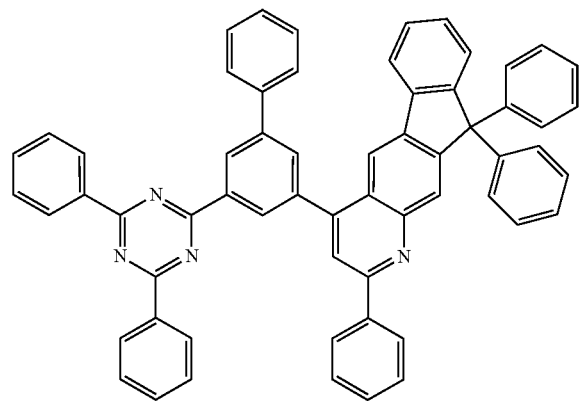
C-92
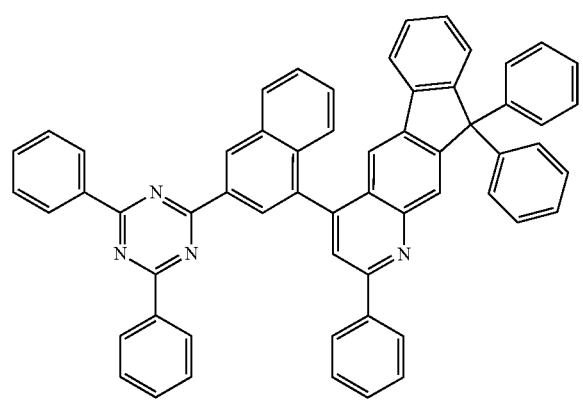
C-93
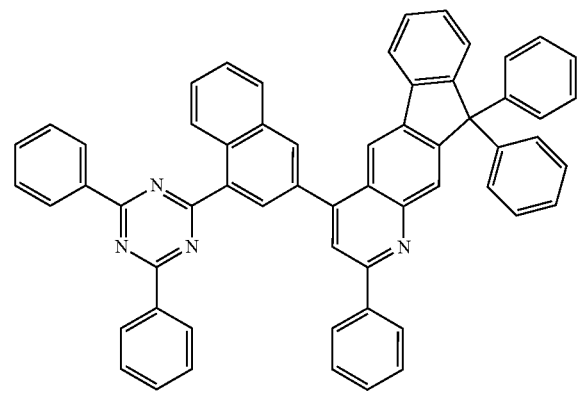
C-94
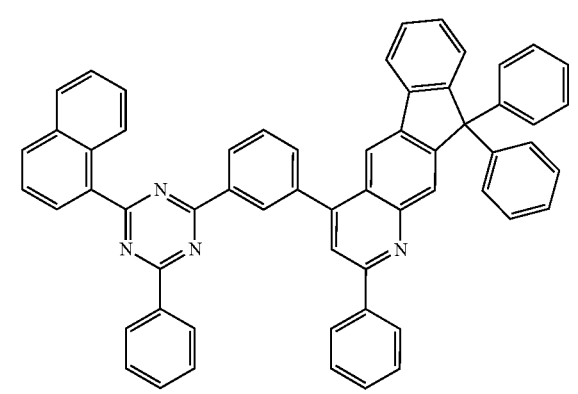
C-95
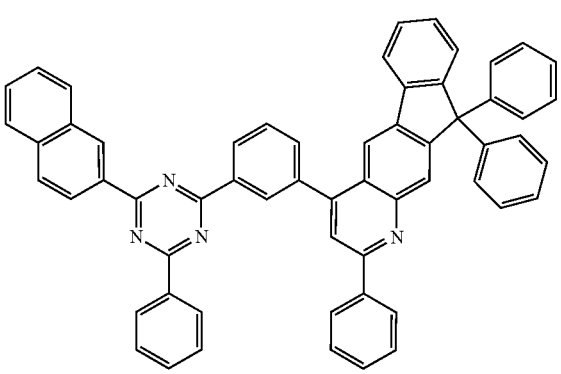
C-96
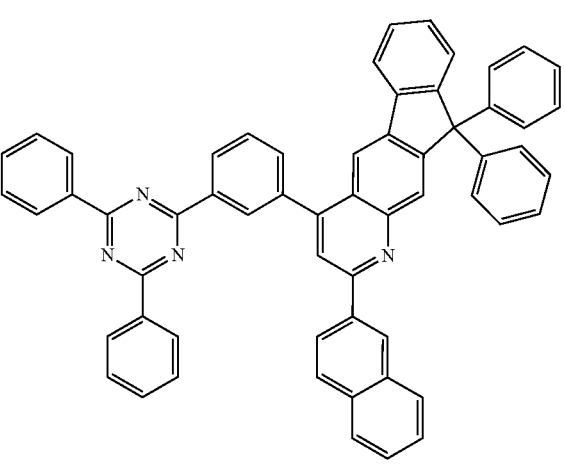
C-97
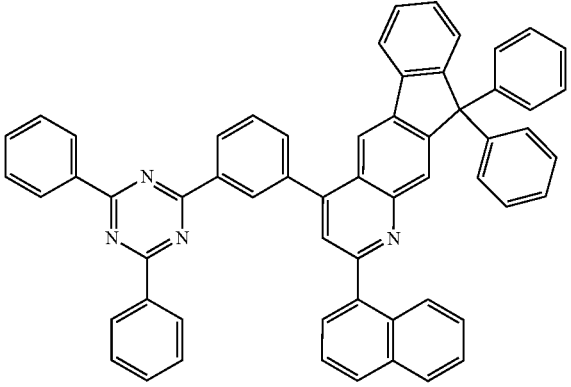

C-98
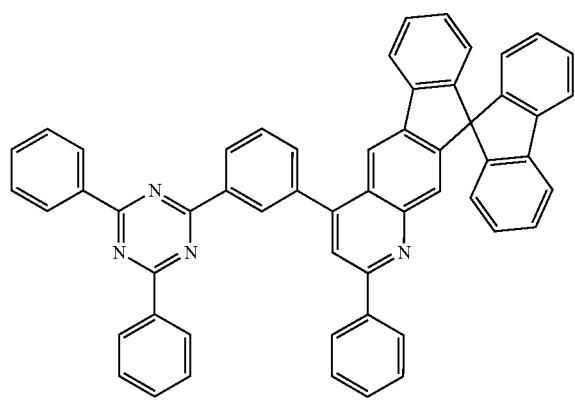
C-101
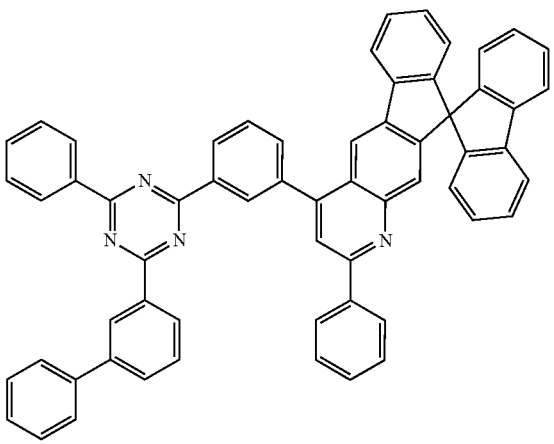
C-99
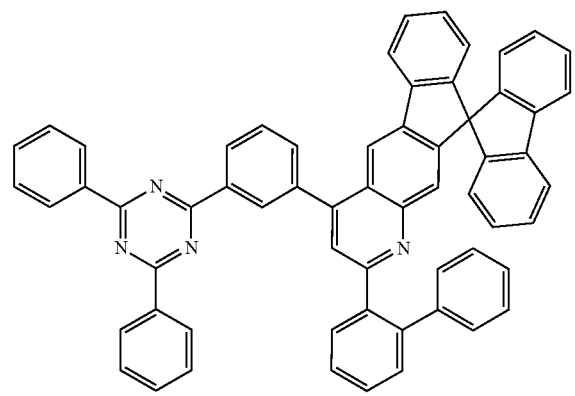
C-102
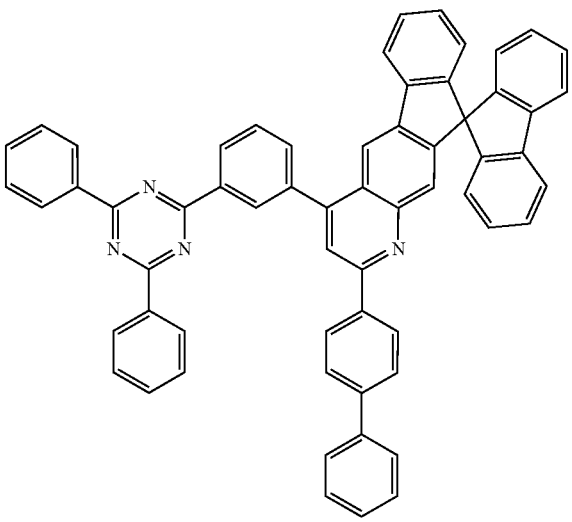
C-100
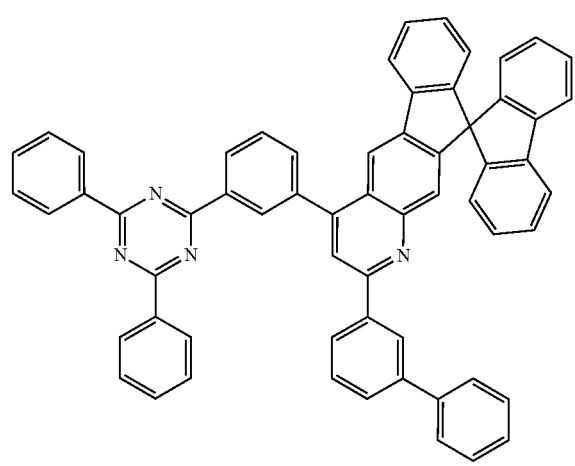
C-103
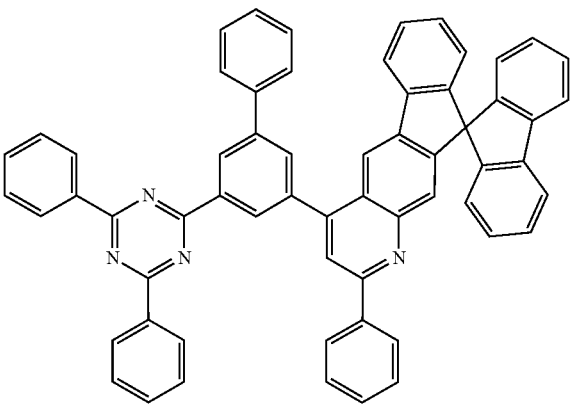

C-104
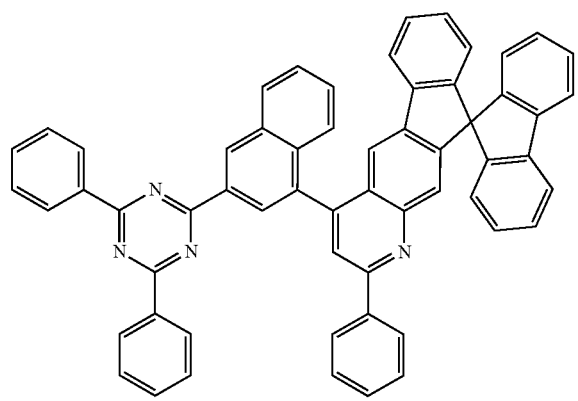
C-105
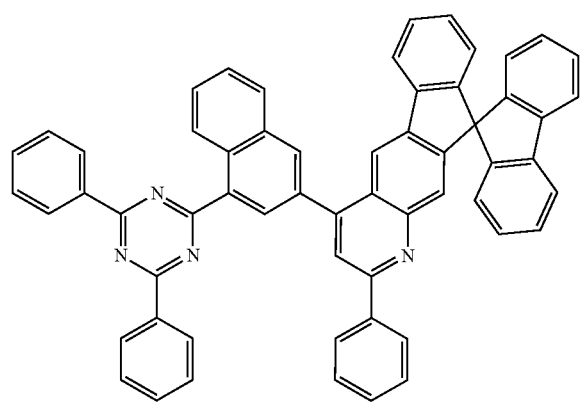
C-106
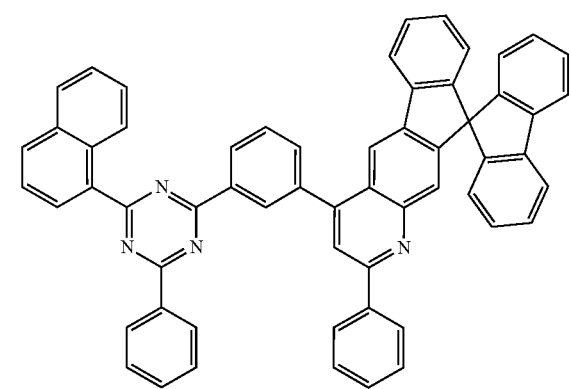
C-107
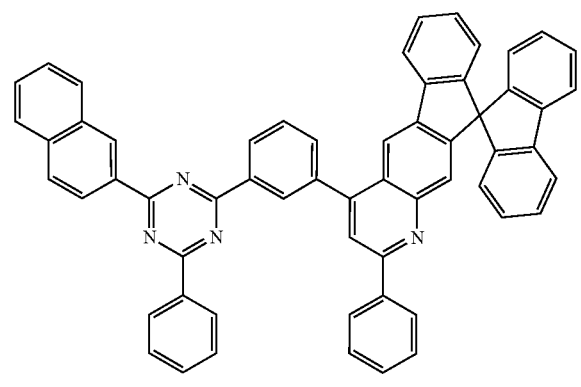
C-108
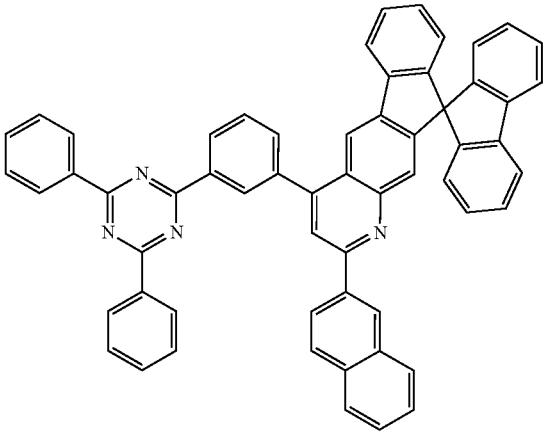
C-109
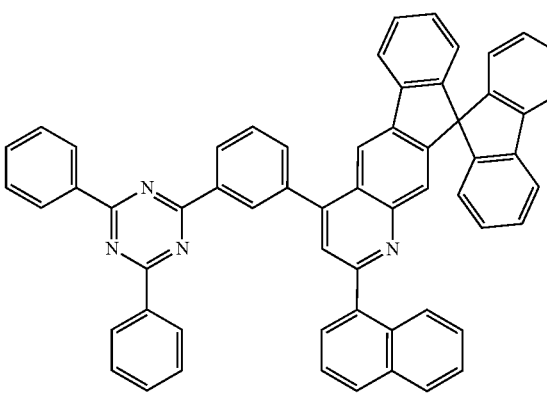
C-110
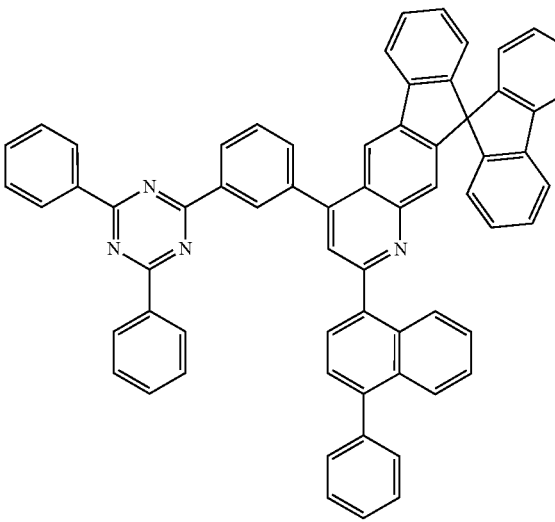

C-111
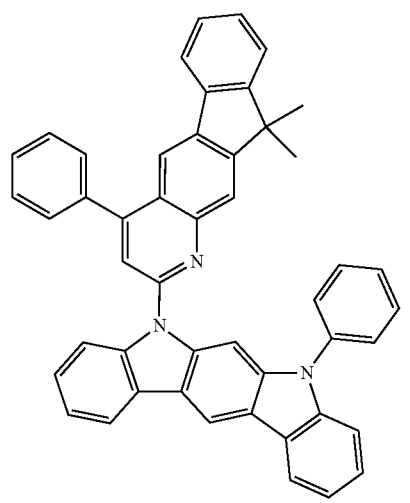
C-112
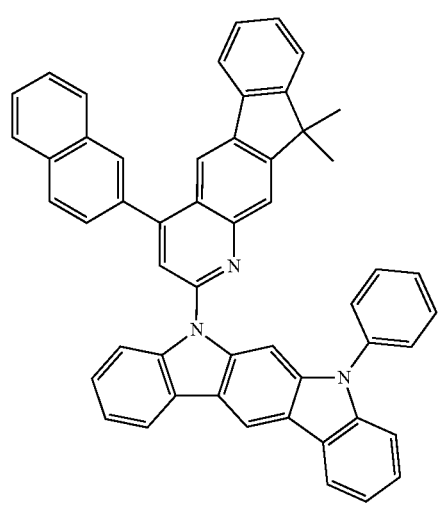
C-113
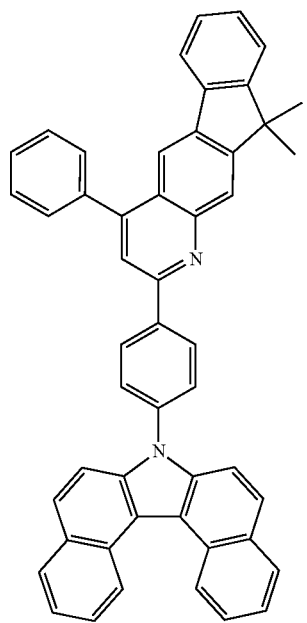
C-114
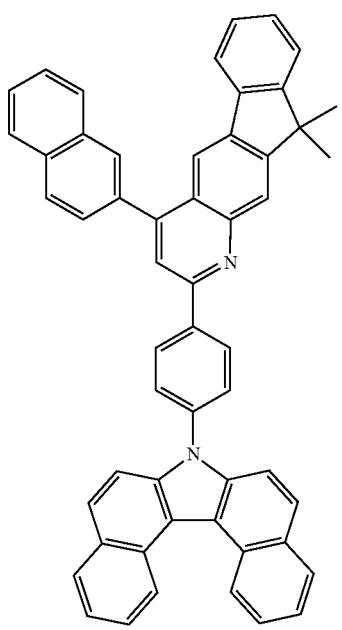
C-115
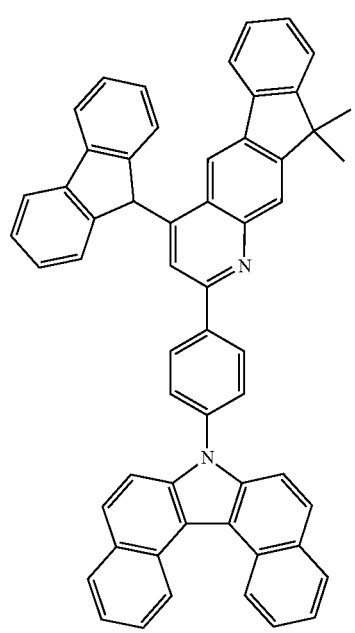

C-116
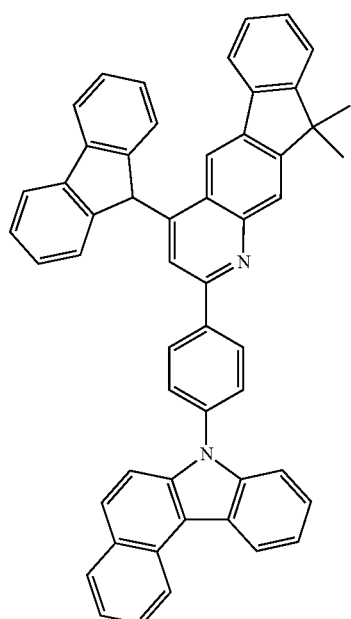
C-117
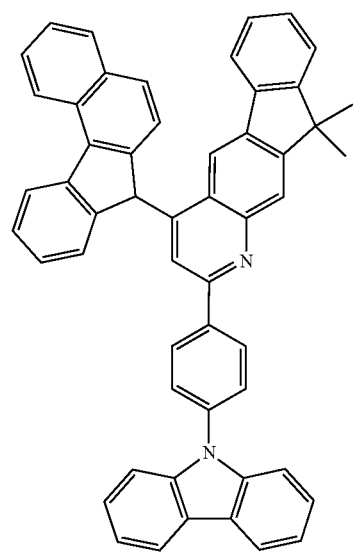
C-118
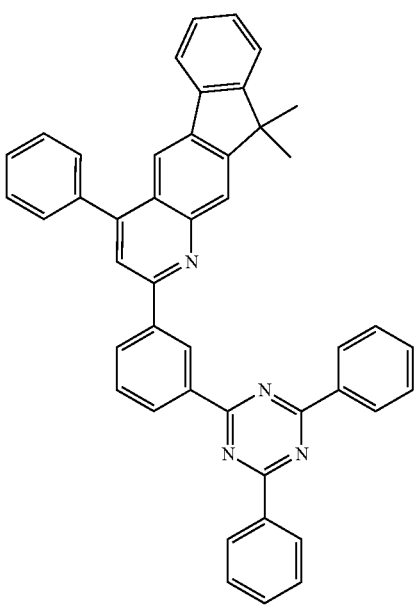
C-119
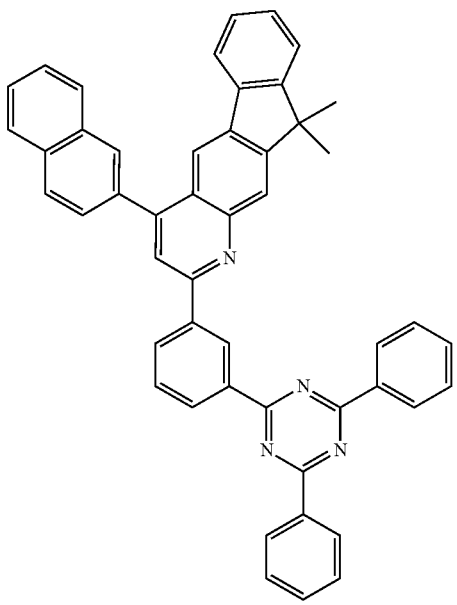

-continued
C-120
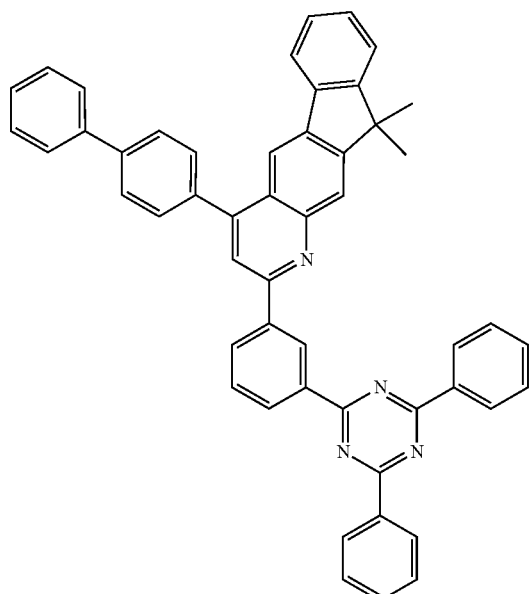
C-122
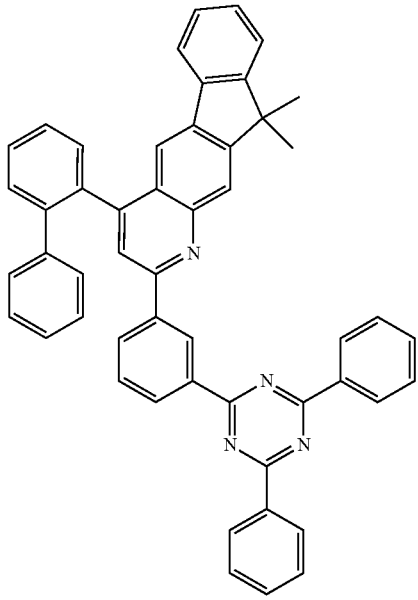
C-121
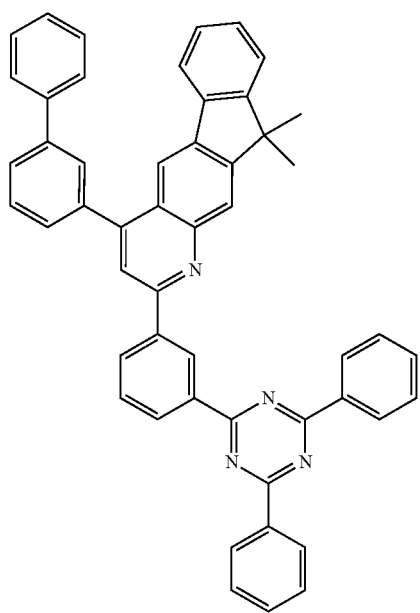
C-123

C-124
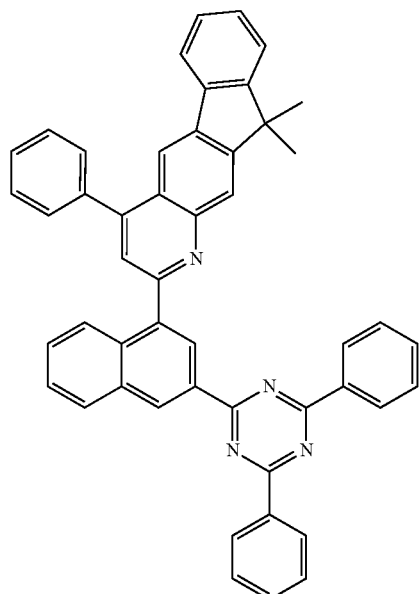
C-125
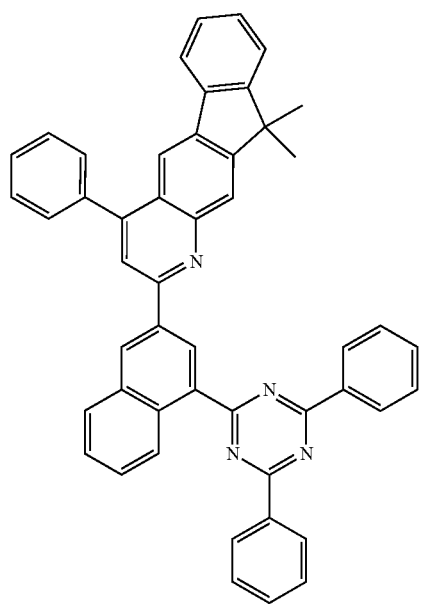
C-126
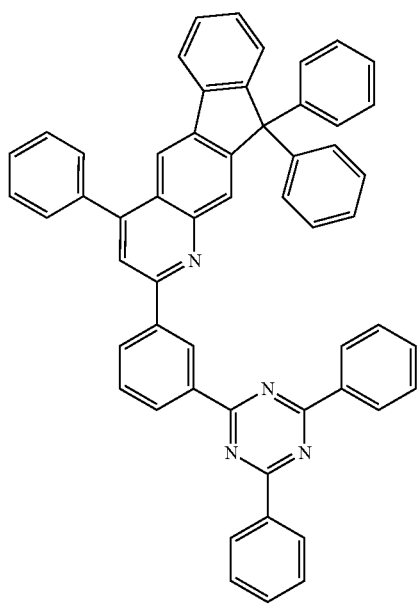
C-127
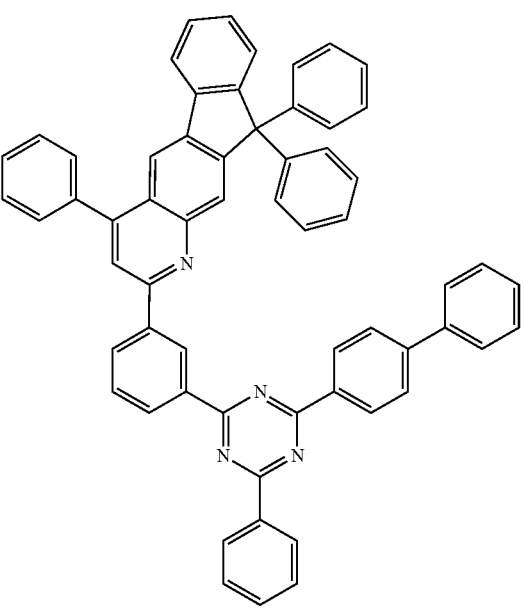

C-128
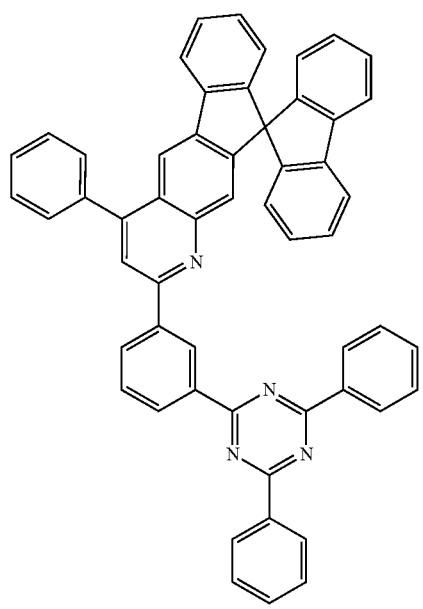
C-130
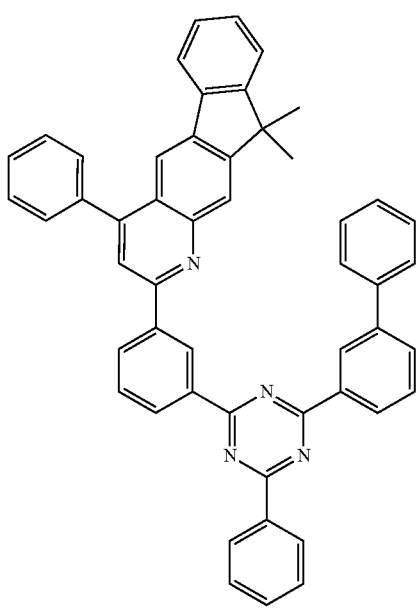
C-129
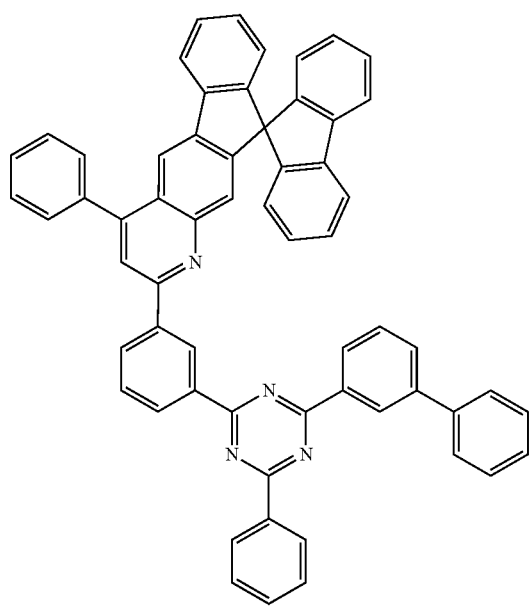
C-131
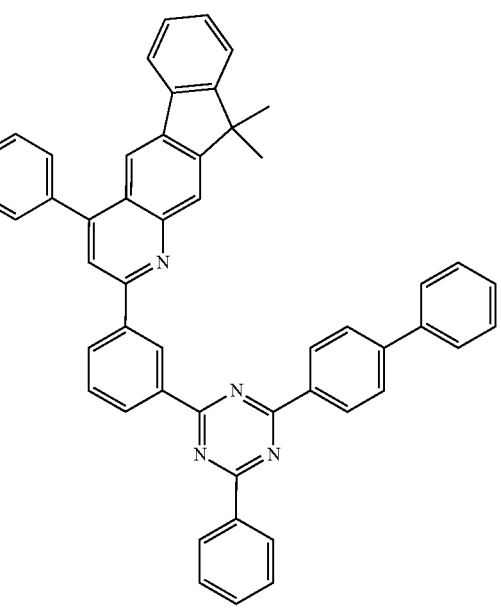

C-132
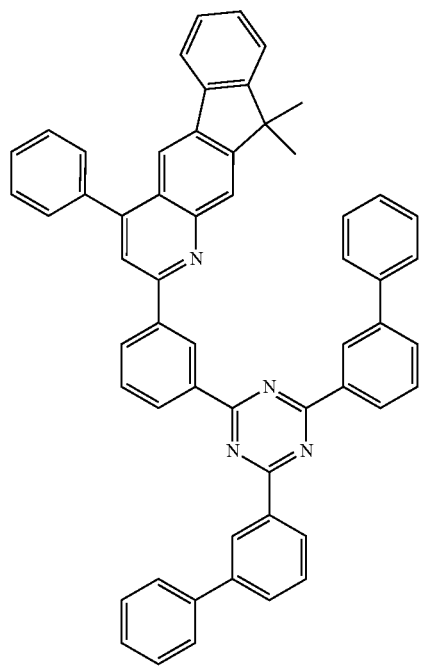
C-133
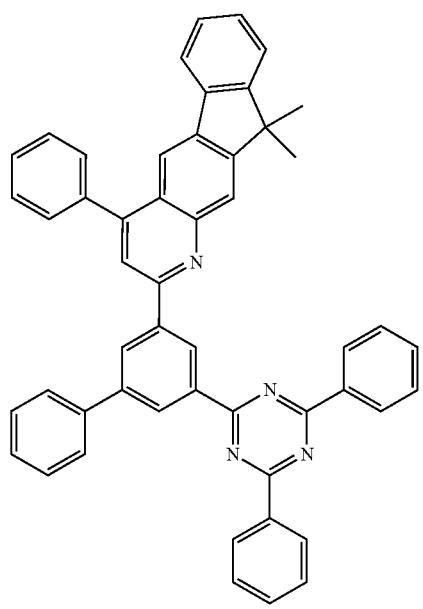
C-134
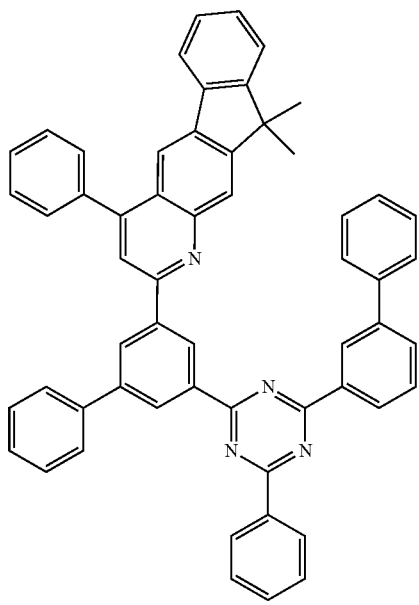
C-135
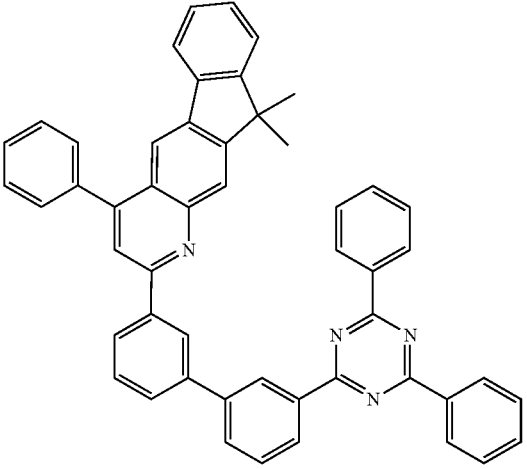

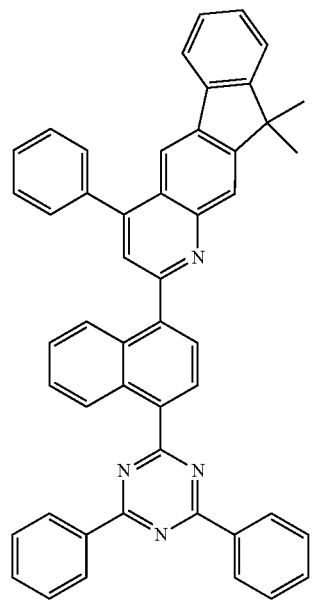
C-136
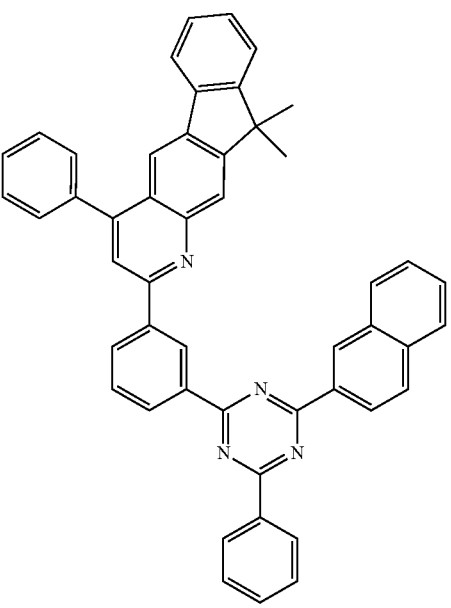
C-138
C-137
C-139

C-140
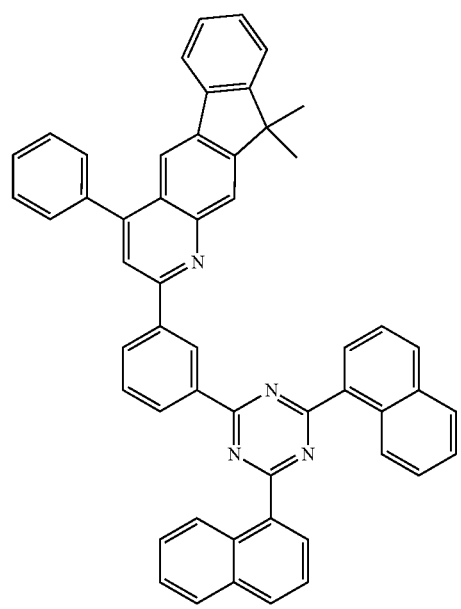
C-142
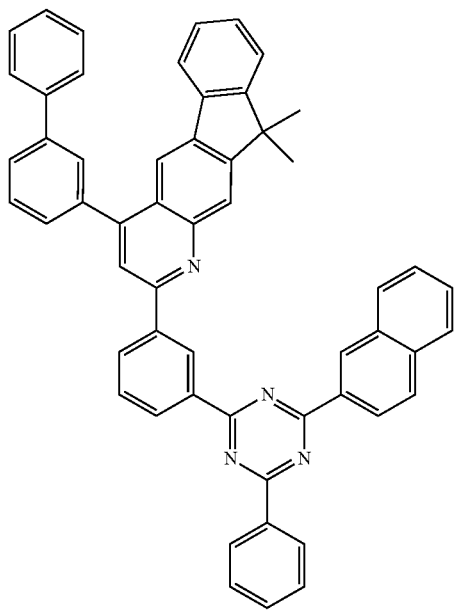
C-143
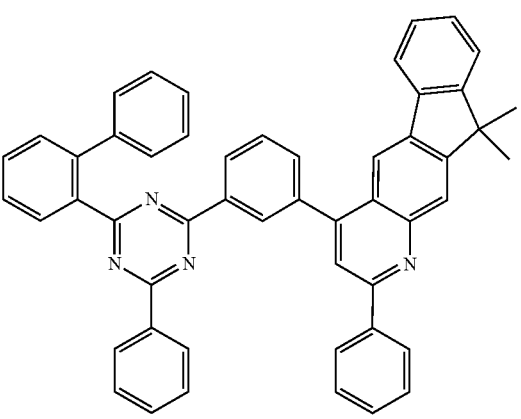
C-141
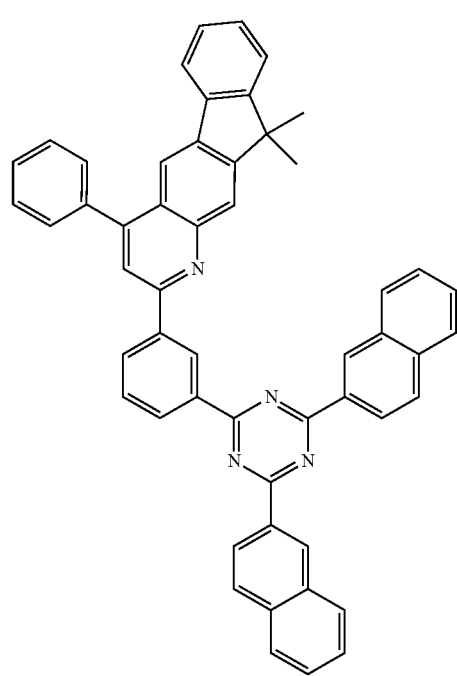
C-144
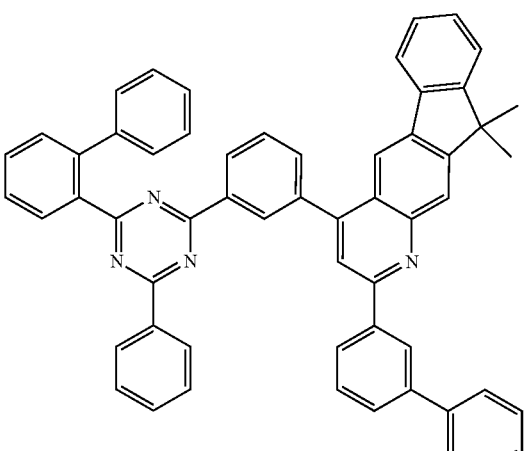

C-145
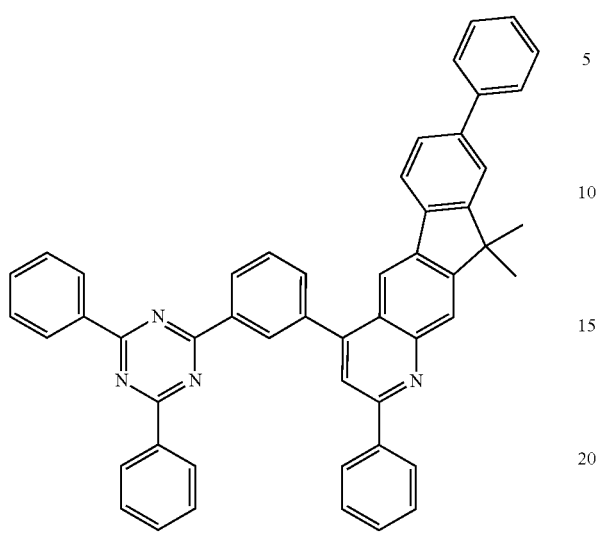
C-148
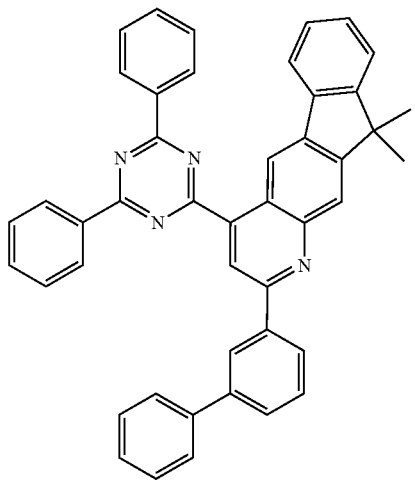
C-146
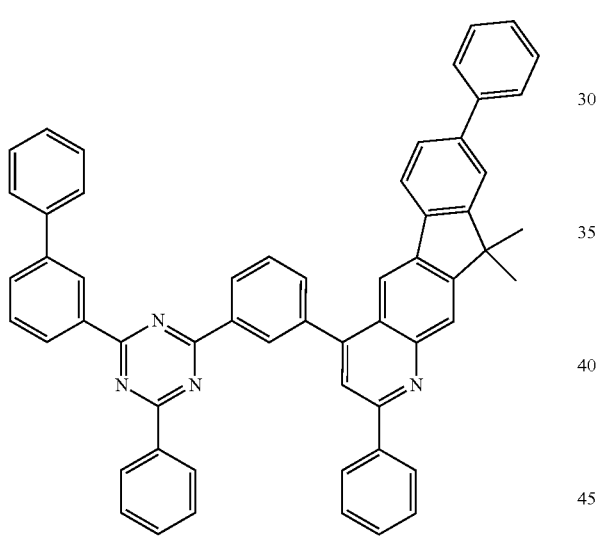
C-149
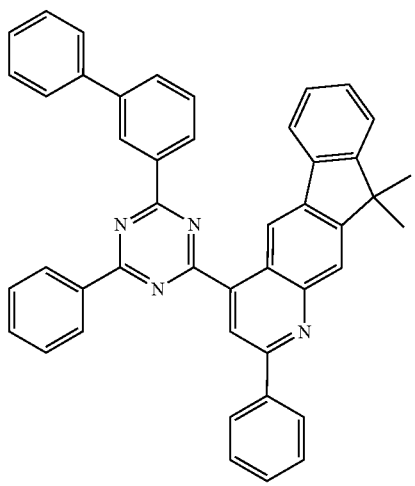
C-147
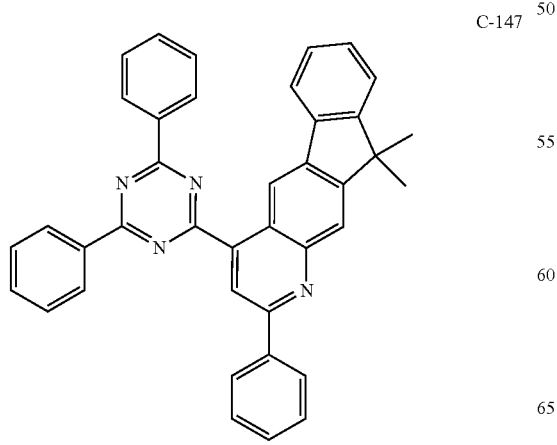
C-150
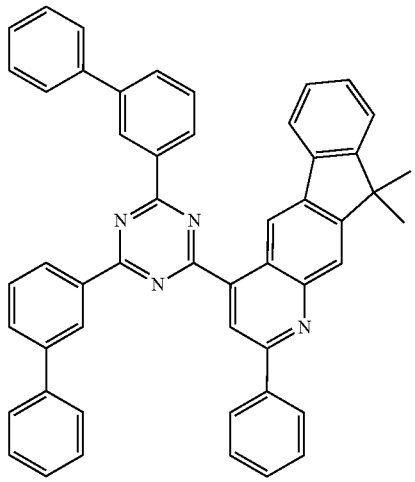

C-151
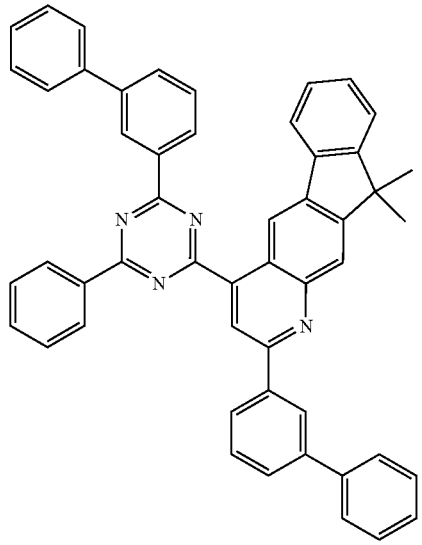
C-152
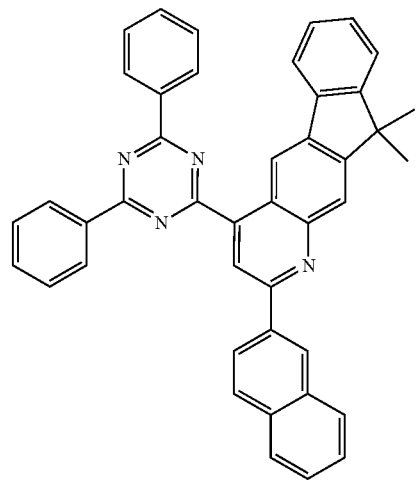
C-153
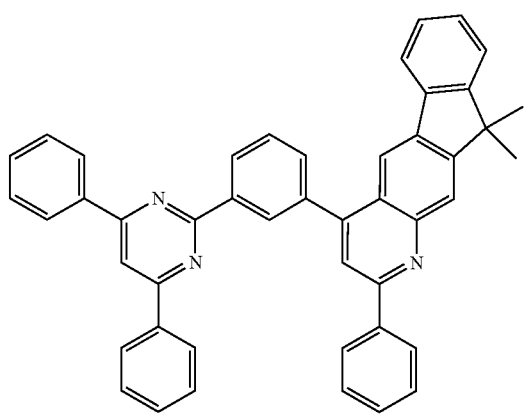
C-154
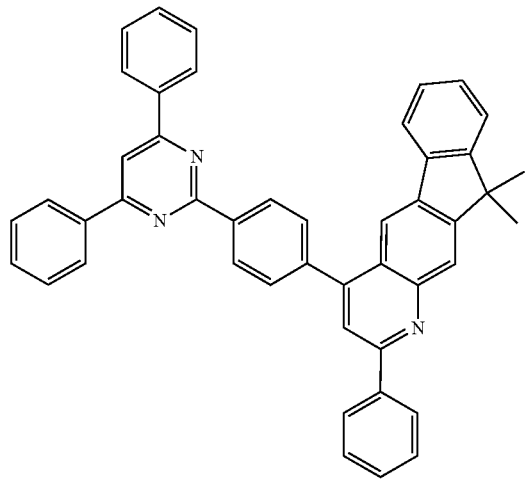
C-155
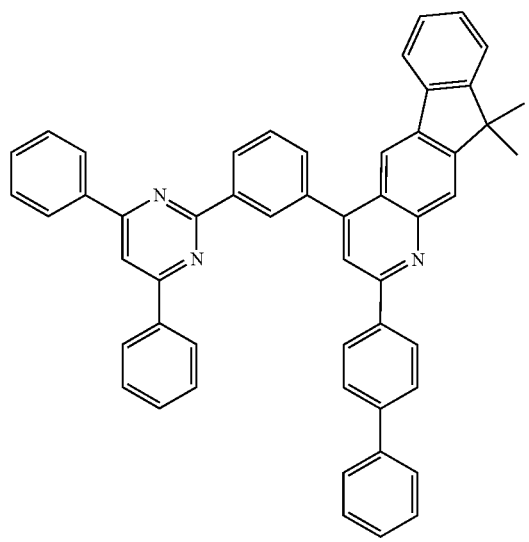
C-156
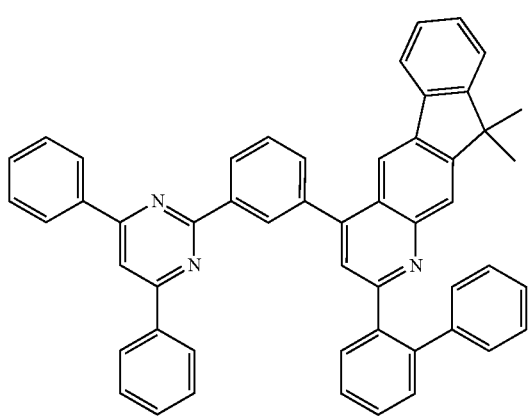

C-157
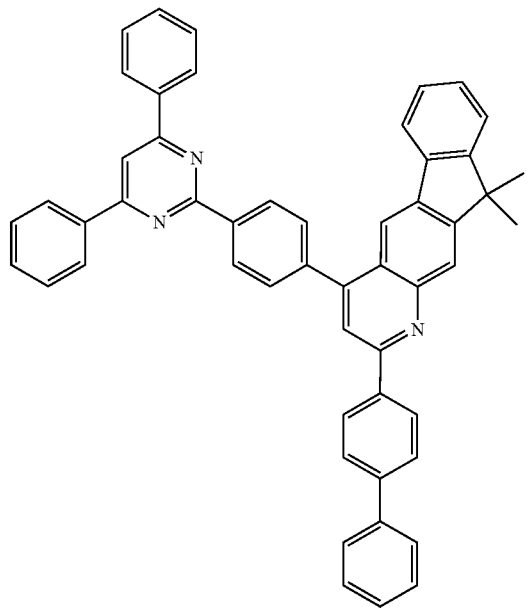
C-158
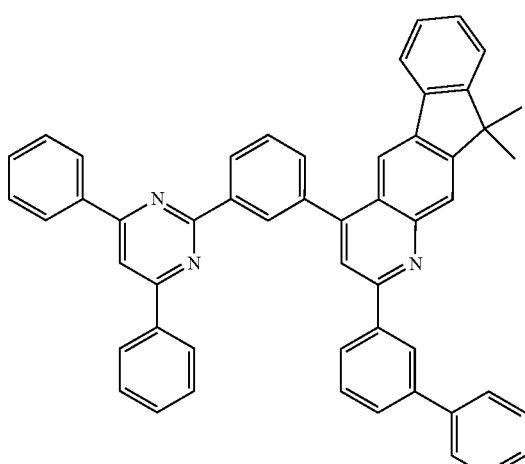
C-159
C-160
C-161
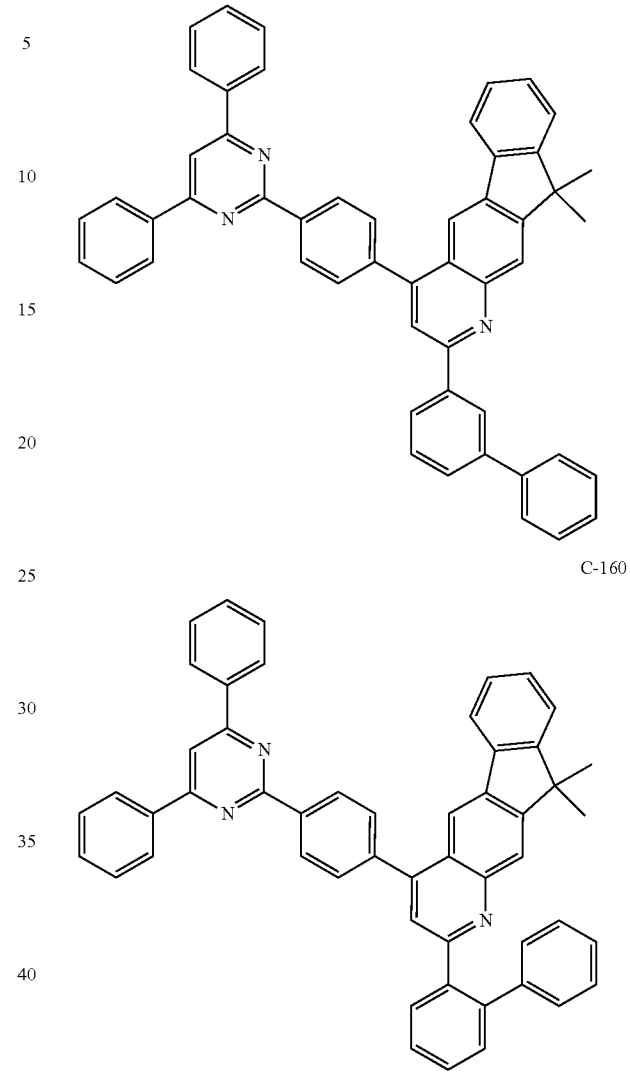
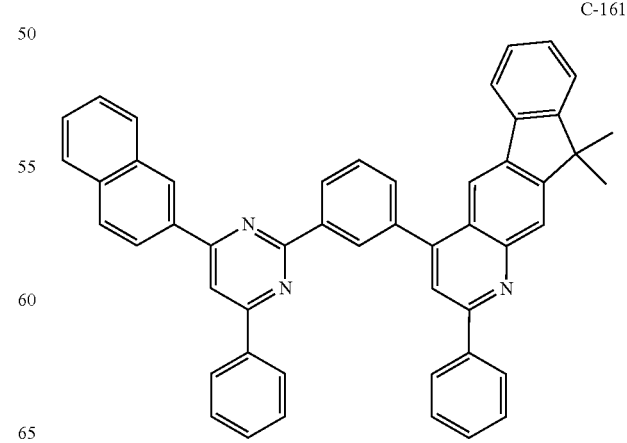

-continued
C-162
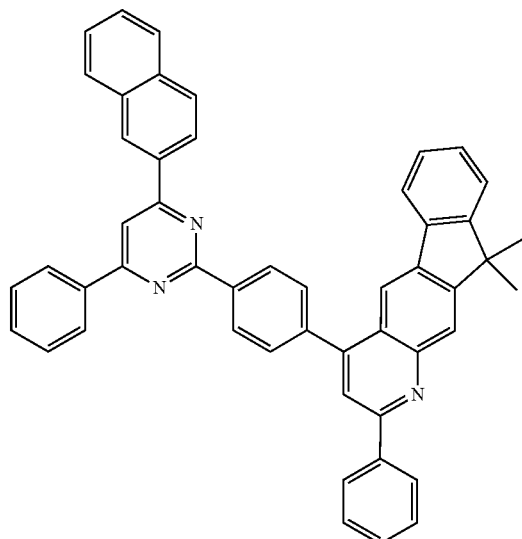
C-163
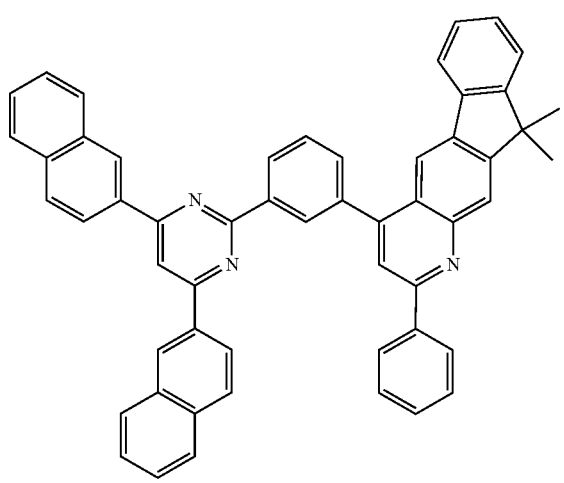
C-164
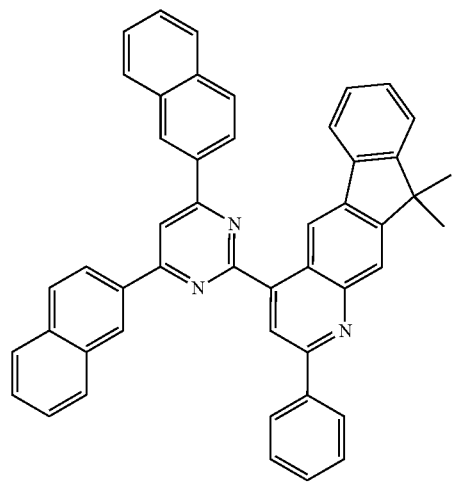
-continued
C-165
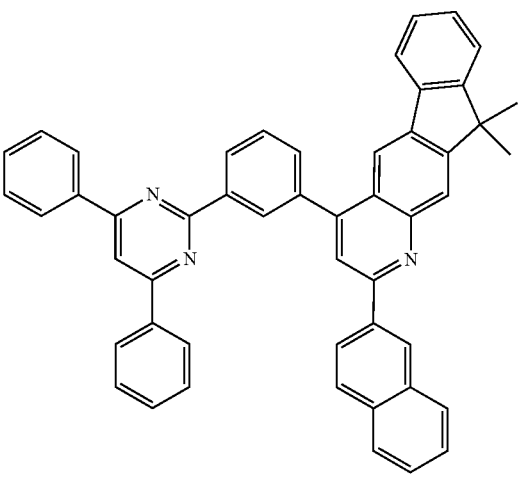
C-166
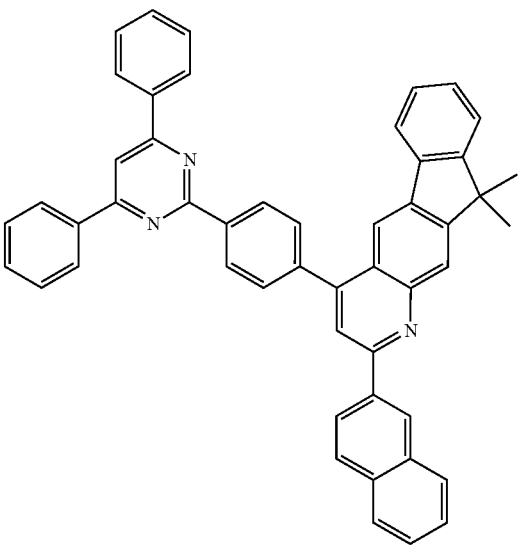
C-167
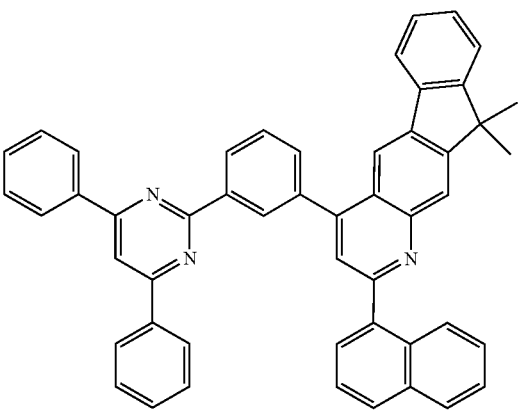

C-168
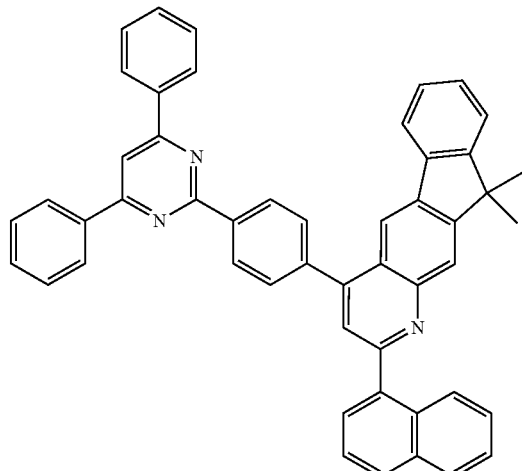
C-169
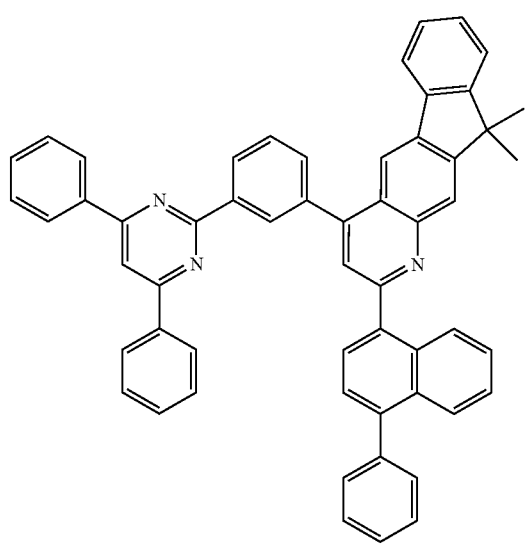
C-170
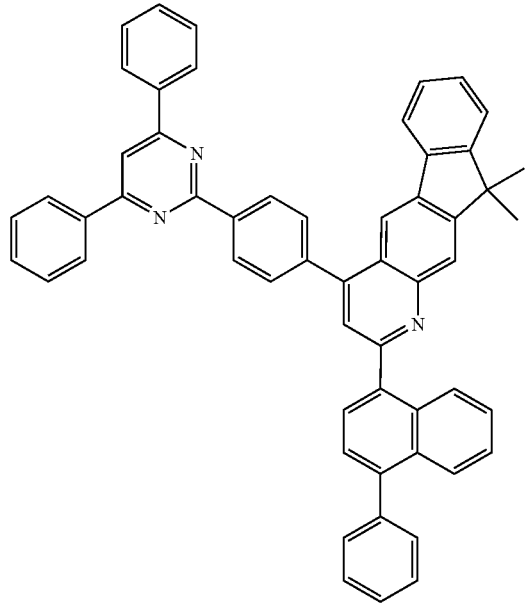
C-171
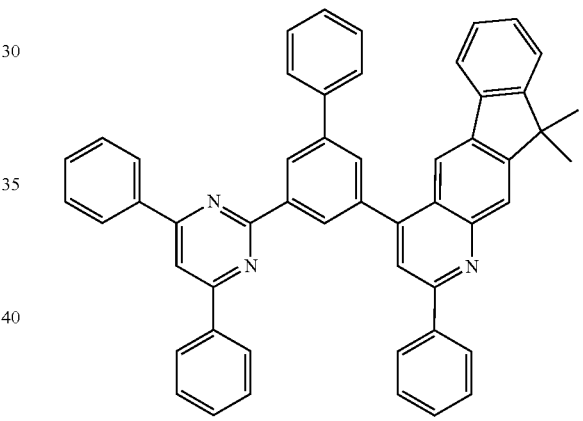
C-172
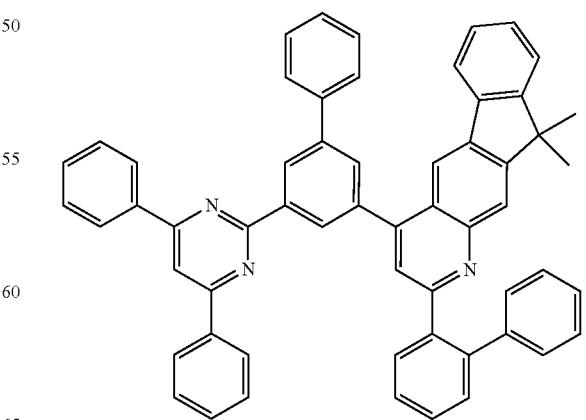

C-173
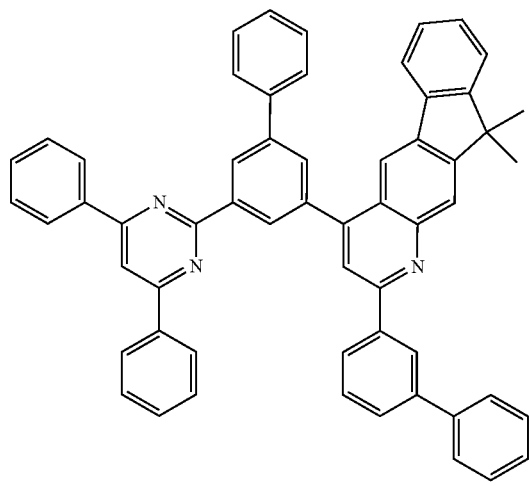
C-174
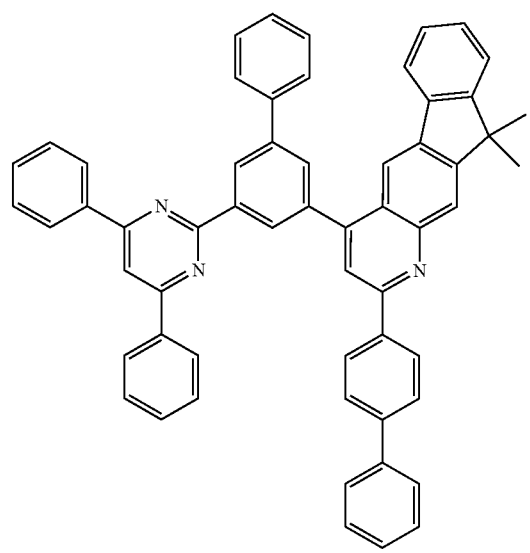
C-175
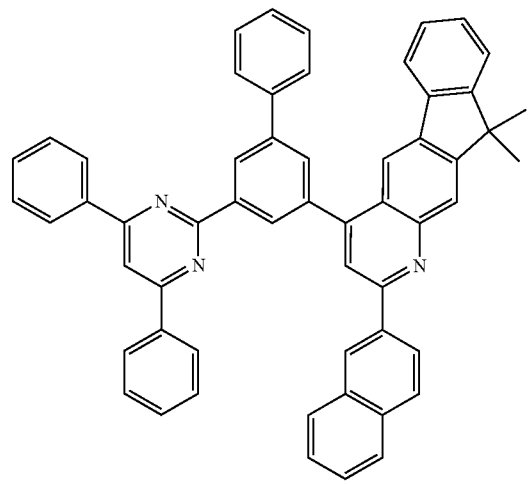
C-176
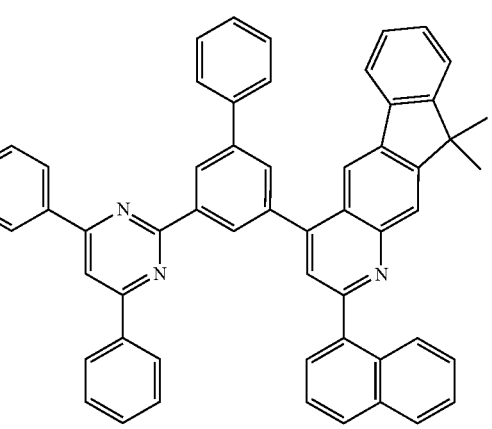
C-177
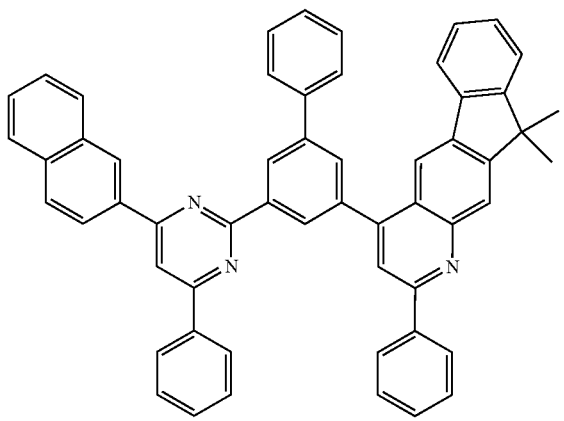
C-178
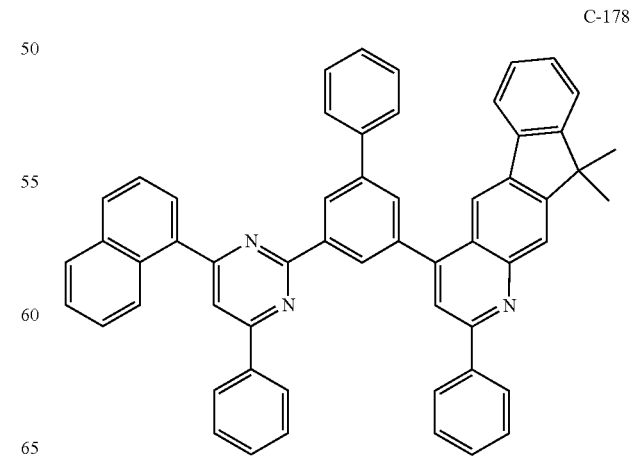

C-179
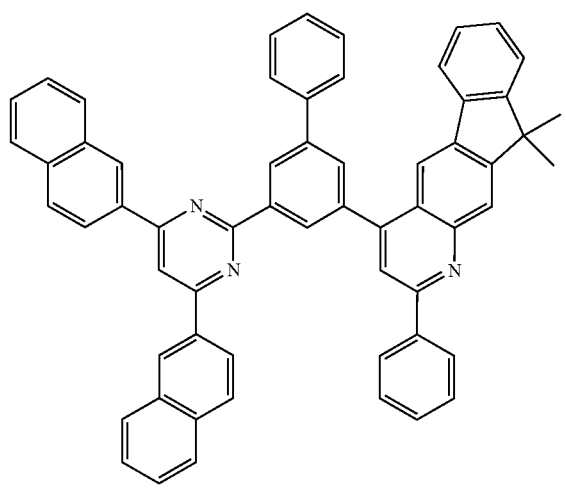
C-180
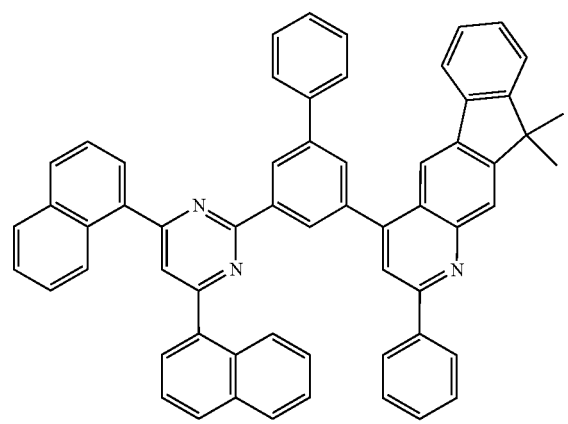
C-181
C-182
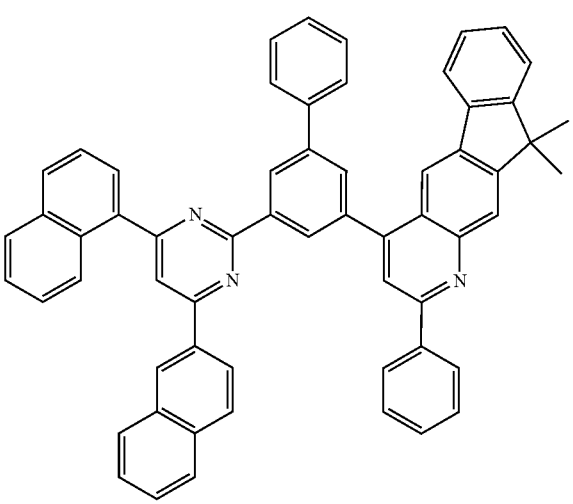
C-183
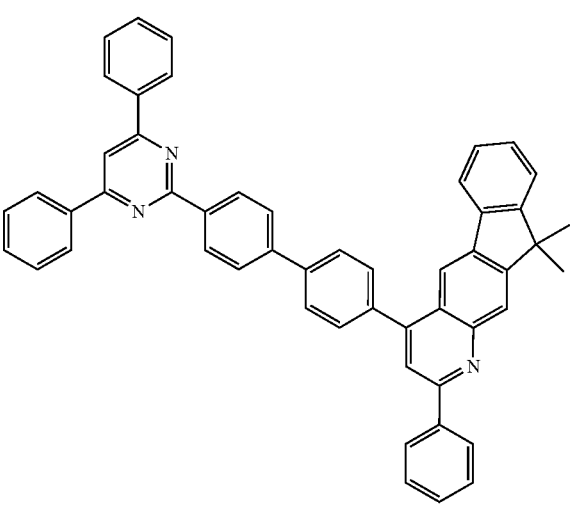
C-184
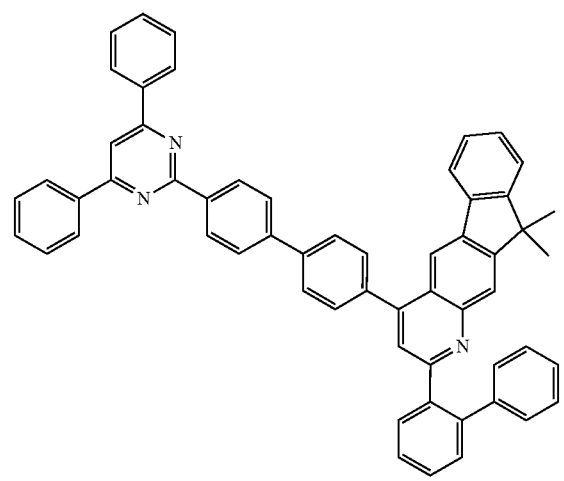

C-185
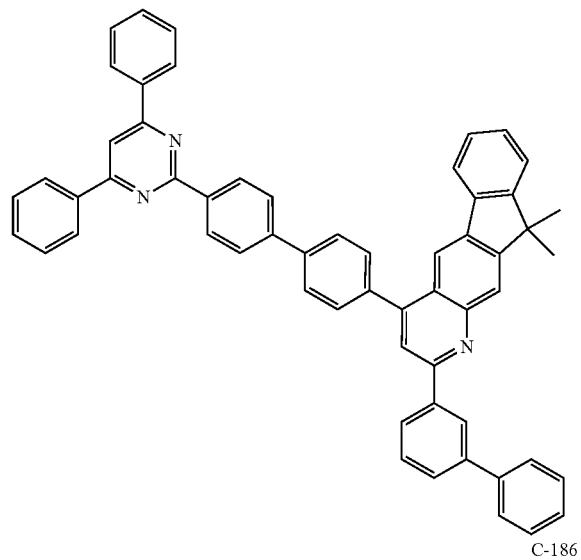
C-188
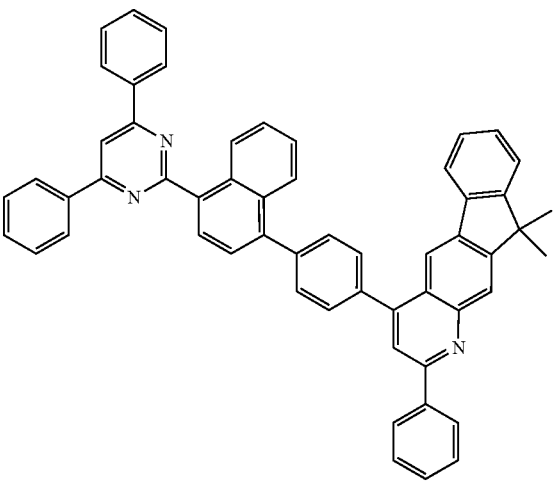
C-186
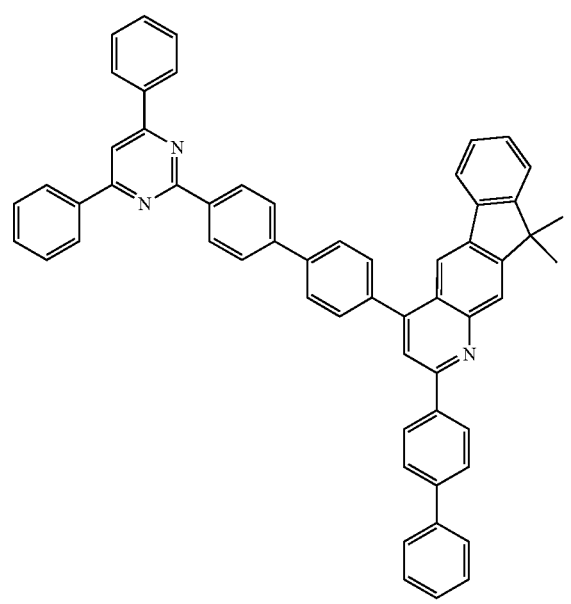
C-189
C-187
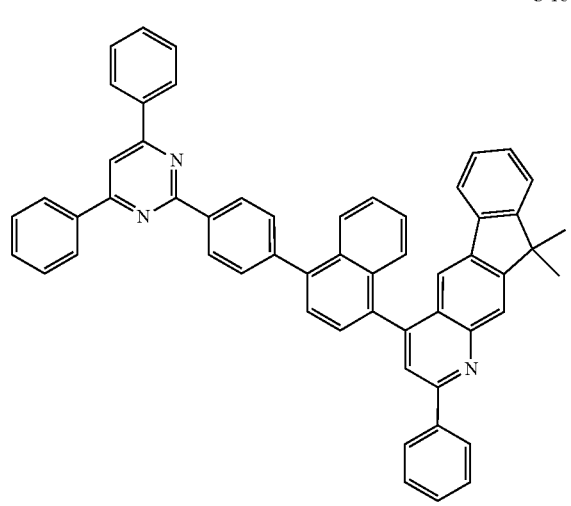
C-190
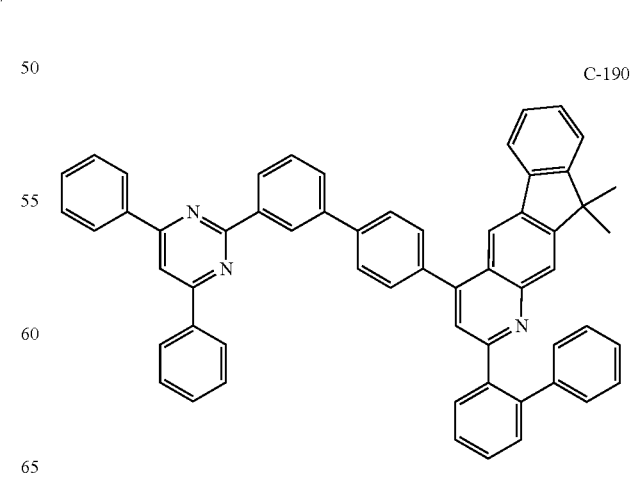

C-191
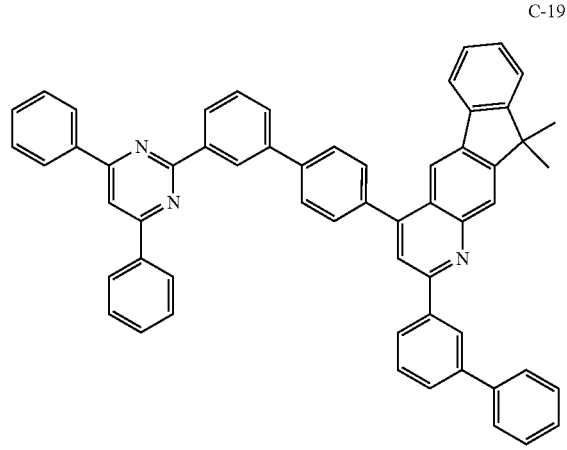
C-194
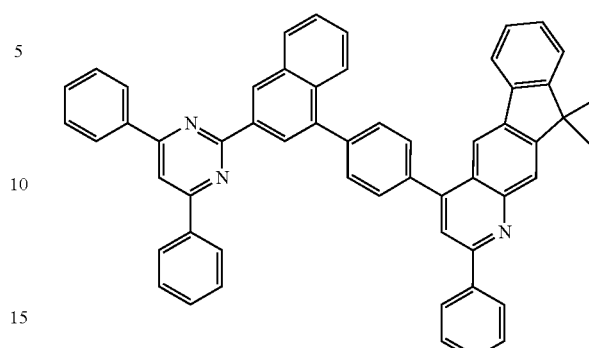
C-195
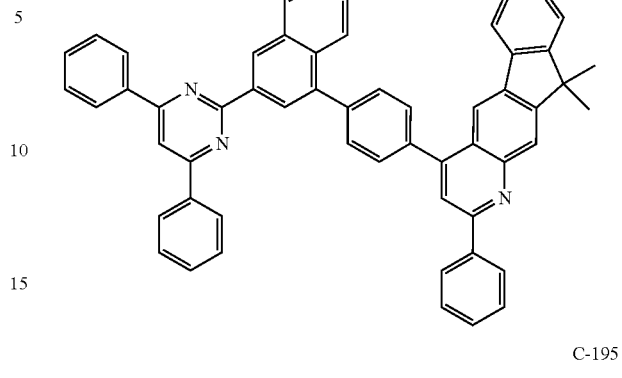
C-192
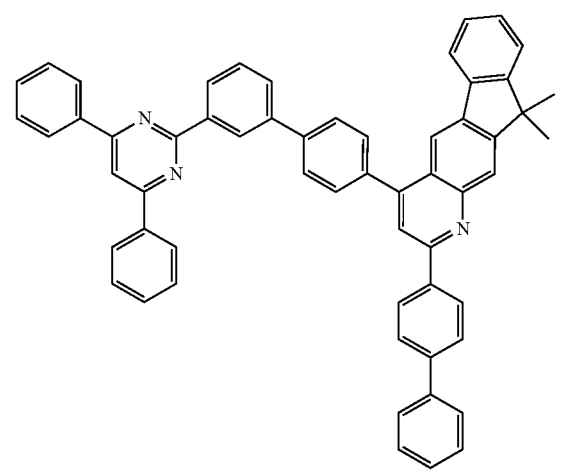
C-196
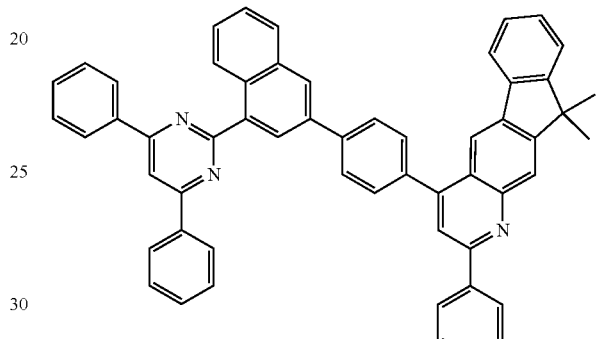
C-193
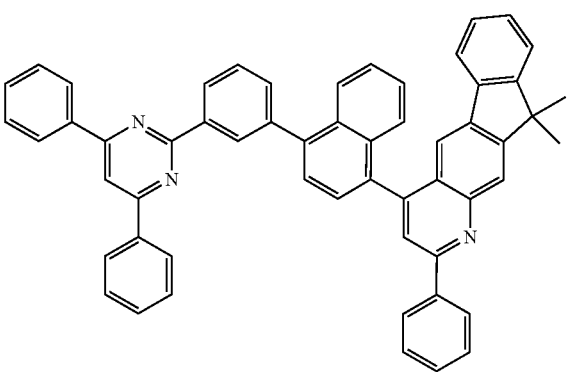
C-197
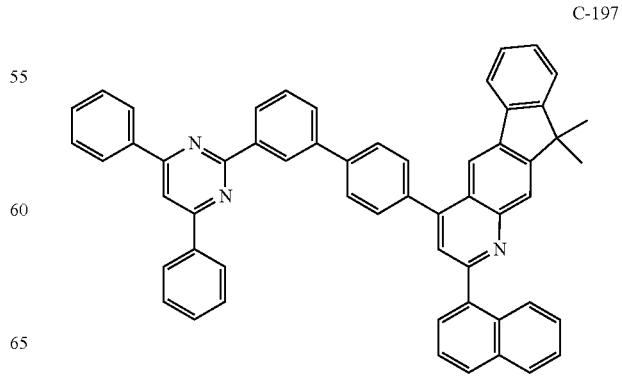

-continued
C-198
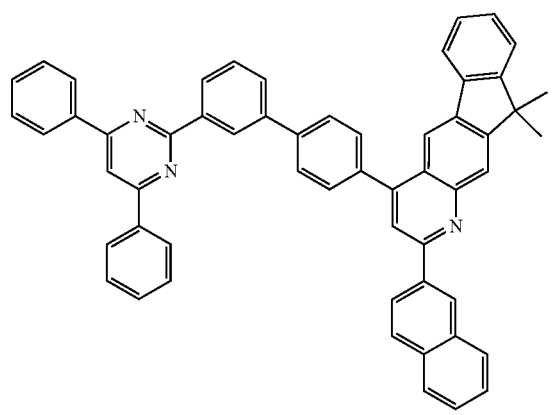
C-199
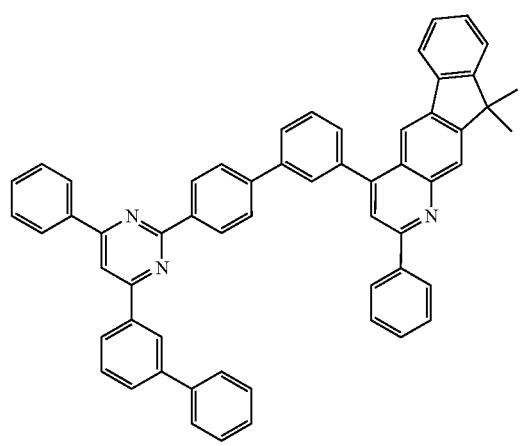
C-200
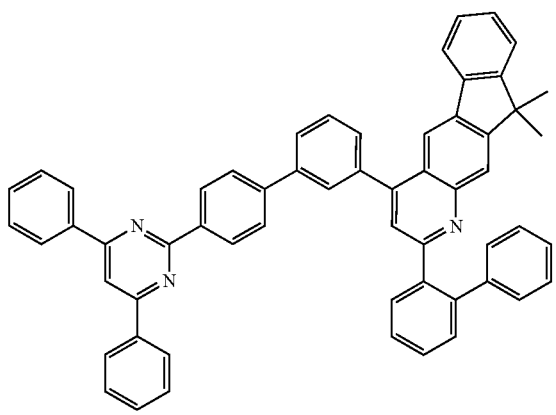
-continued
C-201
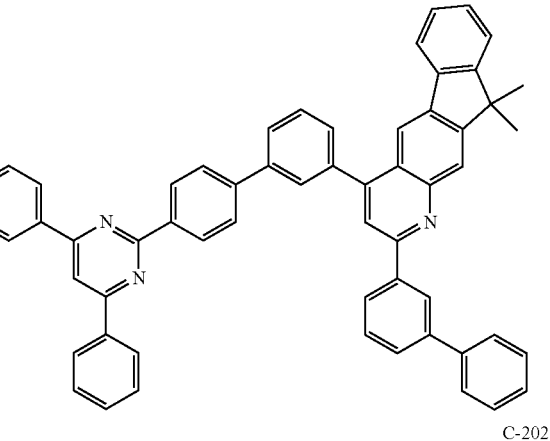
C-202
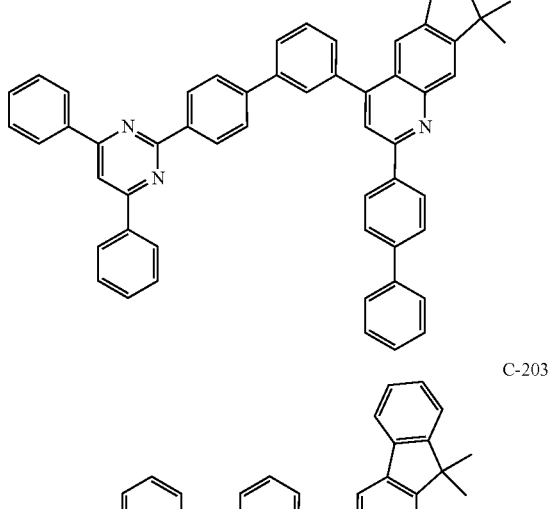
C-203
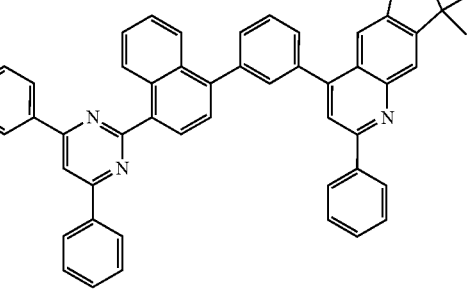
C-204
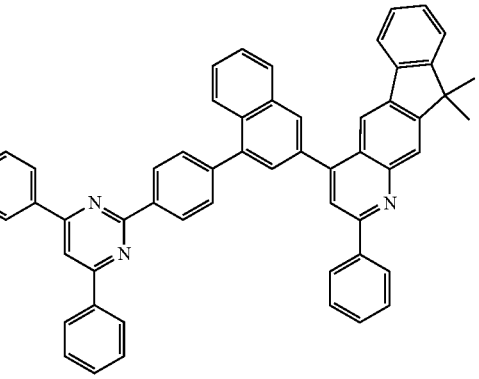

C-205
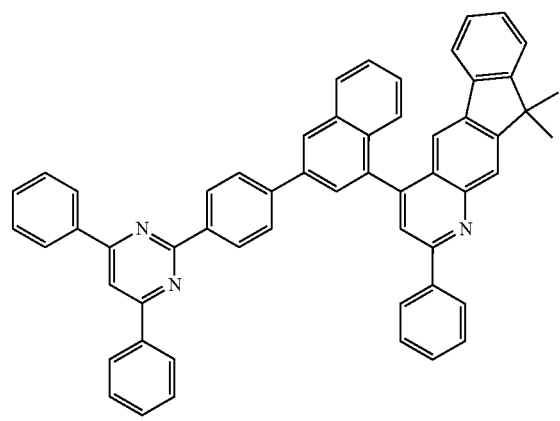
C-206
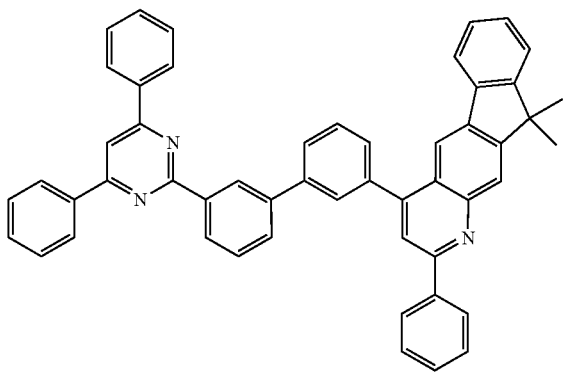
C-207
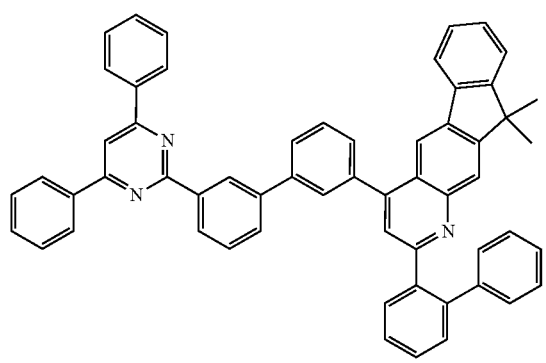
C-208
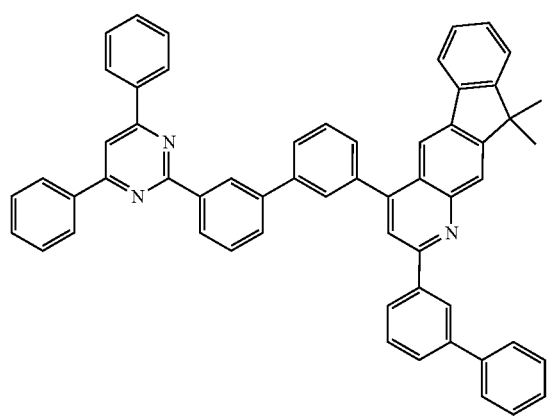
C-209
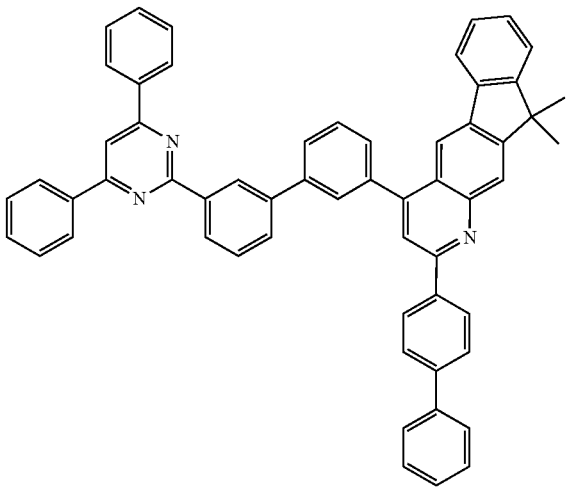
C-210
C-211
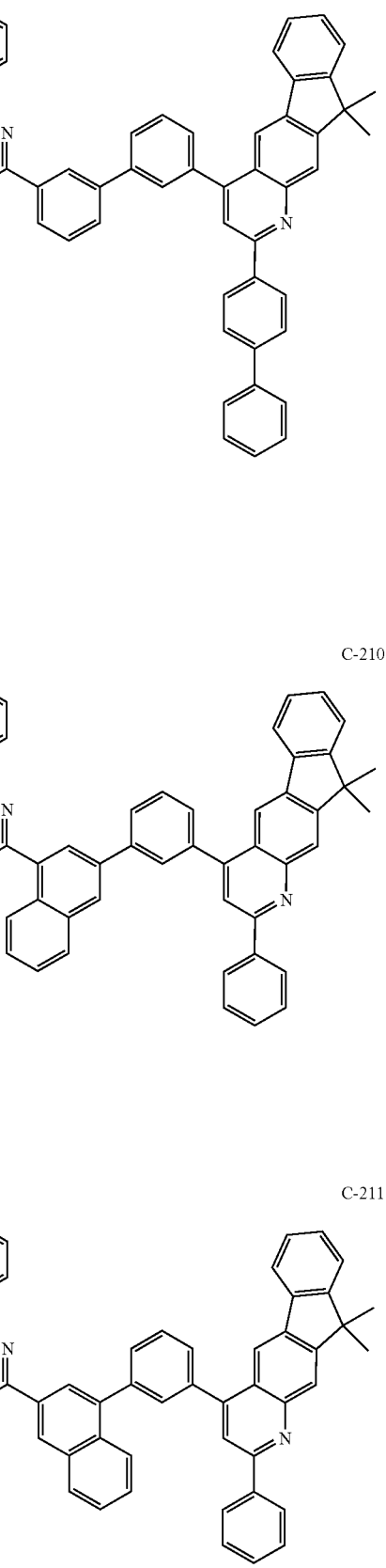

C-212
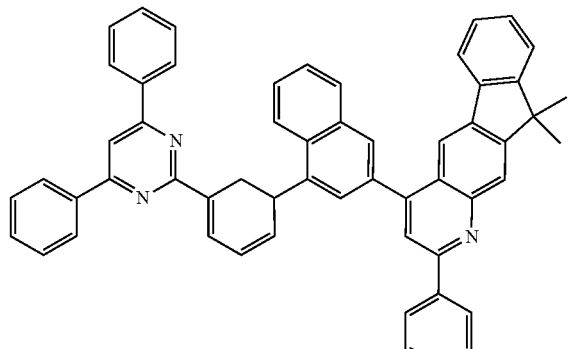
C-213
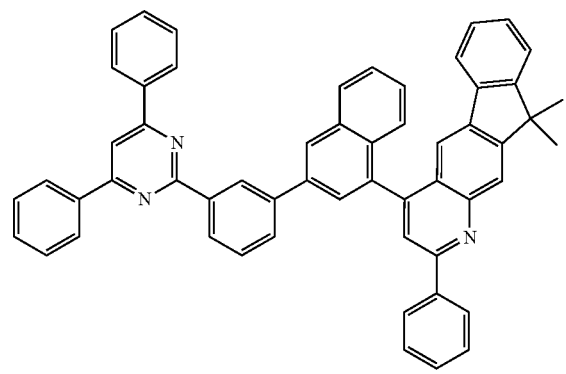
C-214
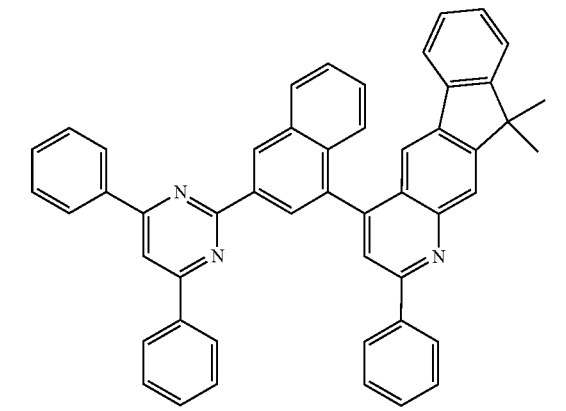
C-215
C-216
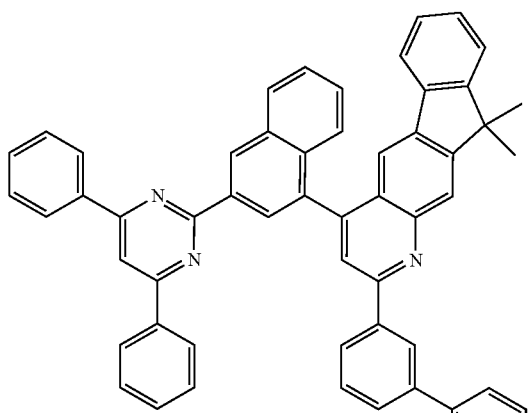
C-217
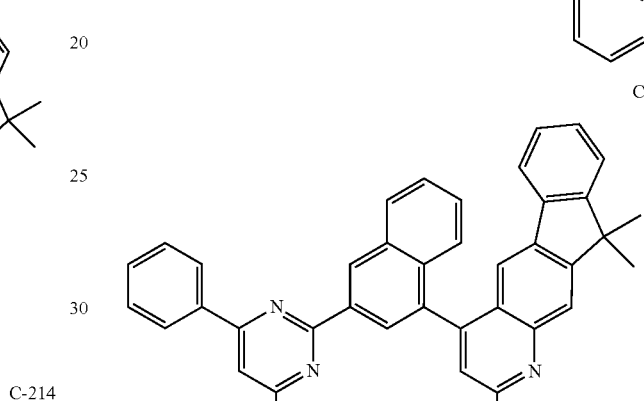
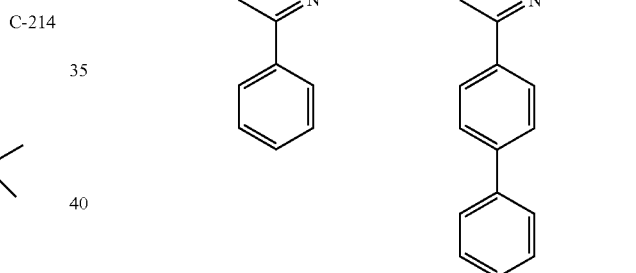
C-218
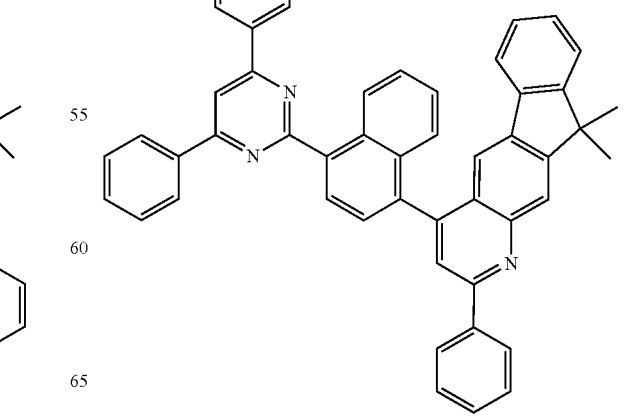

C-219
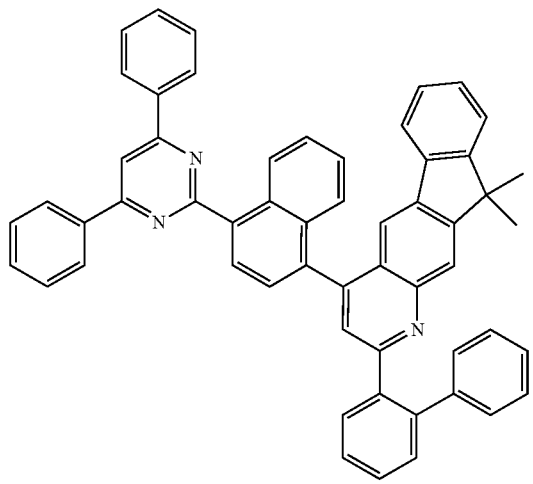
C-220
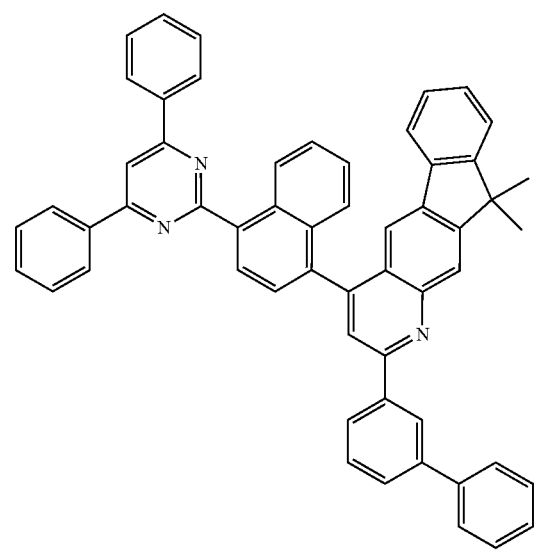
C-221
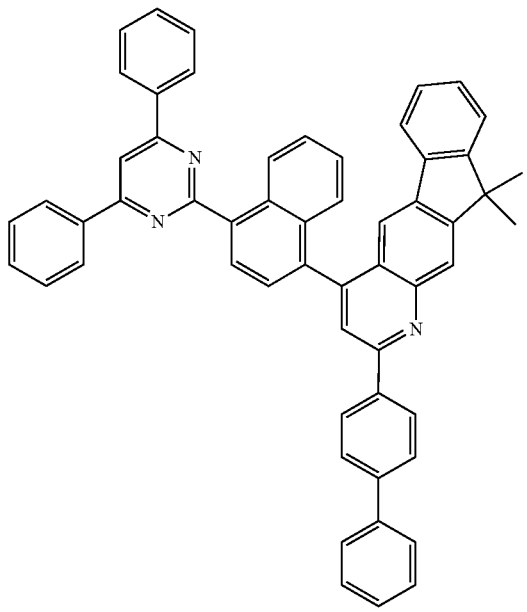
C-222
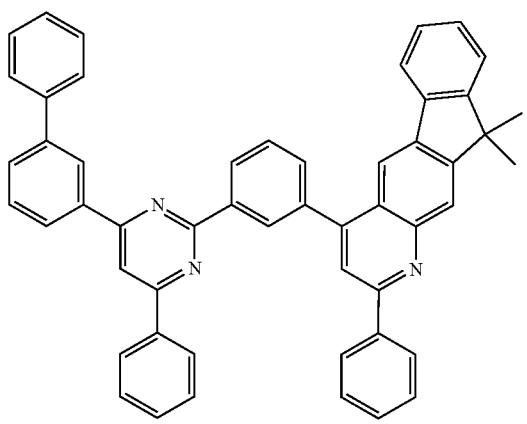
C-223

C-224
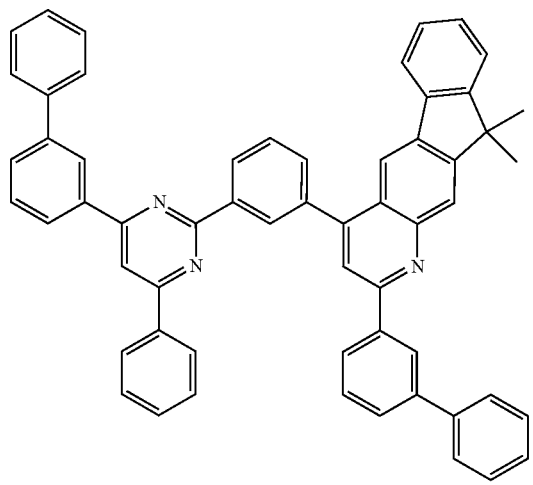
C-227
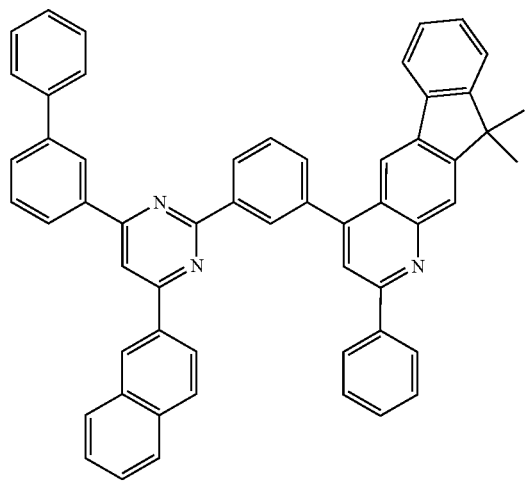
C-225
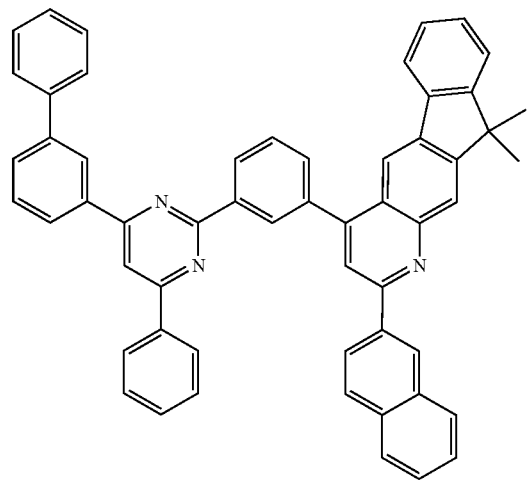
C-228
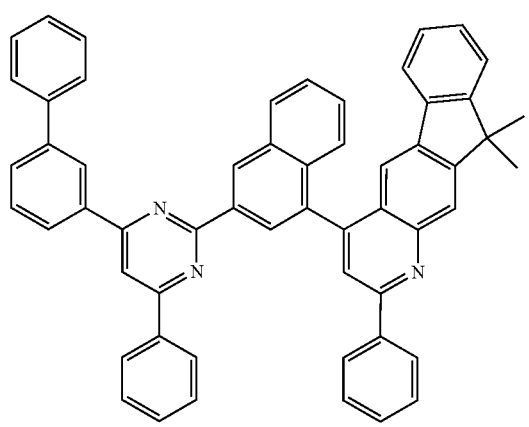
C-226
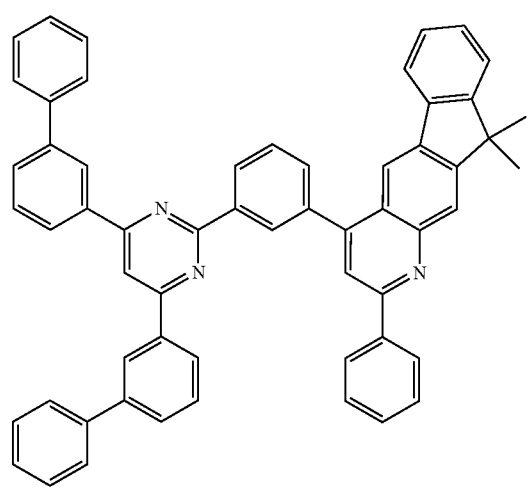
C-229
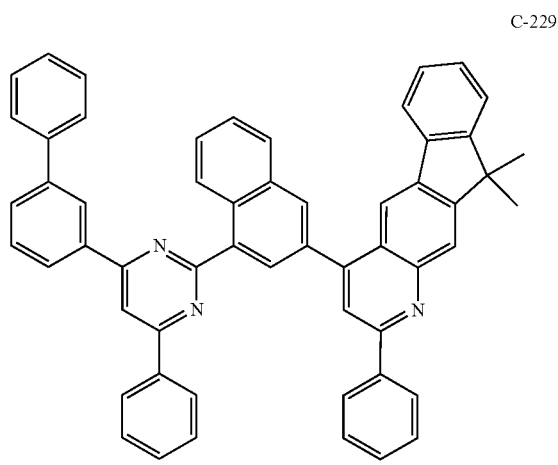

C-230
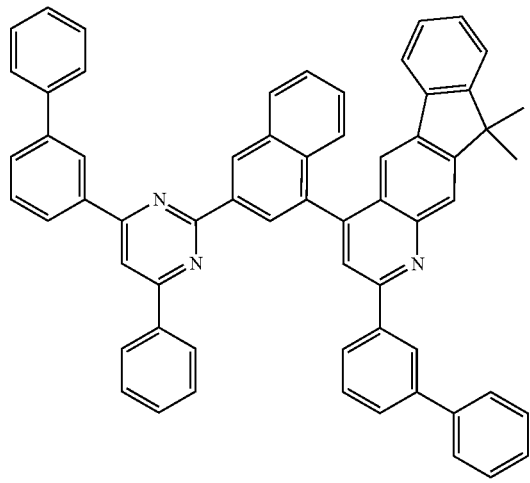
C-233
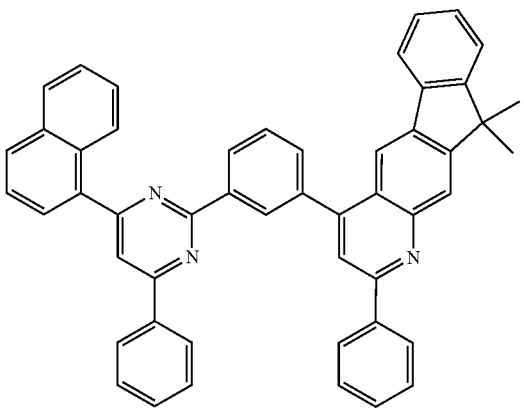
C-231
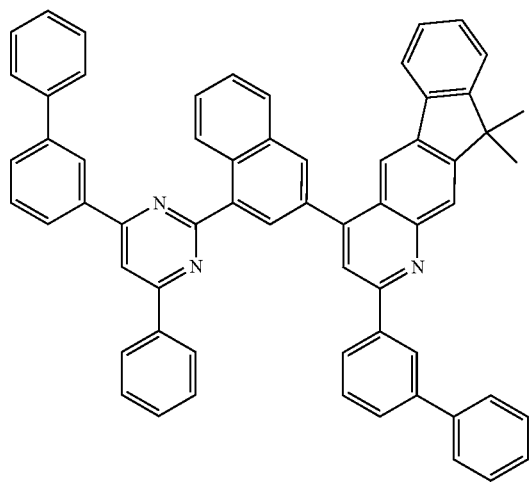
C-234
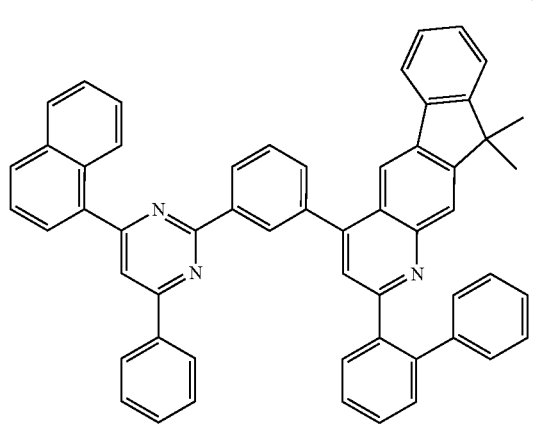
C-232
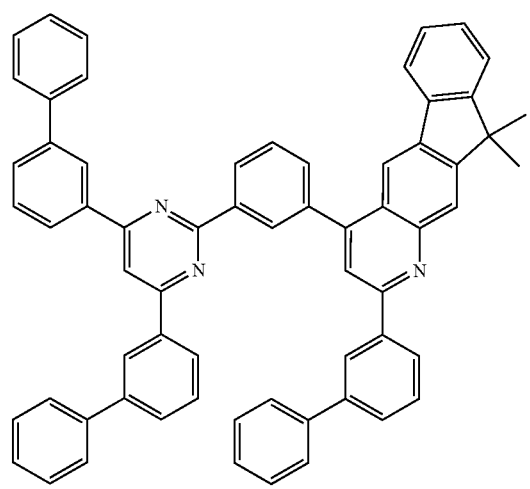
C-235
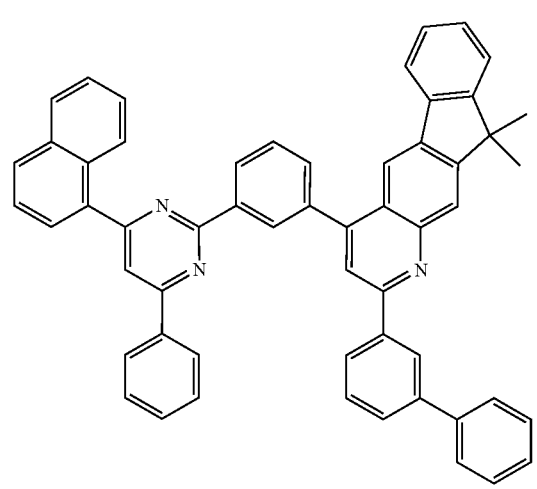

C-236
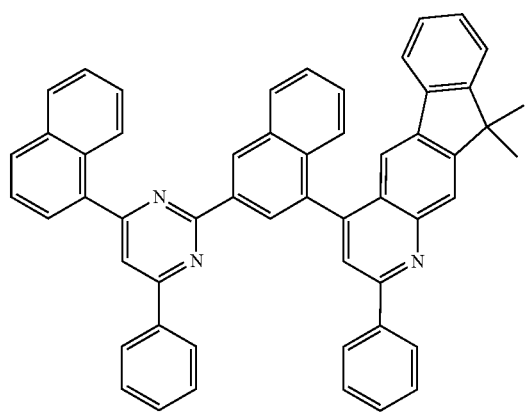
C-237
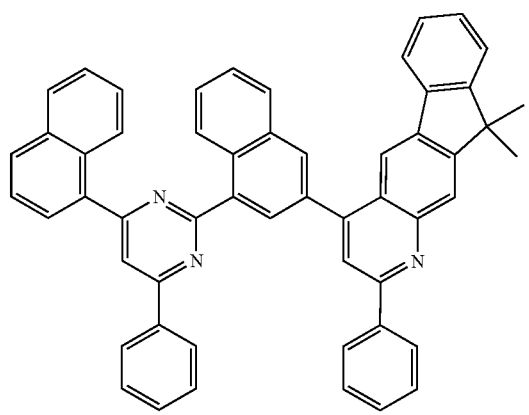
C-238
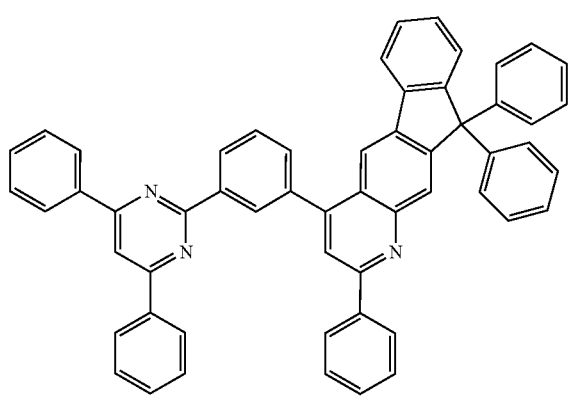
C-239
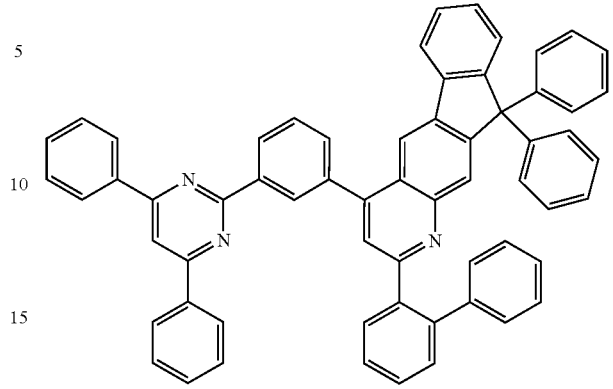
C-240
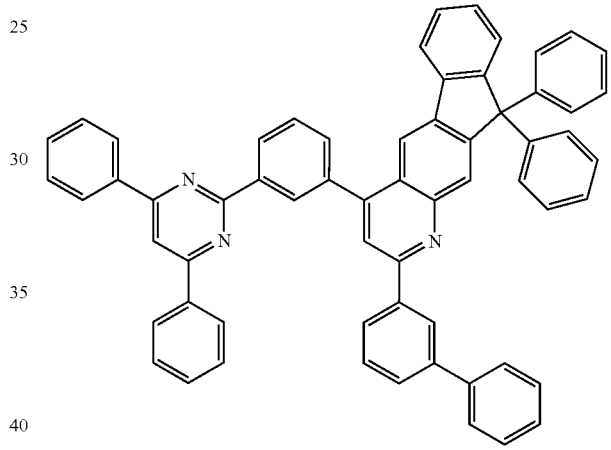
C-241
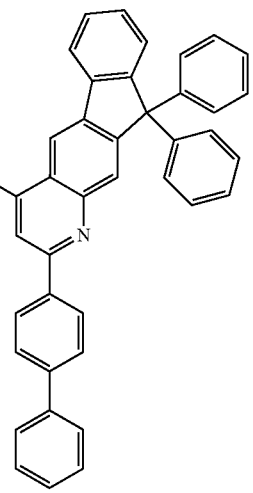

C-242
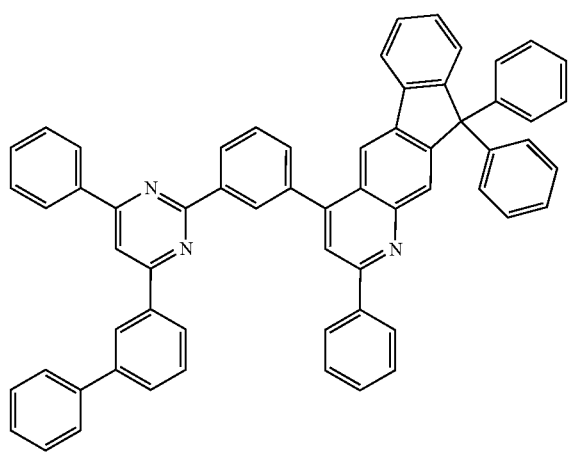
C-245
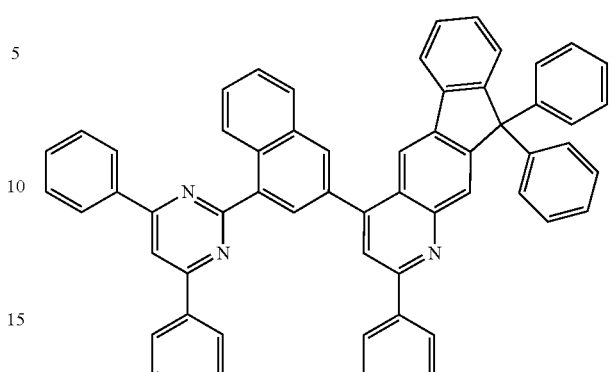
C-243
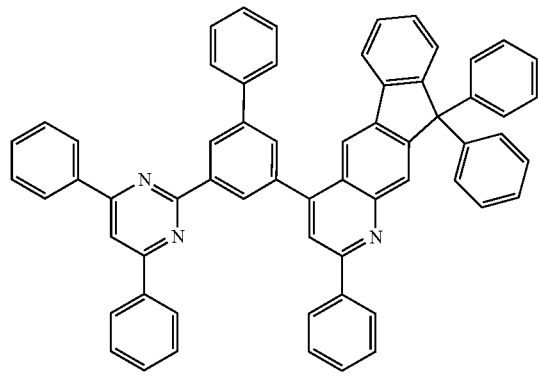
C-246
C-244
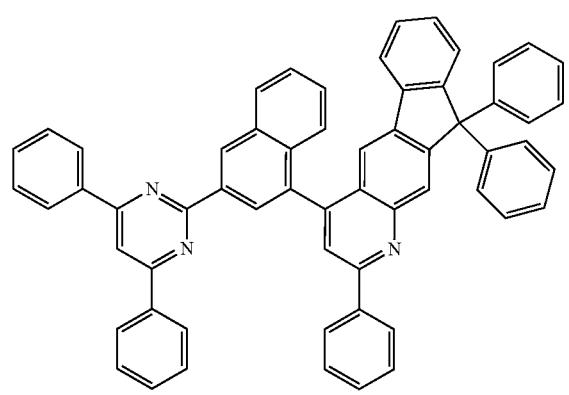
C-247
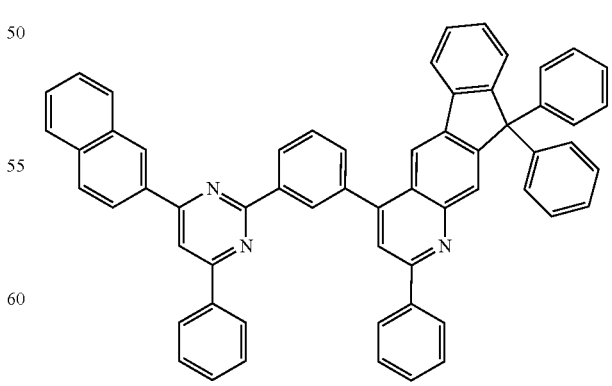

C-248
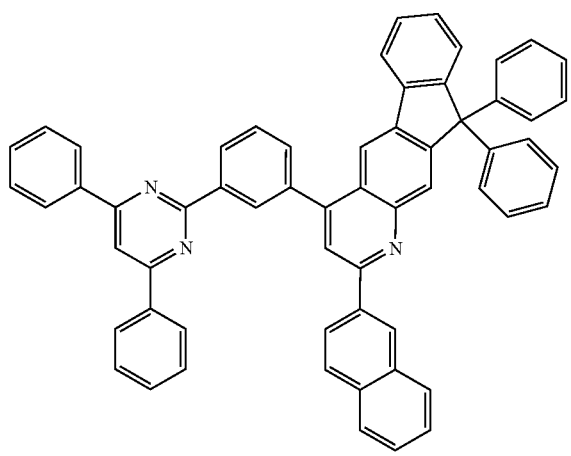
C-251
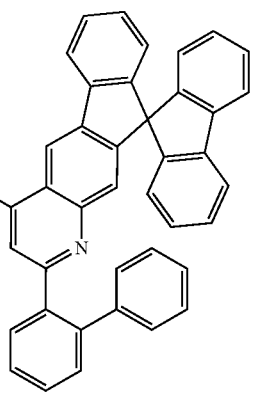
C-249
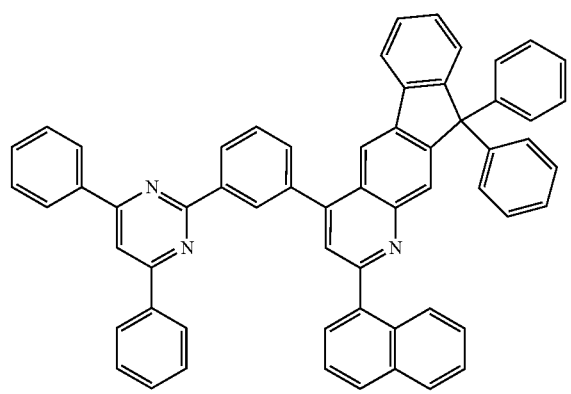
C-252
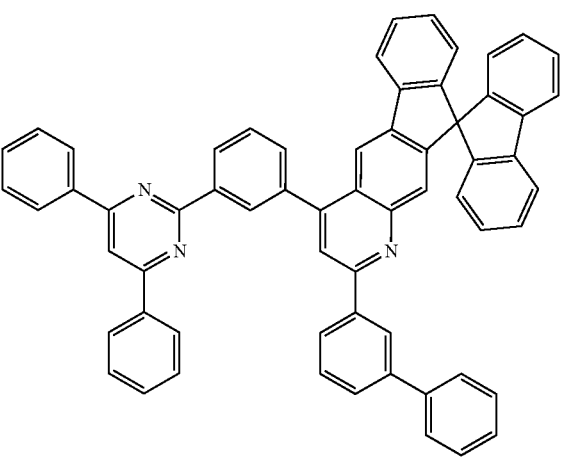
C-250
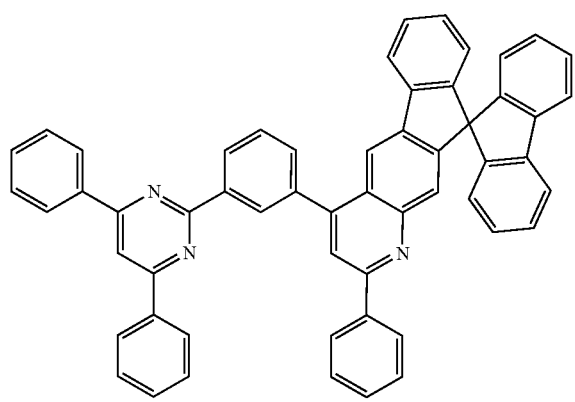
C-253
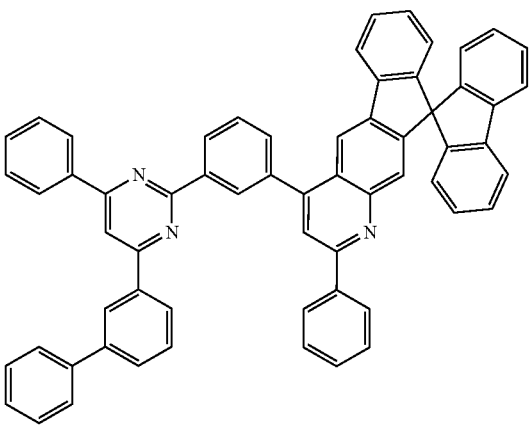

C-254
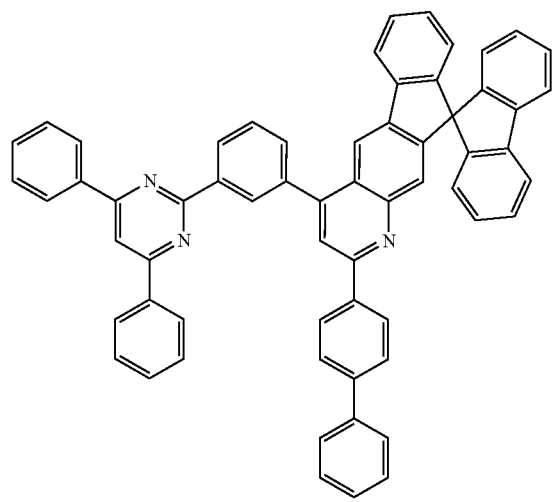
C-255
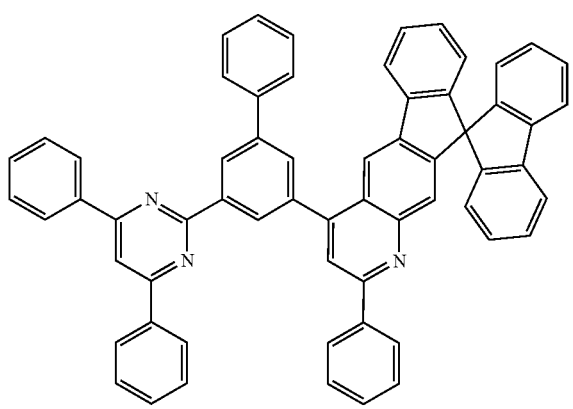
C-256
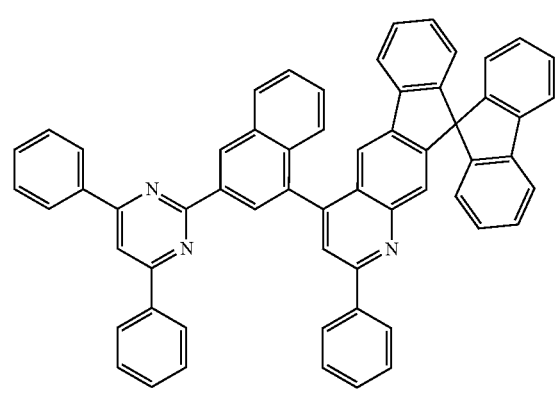
C-257
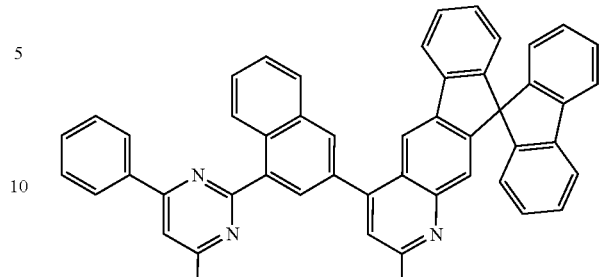
C-258
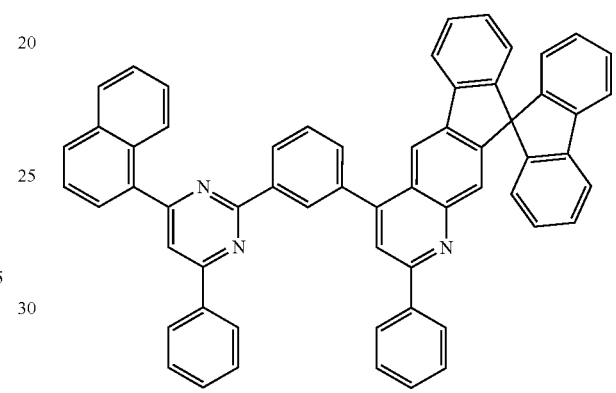
C-259
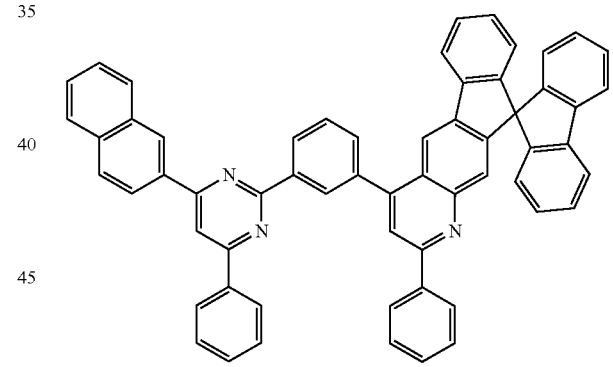
C-260
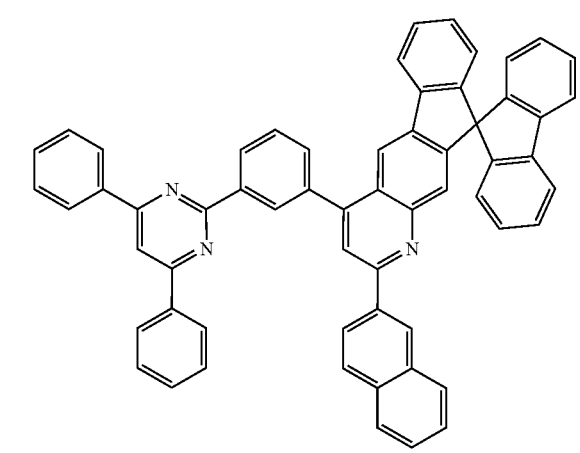

-continued
C-261
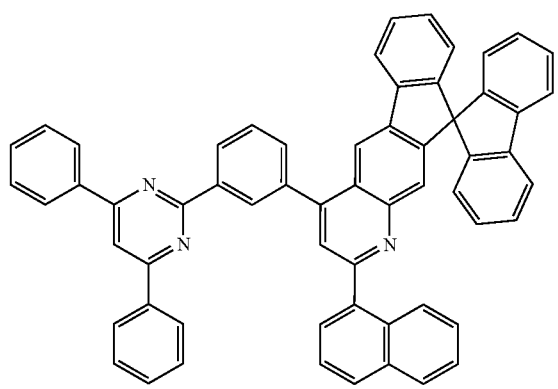
C-262
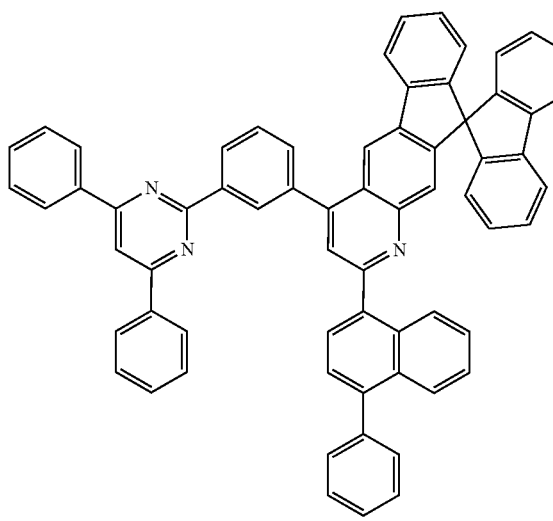
C-263
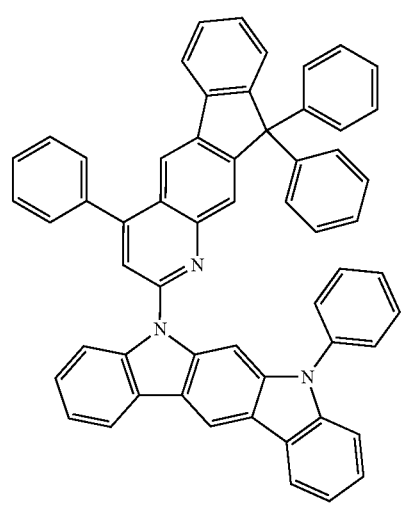
-continued
C-264
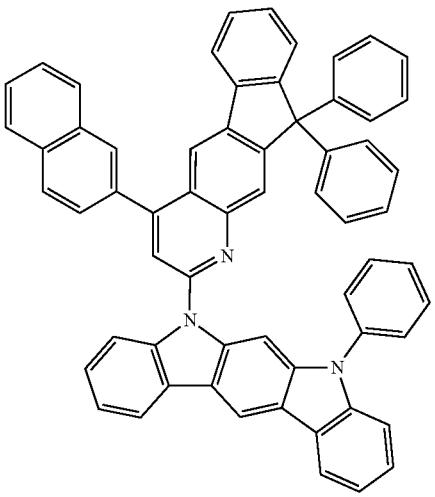
C-265
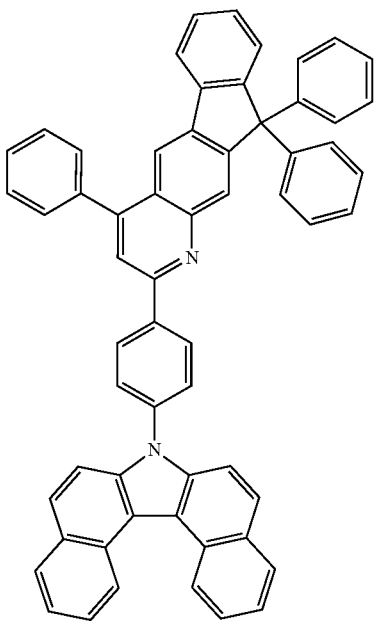

C-266
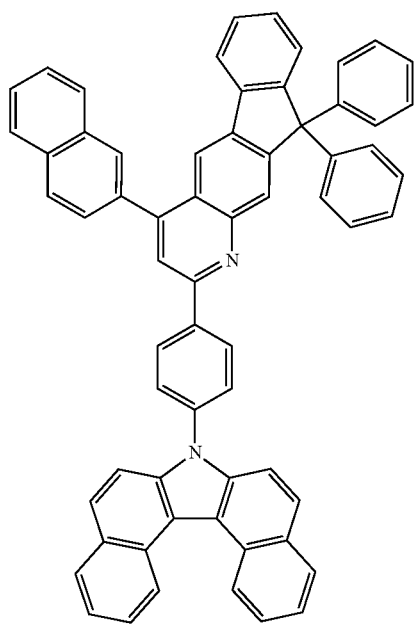
C-267
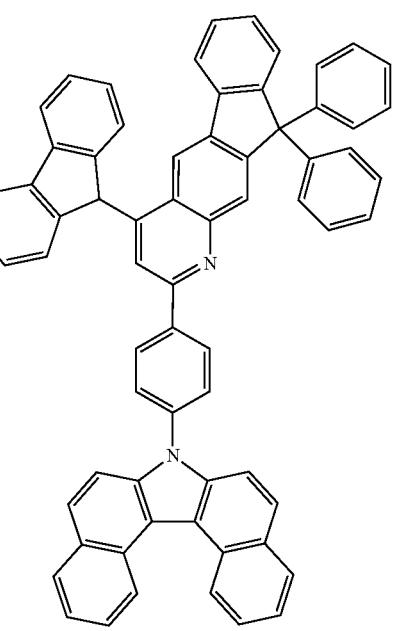
C-268
C-269
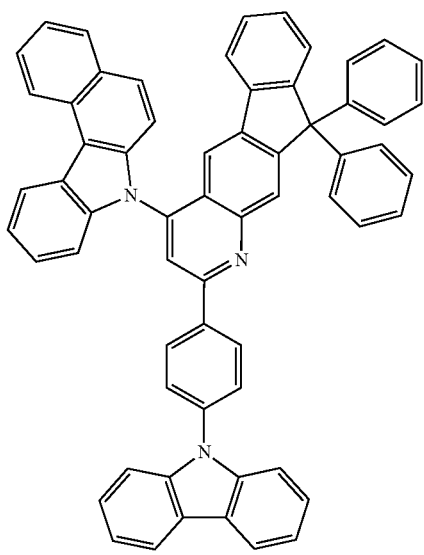

C-270
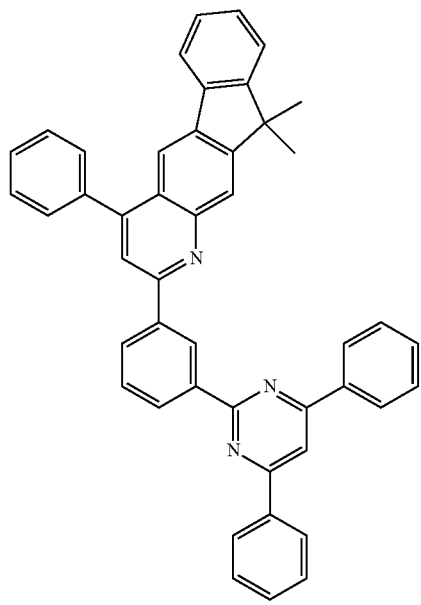
C-272
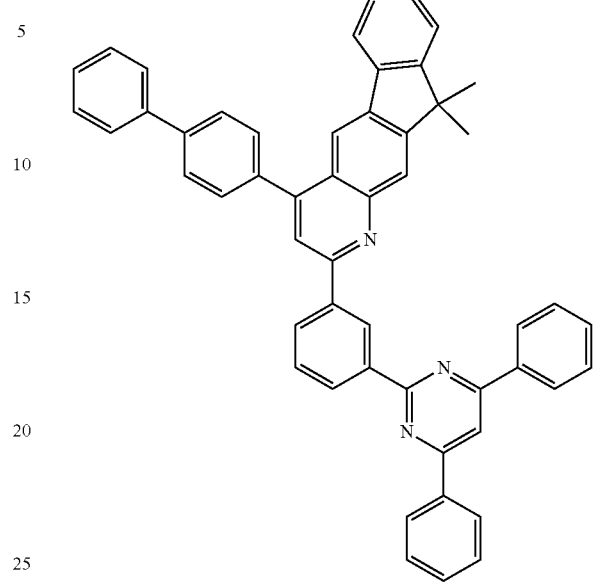
C-271
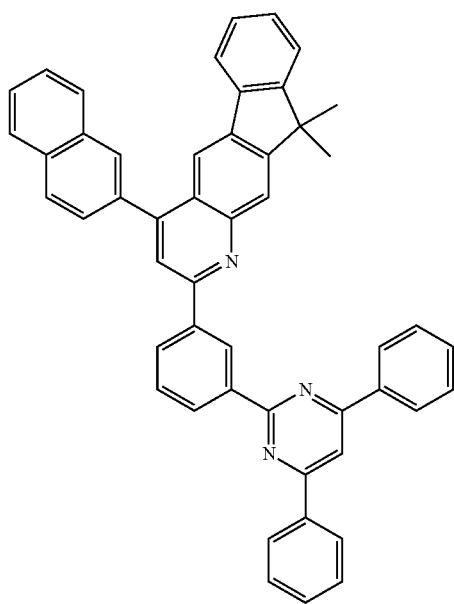
C-273

C-274
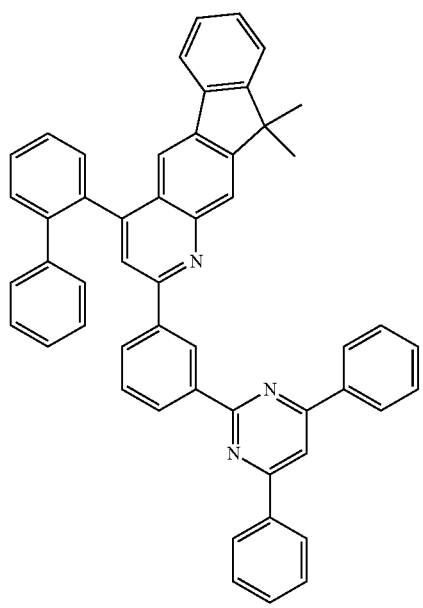
C-275
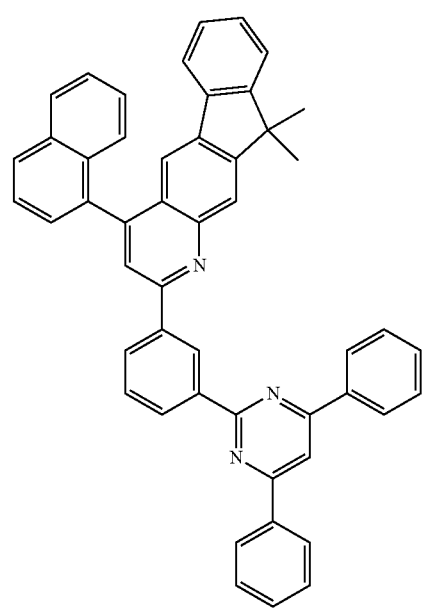
C-276
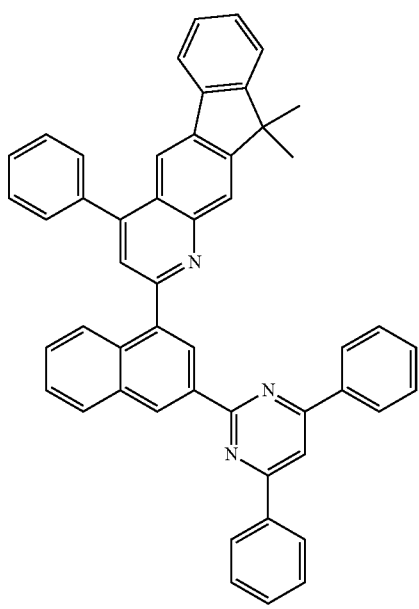
C-277
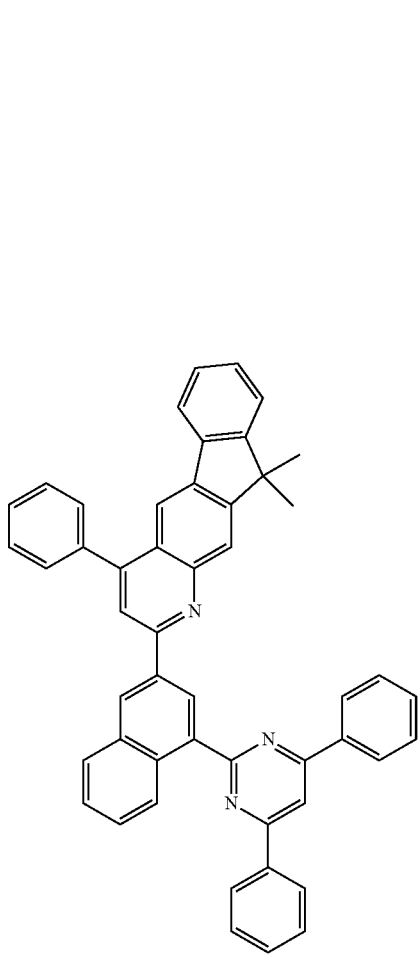

C-278
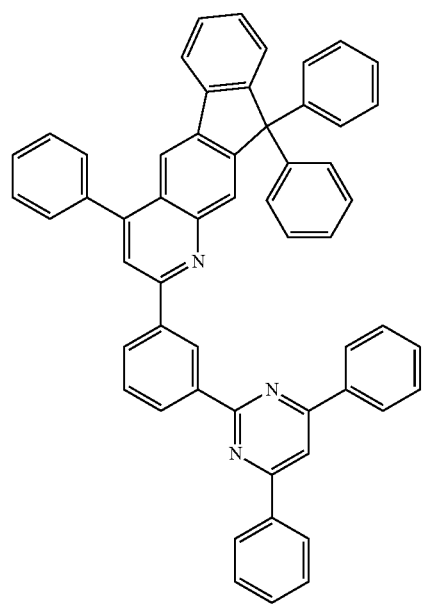
C-280
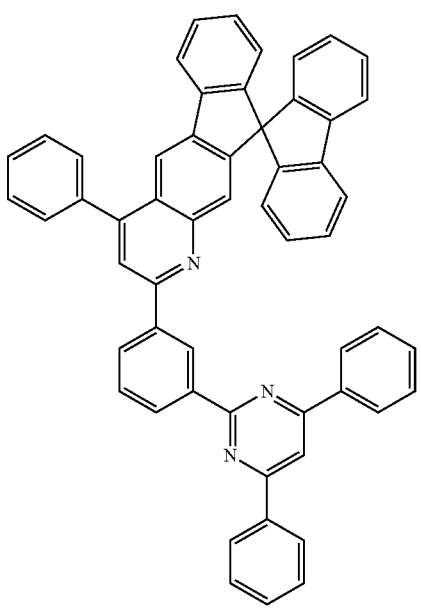
C-279
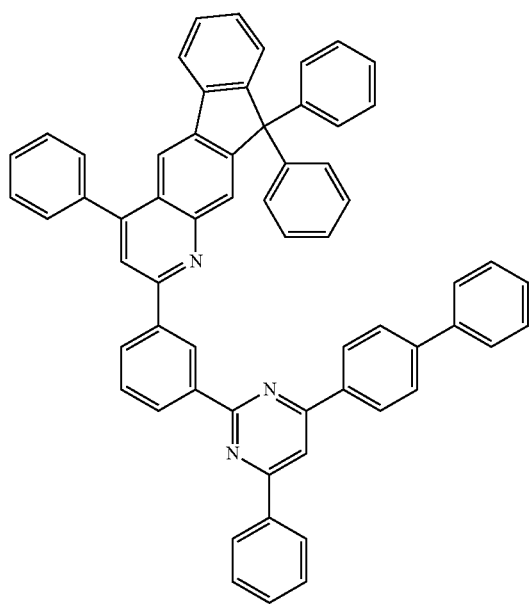
C-281
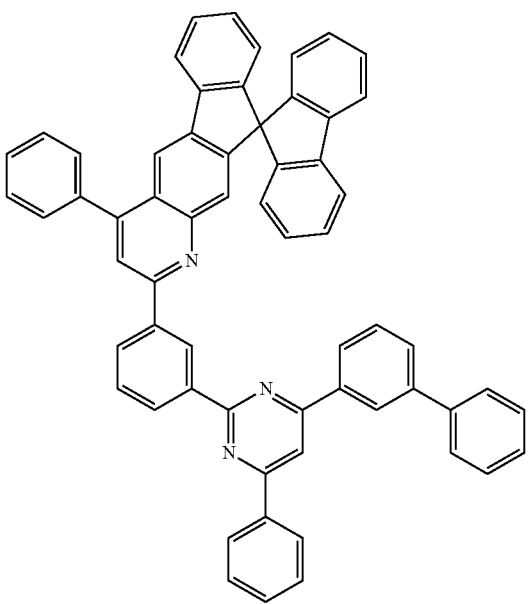

C-282
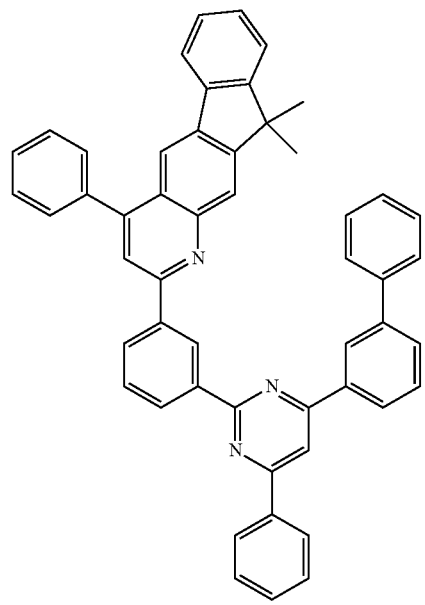
C-283
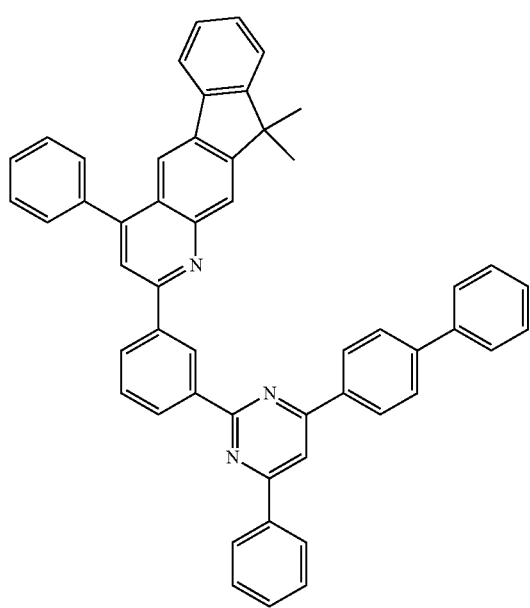
C-284
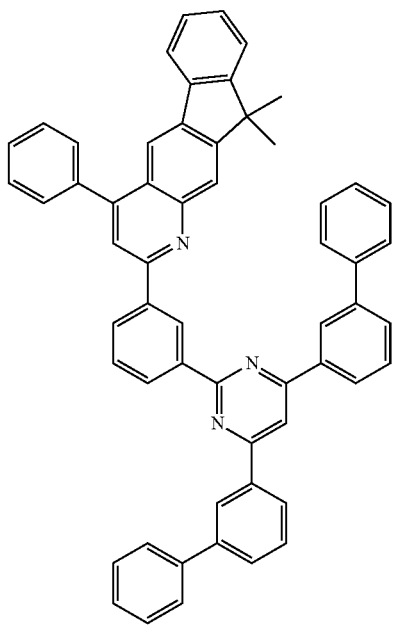
C-285
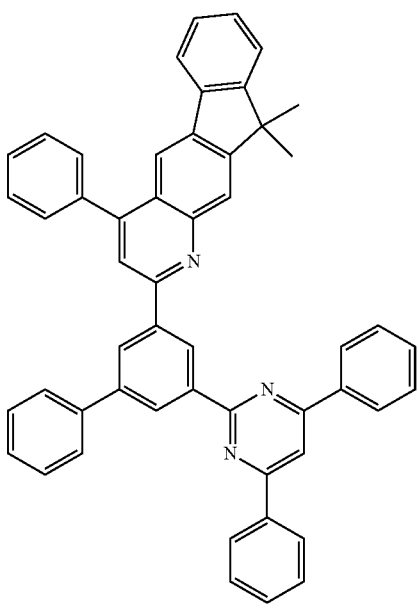

-continued
C-286
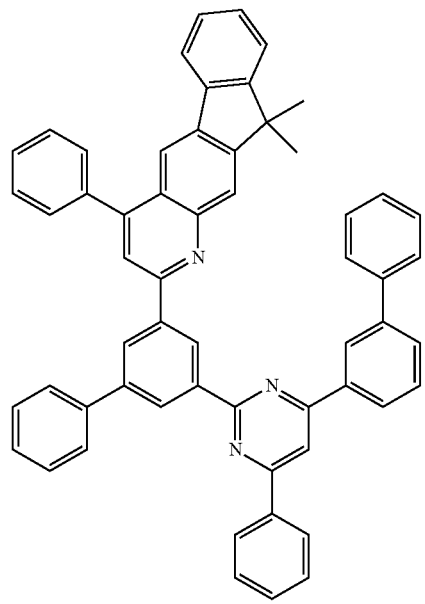
C-287
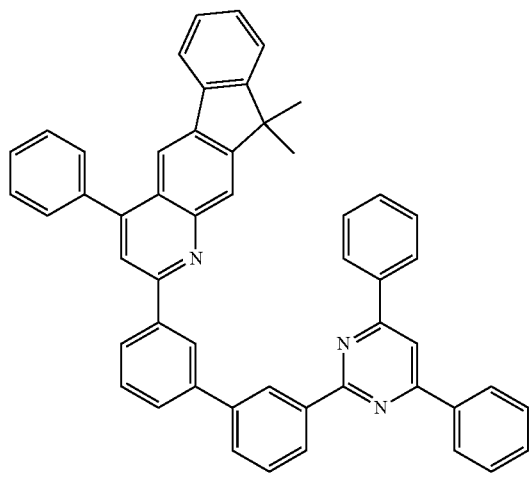
C-288
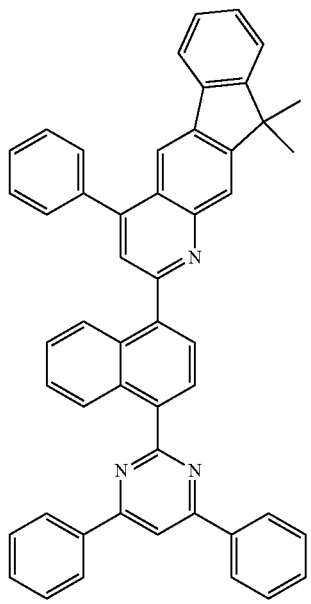
C-289
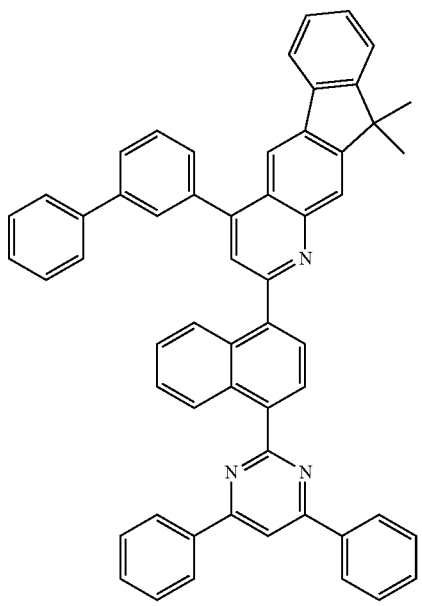

C-290
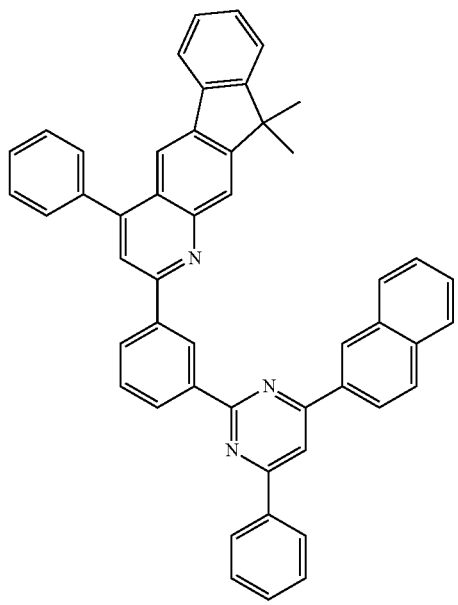
C-292
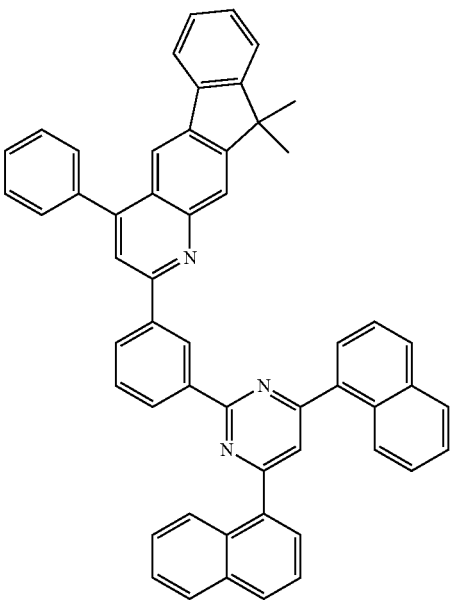
C-291
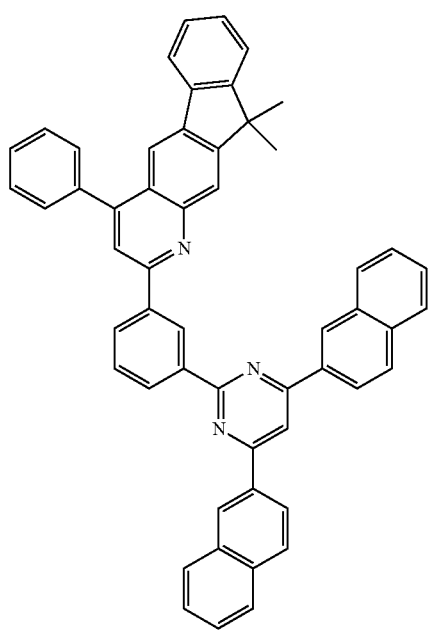
C-293
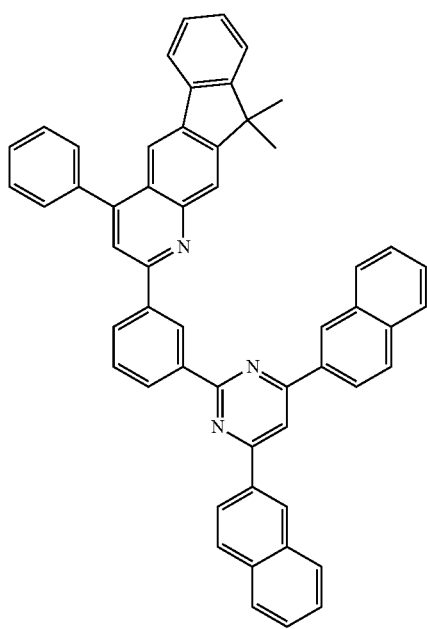

C-294
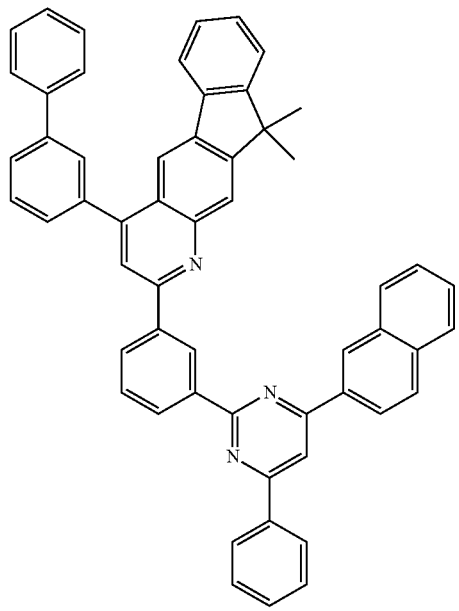
C-295
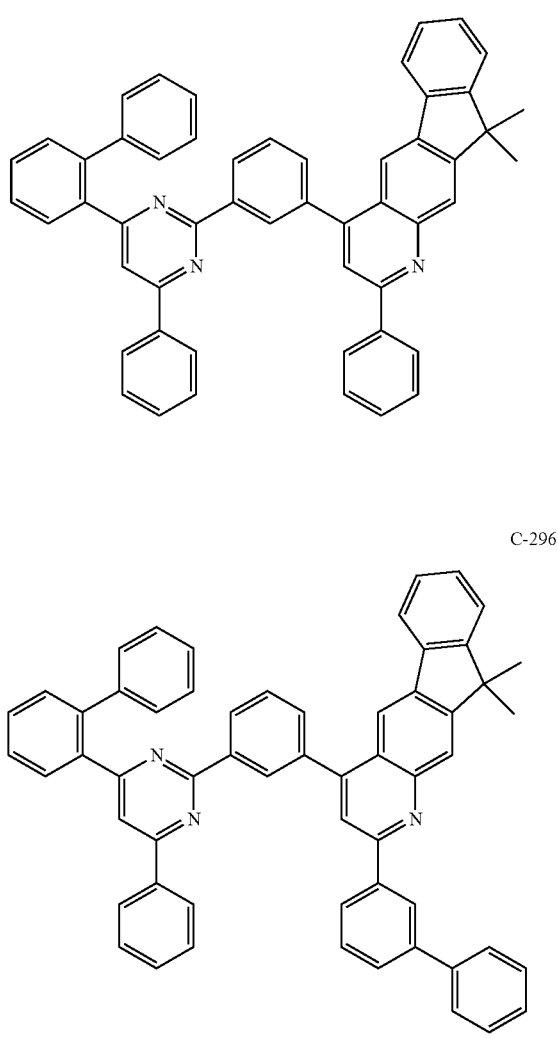
C-296
C-297
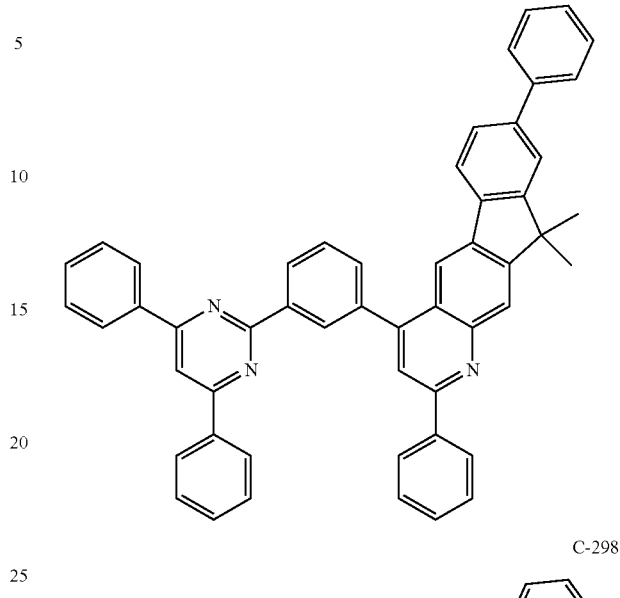
C-298
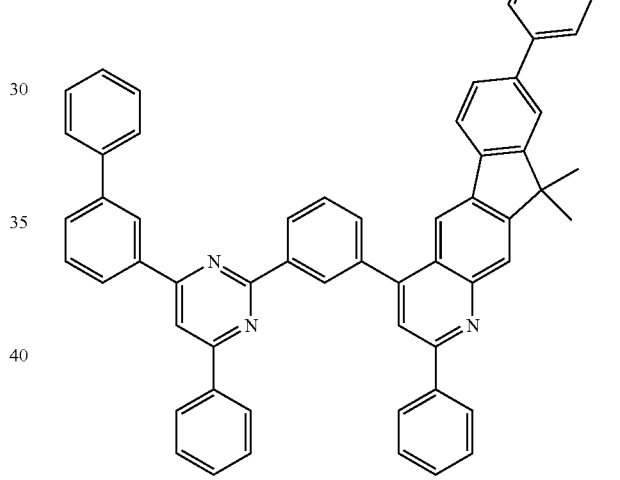
C-299
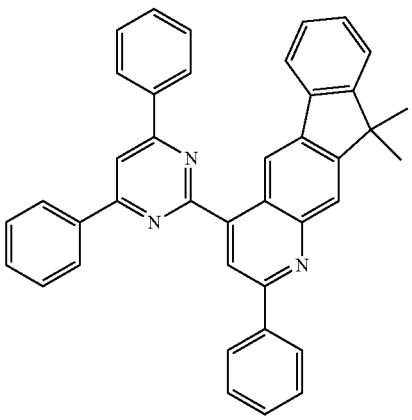

C-300
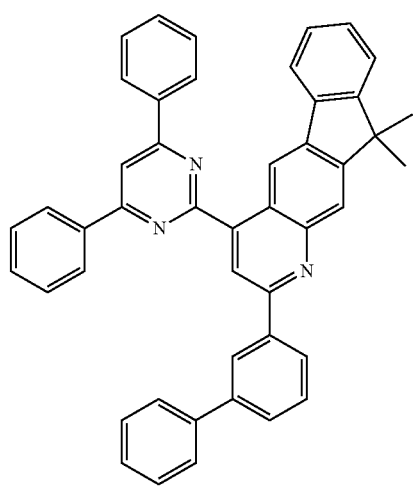
C-303
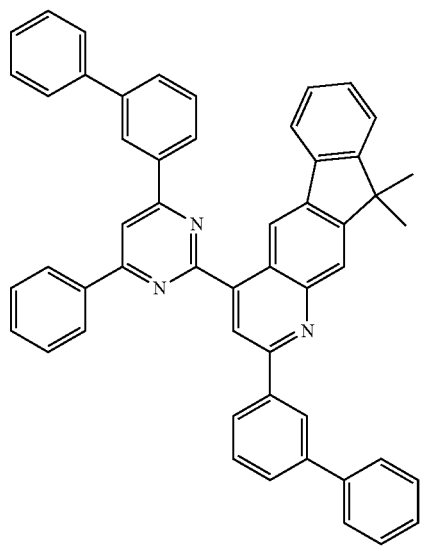
C-301
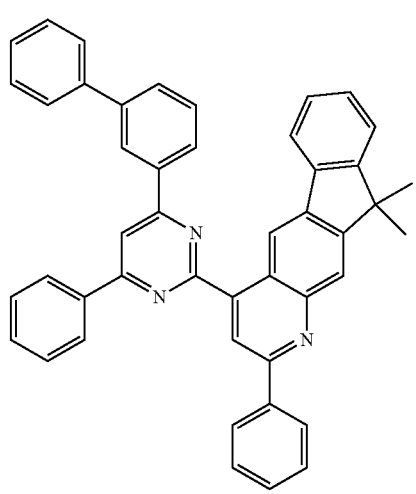
C-304
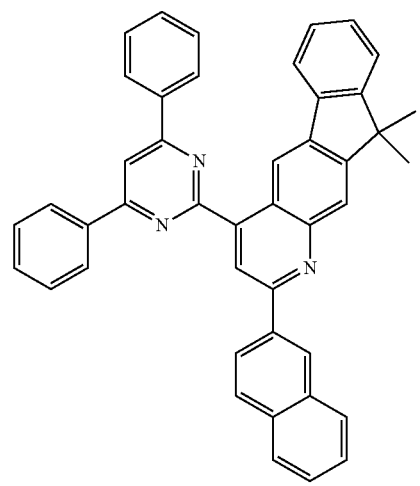
C-302
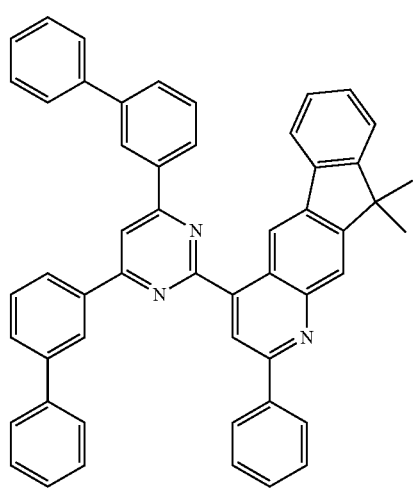
C-305
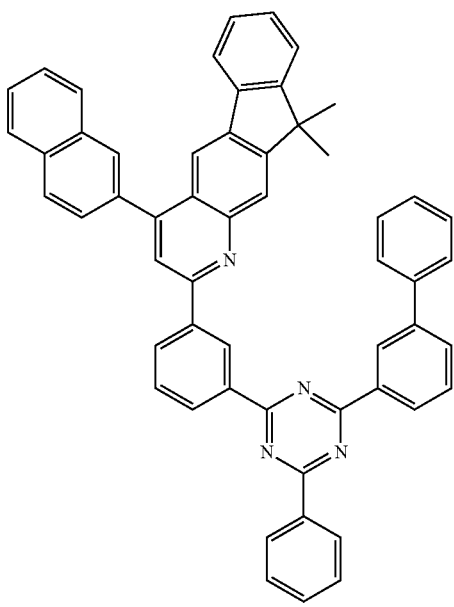

C-306
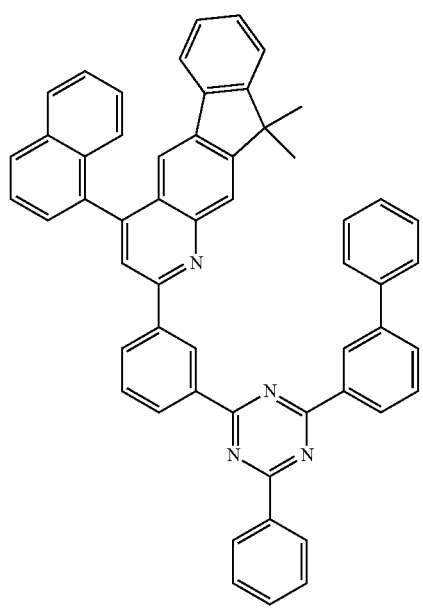
C-309
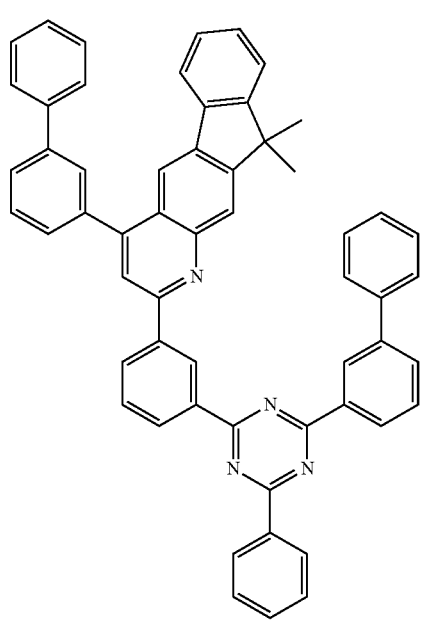
C-307
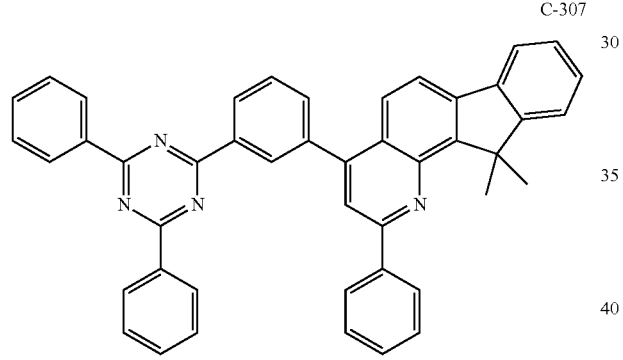
C-308
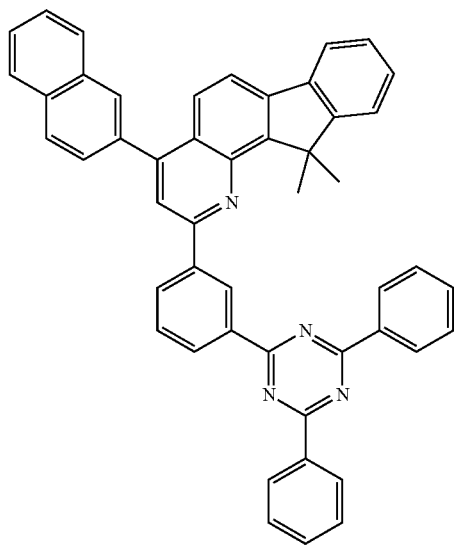
C-310
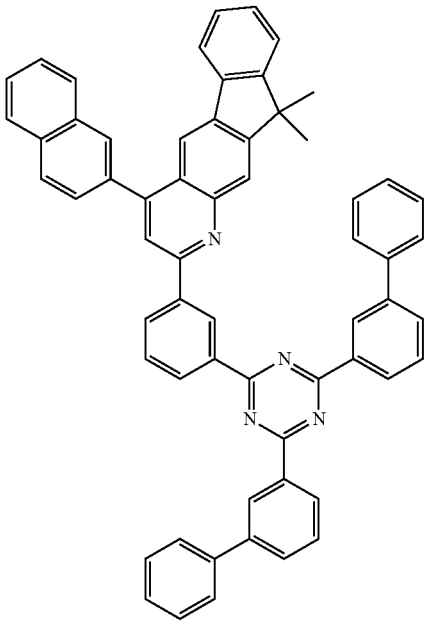

C-311
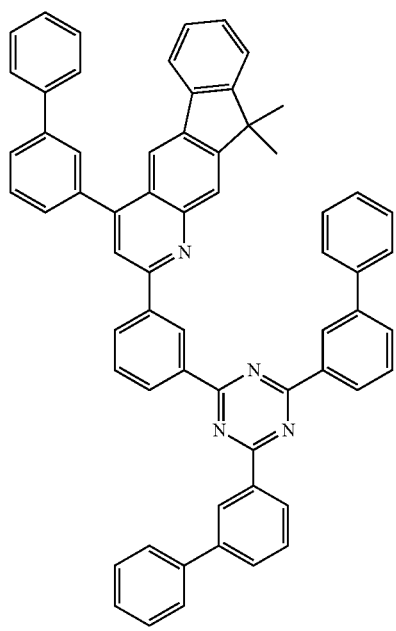
C-312
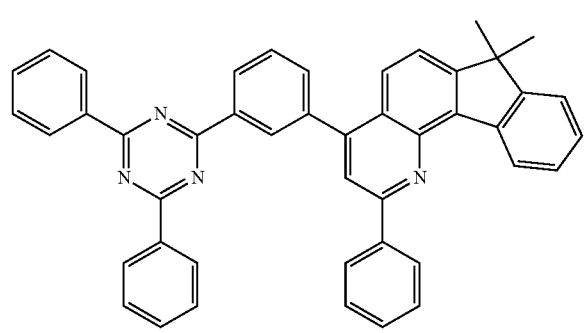
C-313
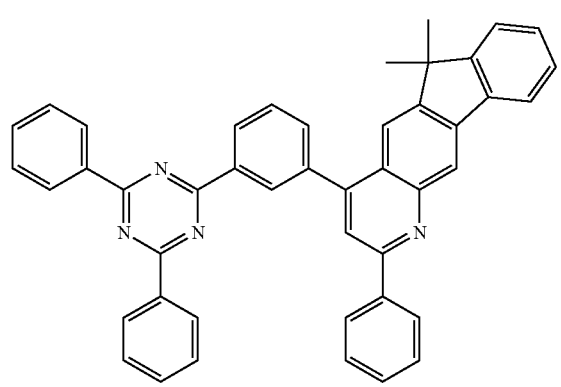
C-314
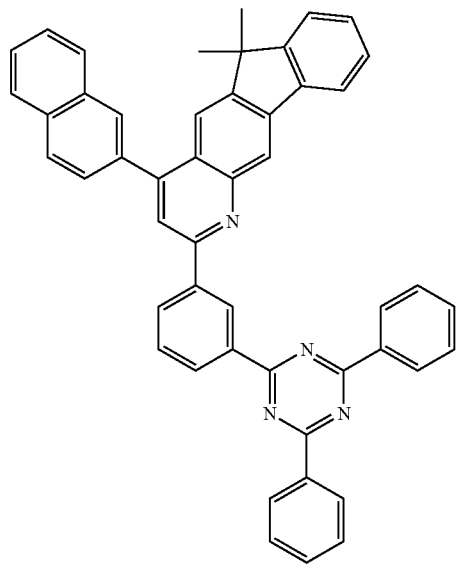
C-315
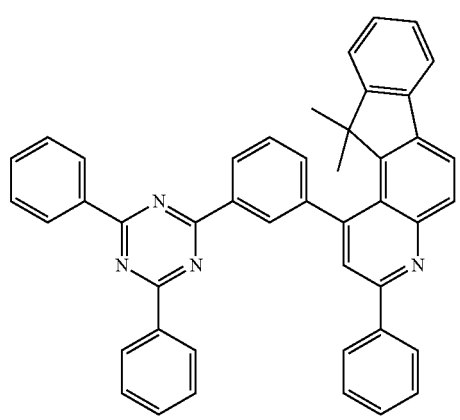
C-316
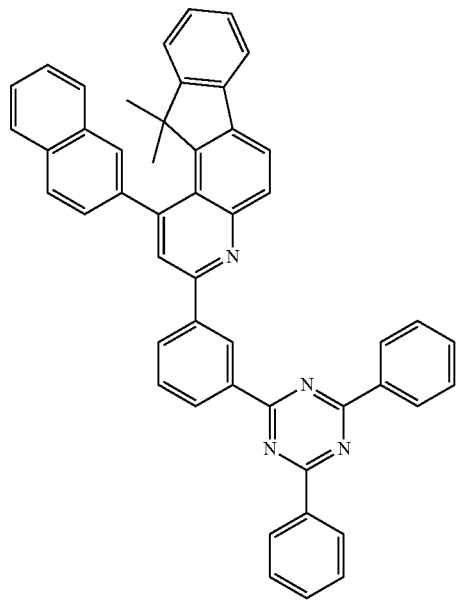

C-317
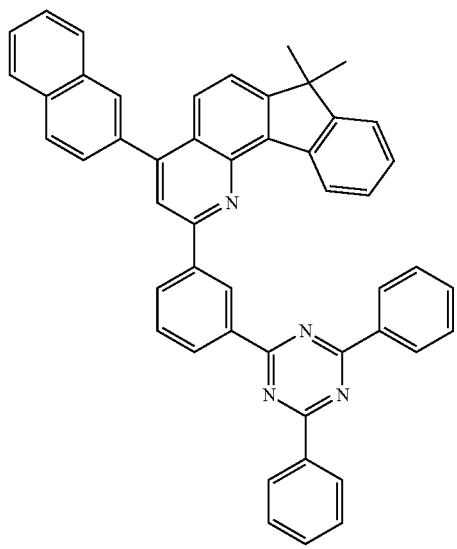
C-318
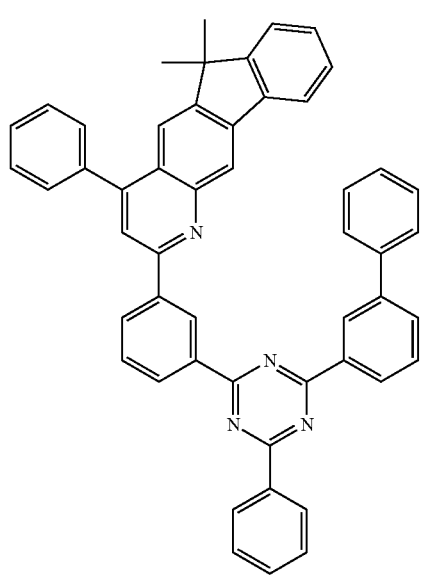
C-319
C-320
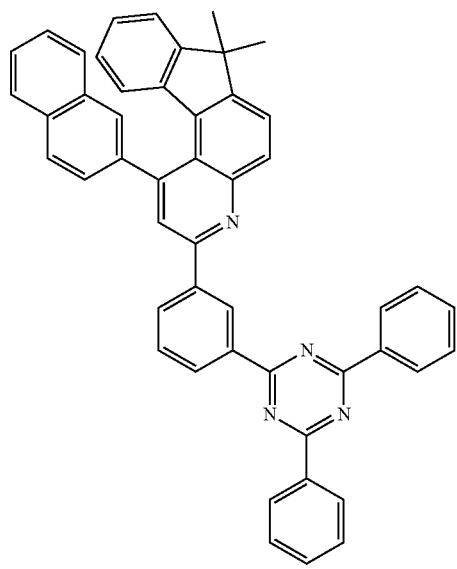
C-321
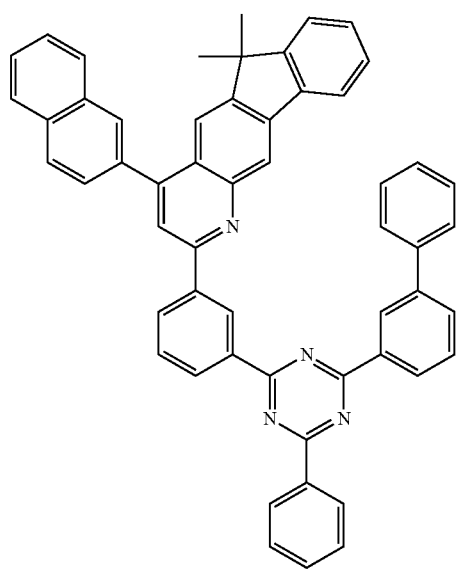

C-322

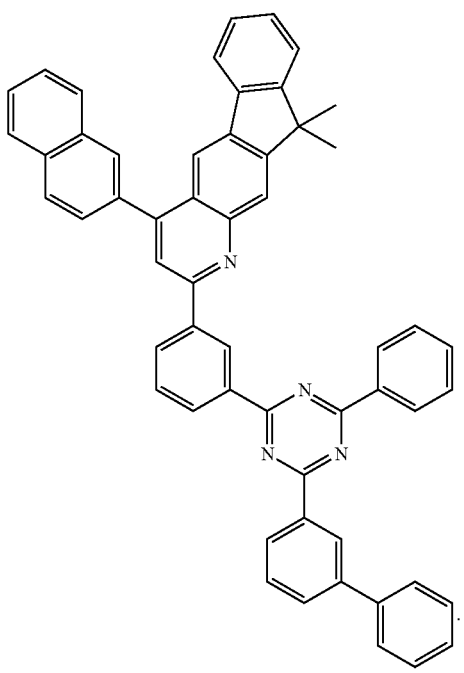

The compounds of formula 1 according to the present disclosure can be prepared by a synthetic method known to one skilled in the art, e.g., the following reaction scheme 1.

[Reaction Scheme 1]

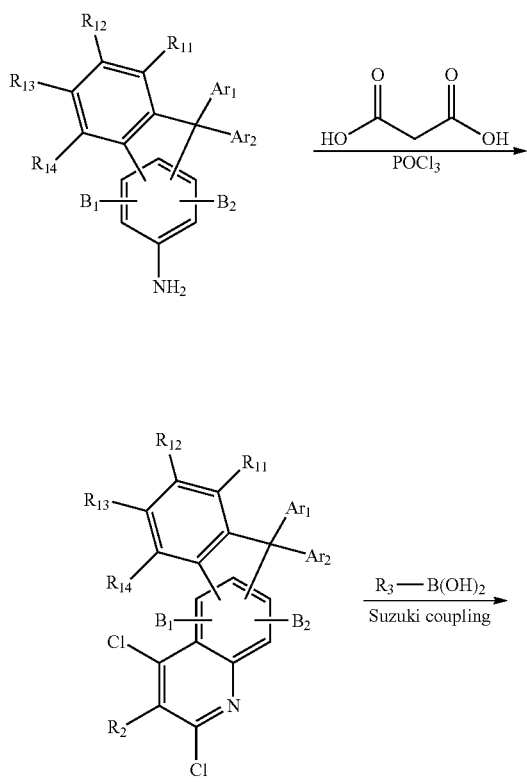

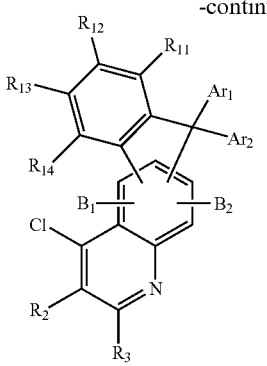

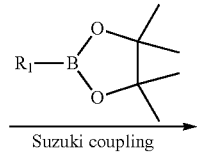

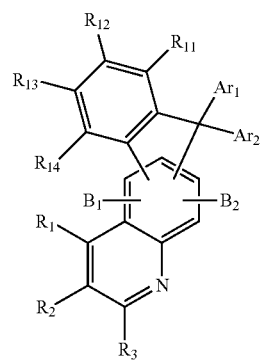

In the reaction scheme 1, $R_1$ to $R_3$, $B_1$, $B_2$, $Ar_1$, $Ar_2$ and $R_{11}$ to $R_{14}$ are as defined in formula 1.

The present disclosure provides an organic electroluminescent material comprising the organic electroluminescent compound of formula 1 and an organic electroluminescent device comprising the organic electroluminescent material.

The organic electroluminescent material may be comprised solely of the organic electroluminescent compound of the present disclosure, or may further comprise conventional materials included in the organic electroluminescent material.

The organic electroluminescent device according to the present disclosure includes a first electrode; a second electrode; and at least one organic layer interposed between the first electrode and the second electrode.

One of the first electrode and the second electrode may be an anode and the other may be a cathode. The organic layer comprises a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

The organic electroluminescent compound represented by formula 1 of the present disclosure may be comprised in at least one layer of the light-emitting layer, the hole injecting layer, the hole transport layer, the hole auxiliary layer, the light-emitting auxiliary layer, the electron transport layer, the electron buffer layer, the electron injection layer, the interlayer, the hole blocking layer, and the electron blocking layer. According to the case, it may be, preferably, comprised in at least one layer of the light-emitting layer, the electron buffer layer, and the electron transport layer. When used in the light-emitting layer, the organic electroluminescent compound of formula 1 of the present disclosure may be comprised as a host material. When used in the electron buffer layer, the organic electroluminescent compound of formula 1 of the present disclosure may be comprised as an electron buffer material. When used in the electron transport layer, the organic electroluminescent compound of formula 1 of the present disclosure may be comprised as an electron transport material.

The light-emitting layer may include at least one host and at least one dopant. If necessary, the light-emitting layer may comprise a co-host material, i.e., a plurality of two or more host materials.

The host compound to be used in the present disclosure may be a phosphorescent host compound or a fluorescent host compound, and the kinds of host compound to be used are not particularly limited. Specifically, the host compound may be a fluorescent host compound, for example, may be an anthracene compound represented by the following formula 11.

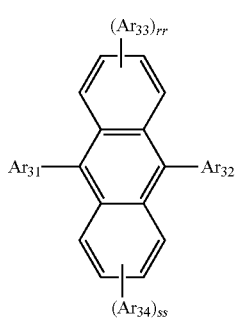

(11)

In formula 11, $Ar_{31}$ and $Ar_{32}$ each independently represent a substituted or unsubstituted (C6-C30)aryl, or a substituted or unsubstituted (5- to 30-membered)heteroaryl; $Ar_{33}$ and $Ar_{34}$ each independently represent hydrogen, deuterium, halogen, cyano, nitro, hydroxy, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted (C1-C30)alkylsilyl, a substituted or unsubstituted (C6-C30)arylsilyl, a substituted or unsubstituted (C6-C30)ar(C1-C30)alkylsilyl, or —$NR_{41}R_{42}$; $R_{41}$ and $R_{42}$ each independently represent hydrogen, a substituted or unsubstituted (C6-C30)aryl, or a substituted or unsubstituted (5- to 30-membered)heteroaryl, or may be bonded to each other to form a (3- to 30-membered) mono- or polycyclic, alicyclic or aromatic ring, or a combination of alicyclic and aromatic rings whose carbon atom may be replaced with at least one heteroatom selected from nitrogen, oxygen, and sulfur; rr and ss each independently represent an integer of 1 to 4; and where rr or ss is an integer of 2 or more, each of $Ar_{33}$ or $Ar_{34}$ may be the same or different.

The compound represented by formula 11 may be specifically illustrated by the following compounds, but is not limited thereto:

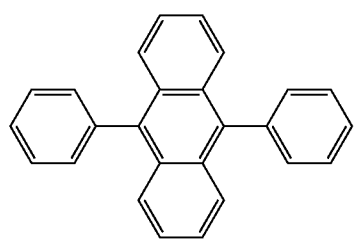

H-1

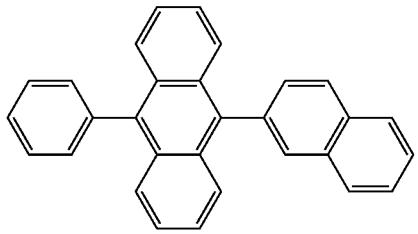

H-2

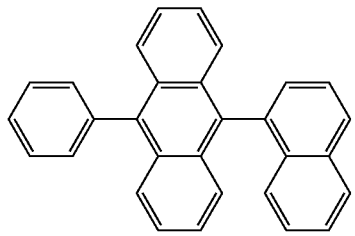

H-3

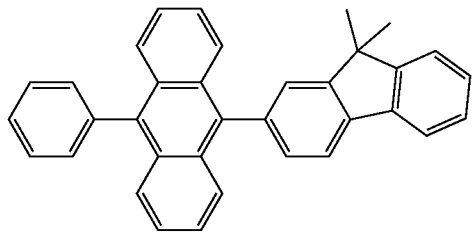

H-4

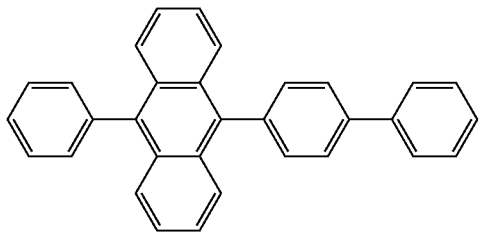

H-5

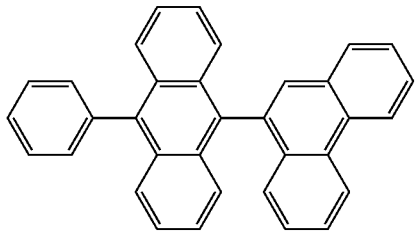

H-6

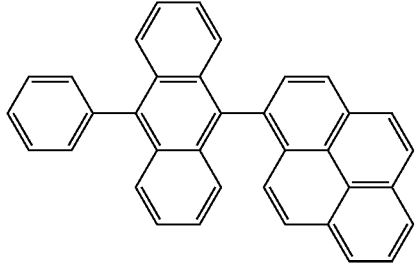

H-7

H-8
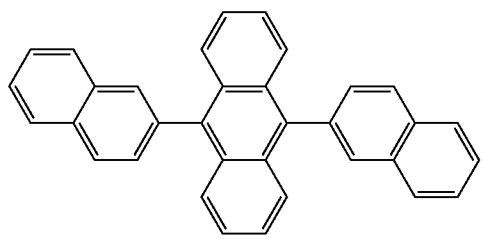
H-9
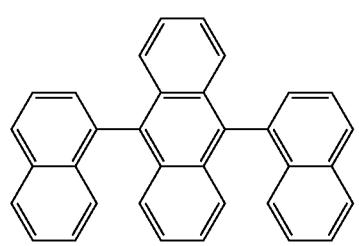
H-10
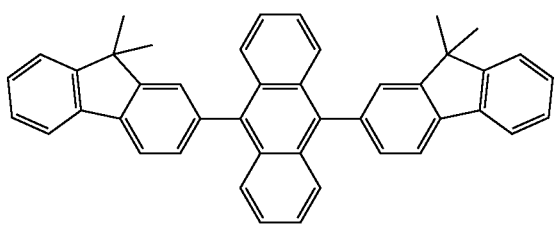
H-11
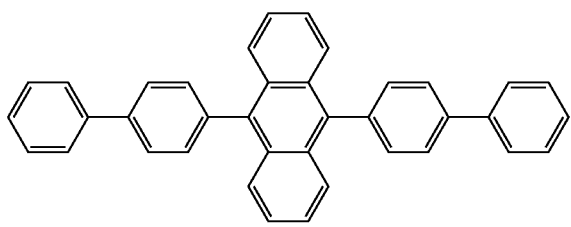
H-12
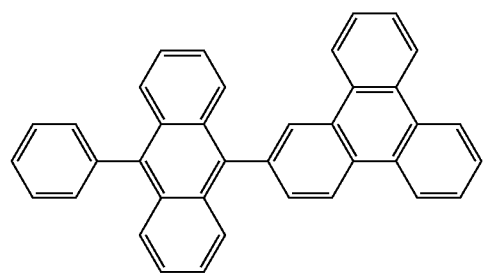
H-13
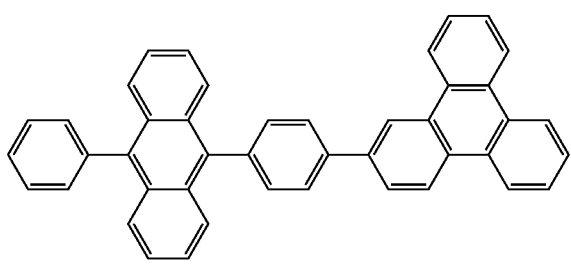
H-14
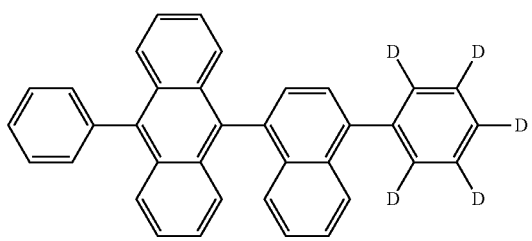
H-15
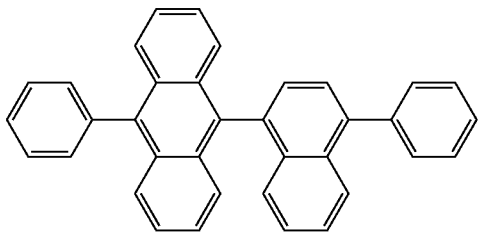
H-16
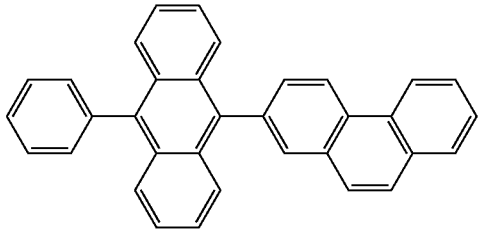
H-17
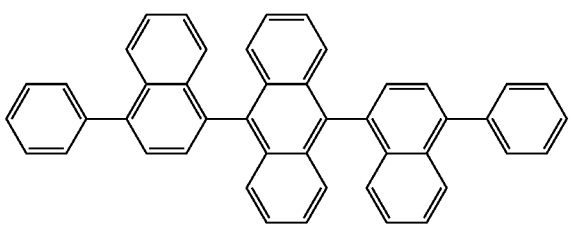
H-18
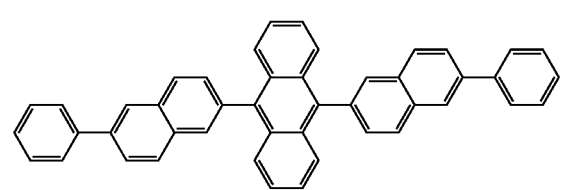
H-19
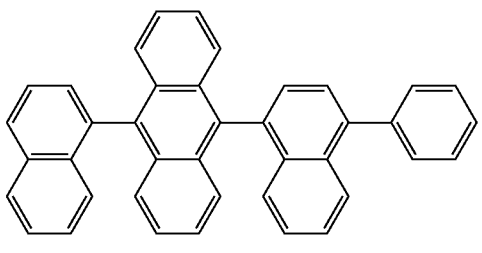

H-20
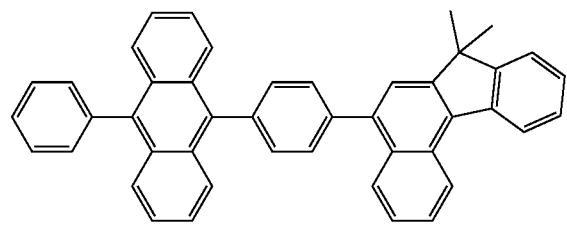
H-21
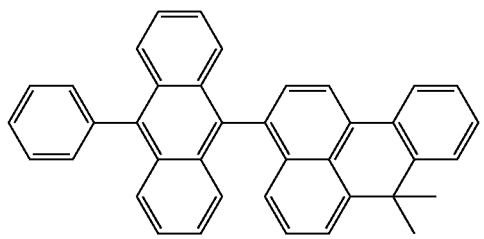
H-22
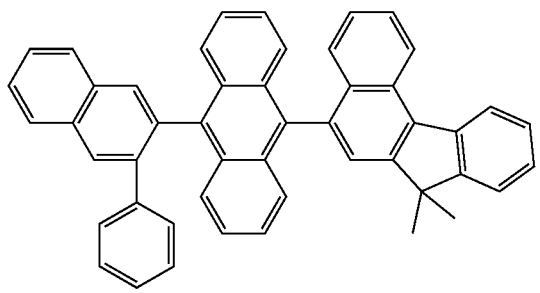
H-23
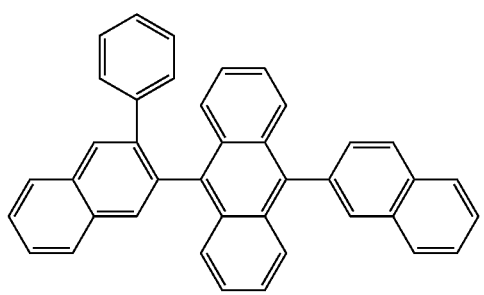
H-24
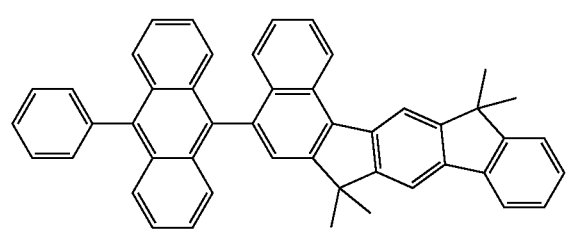
H-25
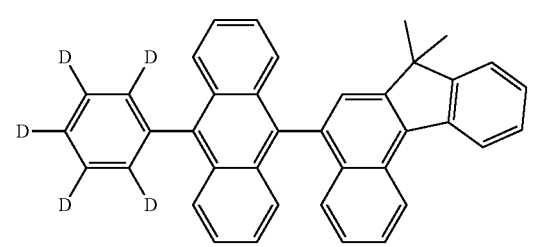
H-26
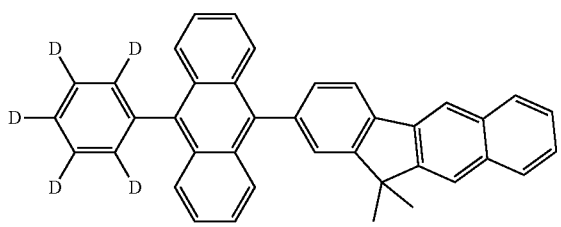
H-27
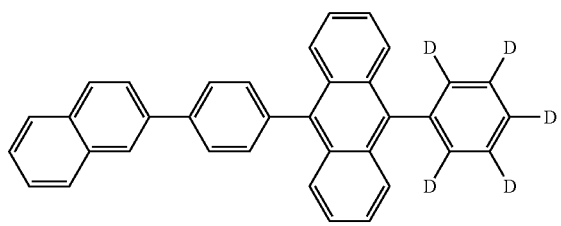
H-28
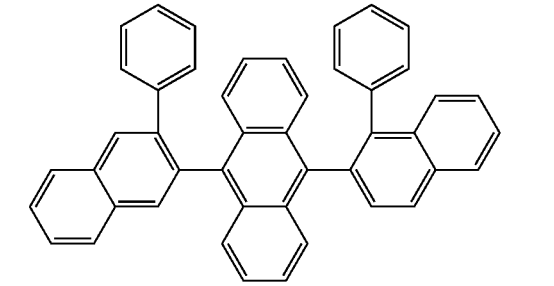
H-29
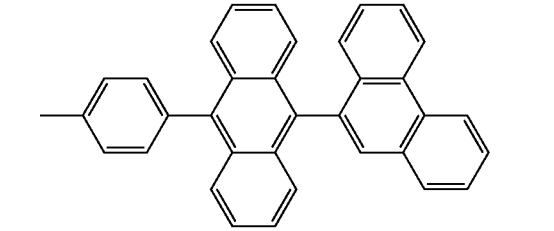
H-30
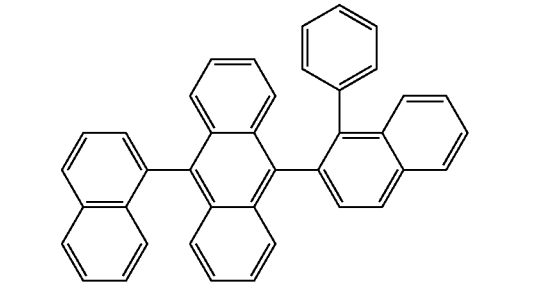
H-31
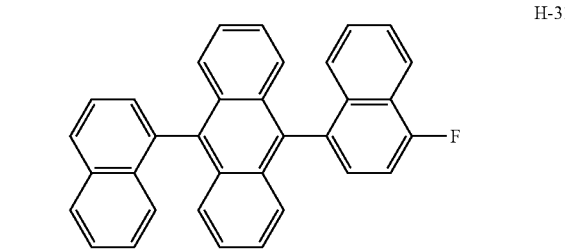

H-32
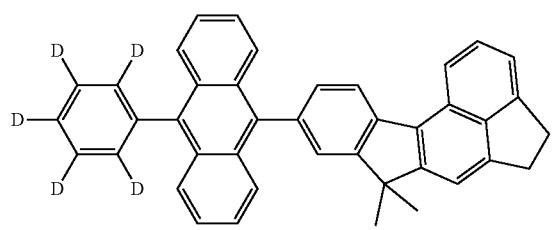
H-33
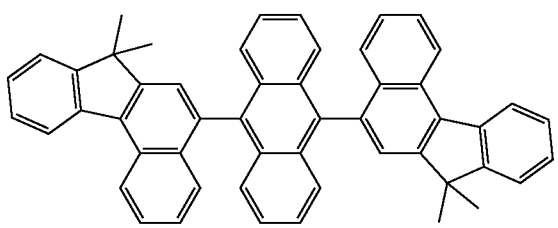
H-34
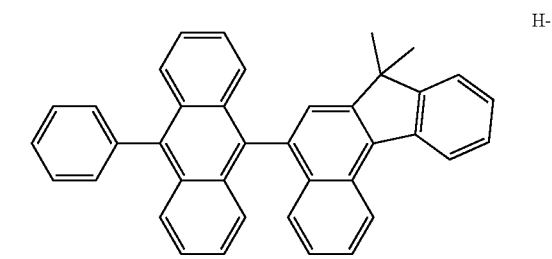
H-35
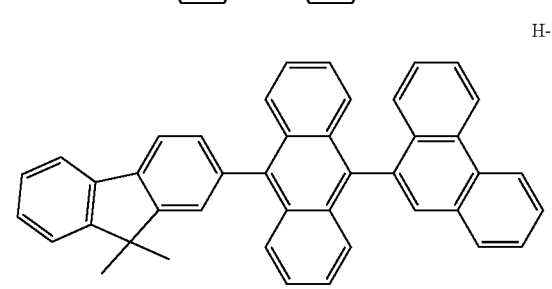
H-36
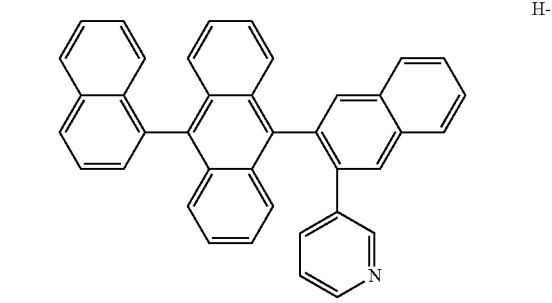
H-37
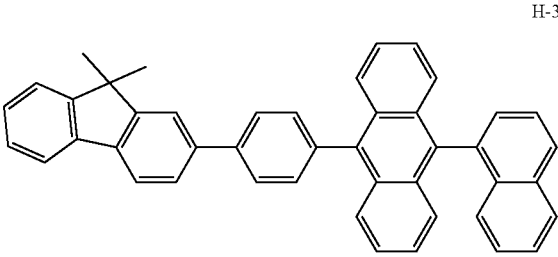
H-38
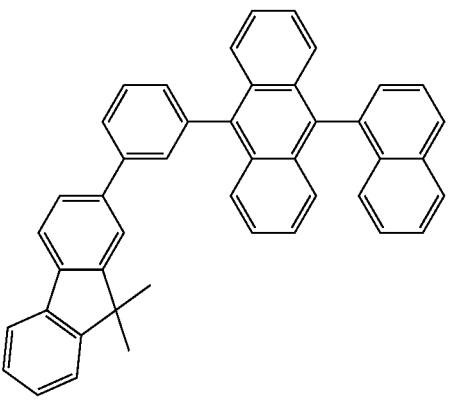
H-39
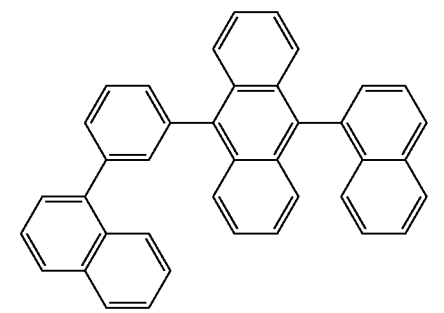
H-40
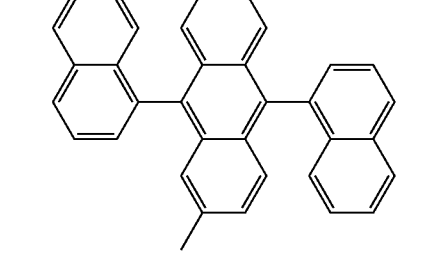
H-41
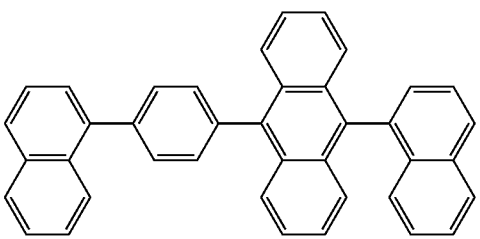
H-42
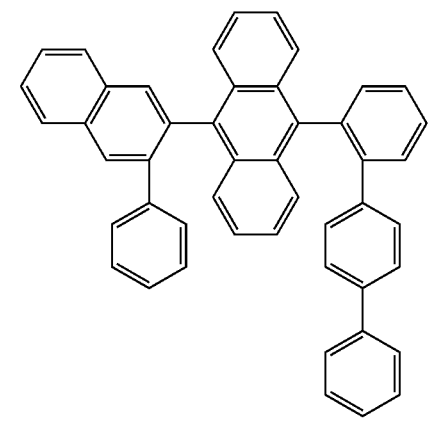

H-43
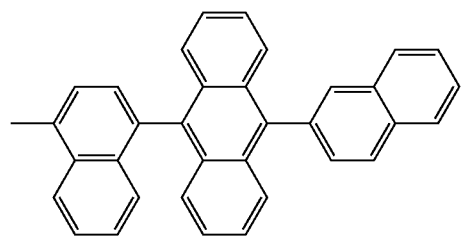
H-44
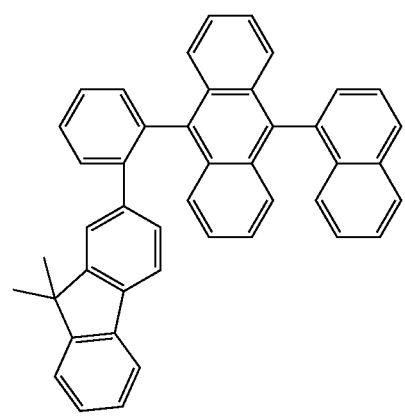
H-45
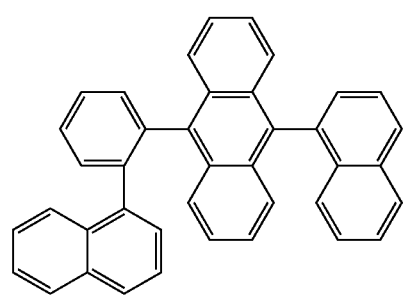
H-46
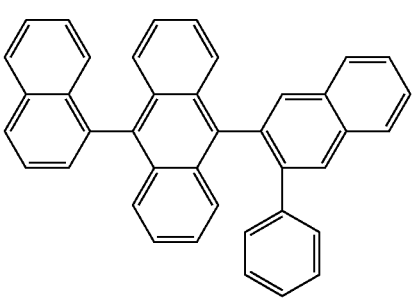
H-47
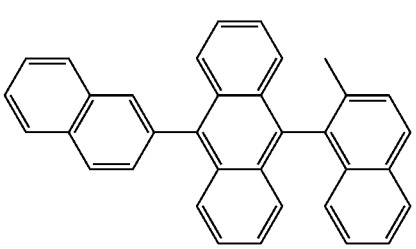
H-48
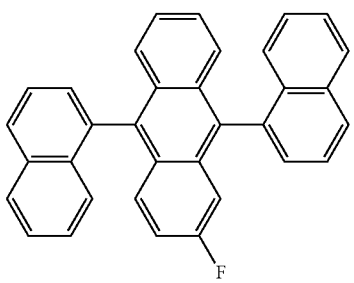
H-49
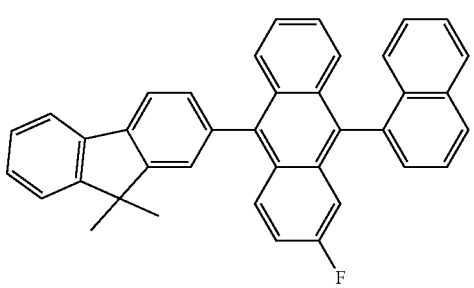
H-50
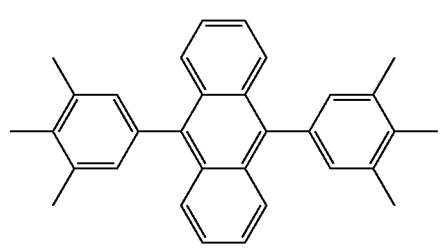
H-51
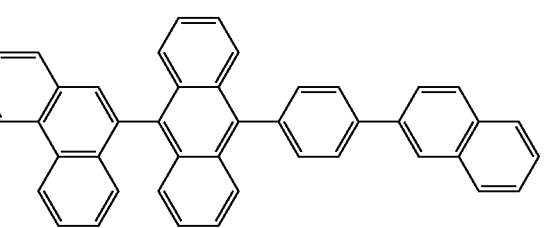
H-52
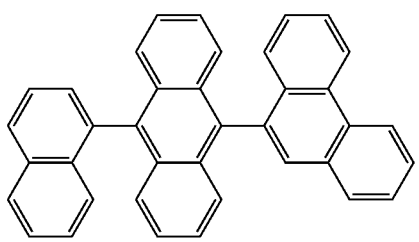
H-53
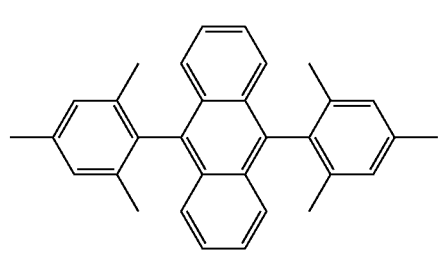

H-54
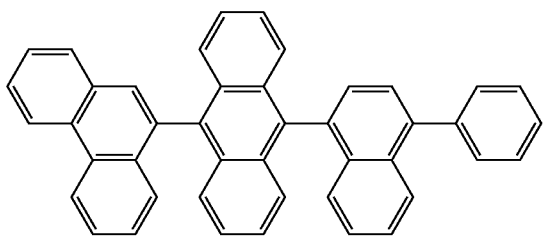
H-55
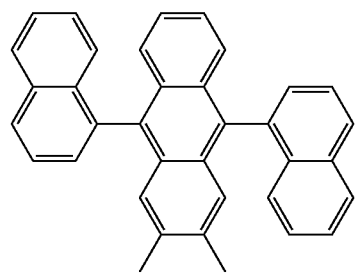
H-56
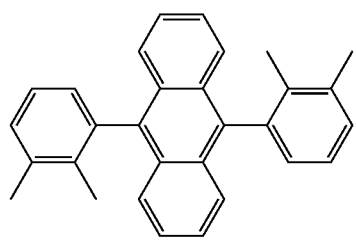
H-57
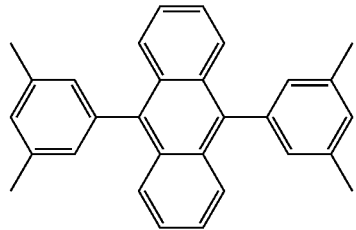
H-58
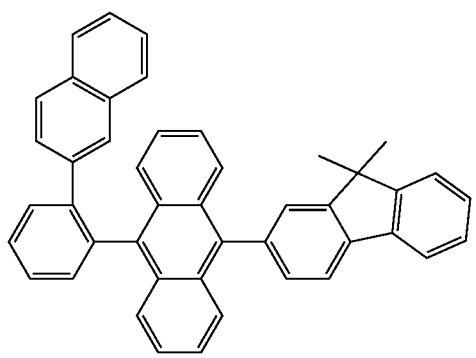
H-59
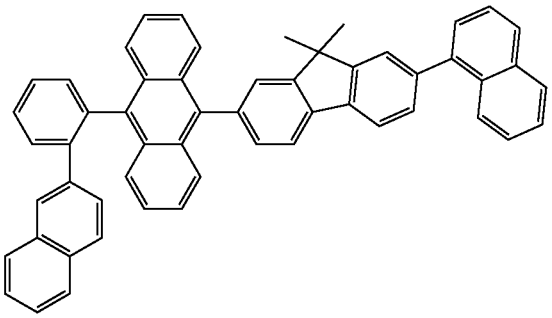
H-60
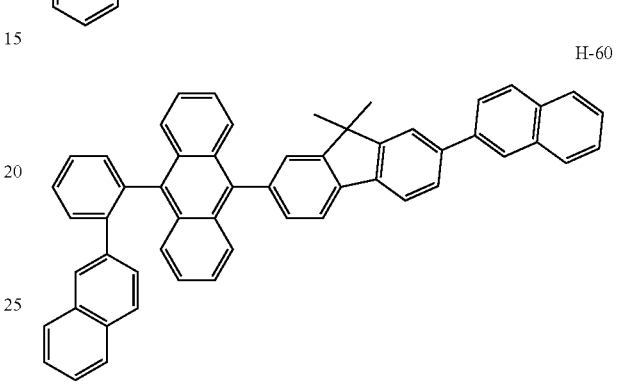
H-61
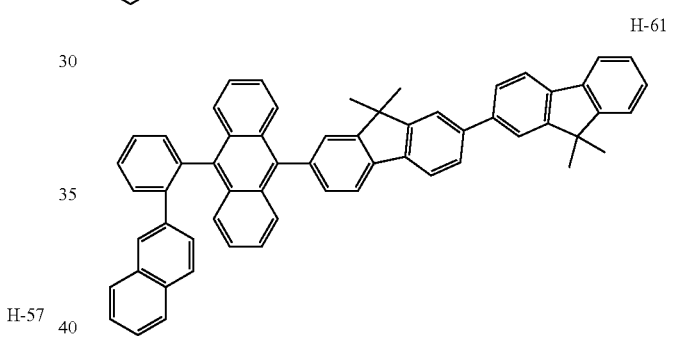
H-62
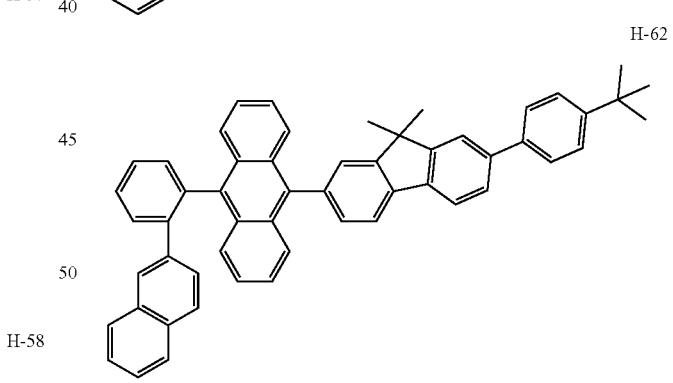
H-63
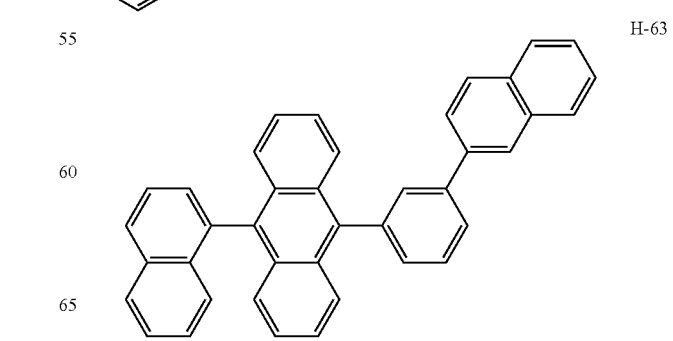

H-64
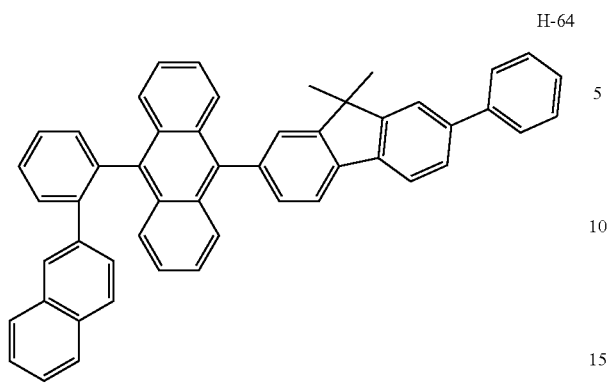
H-65
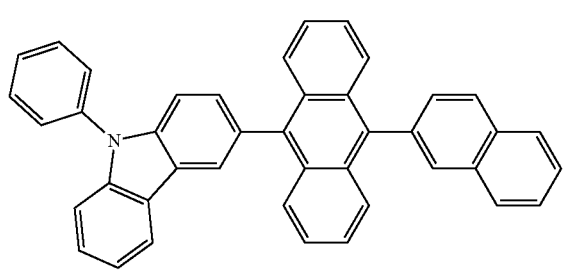
H-66
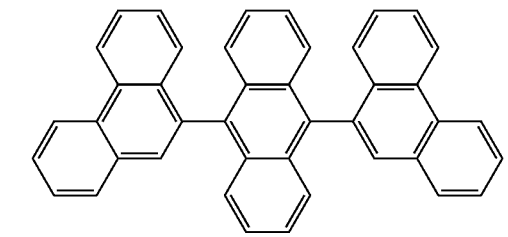
H-67
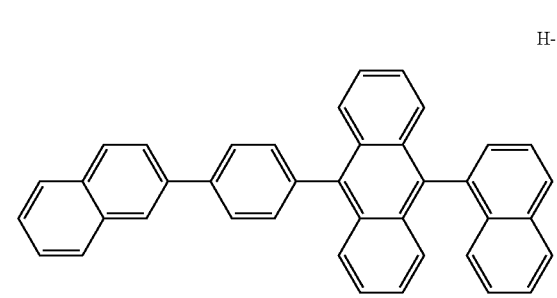
H-68
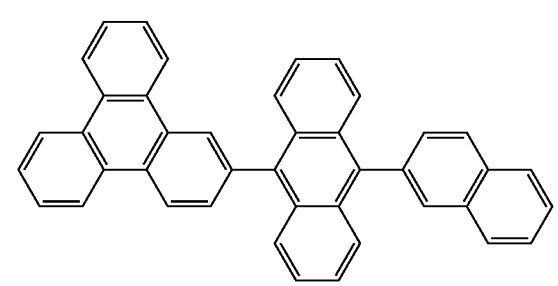
H-69
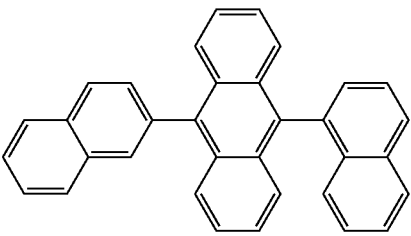
H-70
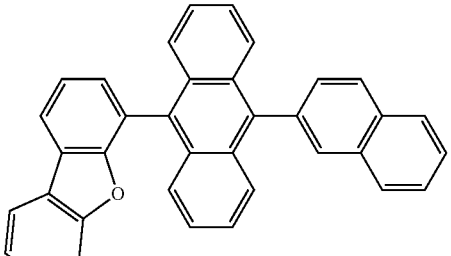
H-71
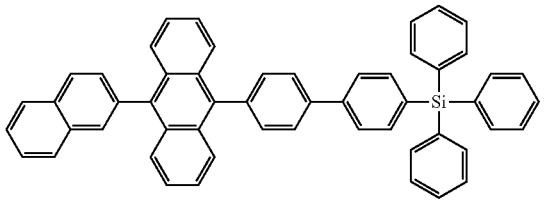
H-72
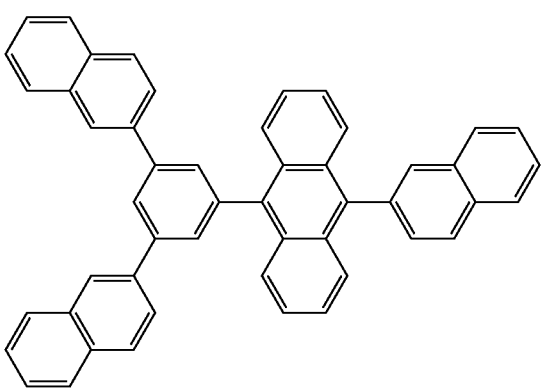
H-73
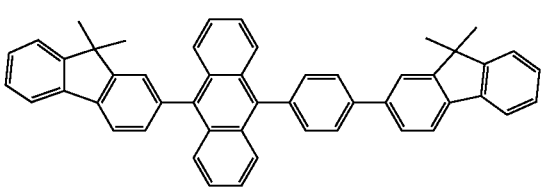

H-74
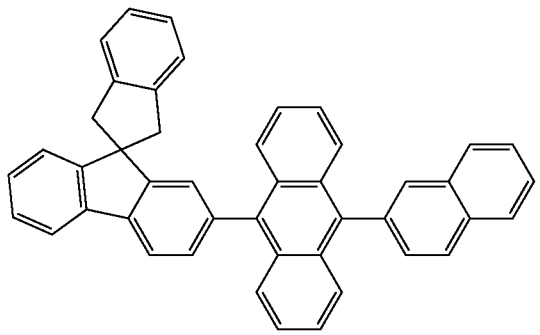
H-75
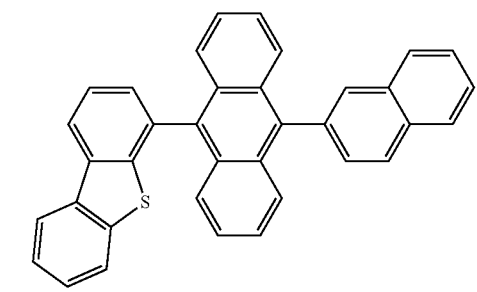
H-76
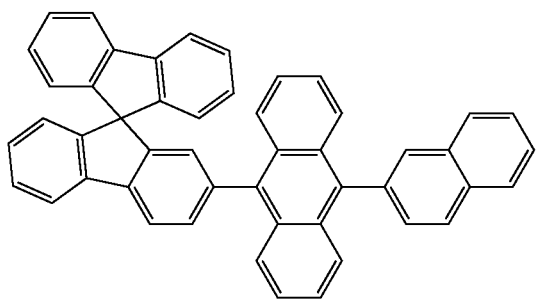
H-77
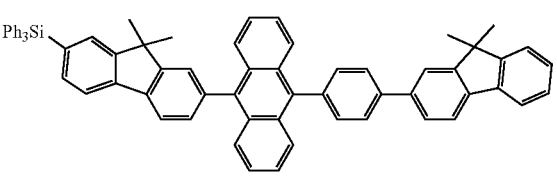
H-78
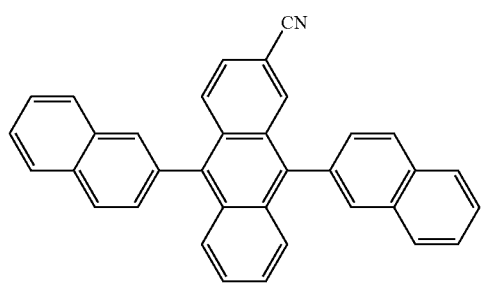
H-79
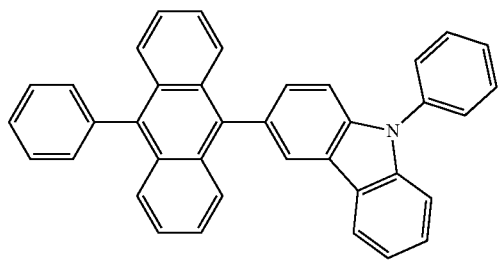
H-80
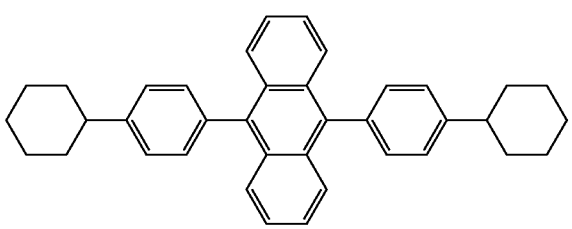
H-81
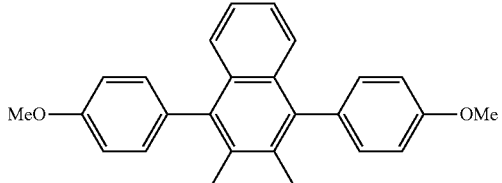
H-82
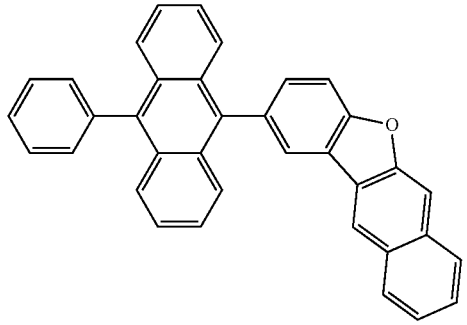
H-83
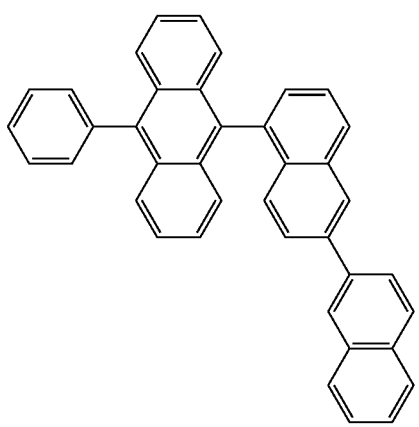

H-84
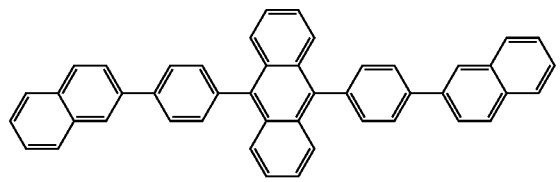
H-85
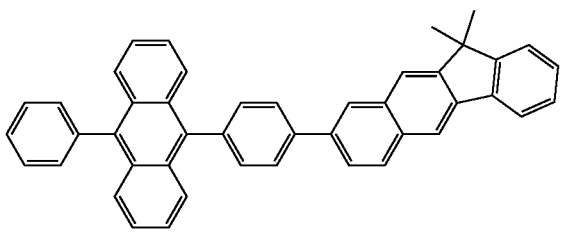
H-86
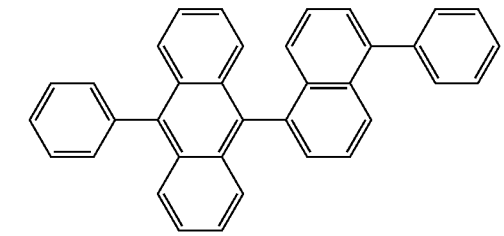
H-87
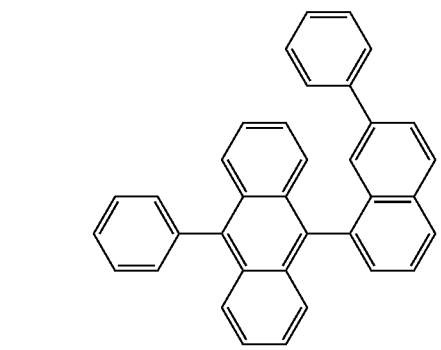
H-88
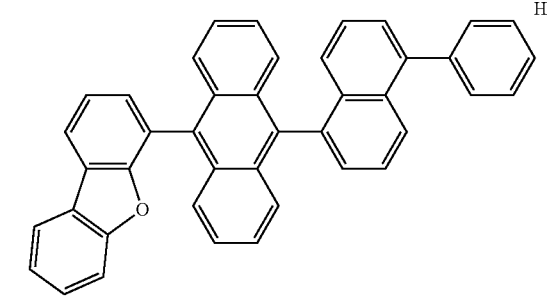
H-89
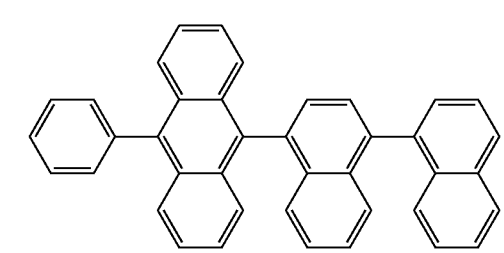
H-90
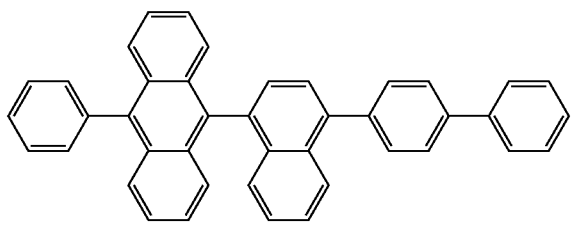
H-91
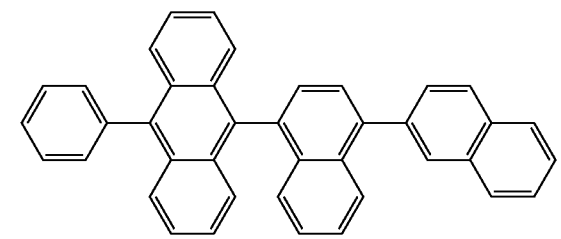
H-92
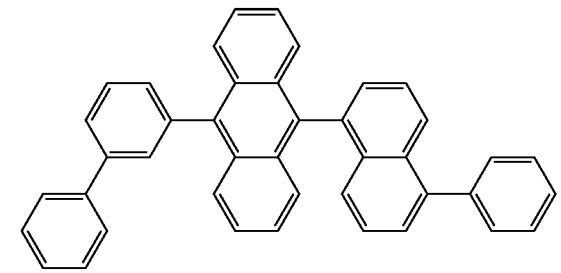
H-93
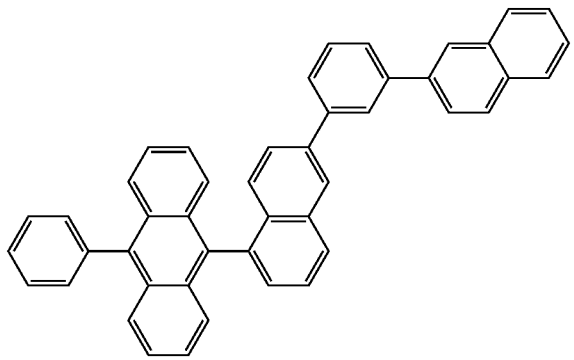
H-94
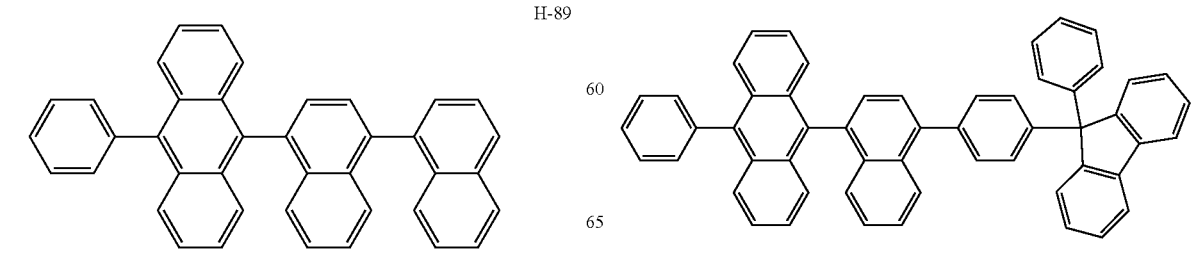

H-95
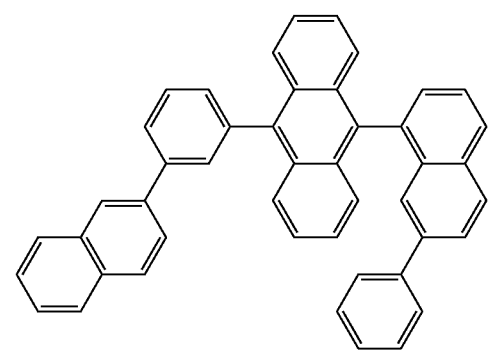
H-96
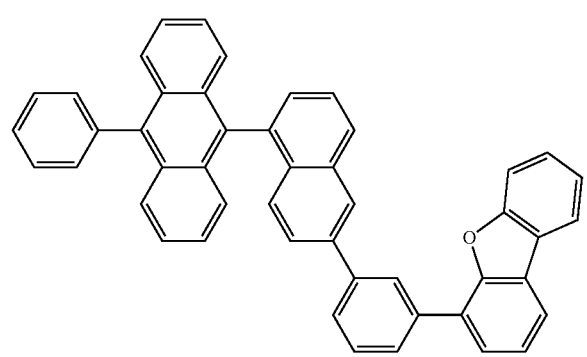
H-97
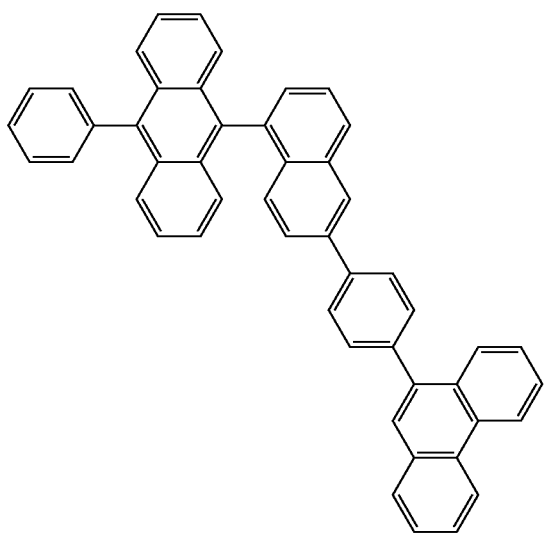
H-98
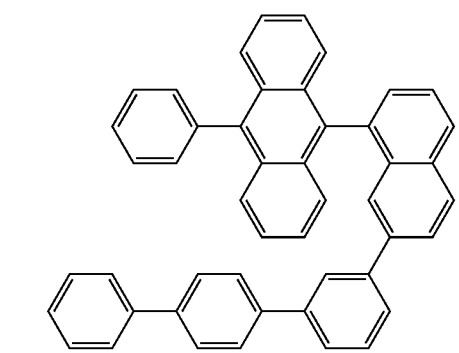
H-99
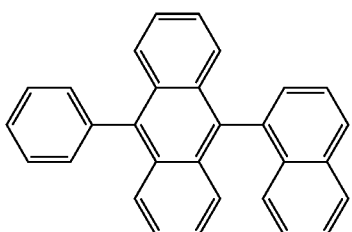
H-100
H-101
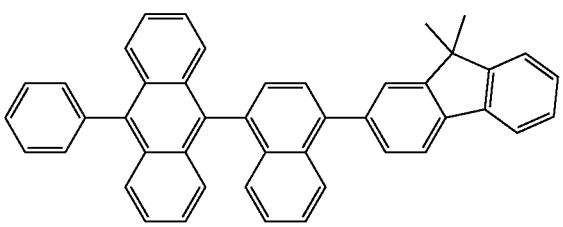
H-102
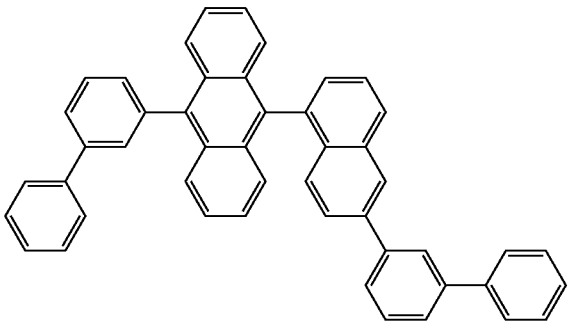

H-103

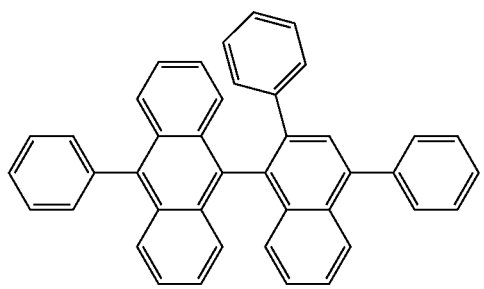

H-104

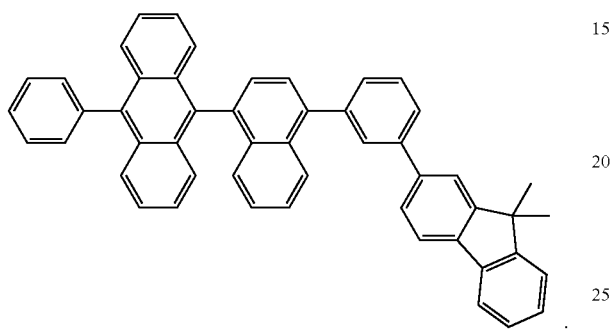

The dopant compound to be used in the present disclosure may be a phosphorescent dopant compound or a fluorescent dopant compound. Specifically, the dopant compound may be a fluorescent dopant compound, for example, may be a condensed polycyclic amine derivative represented by the following formula 21.

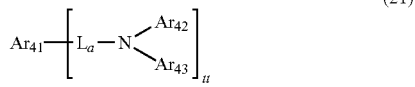 (21)

In formula 21, wherein $Ar_{41}$ represents a substituted or unsubstituted (C6-C50)aryl or styryl; $L_a$ represents a single bond, a substituted or unsubstituted (C6-C30)arylene, or a substituted or unsubstituted (3- to 30-membered)heteroarylene; $Ar_{42}$ and $Ar_{43}$ each independently represent hydrogen, deuterium, halogen, a substituted or unsubstituted (C1-C30) alkyl, a substituted or unsubstituted (C6-C30)aryl, or a substituted or unsubstituted (3- to 30-membered)heteroaryl, or may be linked to an adjacent substituent(s) to form a (3- to 30-membered) mono- or polycyclic, alicyclic or aromatic ring, or a combination thereof whose carbon atom may be replaced with at least one heteroatom selected from nitrogen, oxygen, and sulfur; tt represents 1 or 2; and where tt is 2, each of

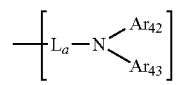

may be the same or different.

A preferable aryl group for $Ar_{41}$ includes a substituted or unsubstituted phenyl, a substituted or unsubstituted fluorenyl, a substituted or unsubstituted anthryl, a substituted or unsubstituted pyrenyl, a substituted or unsubstituted chrysenyl, a substituted or unsubstituted benzofluorenyl, and spiro[fluoren-benzofluorene], etc.

The compound of formula 21 may be illustrated by the following compounds, but is not limited thereto:

D-1

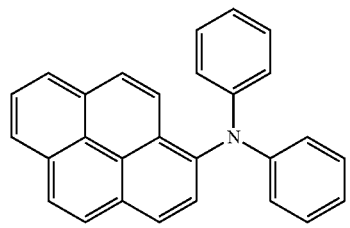

D-2

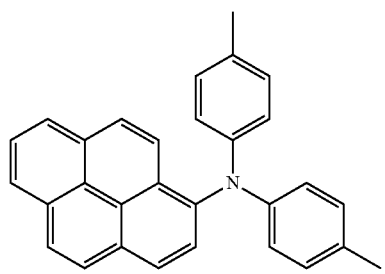

D-3

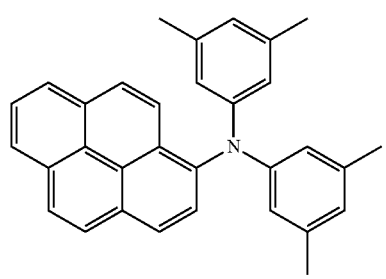

D-4

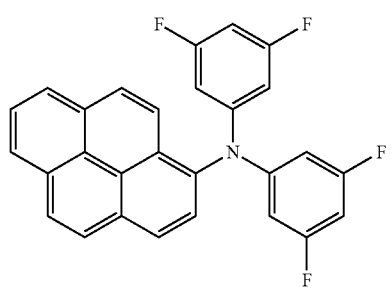

-continued
D-5 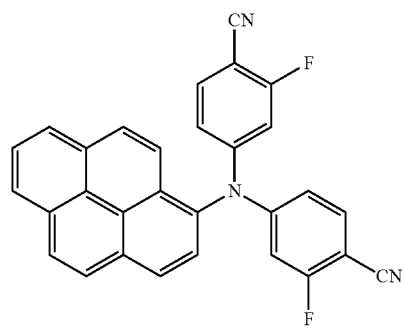
D-6 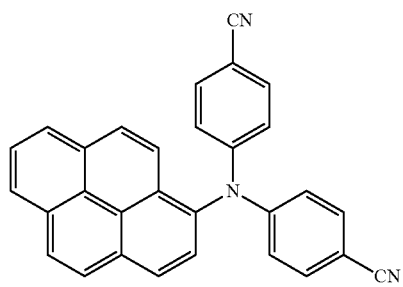
D-7 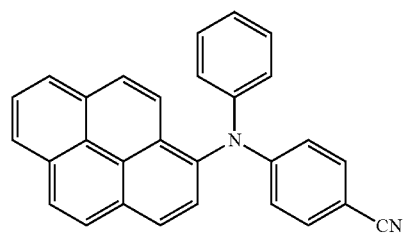
D-8 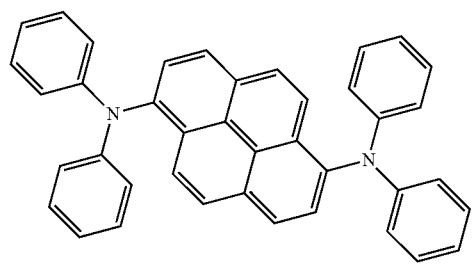
D-9 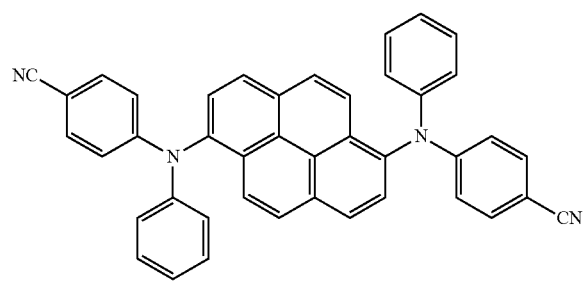
D-10 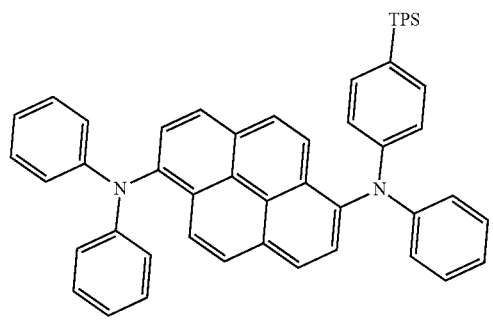
D-11 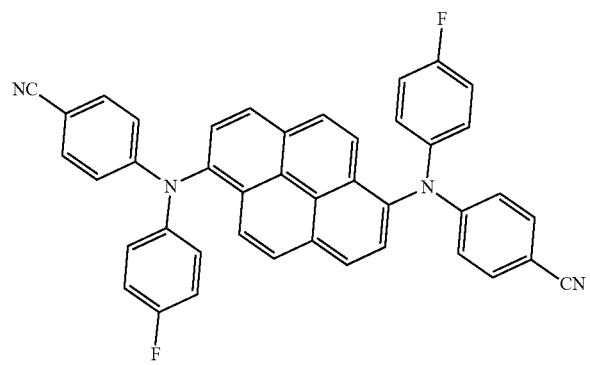
D-12 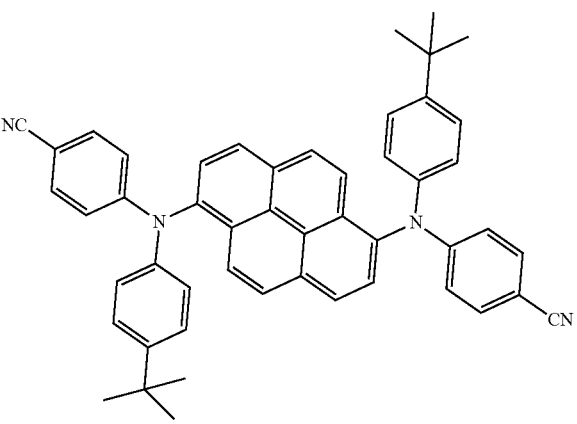

-continued
D-13
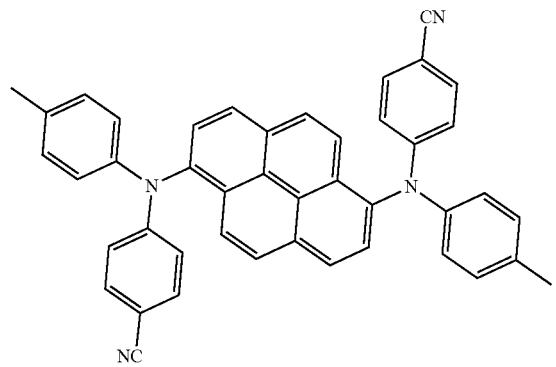
D-14
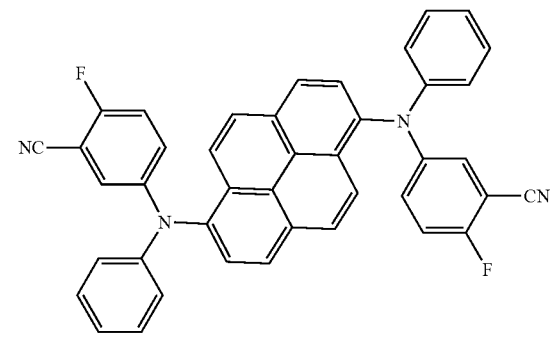
D-15
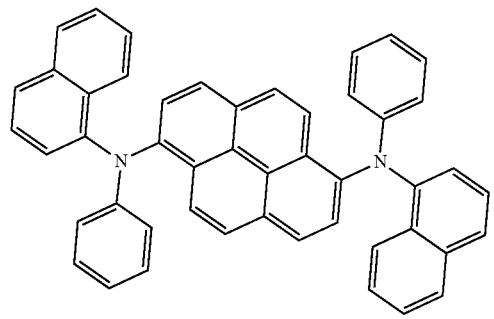
D-16
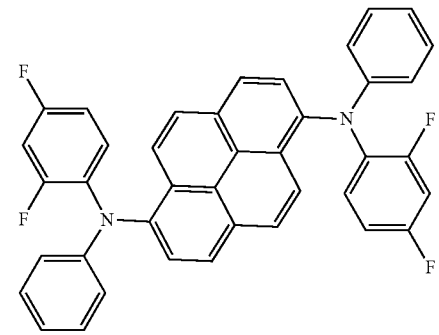
D-17
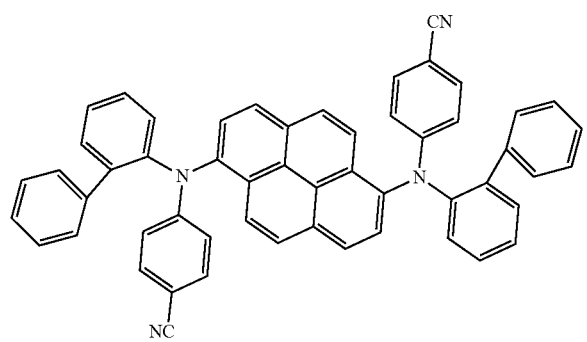
D-18
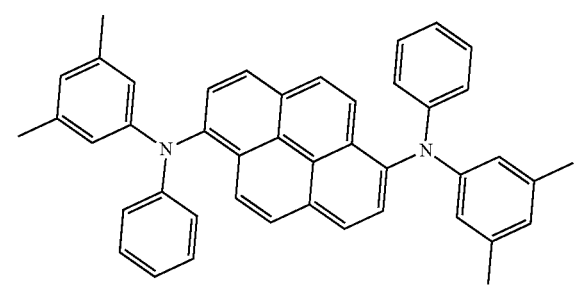
D-19
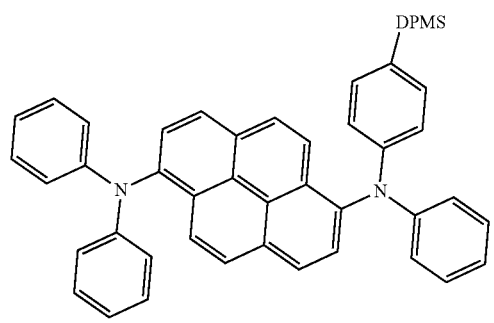
D-20
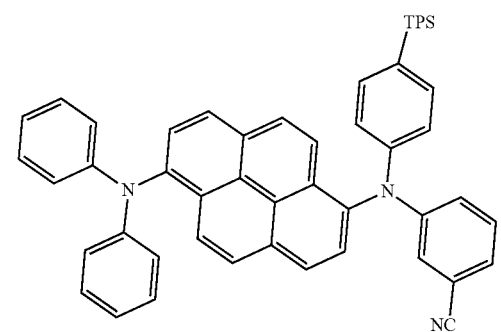

-continued
D-21
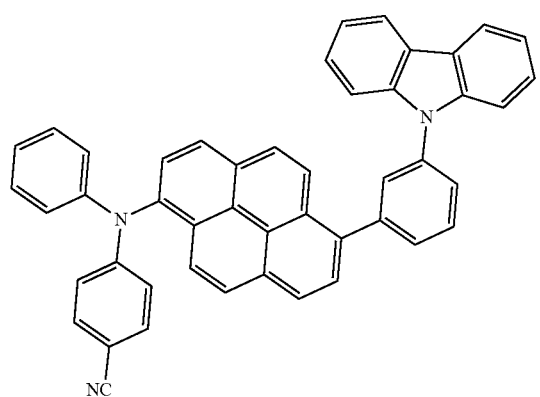
D-22
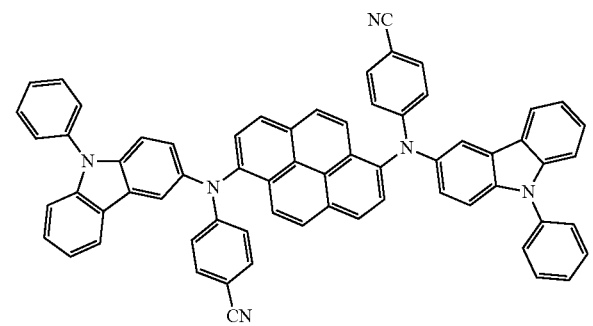
D-23
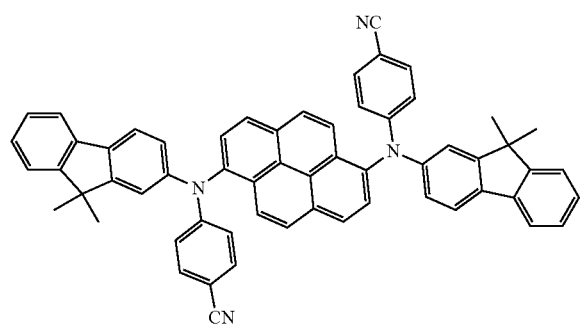
D-24
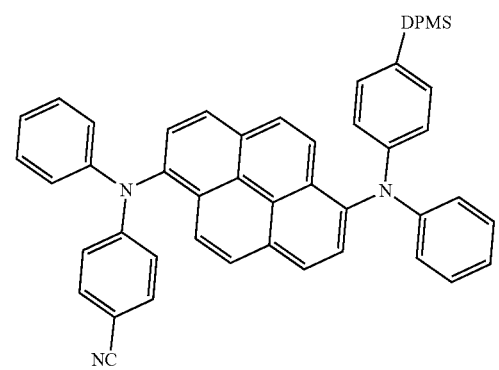
D-25
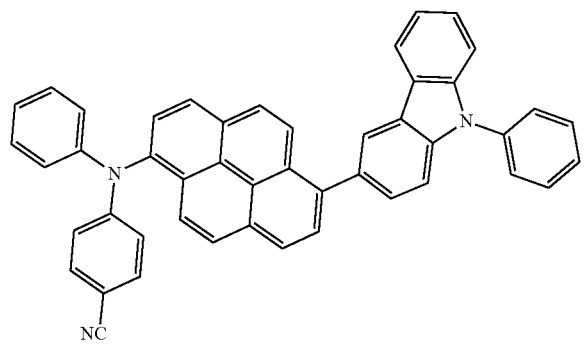
D-26
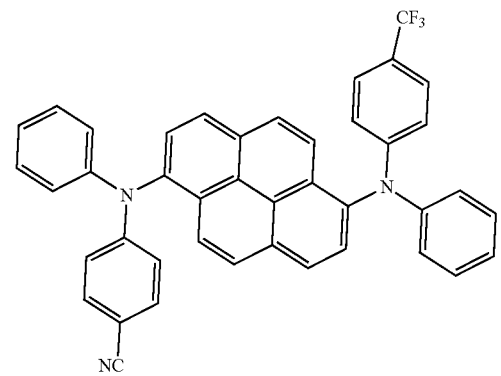
D-27
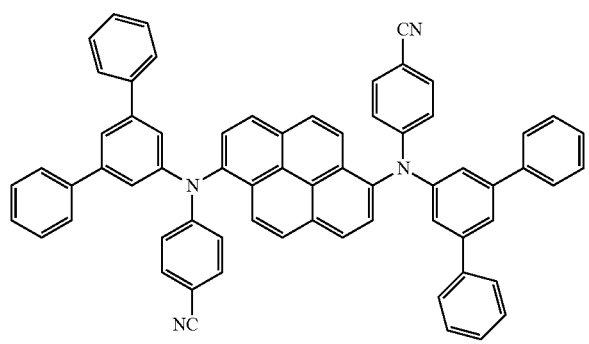
D-28
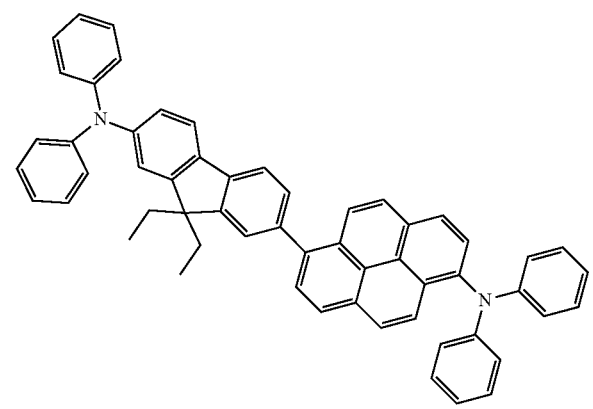

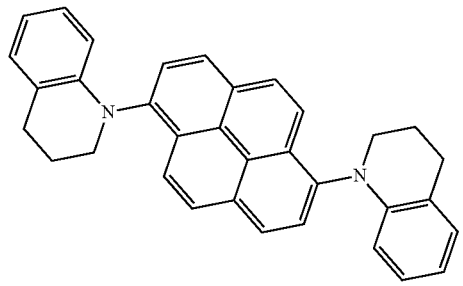
D-29
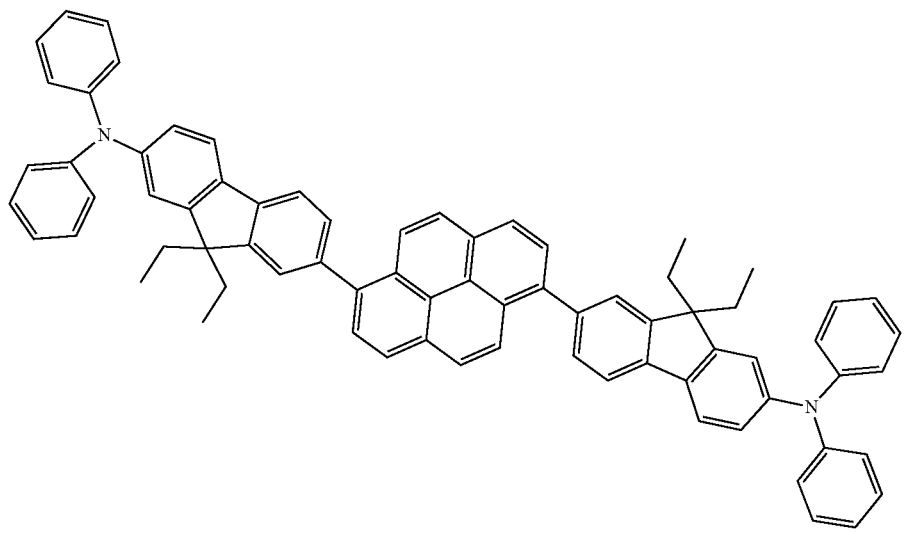
D-30
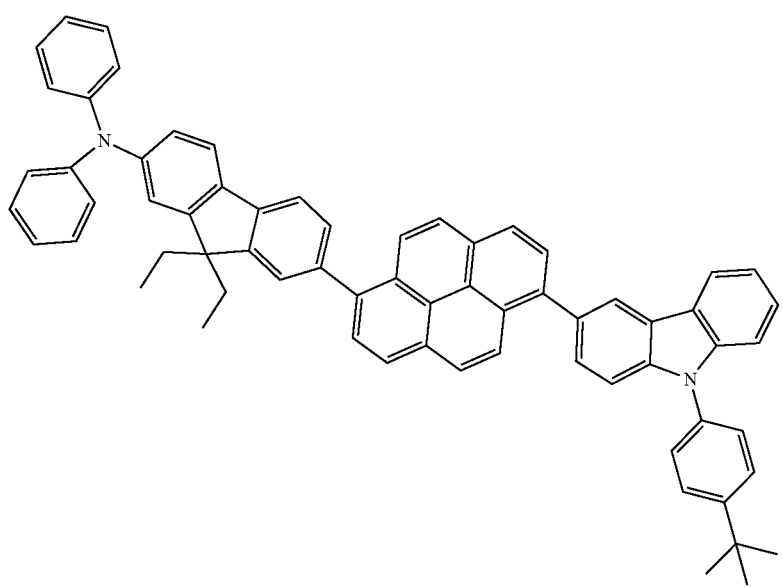
D-31

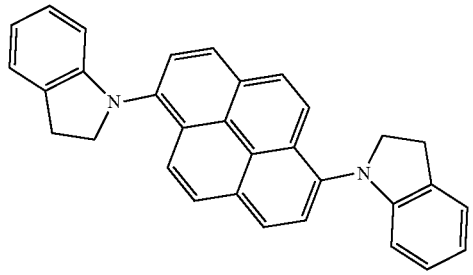
D-32
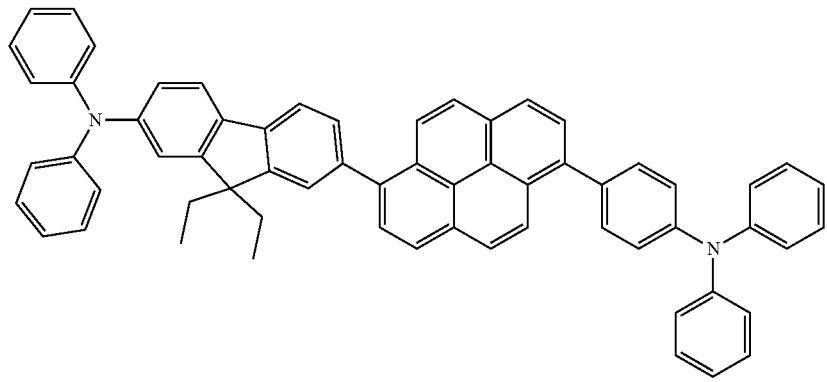
D-33
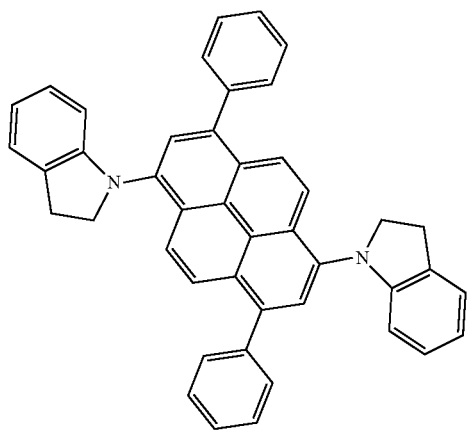
D-34
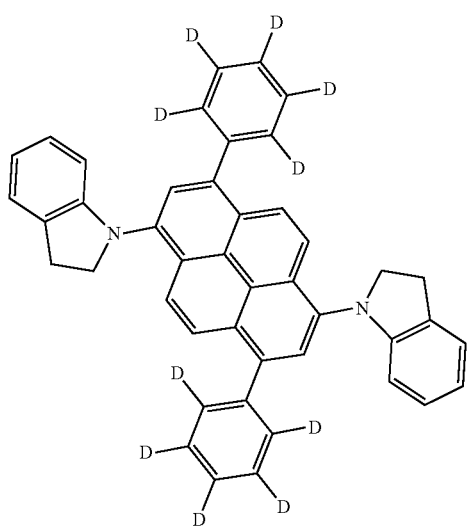
D-35
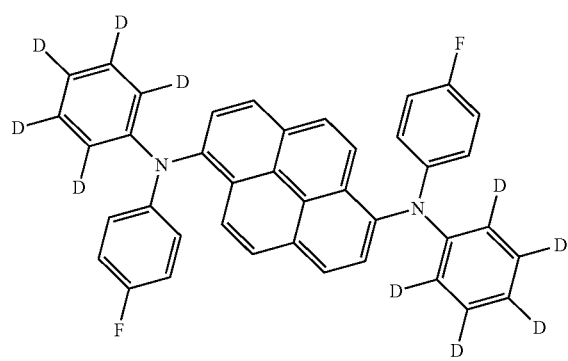
D-36

-continued
D-37
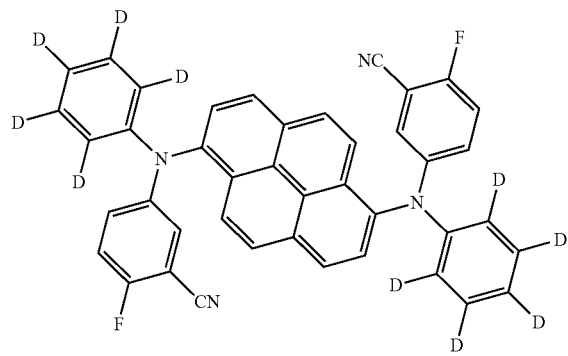
D-38
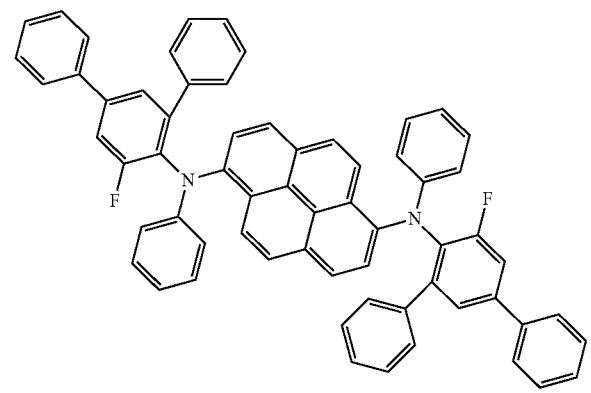
D-39
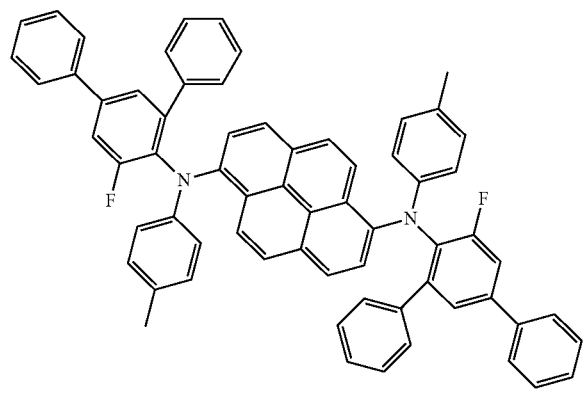
D-40
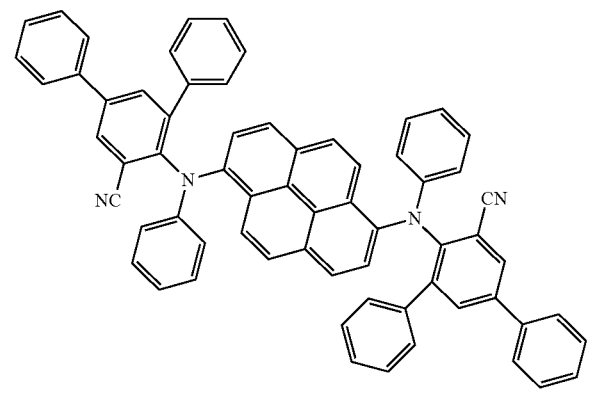
D-41
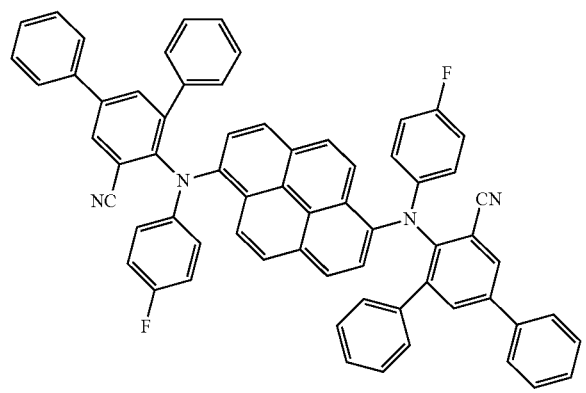
D-42
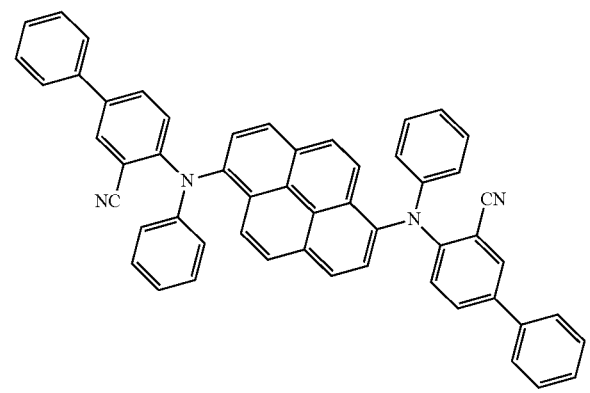

-continued
D-43
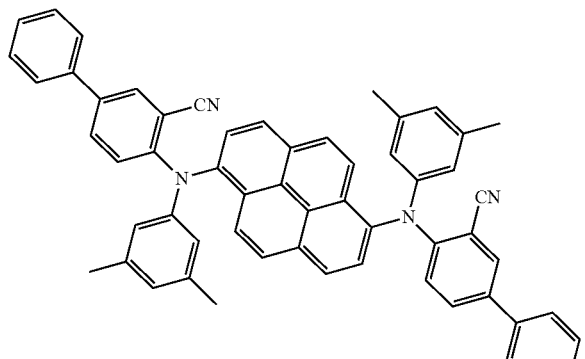
D-44
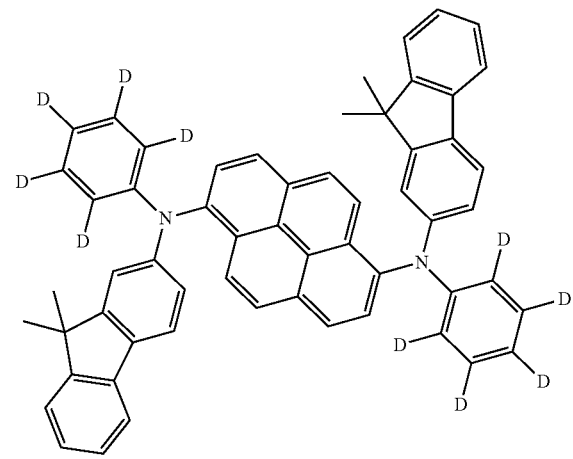
D-45
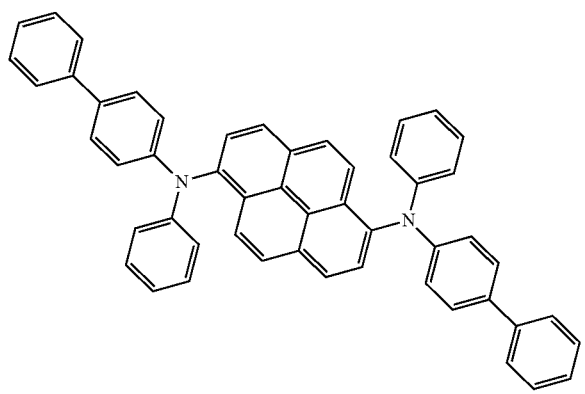
D-46
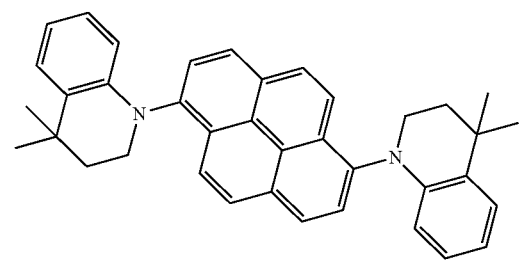
D-47
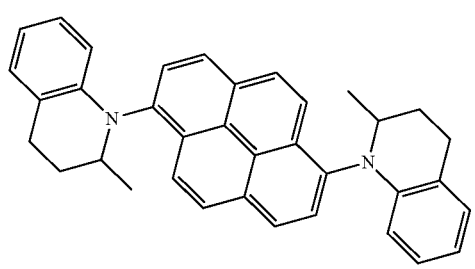
D-48
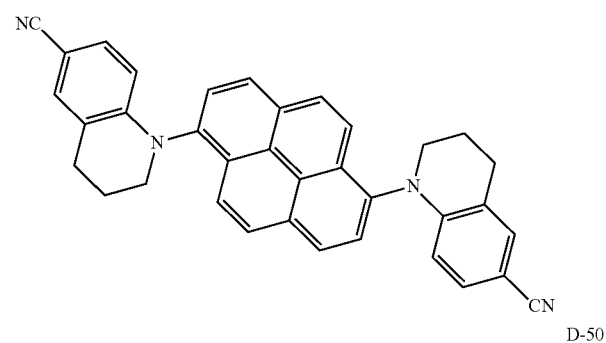
D-49
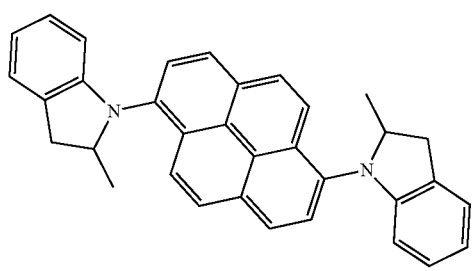
D-50
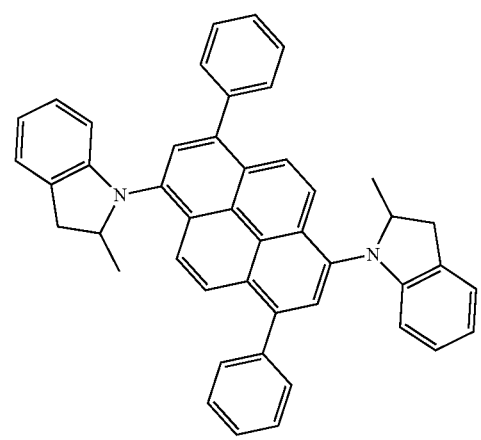

-continued
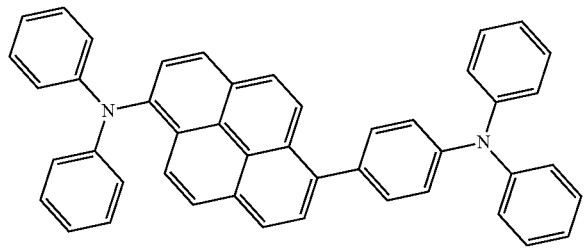
D-51
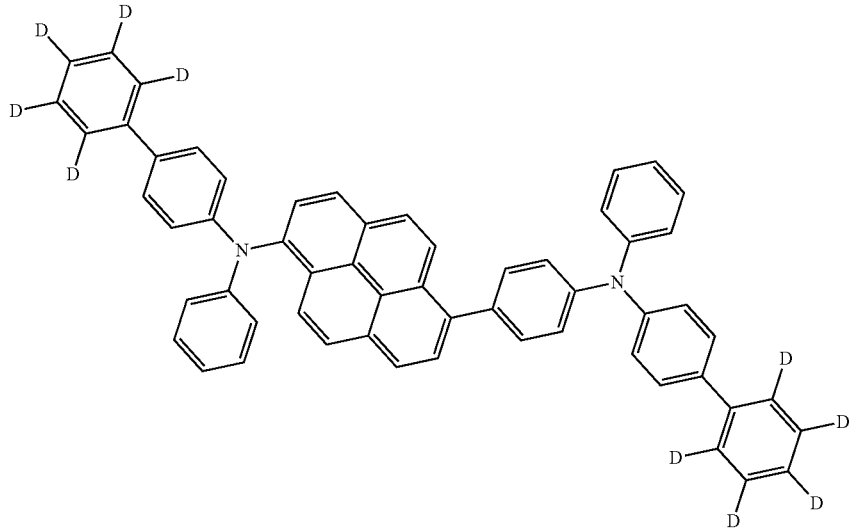
D-52
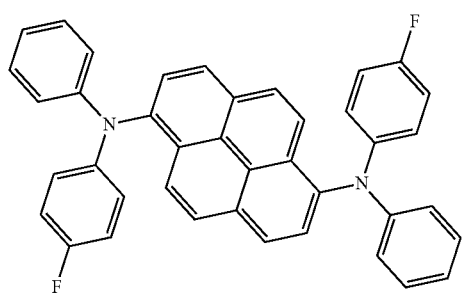
D-53
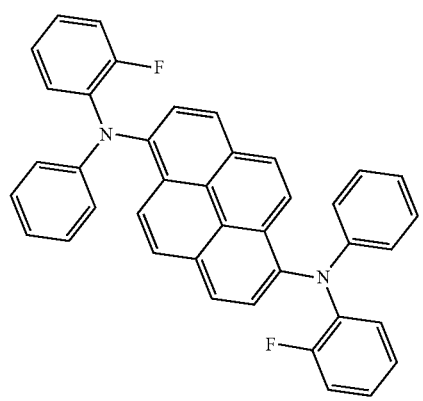
D-54
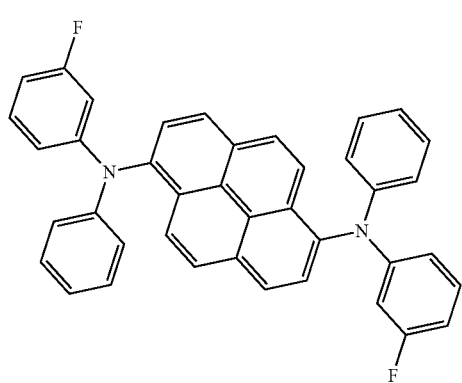
D-55
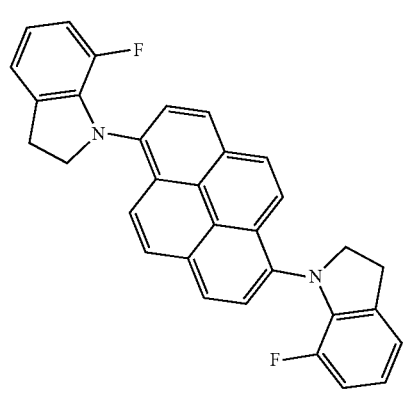
D-56

-continued
| | |
|---|---|
| D-57 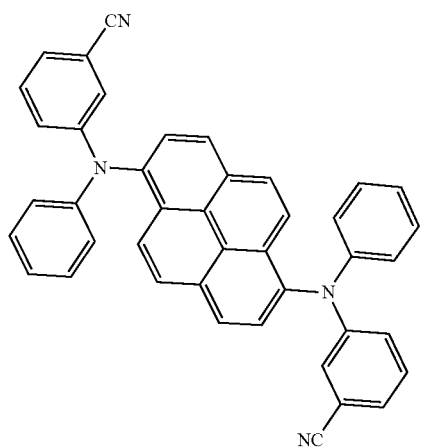 | D-58 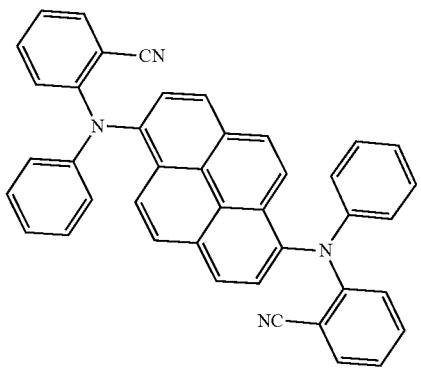 |
| D-59 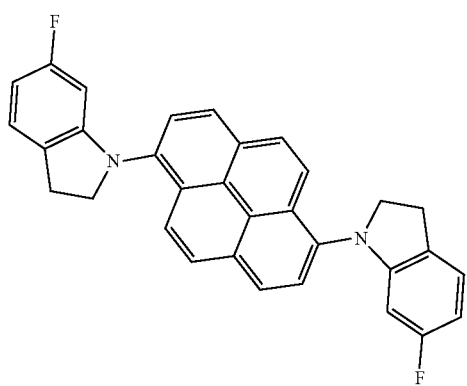 | D-60 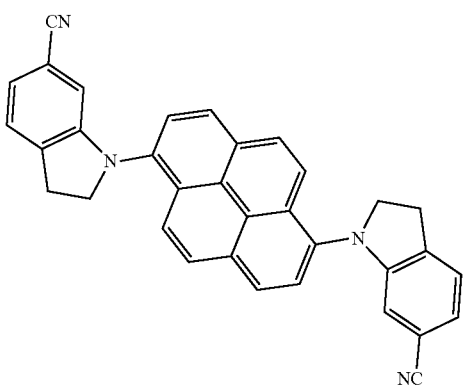 |
| D-61 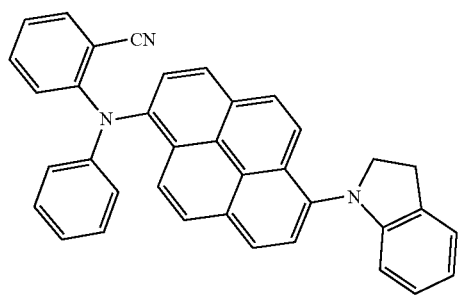 | D-62 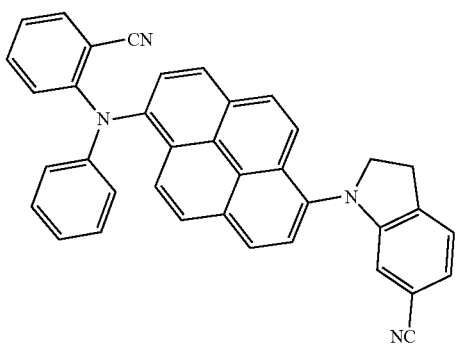 |
| D-63 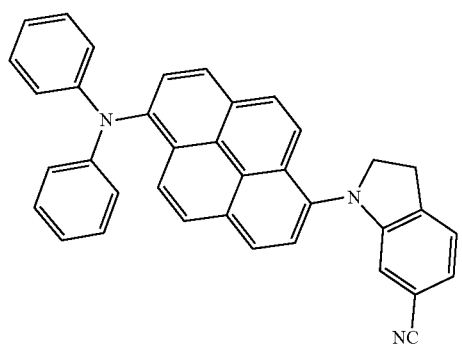 | D-64 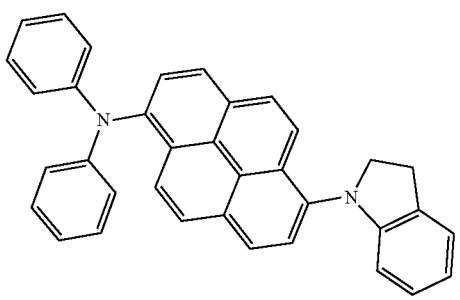 |

-continued
D-65
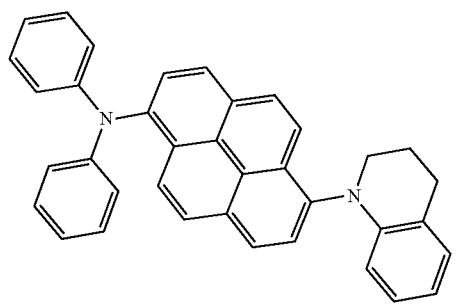
D-66
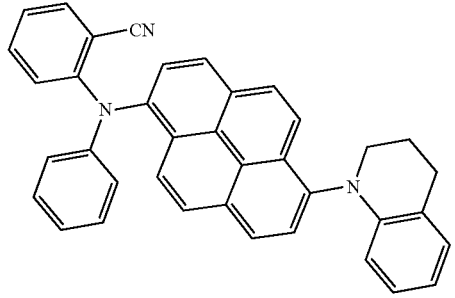
D-67
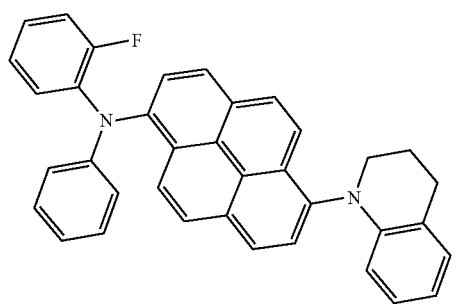
D-68
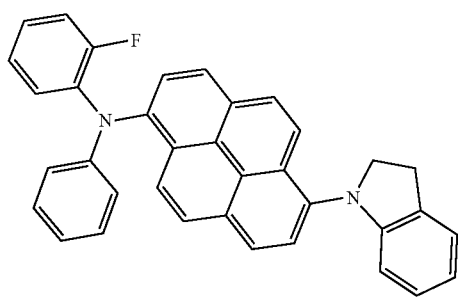
D-69
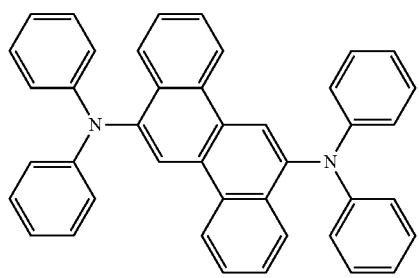
D-70
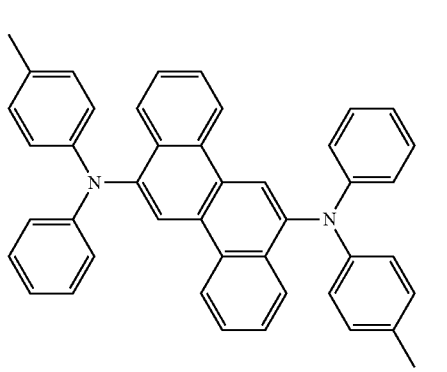
D-71
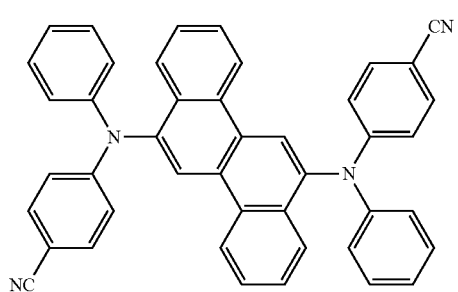
D-72
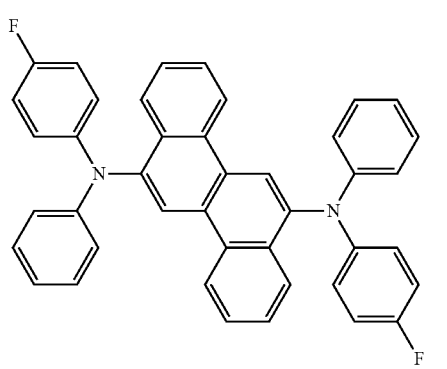
D-73
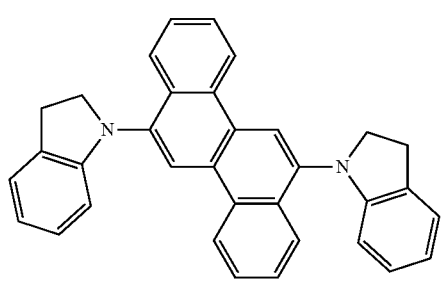
D-74
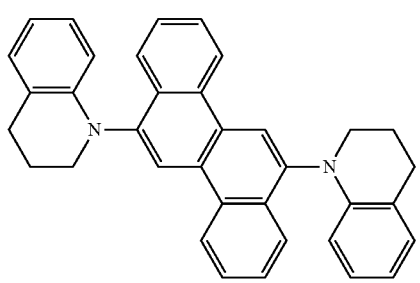

-continued
D-75
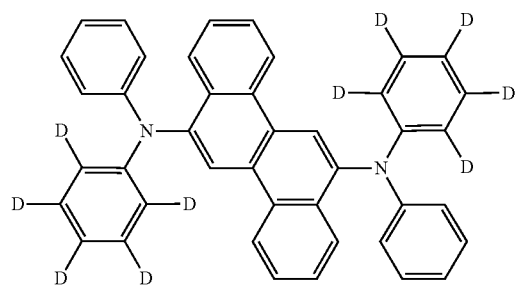
D-76
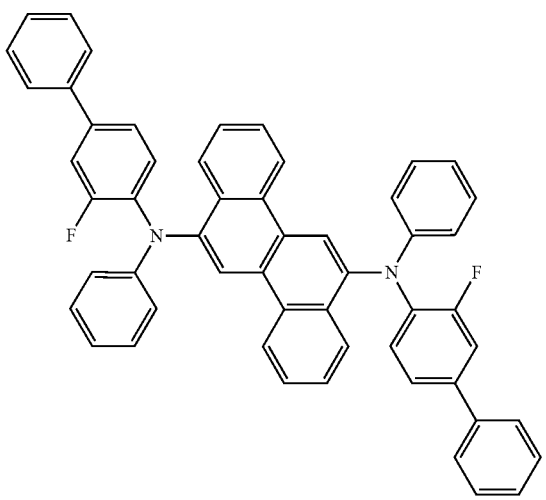
D-77
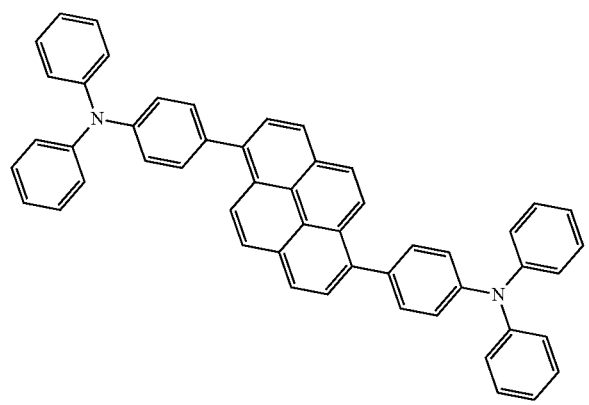
D-78
D-79
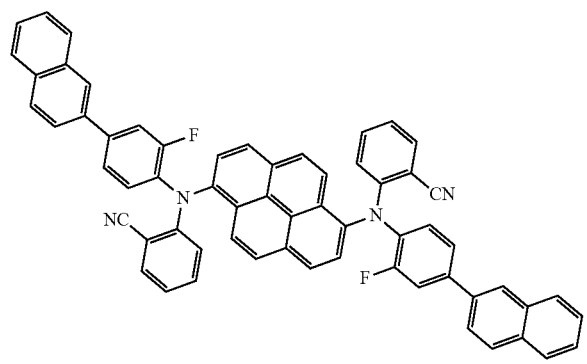
D-80
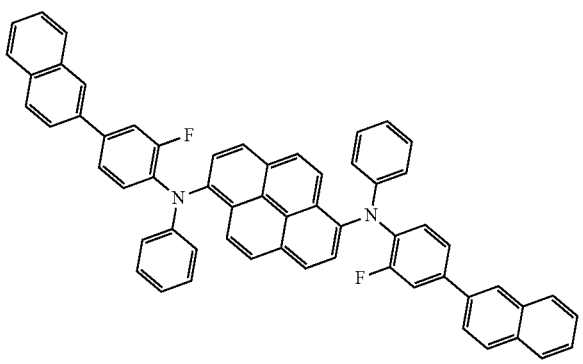

-continued
D-81
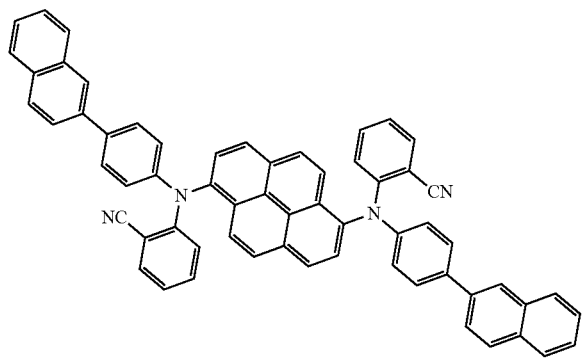
D-82
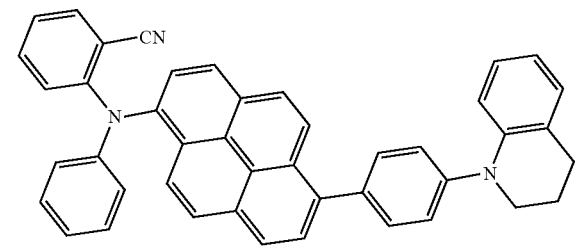
D-83
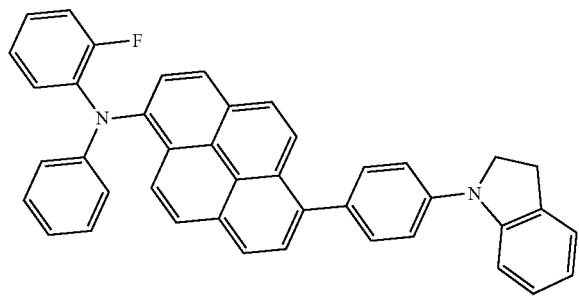
D-84
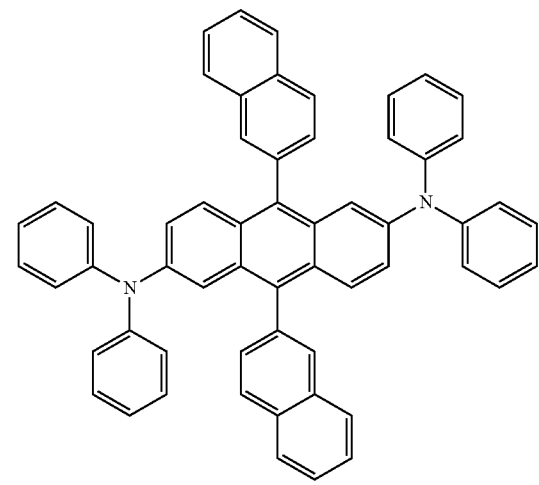
D-85
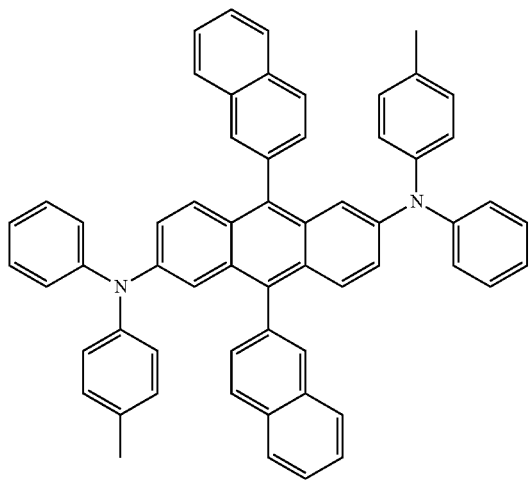
D-86
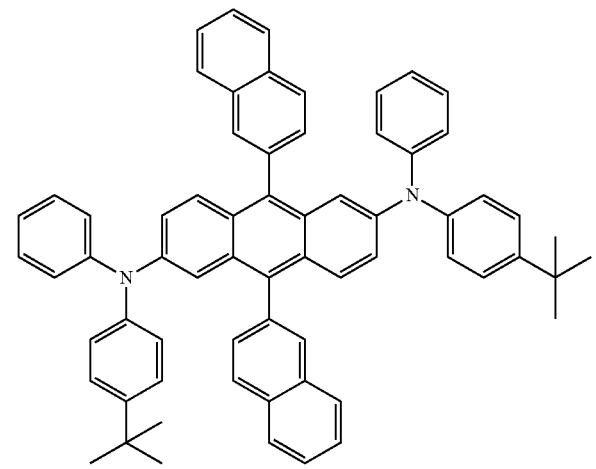

-continued
D-87
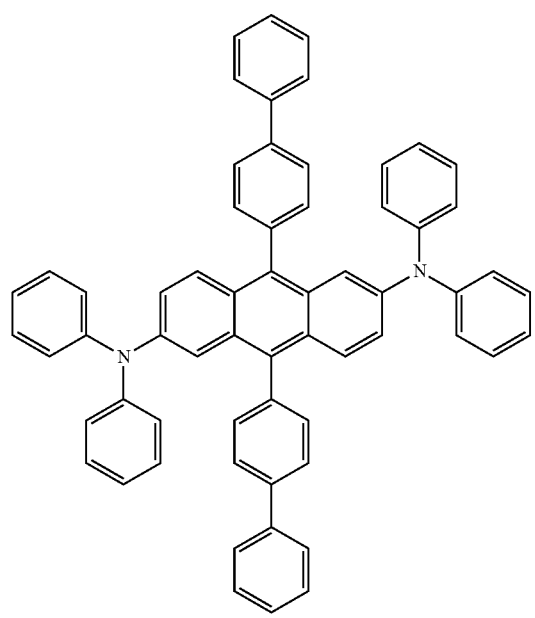
D-88
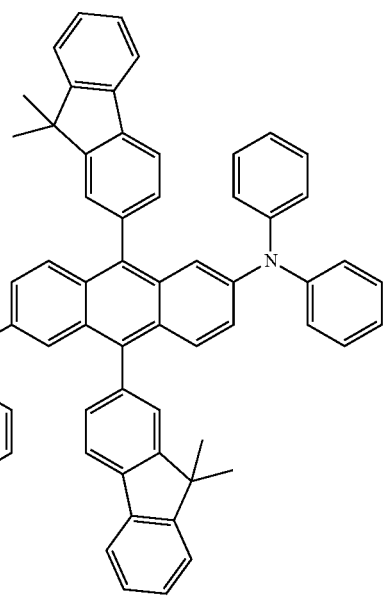
D-89
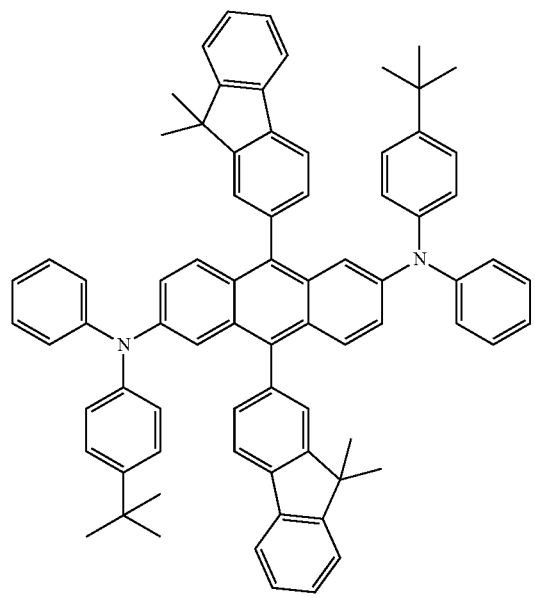
D-90
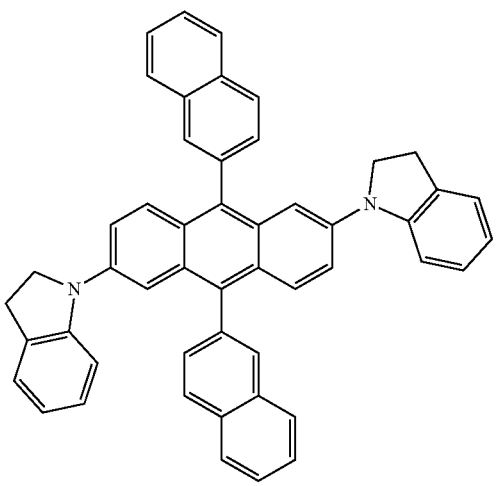

-continued
D-91
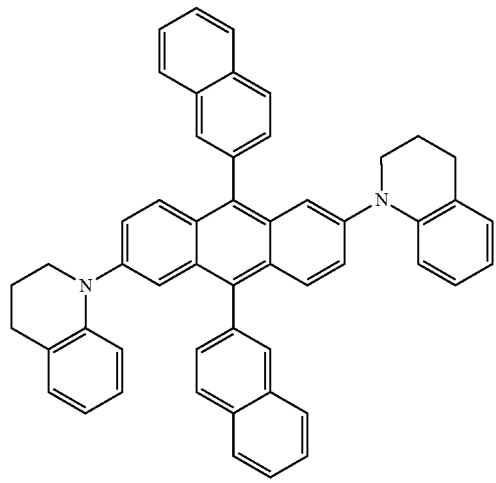
D-92
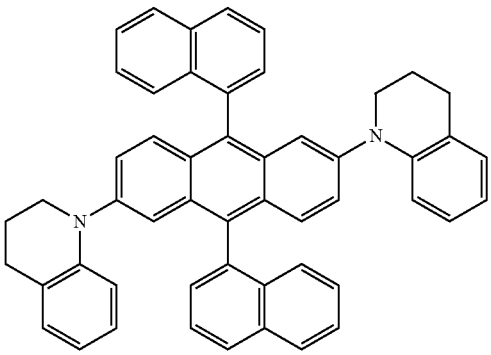
D-93
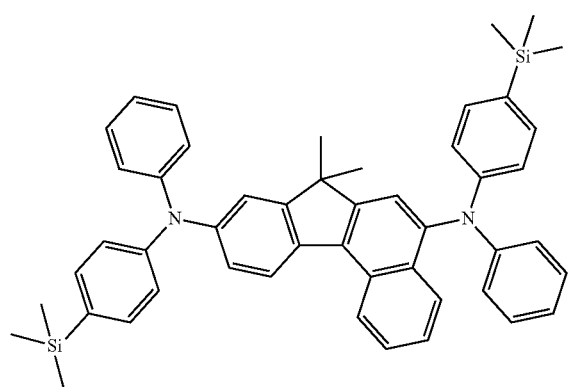
D-94
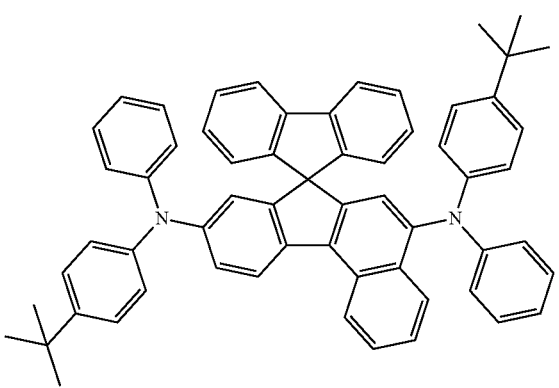
D-95
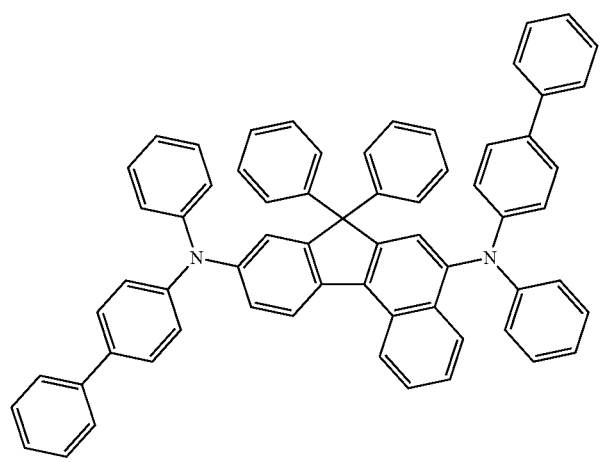

-continued
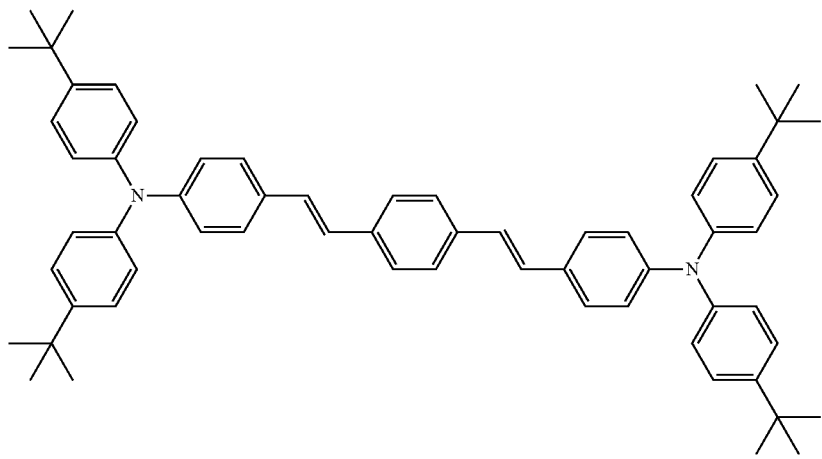
D-96
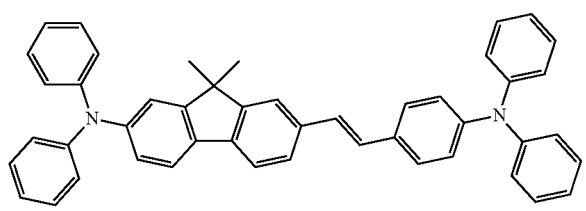
D-97
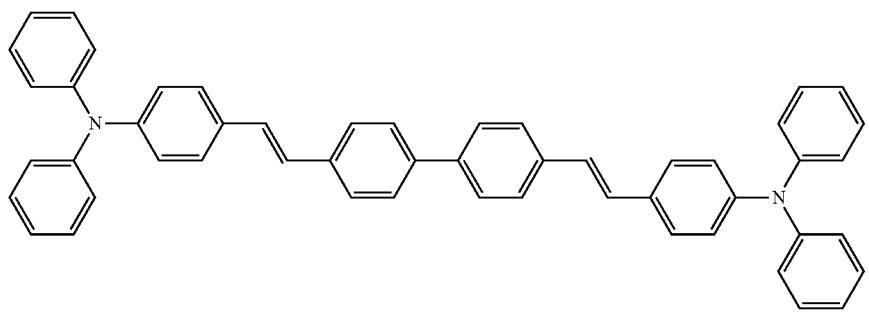
D-98
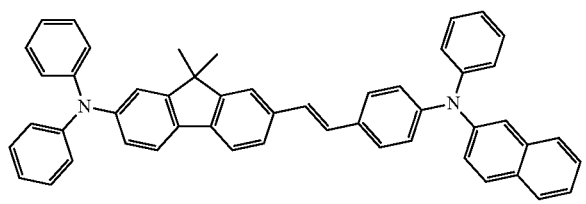
D-99
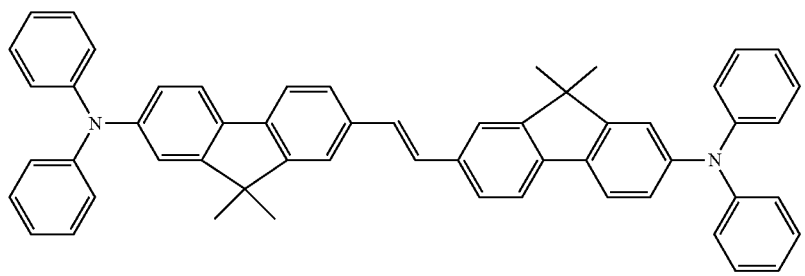
D-100

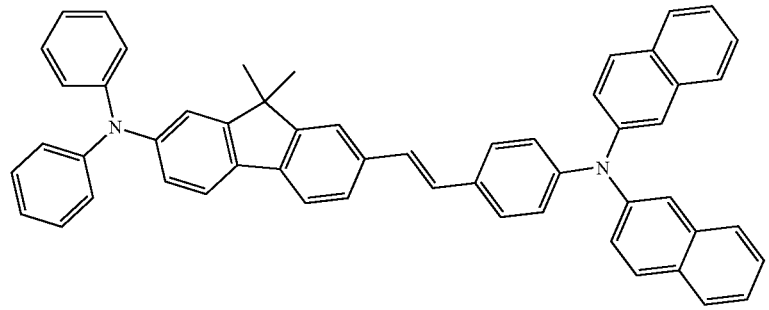
D-101
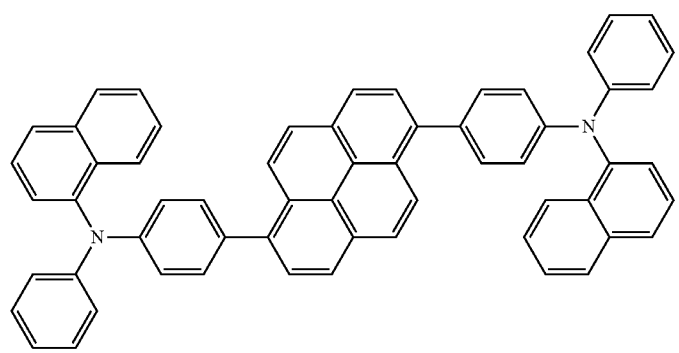
D-102
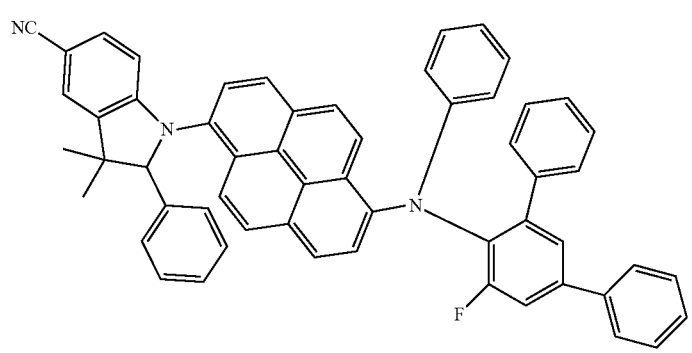
D-103
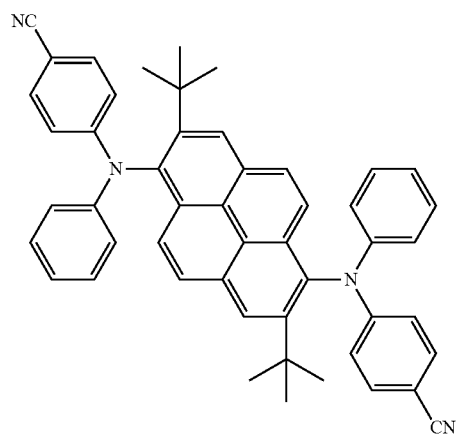
D-104
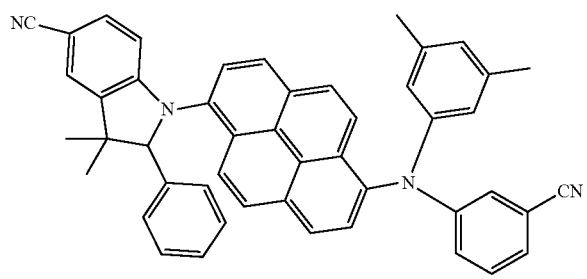
D-105

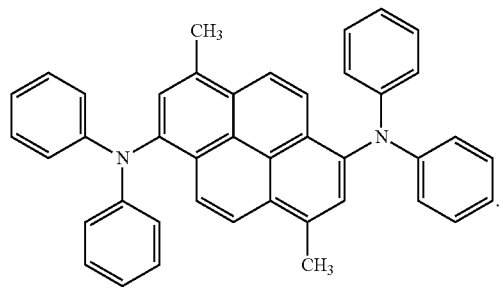

D-106

The organic electroluminescent device according to the present disclosure may further comprise at least one compound selected from the group consisting of an arylamine-based compound and a styrylarylamine-based compound in the organic layer.

Also, in the organic electroluminescent device of the present disclosure, the organic layer may further comprise at least one metal selected from the group consisting of metals of Group 1, metals of Group 2, transition metals of the 4th period, transition metals of the 5th period, lanthanides, and organic metals of the d-transition elements of the Periodic Table, or at least one complex compound comprising such a metal.

In addition, the organic electroluminescent device of the present disclosure further comprises at least one light-emitting layer comprising a blue, red or green light-emitting compound known in the art in addition to the compound of the present disclosure, so that it may emit white light. Further, if necessary, it may further include a yellow or orange light-emitting layer.

In the organic electroluminescent device of the present disclosure, preferably, at least one layer (hereinafter, "a surface layer") selected from a chalcogenide layer, a metal halide layer, and a metal oxide layer may be placed on an inner surface(s) of one or both electrode(s). Specifically, a chalcogenide (including oxides) layer of silicon and aluminum is preferably placed on an anode surface of an electroluminescent medium layer, and a metal halide layer or a metal oxide layer is preferably placed on a cathode surface of an electroluminescent medium layer. The operation stability for the organic electroluminescent device may be obtained by the surface layer. Preferably, the chalcogenide includes $SiO_X(1<X<2)$, $AlO_X(1<X<1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. The hole transport layer or the electron blocking layer may also be multi-layers.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may also be multi-layers, wherein each layer may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes.

In addition, the hole auxiliary layer may be placed between the hole transport layer (or hole injection layer) and the light-emitting layer, and may be effective to promote or block the hole transport rate (or the hole injection rate), thereby enabling the charge balance to be controlled. Also, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as the hole auxiliary layer or the electron blocking layer. The hole auxiliary layer and the electron blocking layer may have an effect of improving the efficiency and/or the lifespan of the organic electroluminescent device.

In addition, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. Also, a reductive dopant layer may be employed as a charge generating layer to produce an organic electroluminescent device having two or more light-emitting layers and emitting white light.

Forming each layer of the organic electroluminescent device of the present disclosure can apply one method of dry film-forming methods such as vacuum evaporation, sputtering, plasma, ion plating methods, etc., or wet film-forming methods such as spin coating, dip coating, flow coating

EXAMPLE 1: PREPARATION OF COMPOUND C-1

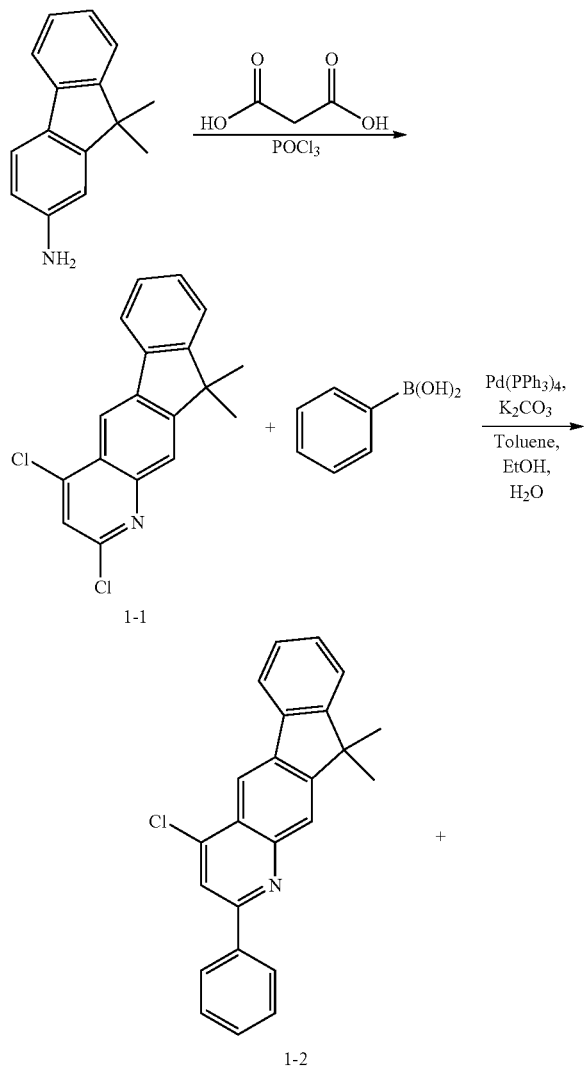

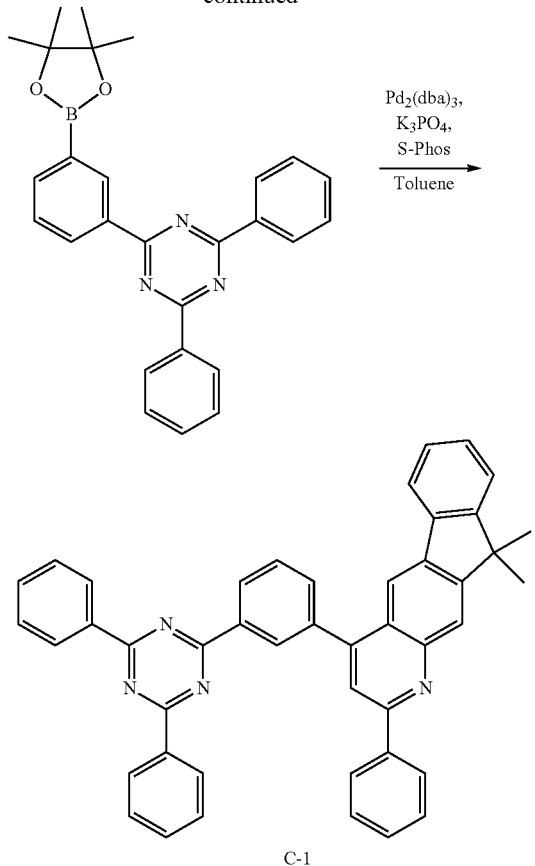

Preparation of Compound 1-1

Malonic acid (75 g, 716.71 mmol) and POCl$_3$ (713 mL, 7.64 mol) were added into a round bottom flask (RBF) of 500 mL and stirred for 10 minutes. 9,9-dimethyl-9H-fluoren-2-amine (100 g, 478 mmol) was slowly added to the reaction mixture and refluxed at 150° C. for 2 hours and then cooled to room temperature. The reaction mixture was slowly added to ice water and the resulting solid was filtered. The filtered solid was dissolved in CHCl$_3$ and the organic layer was separated and treated with MgSO$_4$. Thereafter, the reaction mixture was purified by column chromatography to obtain compound 1-1 (74 g, 49%).

Preparation of Compound 1-2

Compound 1-1 (10 g, 32 mmol), phenylboronic acid (2.70 g, 35 mmol), Pd(PPh$_3$)$_4$ (2.21 g, 2.0 mmol), K$_2$CO$_3$ (13.20 g, 95 mmol), toluene (133 mL, 0.24 M), EtOH (48 mL), and water (48 mL, 2 M) were added to RBF of 500 mL and refluxed. After completion of the reaction, the reaction mixture was cooled to room temperature and then was extracted with dichloromethane and treated with MgSO$_4$. Thereafter, the reaction mixture was purified by column chromatography to obtain compound 1-2 (8.0 g, 71%).

Preparation of Compound C-1

Compound 1-2 (8.0 g, 22.0 mmol), 2,4-diphenyl-6-(3-(4,4,5,5-tetramethyl-1,3,2-dioxaborolan-2-yl)phenyl)-1,3,5-triazine (19.57 g, 45.0 mmol), K$_3$PO$_4$ (23.38 g, 110 mmol), 2-dicyclohexylphosphino-2',6'-dimethoxybiphenyl (s-phos) (0.74 g, 2.0 mmol), and toluene (173 mL, 0.13 M) were added to RBF of 500 mL and stirred at 140° C. for 30 minutes. Pd$_2$(dba)$_3$ (0.823 g, 2.0 mmol) was then added to the reaction mixture, followed by reflux for 3 hours. After completion of the reaction, the reaction mixture was cooled to room temperature and then was extracted with ethyl acetate and treated with MgSO$_4$. Thereafter, the reaction mixture was purified by column chromatography to obtain compound C-1 (5.1 g, 36%).

|     | MW     | UV     | PL     | M.P.    |
| --- | ------ | ------ | ------ | ------- |
| C-1 | 628.78 | 280 nm | 403 nm | 305° C. |

EXAMPLE 2: PREPARATION OF COMPOUND C-119

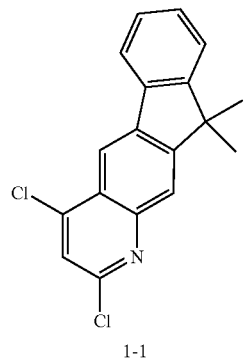

1-1

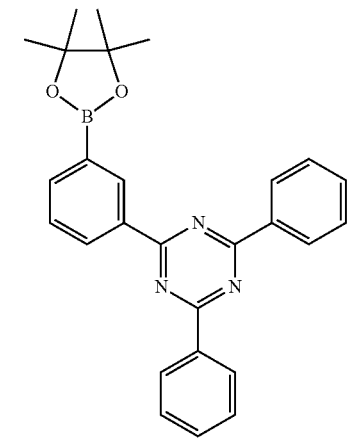

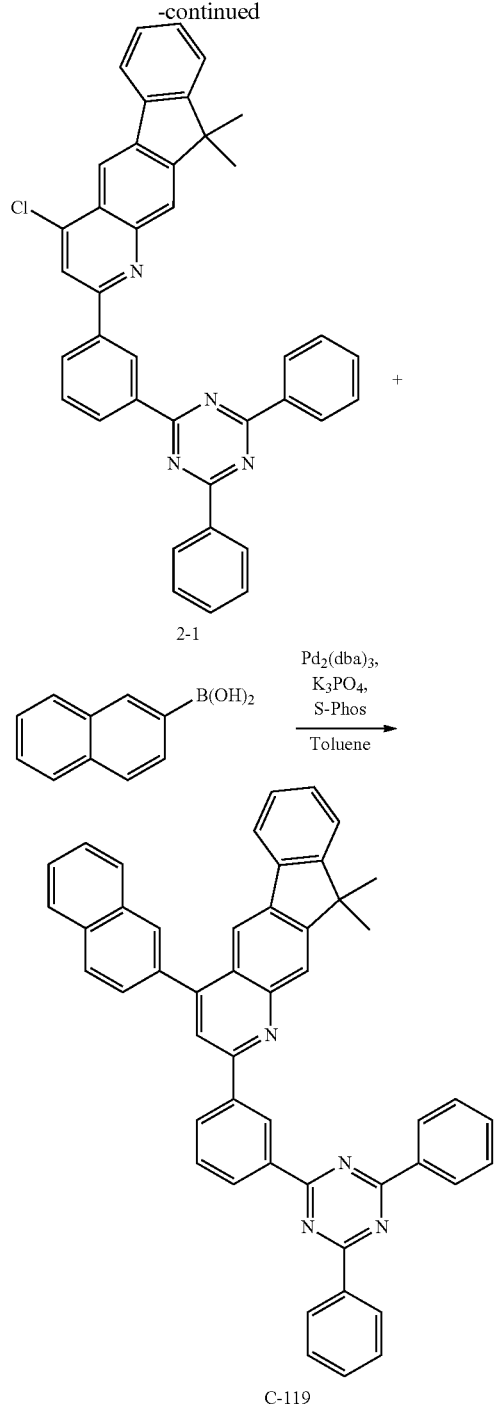

Preparation of Compound 2-1

Compound 1-1 (5 g, 16 mmol), 2,4-diphenyl-6-(3-(4,4,5,5-tetramethyl-1,3,2-dioxaborolan-2-yl)phenyl)-1,3,5-triazine (7.62 g, 18 mmol), Pd(PPh$_3$)$_4$ (1.10 g, 0.96 mmol), K$_2$CO$_3$ (6.60 g, 48 mmol), toluene (70 mL, 0.23 M), EtOH (24 mL), and water (24 mL, 2 M) were added to RBF of 500 mL and refluxed. After completion of the reaction, the reaction mixture was cooled to room temperature and then was extracted with dichloromethane and treated with MgSO$_4$. Thereafter, the reaction mixture was purified by column chromatography to obtain compound 2-1 (8.0 g, 85%).

Preparation of Compound C-119

Compound 2-1 (7.5 g, 13.0 mmol), 2-naphthylboronic acid (3.25 g, 26 mmol), K₃PO₄ (13.29 g, 63 mmol), s-phos (0.42 g, 1.0 mmol), and toluene (100 mL, 0.13 M) were added into RBF of 500 mL, and the reaction mixture was stirred at 140° C. for 30 minutes. Pd$_2$(dba)$_3$ (0.468 g, 0.511 mmol) was then added thereto, followed by refluxing for 3 hours. After completion of the reaction, the reaction mixture was cooled to room temperature and then was extracted with ethyl acetate and treated with MgSO$_4$. Thereafter, the reaction mixture was purified by column chromatography to obtain compound C-119 (7.5 g, 86%).

|  | MW | UV | PL | M.P. |
|---|---|---|---|---|
| C-119 | 678.84 | 282 nm | 407 nm | 230° C. |

EXAMPLE 3: PREPARATION OF COMPOUND C-135

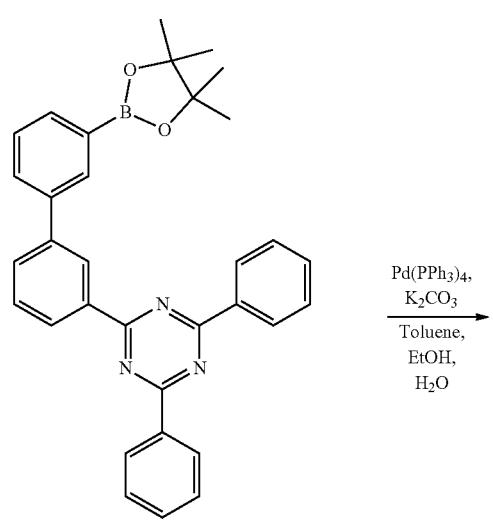

1-1

+

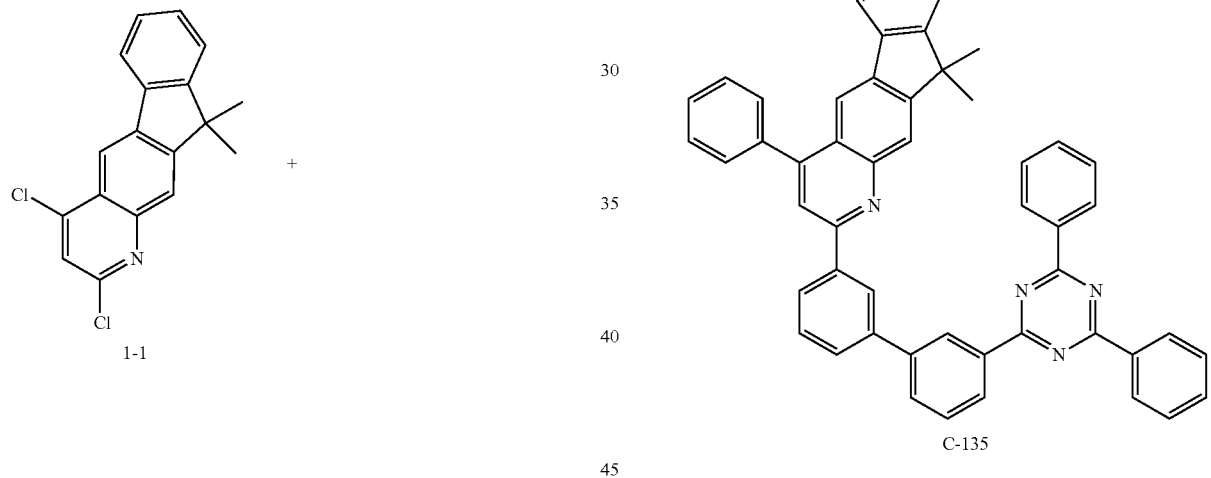

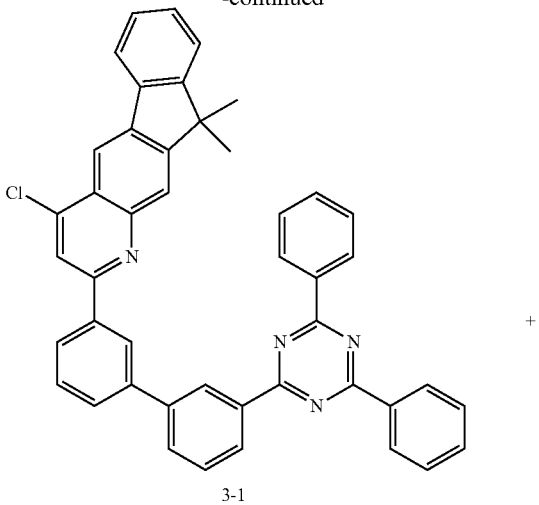

3-1

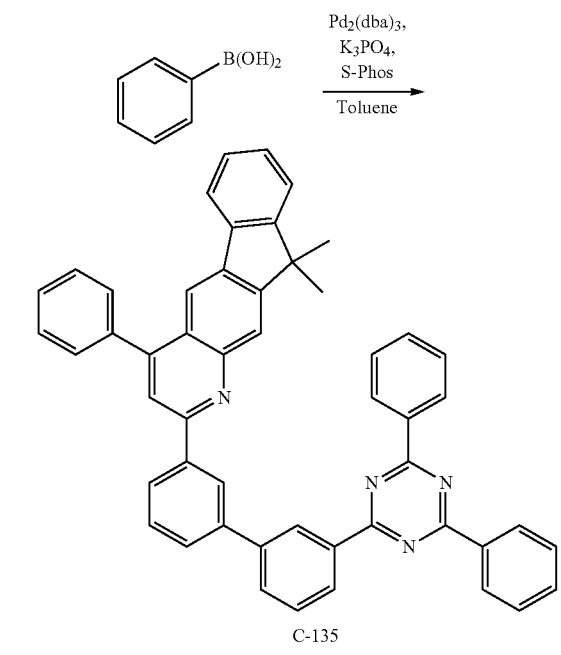

C-135

Preparation of Compound 3-1

Compound 1-1 (4 g, 13 mmol), 2,4-diphenyl-6-(3'-(4,4,5,5-tetramethyl-1,3,2-dioxaborolan-2-yl)-[1,1'-biphenyl]-3-yl)-1,3,5-triazine (7.16 g, 14 mmol), Pd(PPh$_3$)$_4$ (0.883 g, 0.764 mmol), K$_2$CO$_3$ (5.28 g, 38 mmol), toluene (60 mL, 0.21 M), EtOH (20 mL), and water (19 mL, 2 M) were added to RBF of 250 mL and refluxed. After completion of the reaction, the reaction mixture was cooled to room temperature and then was extracted with dichloromethane and treated with MgSO$_4$. Thereafter, the reaction mixture was purified by column chromatography to obtain compound 3-1 (5.5 g, 64%).

Preparation of Compound C-135

Compound 3-1 (2.5 g, 4.0 mmol), phenylboronic acid (0.919 g, 8.0 mmol), K$_3$PO$_4$ (3.921 g, 18 mmol), s-phos (0.124 g, 0.302 mmol), and toluene (30 mL, 0.126 M) were added to RBF of 100 mL, and the reaction mixture was stirred at 140° C. for 30 minutes. Pd$_2$(dba)$_3$ (0.138 g, 0.151 mmol) was then added thereto, followed by refluxing for 3 hours. After completion of the reaction, the reaction mixture was cooled to room temperature and then was extracted with ethyl acetate and treated with MgSO₄. Thereafter, the reaction mixture was purified by column chromatography to obtain compound C-135 (1.5 g, 56%).

|  | MW | UV | PL | M.P. |
|---|---|---|---|---|
| C-135 | 704.86 | 282 nm | 399 nm | 292° C. |

EXAMPLE 4: PREPARATION OF COMPOUND C-322

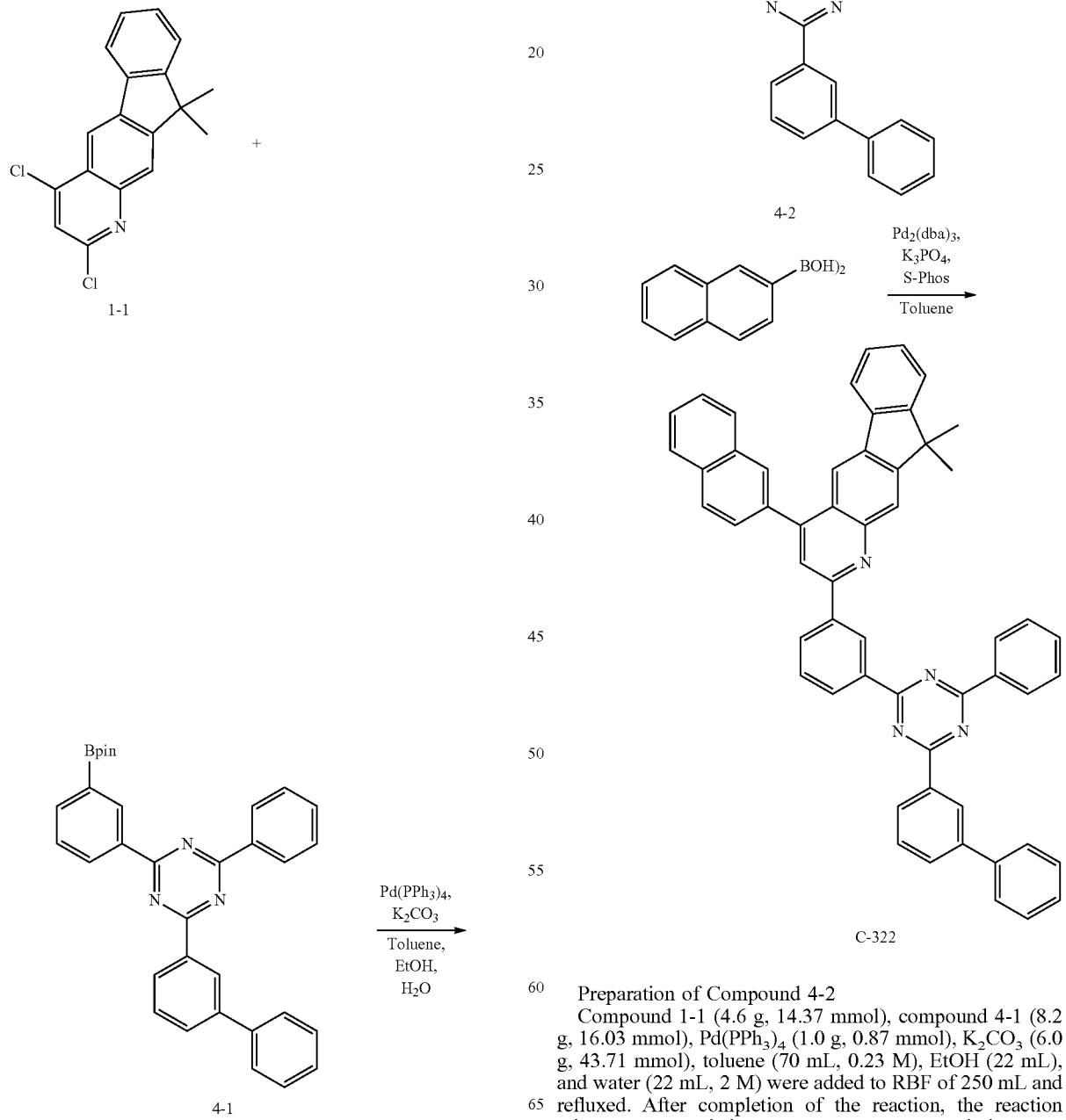

Preparation of Compound 4-2

Compound 1-1 (4.6 g, 14.37 mmol), compound 4-1 (8.2 g, 16.03 mmol), Pd(PPh₃)₄ (1.0 g, 0.87 mmol), K₂CO₃ (6.0 g, 43.71 mmol), toluene (70 mL, 0.23 M), EtOH (22 mL), and water (22 mL, 2 M) were added to RBF of 250 mL and refluxed. After completion of the reaction, the reaction mixture was cooled to room temperature and then was extracted with dichloromethane and treated with MgSO₄.

Thereafter, the reaction mixture was purified by column chromatography to obtain compound 4-2 (8.2 g, 86%).

Preparation of Compound C-322

Compound 4-2 (8.0 g, 12.06 mmol), compound 4-3 (4.1 g, 24.12 mmol), $K_3PO_4$ (12.54 g, 59.1 mmol), s-phos (0.4 g, 0.96 mmol), and toluene (142 mL, 0.0852 M) were added to RBF of 250 mL, and the reaction mixture was stirred at 140° C. for 30 minutes. $Pd_2(dba)_3$ (0.44 g, 0.48 mmol) was then added thereto, followed by refluxing for 3 hours. After completion of the reaction, the reaction mixture was cooled to room temperature and then was extracted with ethyl acetate and treated with $MgSO_4$. Thereafter, the reaction mixture was purified by column chromatography to obtain compound C-322 (7.5 g, 82%).

|  | MW | M.P. |
| --- | --- | --- |
| C-322 | 754.94 g/mol | 283° C. |

[COMPARATIVE EXAMPLE 1] PRODUCING A BLUE LIGHT-EMITTING ORGANIC ELECTROLUMINESCENT DEVICE NOT ACCORDING TO THE PRESENT DISCLOSURE

An OLED device was produced not according to the present disclosure. First, a transparent electrode ITO thin film (10 Ω/sq) on a glass substrate for an OLED (GEOMATEC CO., LTD.) was subjected to an ultrasonic washing with acetone and isopropyl alcohol, sequentially, and then was stored in isopropanol. Next, the ITO substrate was mounted on a substrate holder of a vacuum vapor deposition apparatus. Compound HI-1 was introduced into a cell of the vacuum vapor deposition apparatus, and the pressure in the chamber of the apparatus was then controlled to $10^{-7}$ torr. Thereafter, an electric current was applied to the cell to evaporate the introduced material, thereby forming a first hole injection layer having a thickness of 60 nm on the ITO substrate. Compound HI-2 was then introduced into another cell of the vacuum vapor deposition apparatus, and an electric current was applied to the cell to evaporate the introduced material, thereby forming a second hole injection layer having a thickness of 5 nm on the first hole injection layer. Compound HT-1 was introduced into another cell of the vacuum vapor deposition apparatus. Thereafter, an electric current was applied to the cell to evaporate the introduced material, thereby forming a first hole transport layer having a thickness of 20 nm on the second hole injection layer. Compound HT-2 was then introduced into another cell of the vacuum vapor deposition apparatus, and an electric current was applied to the cell to evaporate the introduced material, thereby forming a second hole transport layer having a thickness of 5 nm on the first hole transport layer. After forming the hole injection layers and the hole transport layers, a light-emitting layer was then deposited as follows. Compound H-15 as a host was introduced into one cell of the vacuum vapor deposition apparatus and compound D-38 as a dopant was introduced into another cell of the apparatus. The two materials were evaporated at a different rate and the dopant was deposited in a doping amount of 2 wt %, based on the total weight of the host and dopant, to form a light-emitting layer having a thickness of 20 nm on the second hole transport layer. Next, compound ET-1 as an electron transport material was introduced into one cell and compound EI-1 was introduced into another cell were evaporated in a weight ratio of 1:1 and deposited to form an electron transport layer having a thickness of 35 nm. After depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED device was produced. For each of the materials, each of the compounds was used by purifying by vacuum sublimation at $10^{-6}$ torr.

The results of the driving voltage, the luminous efficiency, and the CIE color coordinates of the organic electroluminescent device produced as described above at a luminance of 1,000 nits are shown in the following Table 1.

[COMPARATIVE EXAMPLE 2] PRODUCING A BLUE LIGHT-EMITTING ORGANIC ELECTROLUMINESCENT DEVICE NOT ACCORDING TO THE PRESENT DISCLOSURE

In Comparative Example 2, an OLED device was produced in the same manner as in Comparative Example 1, except that the thickness of the electron transport layer was reduced to 25 nm and the compound of the following Table 1 was inserted as an electron buffer layer having a thickness of 5 nm between the light-emitting layer and the electron transport layer. The evaluation results of the organic electroluminescent devices produced in Comparative Example 2 are shown in Table 1 below.

[DEVICE EXAMPLES 1 TO 3] PRODUCING A BLUE LIGHT-EMITTING ORGANIC ELECTROLUMINESCENT DEVICE COMPRISING THE COMPOUND OF THE PRESENT DISCLOSURE AS AN ELECTRON BUFFER MATERIAL

In Device Examples 1 to 3, an OLED device was produced in the same manner as in Comparative Example 1, except that the thickness of the electron transport layer was reduced to 25 nm and the compound of the following Table 1 was inserted as an electron buffer layer having a thickness of 5 nm between the light-emitting layer and the electron transport layer. The evaluation results of the organic electroluminescent devices produced in Device Examples 1 to 3 are shown in Table 1 below.

TABLE 1

|  | Electron Buffer Material | Driving Voltage (V) | Luminous Efficiency (cd/A) | Color Coordinates | |
| --- | --- | --- | --- | --- | --- |
|  |  |  |  | (x) | (y) |
| Comparative Example 1 | — | 4.4 | 6.5 | 0.139 | 0.096 |
| Comparative Example 2 | Compound X | 5.0 | 5.7 | 0.139 | 0.095 |
| Device Example 1 | C-119 | 4.2 | 7.1 | 0.139 | 0.095 |
| Device Example 2 | C-1 | 4.2 | 7.2 | 0.139 | 0.093 |
| Device Example 3 | C-135 | 4.1 | 7.2 | 0.139 | 0.093 |

It was confirmed that the organic electroluminescent device including the present compound as an electron buffer material is excellent in terms of driving voltage and/or luminous efficiency while maintaining the same level of color coordinates compared with the organic electroluminescent device not including an electron buffer material or including a conventional material as an electron buffer material.

[COMPARATIVE EXAMPLES 3 AND 4] PRODUCING A BLUE LIGHT-EMITTING ORGANIC ELECTROLUMINESCENT DEVICE NOT ACCORDING TO THE PRESENT DISCLOSURE

In Comparative Examples 3 and 4, an OLED device was produced in the same manner as in Comparative Example 1, except that the electron transport material was changed to the compound of the following Table 2. The evaluation results of the organic electroluminescent devices produced in Comparative Examples 3 and 4 are shown in Table 2 below.

[DEVICE EXAMPLES 4 TO 7] PRODUCING A BLUE LIGHT-EMITTING ORGANIC ELECTROLUMINESCENT DEVICE COMPRISING THE COMPOUND OF THE PRESENT DISCLOSURE AS AN ELECTRON TRANSPORT MATERIAL

In Device Examples 4 to 7, an OLED device was produced in the same manner as in Comparative Example 1, except that the electron transport material was changed to the compound of the following Table 2. The evaluation results of the organic electroluminescent devices produced in Device Examples 4 to 7 are shown in Table 2 below.

TABLE 2

| | Electron Transport Material | Driving Voltage (V) | Luminous Efficiency (cd/A) | Color Coordinates | |
|---|---|---|---|---|---|
| | | | | (x) | (y) |
| Comparative Example 3 | Compound X | 4.3 | 4.8 | 0.139 | 0.088 |
| Comparative Example 4 | Compound Y | 4.4 | 4.5 | 0.139 | 0.086 |
| Device Example 4 | C-119 | 3.8 | 6.2 | 0.139 | 0.088 |
| Device Example 5 | C-1 | 3.8 | 5.9 | 0.139 | 0.086 |
| Device Example 6 | C-135 | 4.1 | 6.8 | 0.139 | 0.088 |
| Device Example 7 | C-322 | 3.9 | 6.8 | 0.139 | 0.091 |

It was confirmed that the organic electroluminescent device including the present compound as an electron transport material is excellent in terms of driving voltage and/or luminous efficiency while maintaining the same level of color coordinates compared with the organic electroluminescent device including a conventional material as an electron transport material.

TABLE 3

| The compounds used in the Device Examples and Comparative Examples |
|---|
| Hole Injection Layer/Hole Transport Layer |

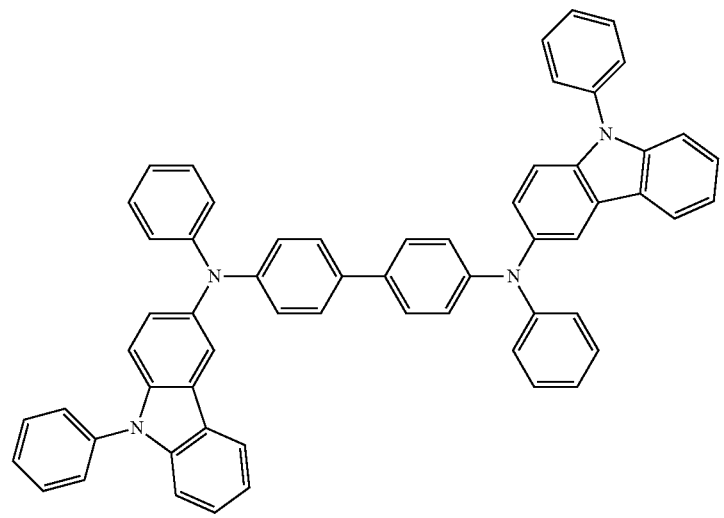

HI-1

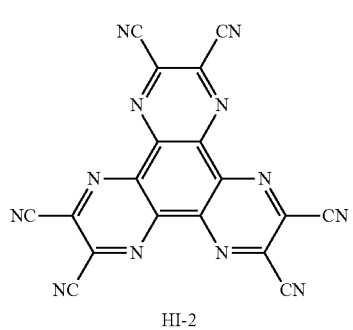

HI-2

TABLE 3-continued
The compounds used in the Device Examples and Comparative Examples
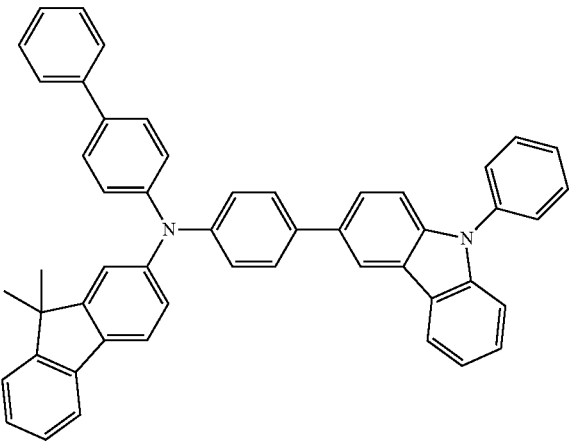
HT-1
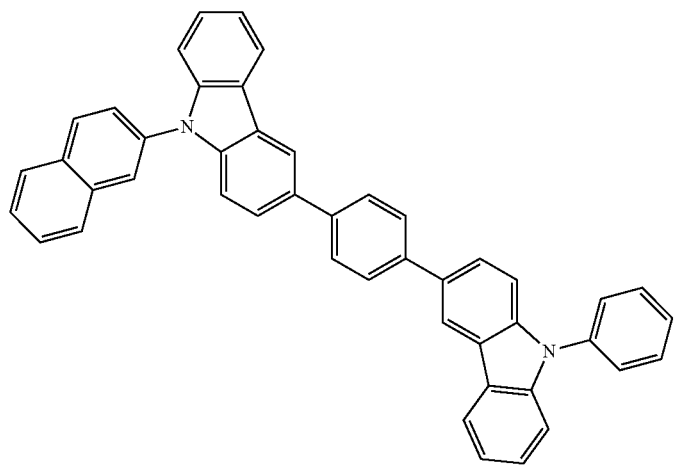
HT-2
Light-Emitting Layer
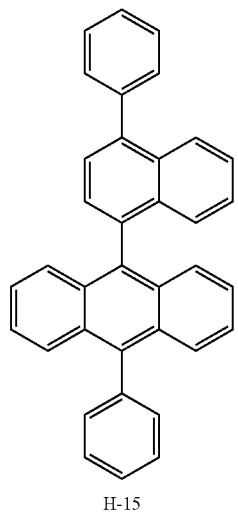
H-15

TABLE 3-continued
The compounds used in the Device Examples and Comparative Examples
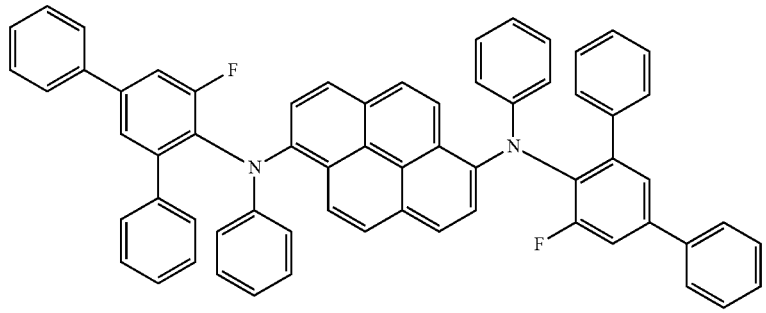
D-38
Electron Buffer Layer/ Electron Transport Layer/ Electron/ Injection Layer
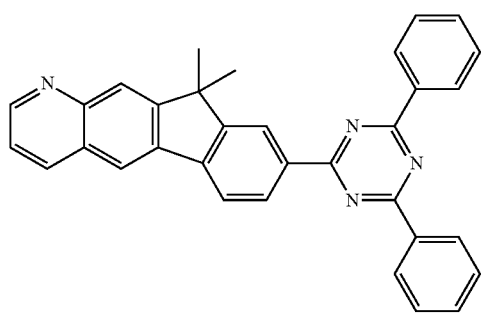
Compound X
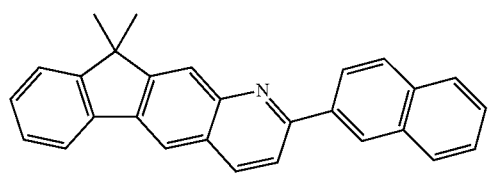
Compound Y
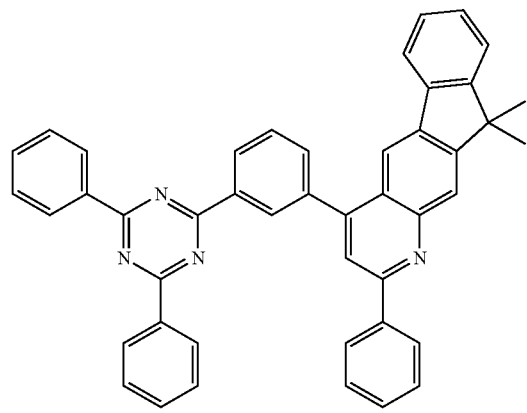
C-1

TABLE 3-continued
The compounds used in the Device Examples and Comparative Examples
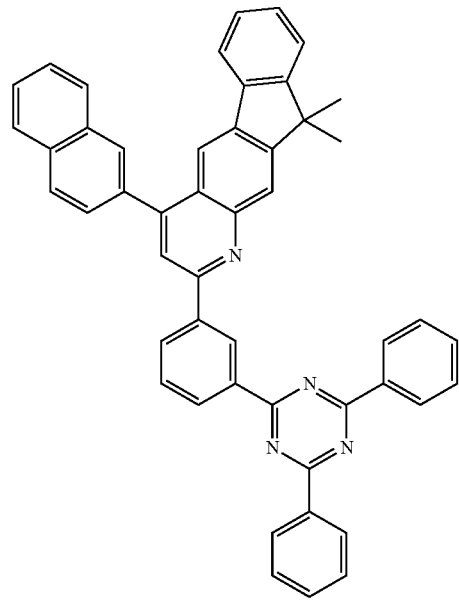
C-119
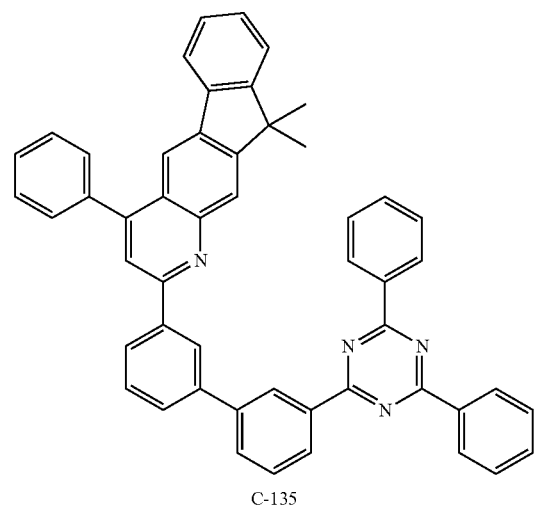
C-135

TABLE 3-continued
The compounds used in the Device Examples and Comparative Examples
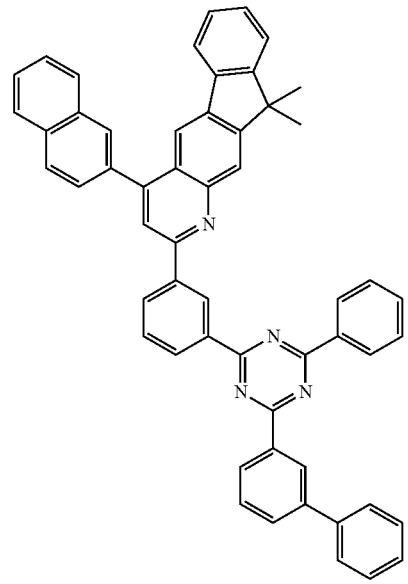
C-322
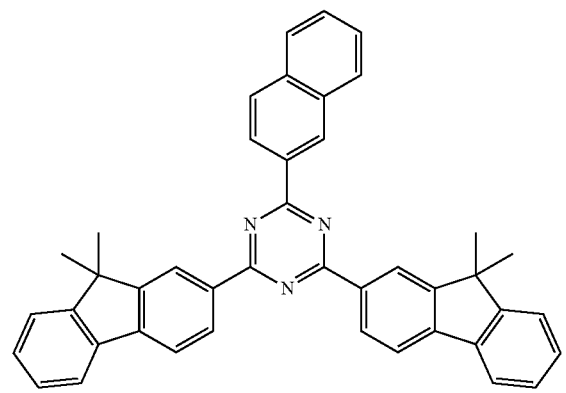
ET-1
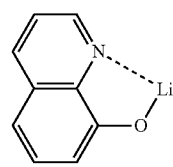
EI-1

The invention claimed is:
1. An organic electroluminescent compound represented by the following formula 7:

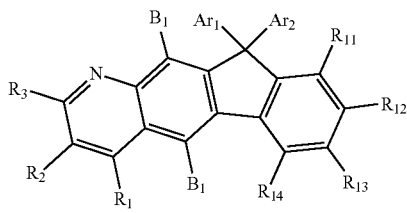

(7)

wherein,
$R_1$ to $R_3$ each independently represent hydrogen, deuterium, halogen, cyano, a substituted or unsubstituted (C1-C30)alkyl, a substituted or unsubstituted (C6-C30)aryl, or a substituted or unsubstituted (5- to 30-membered)heteroaryl, provided that at least two of $R_1$ to $R_3$ each independently represent a substituted or unsubstituted (C1-C30)alkyl, a substituted or unsubstituted (C6-C30)aryl, or a substituted or unsubstituted (5- to 30-membered)heteroaryl;
$B_1$ and $B_2$ each independently represent hydrogen, deuterium, halogen, cyano, a substituted or unsubstituted (C1-C30)alkyl, a substituted or unsubstituted (C6-C30)aryl, a substituted or unsubstituted (5- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino;
$Ar_1$ and $Ar_2$ each independently represent halogen, a substituted or unsubstituted (C1-C30)alkyl, a substituted or unsubstituted (C6-C30)aryl, or a substituted or unsubstituted (5- to 30-membered)heteroaryl; or may be linked to an adjacent substituent to form a substituted or unsubstituted (3- to 30-membered) mono- or polycyclic, alicyclic or aromatic ring, or a combination thereof; and
$R_{11}$ to $R_{14}$ each independently represent hydrogen, deuterium, halogen, cyano, a substituted or unsubstituted (C1-C30)alkyl, a substituted or unsubstituted (C6-C30)aryl, a substituted or unsubstituted (5- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or may be linked to an adjacent substituent to form a substituted or unsubstituted (3- to 30-membered) mono- or polycyclic, alicyclic or aromatic ring, or a combination thereof.

2. The organic electroluminescent compound according to claim 1, wherein the substituents of the substituted alkyl, the substituted aryl, the substituted heteroaryl, the substituted cycloalkyl, the substituted alkoxy, the substituted trialkylsilyl, the substituted dialkylarylsilyl, the substituted alkyldiarylsilyl, the substituted arylsilyl, the substituted mono- or di-alkylamino, the substituted mono- or di-arylamino, the substituted alkylarylamino, and the substituted mono- or polycyclic, alicyclic, aromatic ring, or the combination thereof, in $R_1$ to $R_3$, $B_1$, $B_2$, $Ar_1$ $Ar_2$, and $R_{11}$ to $R_{14}$, are each independently at least one selected from the group consisting of deuterium; halogen; cyano; carboxyl; nitro; hydroxyl; (C1-C30)alkyl; halo(C1-C30)alkyl; (C2-C30)alkenyl; (C2-C30)alkynyl; (C1-C30)alkoxy; (C1-C30)alkylthio; (C3-C30)cycloalkyl; (C3-C30)cycloalkenyl; (3- to 7-membered) heterocycloalkyl; (C6-C30)aryloxy; (C6-C30)arylthio; (C6-C30)aryl-substituted or unsubstituted (5- to 30-membered) heteroaryl; (5- to 30-membered)heteroaryl-substituted or unsubstituted (C6-C30)aryl; tri(C1-C30)alkylsilyl; tri(C6-C30)arylsilyl; di(C1-C30)alkyl(C6-C30)arylsilyl; (C1-C30) alkyldi(C6-C30)arylsilyl; amino; a mono- or di-(C1-C30) alkylamino; (C1-C30)alkyl-substituted or unsubstituted mono- or di-(C6-C30)arylamino; (C1-C30)alkyl(C6-C30) arylamino; (C1-C30)alkylcarbonyl; (C1-C30)alkoxycarbonyl; (C6-C30)arylcarbonyl; di(C6-C30)arylboronyl, di(C1-C30)alkylboronyl, (C1-C30)alkyl(C6-C30)arylboronyl; (C6-C30)ar(C1-C30)alkyl; and (C1-C30)alkyl(C6-C30) aryl.

3. The organic electroluminescent compound according to claim 1, wherein, $R_1$ and $R_3$ each independently represent a substituted or unsubstituted (C6-C20)aryl, or a substituted or unsubstituted (5- to 20-membered)heteroaryl;
$R_2$ represents hydrogen;
$B_1$ and $B_2$ represent hydrogen;
$Ar_1$ and $Ar_2$ each independently represent a substituted or unsubstituted (C1-C6)alkyl, or a substituted or unsubstituted (C6-C12)aryl, or may be linked to an adjacent substituent to form a substituted or unsubstituted (5- to 15-membered) polycyclic, alicyclic, or aromatic ring, or a combination thereof; and
$R_{11}$ to $R_{14}$ each independently represent hydrogen or a substituted or unsubstituted (C6-C12)aryl.

4. The organic electroluminescent compound according to claim 1, wherein, $R_1$ and $R_3$ each independently represent a substituted or unsubstituted (C6-C20)aryl, or a substituted or unsubstituted (5- to 20-membered)heteroaryl, wherein the substituents of the substituted aryl are each independently (C6-C15)aryl-substituted or unsubstituted (5- to 25-membered)heteroaryl, and wherein the substituents of the substituted heteroaryl are each independently (C6-C15)aryl;
$R_2$ represents hydrogen;
$B_1$ and $B_2$ represent hydrogen;
$Ar_1$ and $Ar_2$ each independently represent an unsubstituted (C1-C6)alkyl, or an unsubstituted (C6-C12)aryl; or may be linked to an adjacent substituent to form an unsubstituted (5- to 15-membered) polycyclic aromatic ring; and
$R_{11}$ to $R_{14}$ each independently represent halogen or an unsubstituted (C6-C12)aryl.

5. The organic electroluminescent compound according to claim 1, wherein the compound represented by formula 7 is selected from the group consisting of:

C-1
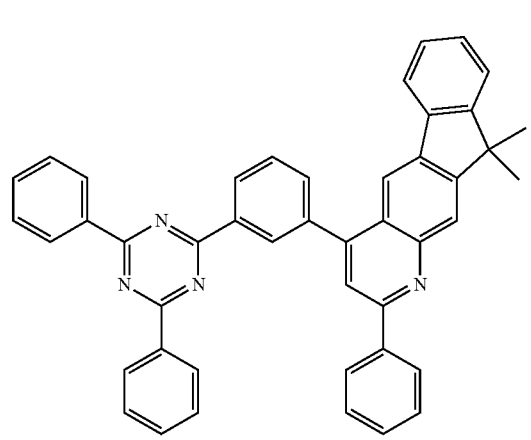
C-2
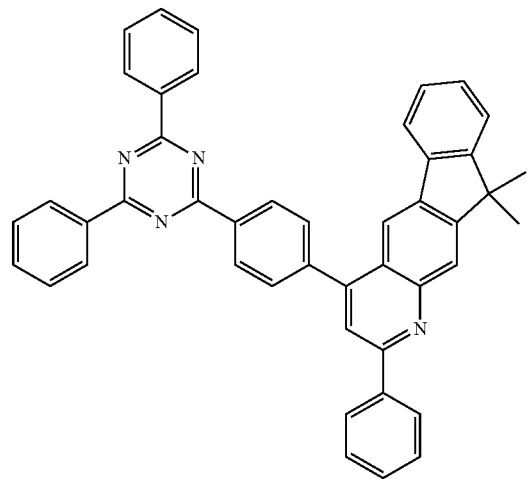
C-3
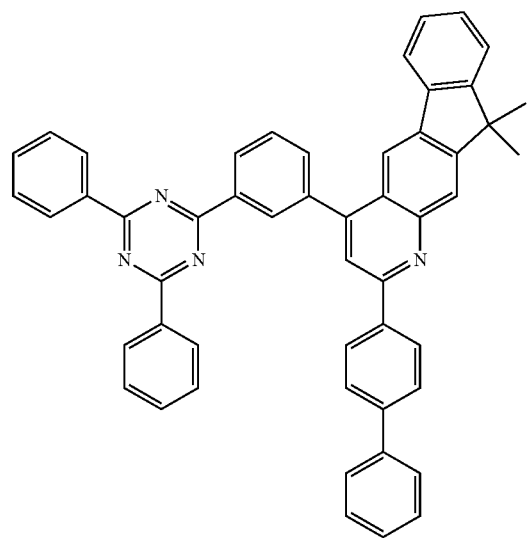
C-4
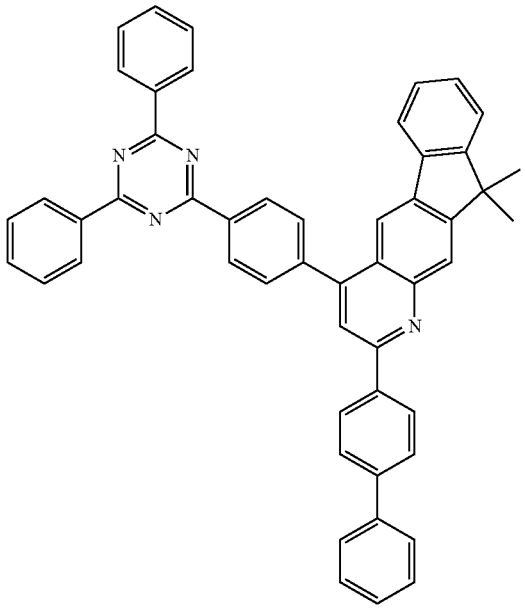
C-5
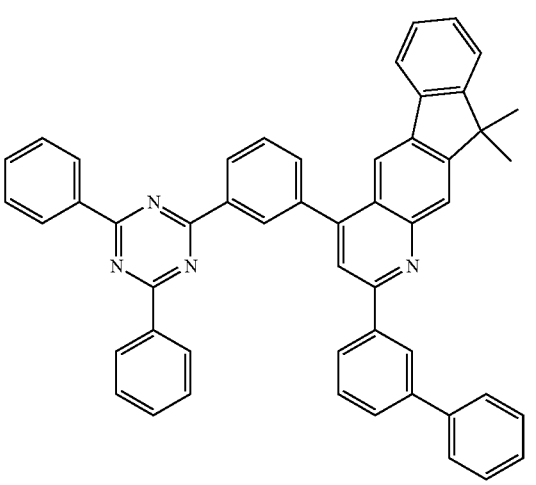
C-6
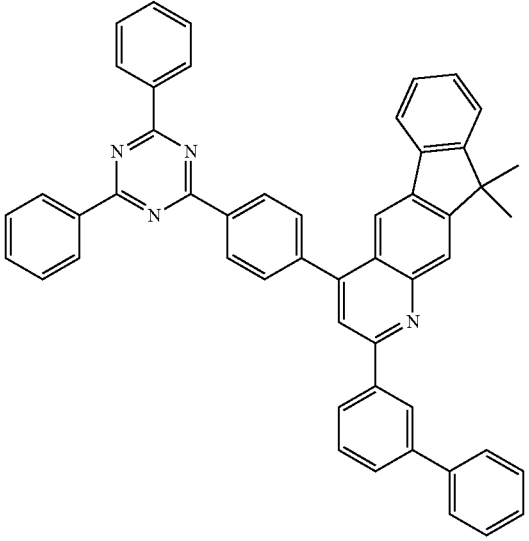

C-7
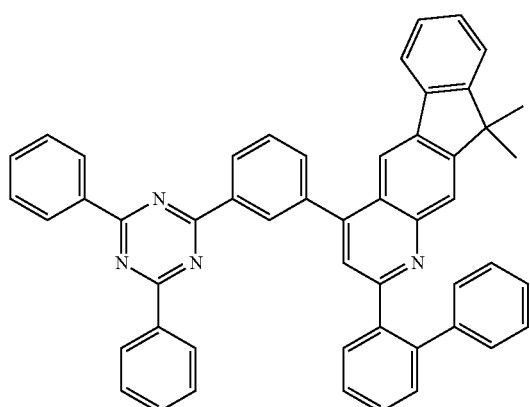
C-8
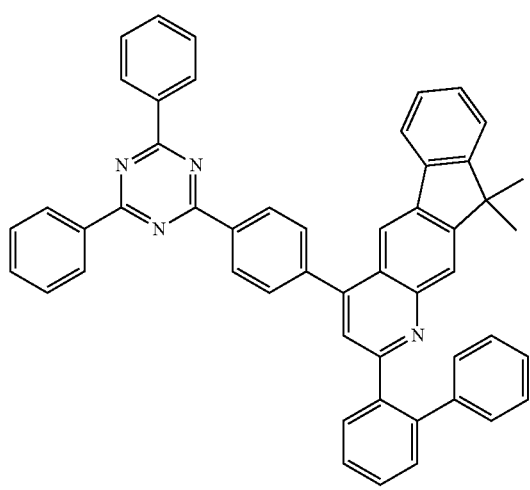
C-9
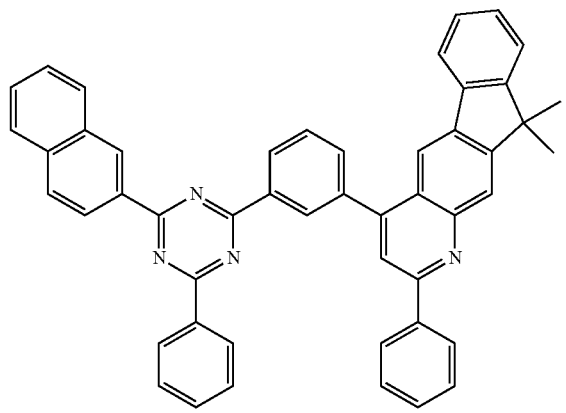
C-10
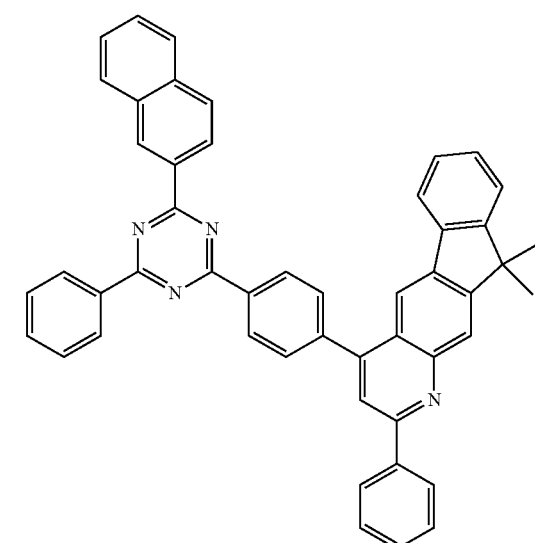
C-11
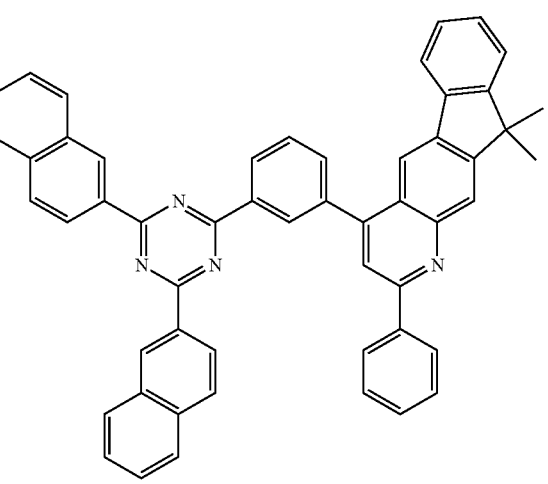
C-12
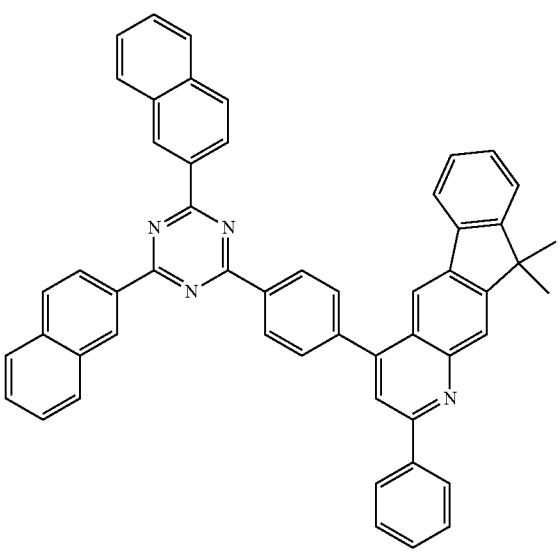

C-13
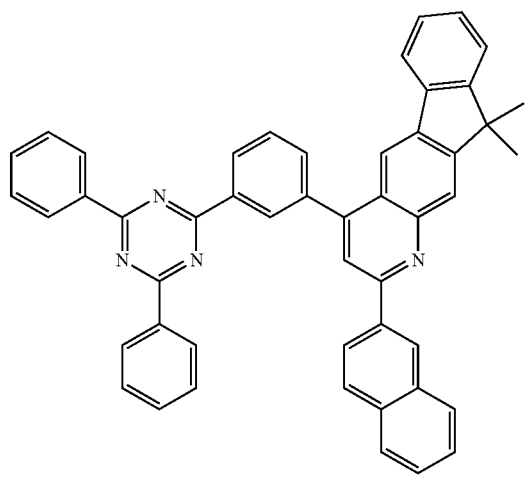
C-16
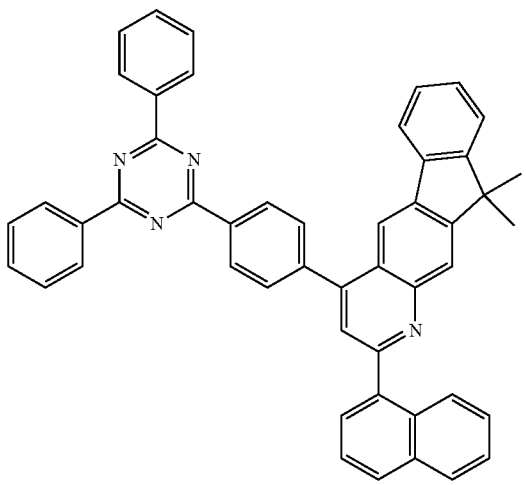
C-14
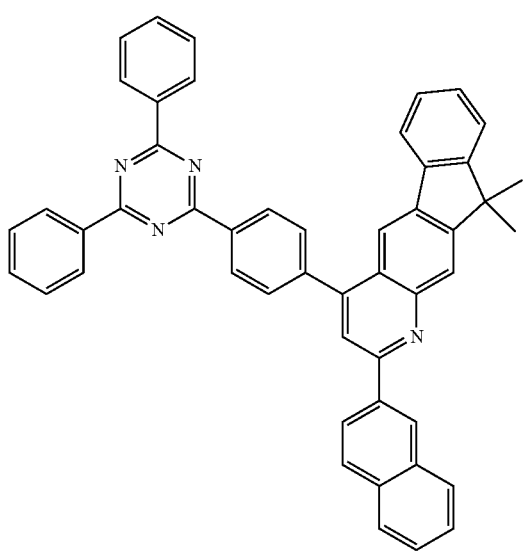
C-17
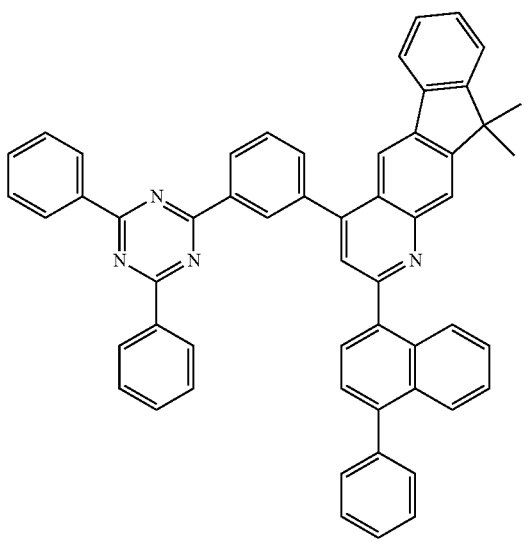
C-15
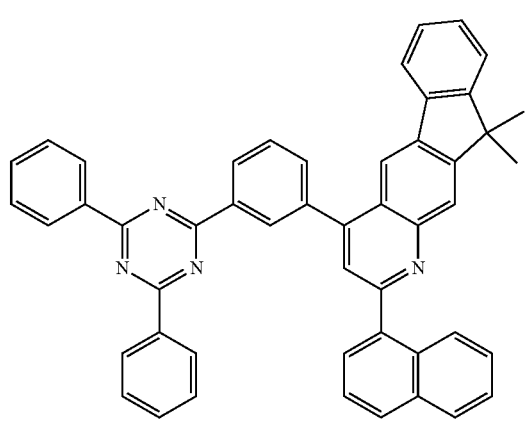

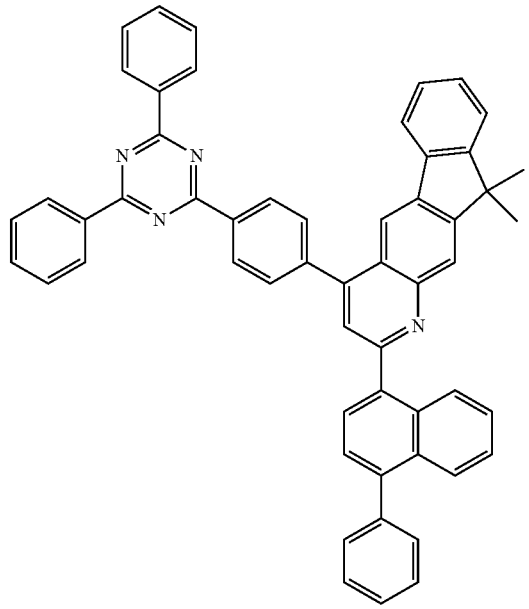
C-18
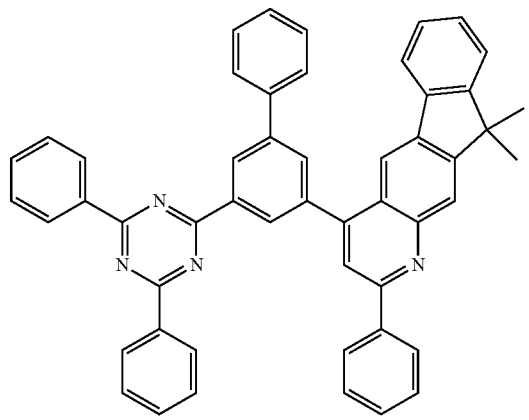
C-19
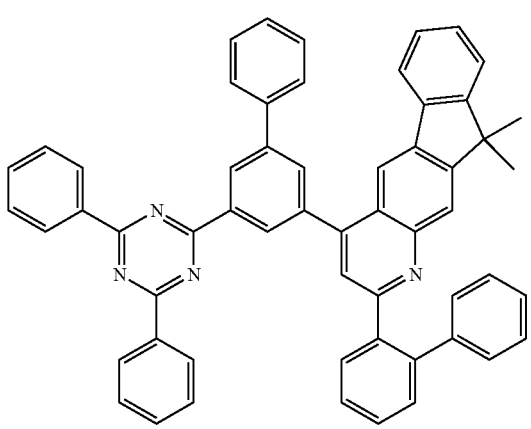
C-20
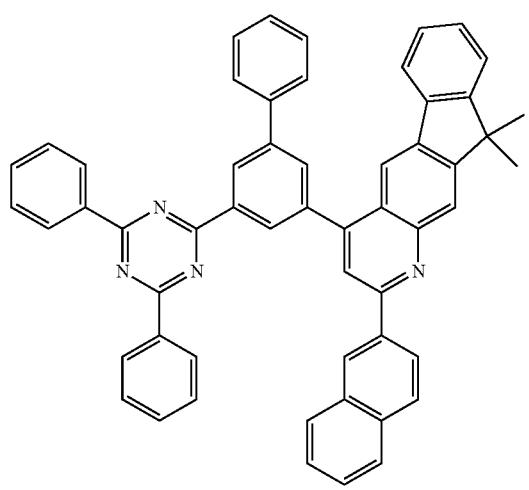
C-21
C-22
C-23

C-24
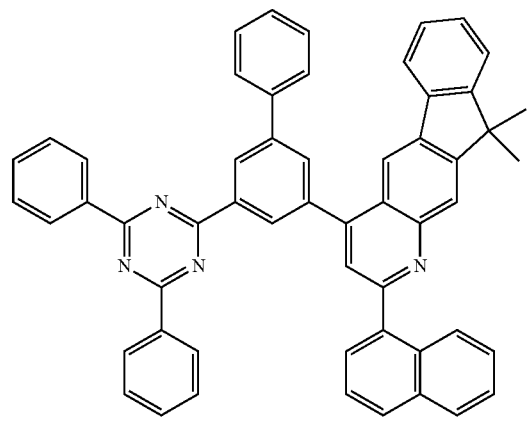
C-25
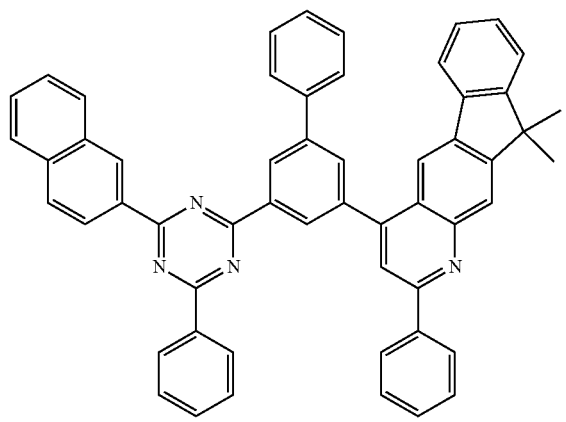
C-26
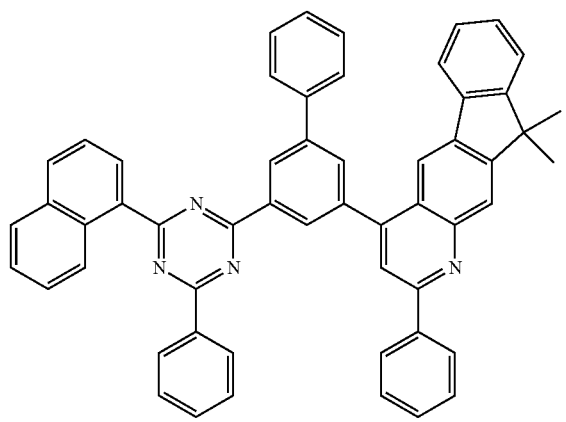
C-27
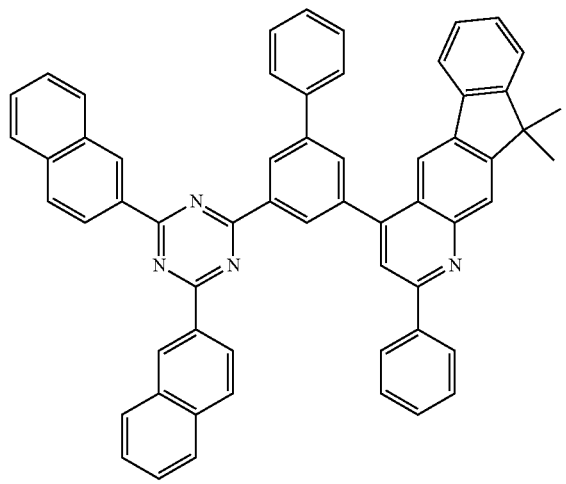
C-28
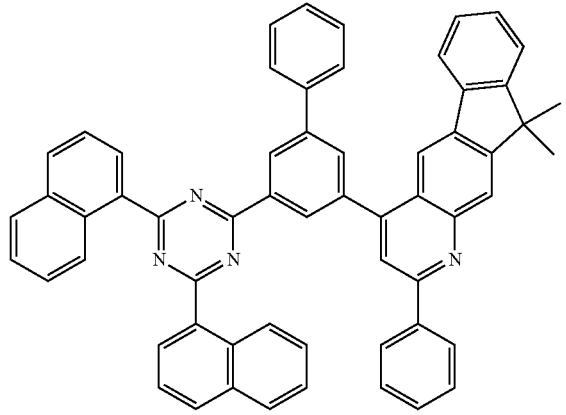
C-29
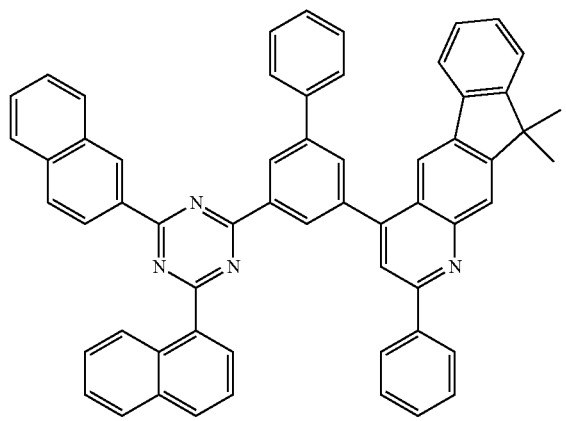

C-30
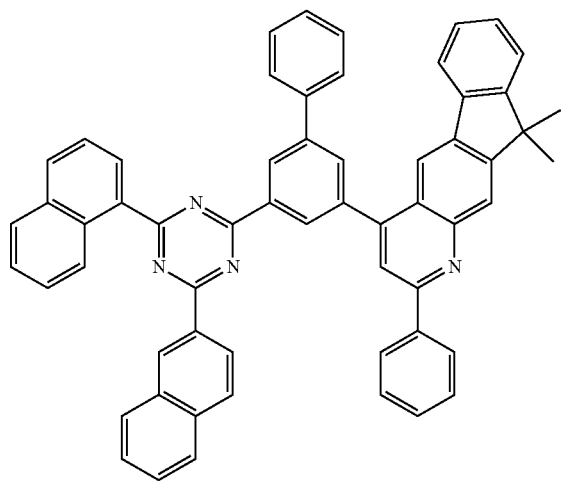
C-31
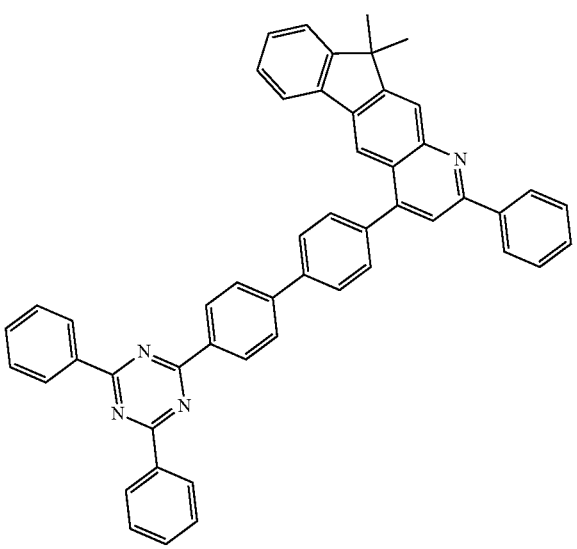
C-32
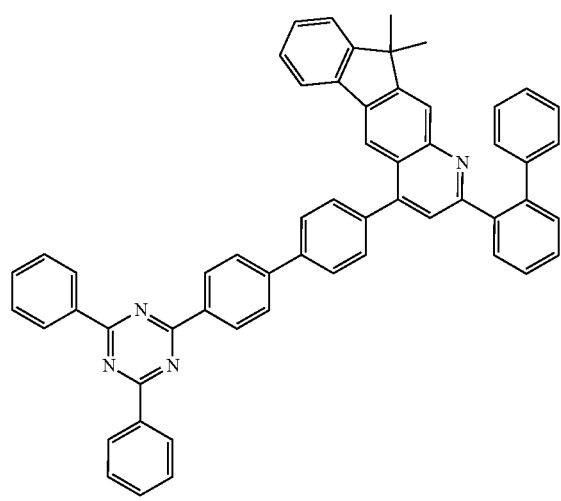
C-33
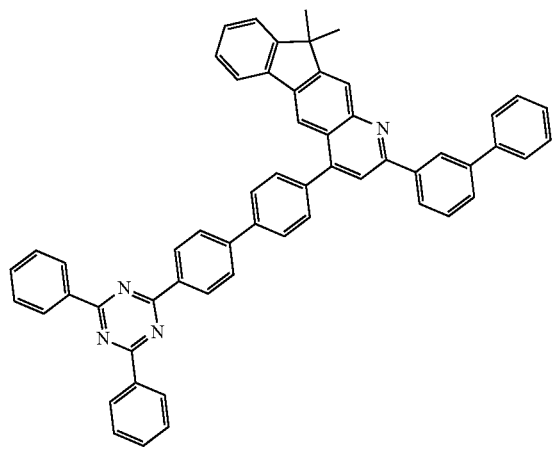
C-34
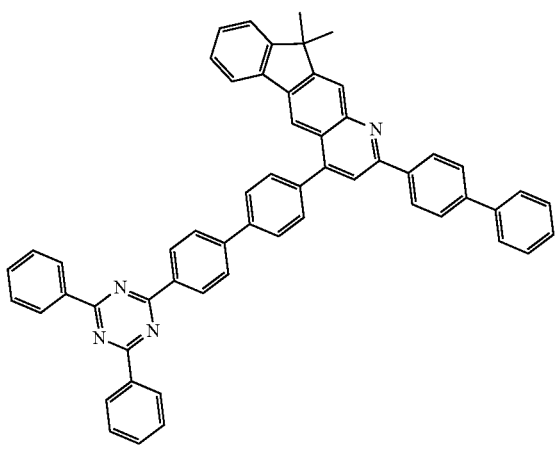
C-35
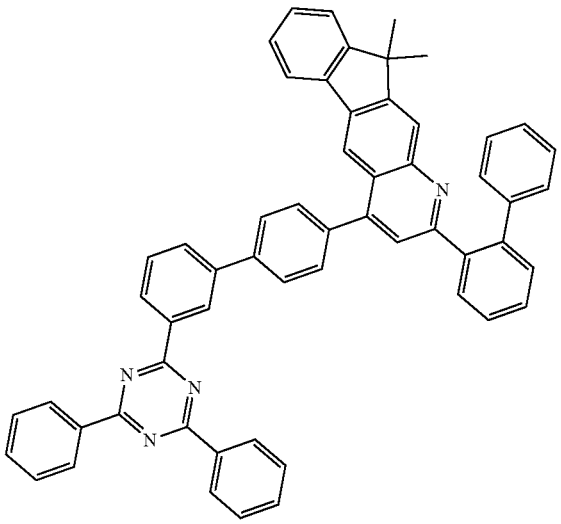

C-36
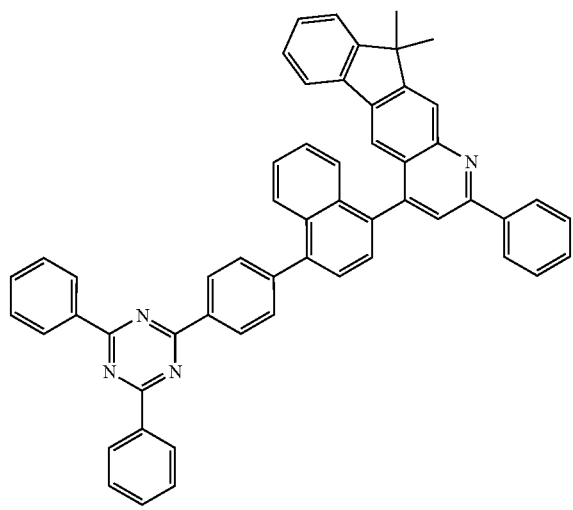
C-37
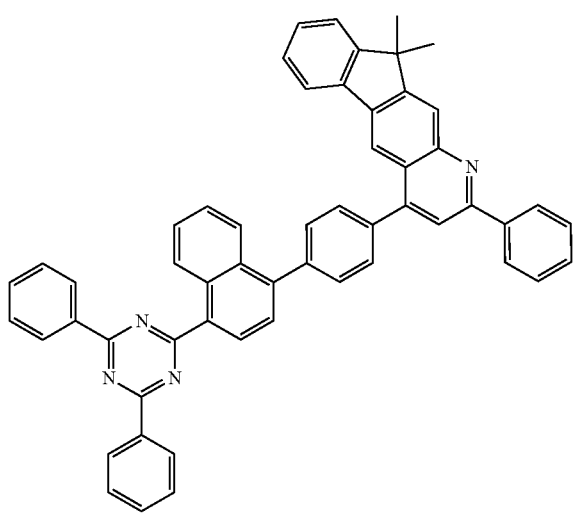
C-38
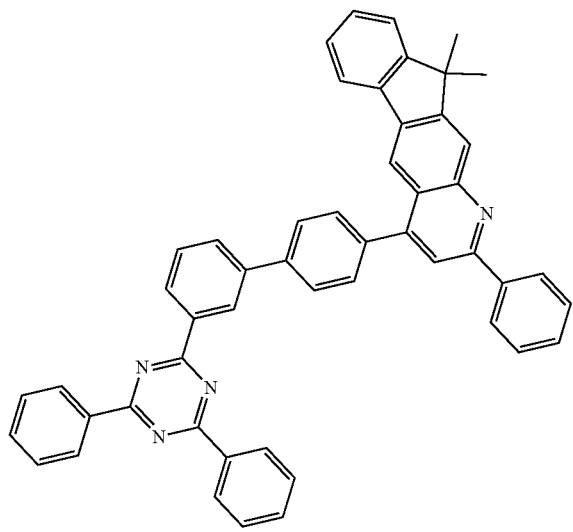
C-39
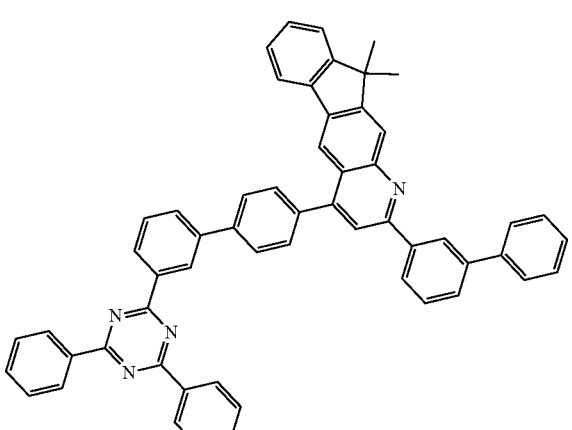
C-40
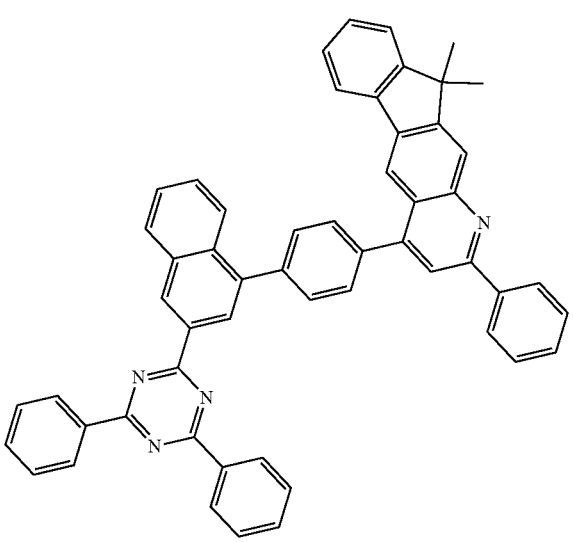
C-41
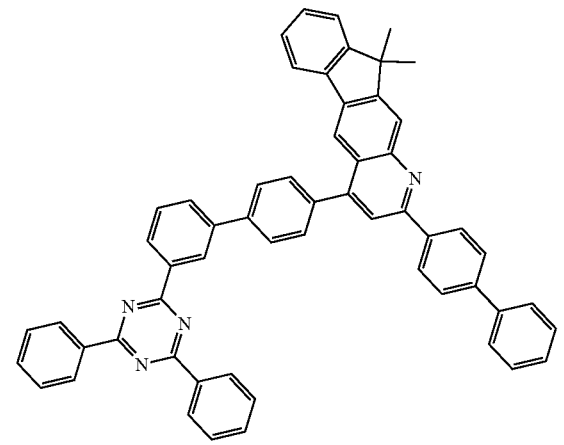

C-42
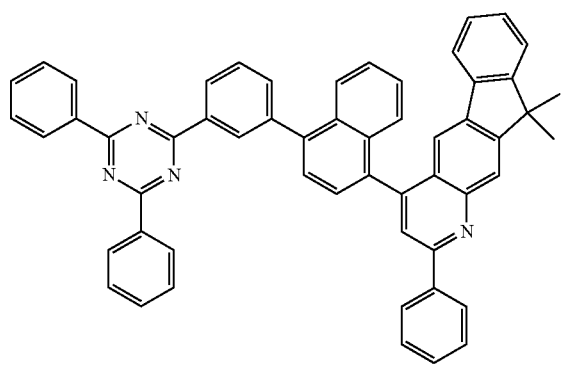
C-43
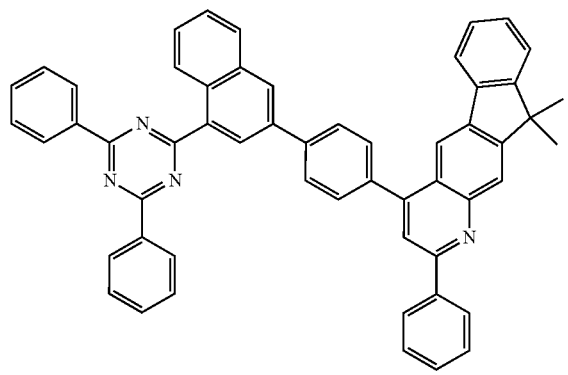
C-44
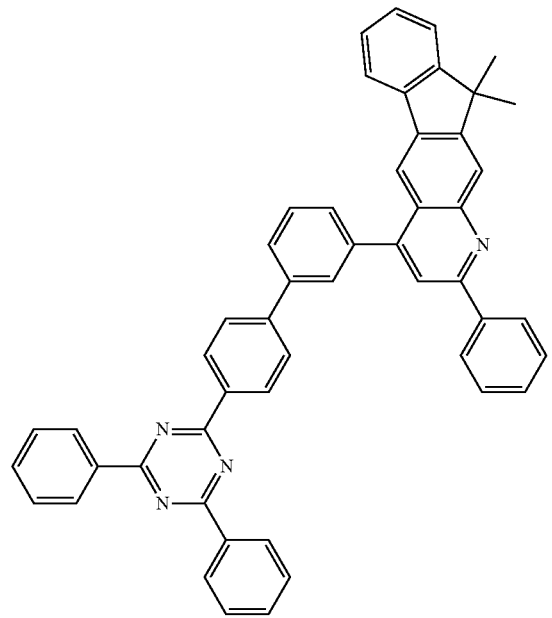
C-45
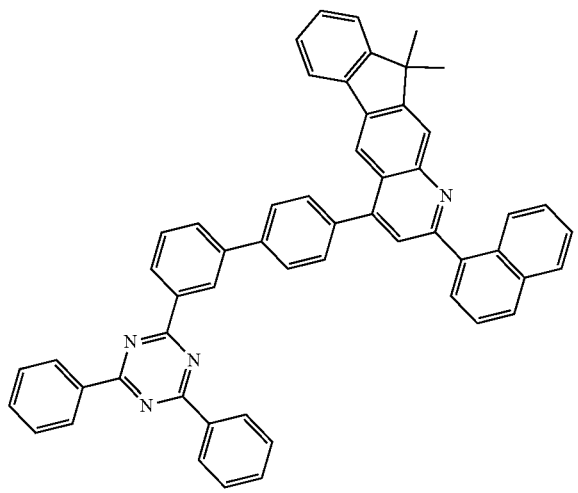
C-46
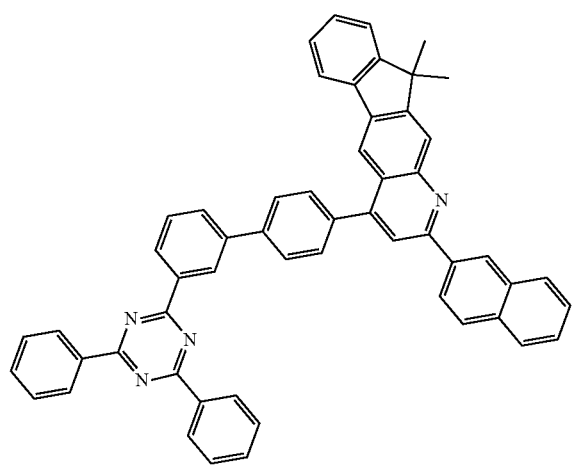
C-47
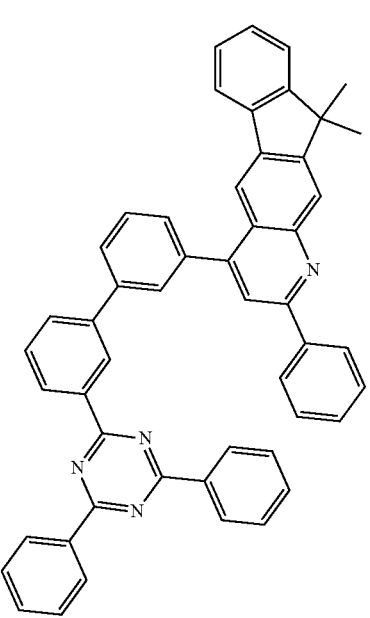

C-48
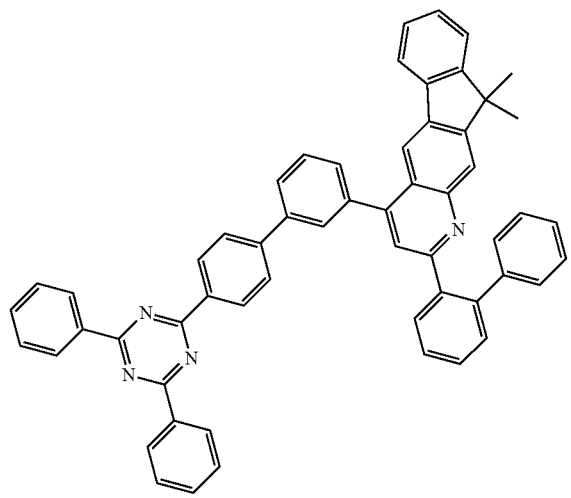
C-49
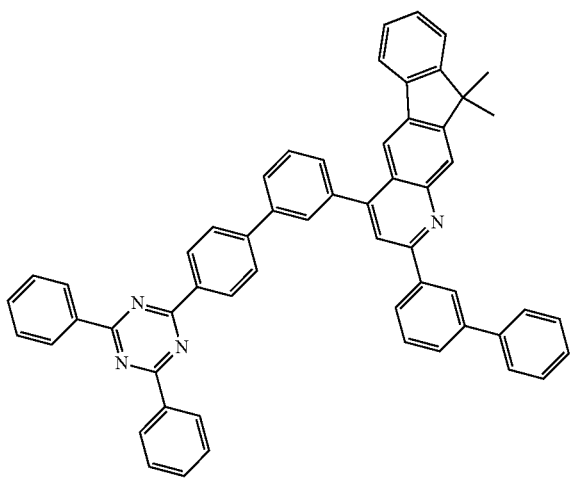
C-50
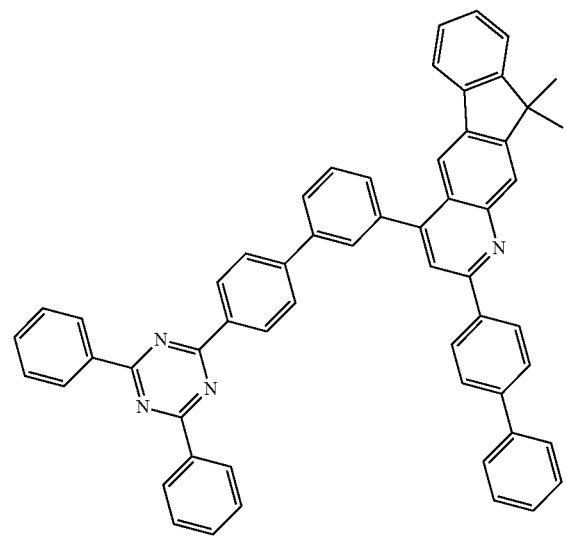
C-51
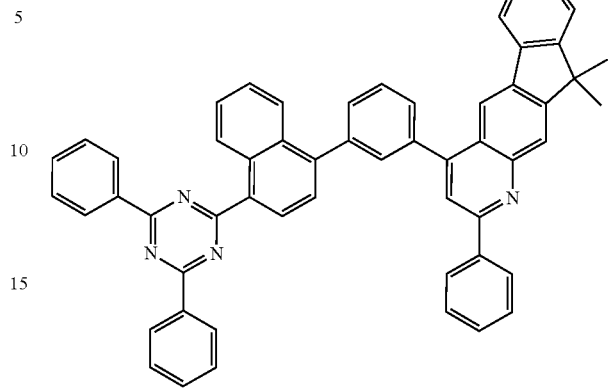
C-52
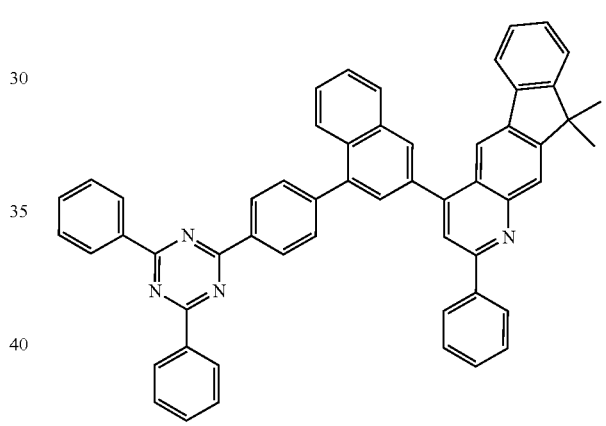
C-53
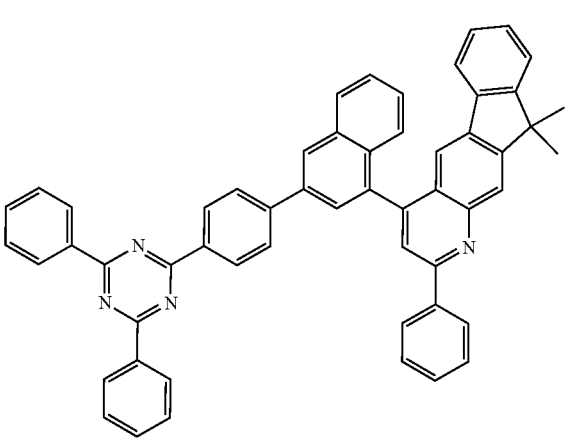

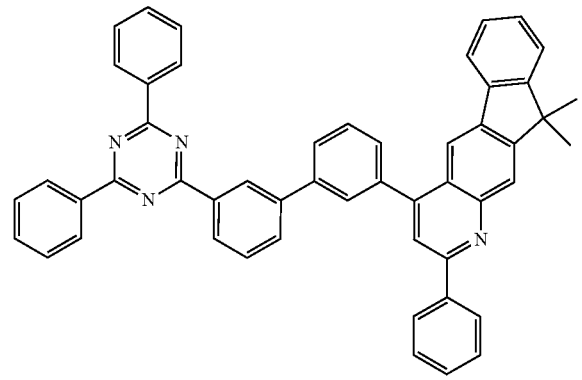
C-54
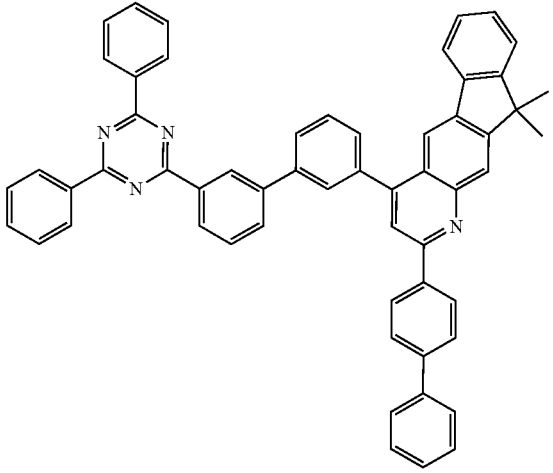
C-57
C-55
C-58
C-56
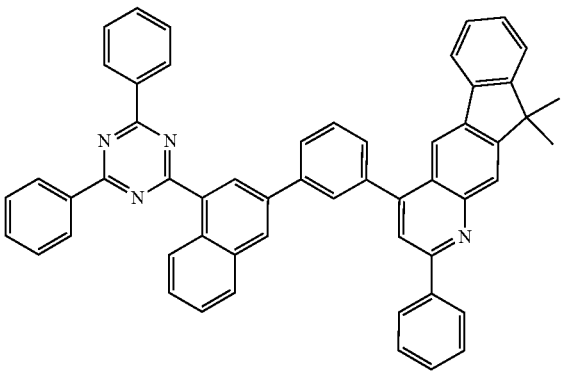
C-59
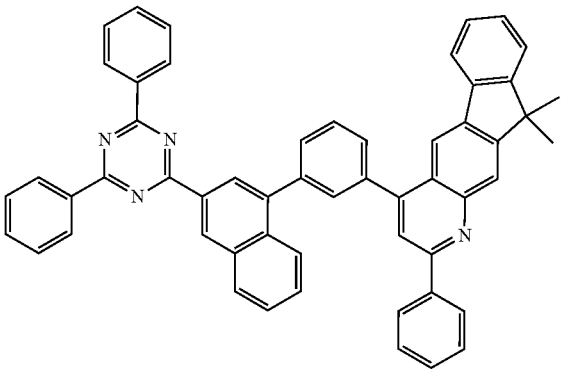
C-60
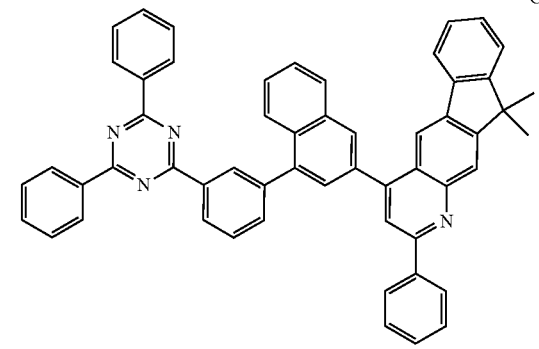

C-61
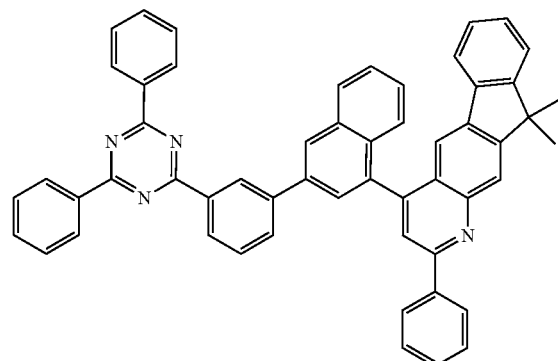
C-62
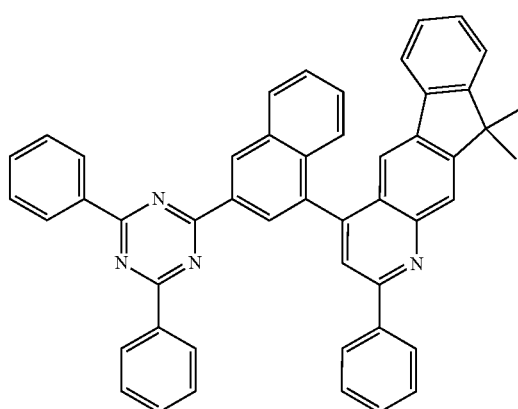
C-63
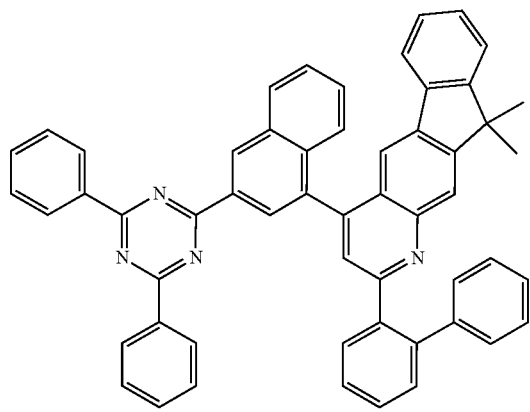
C-64
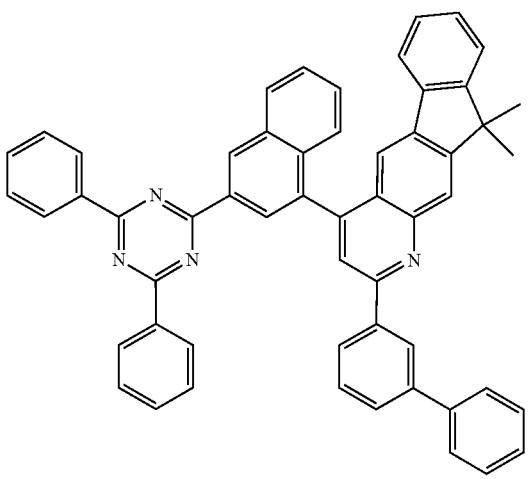
C-65
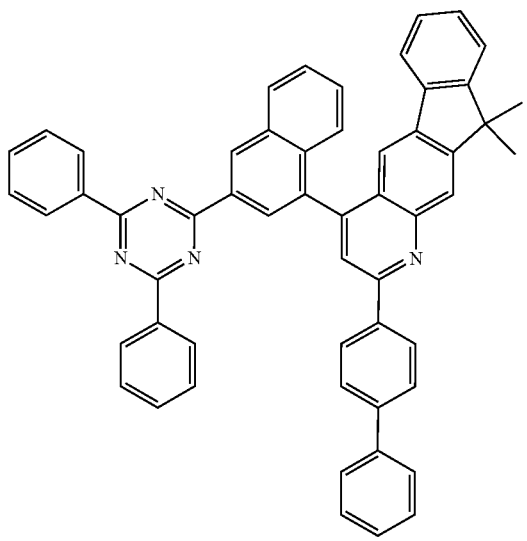
C-66
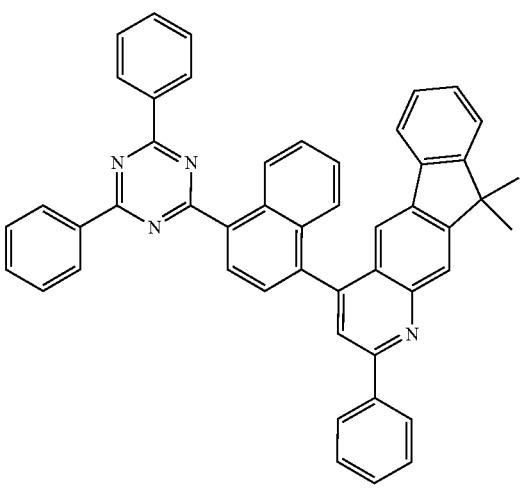

C-67
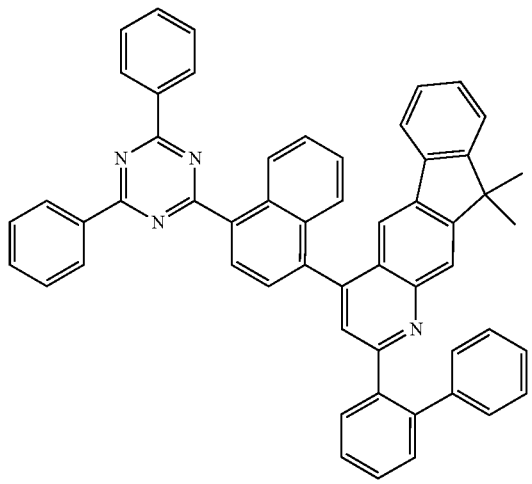
C-68
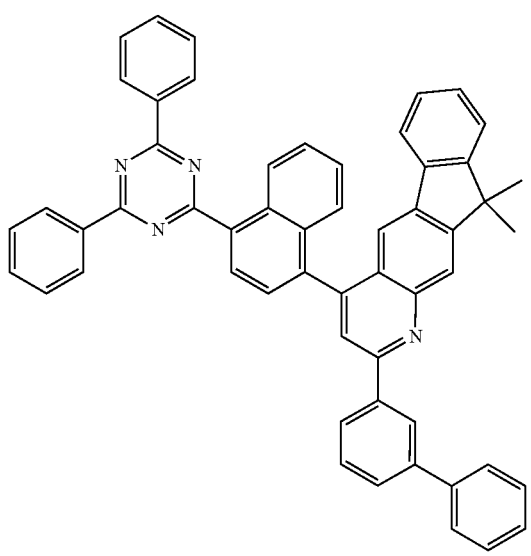
C-69
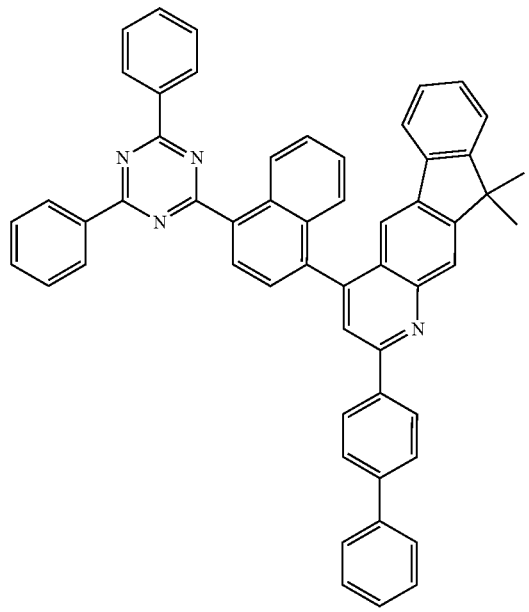
C-70
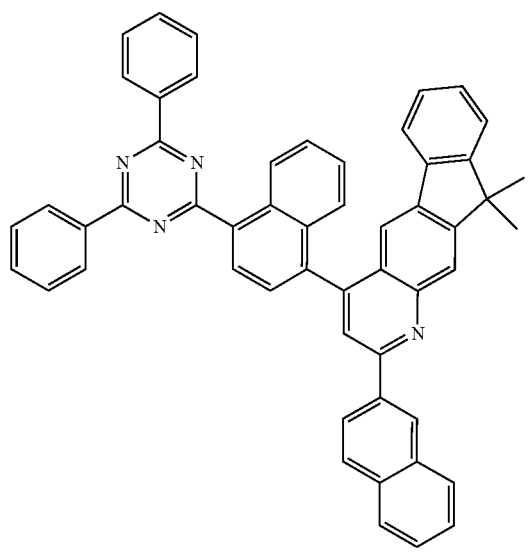
C-71
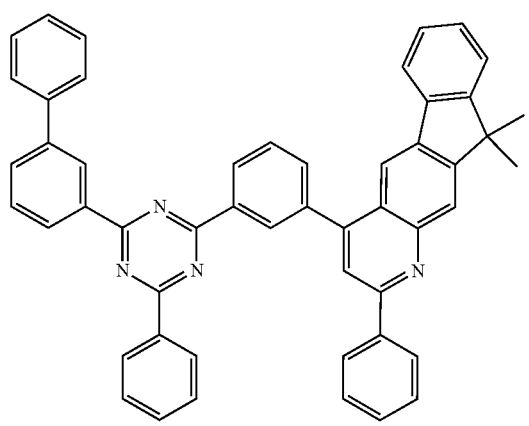

C-72
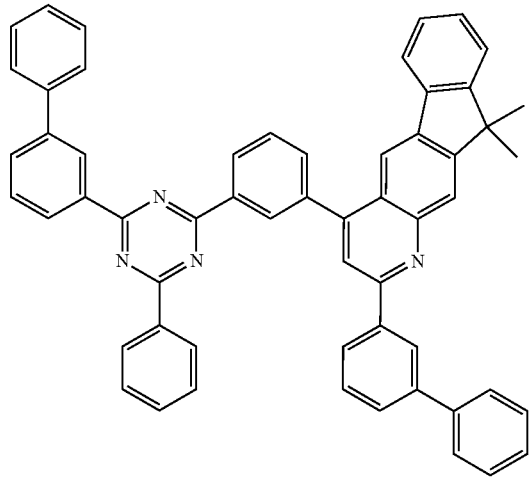
C-73
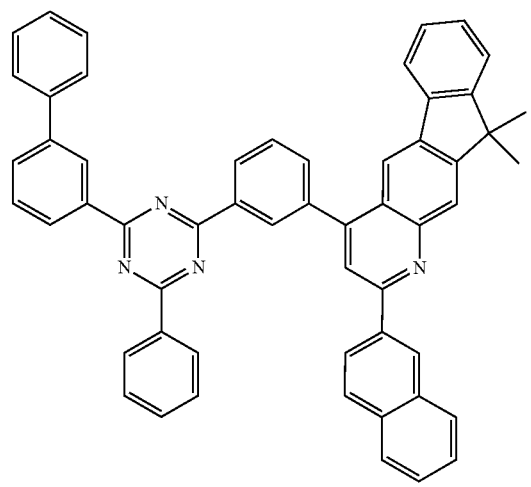
C-74
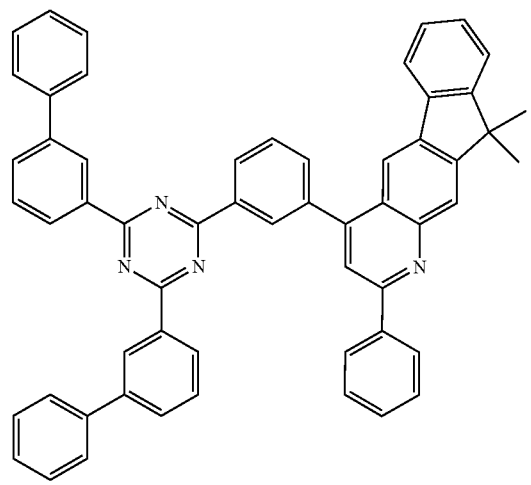
C-75
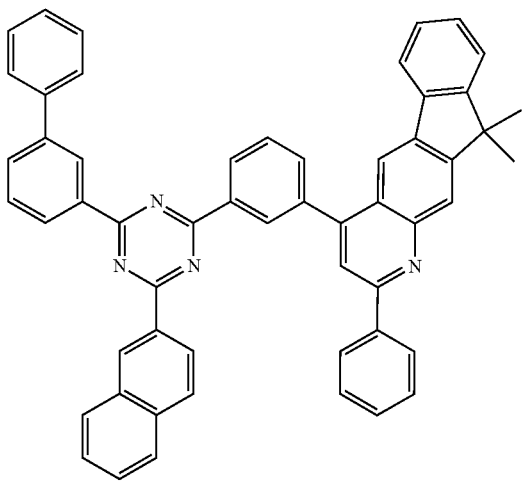
C-76
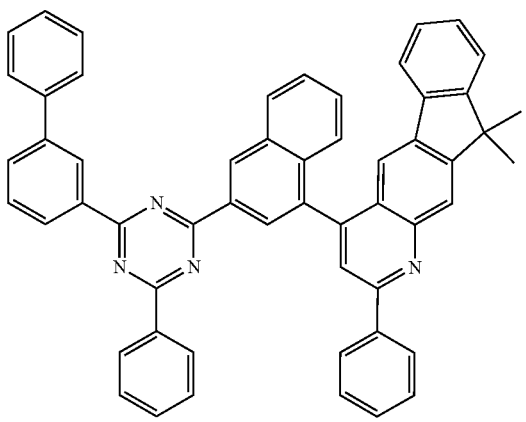
C-77
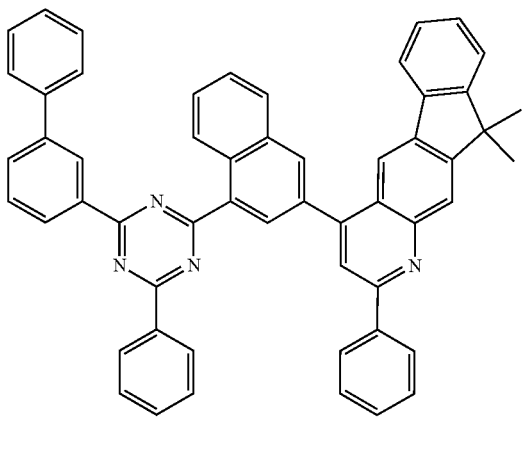

-continued
C-78
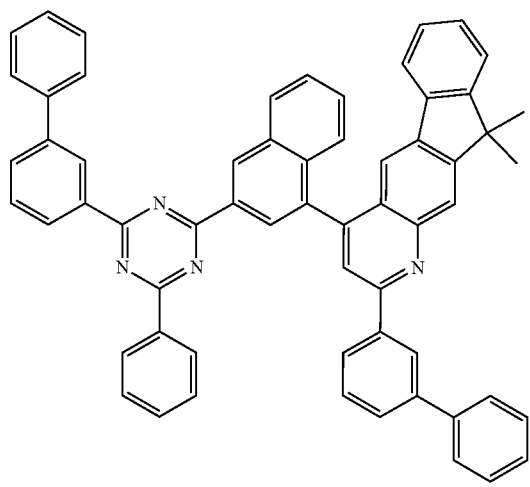
C-79
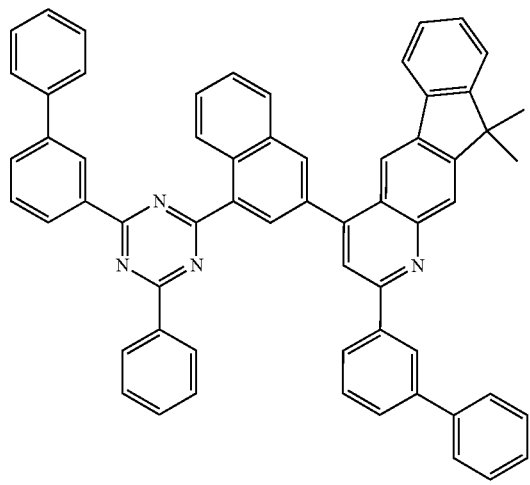
C-80
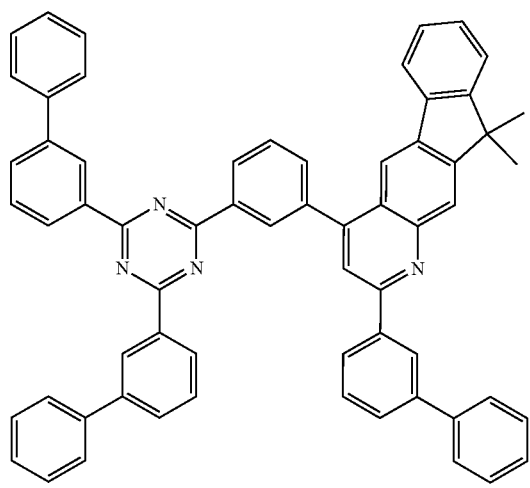
-continued
C-81
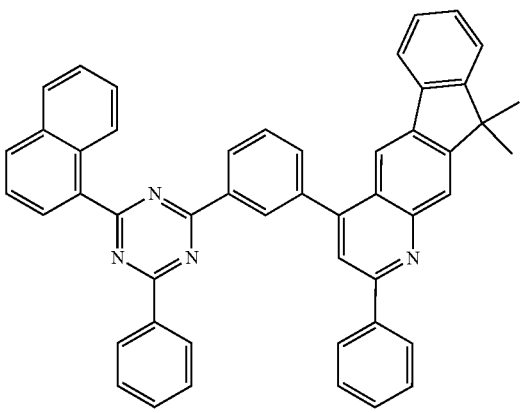
C-82
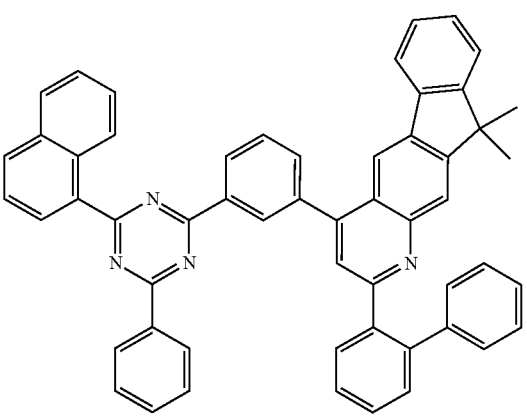
C-83
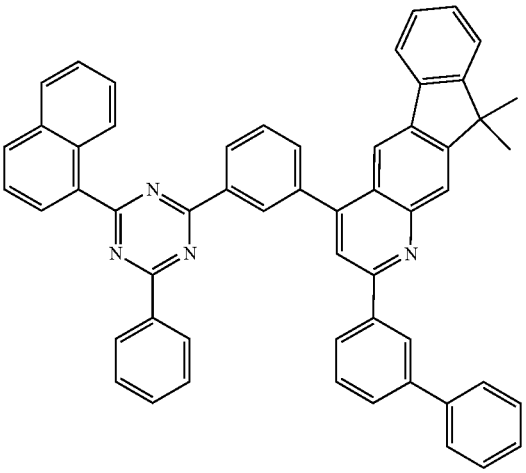

-continued
C-84
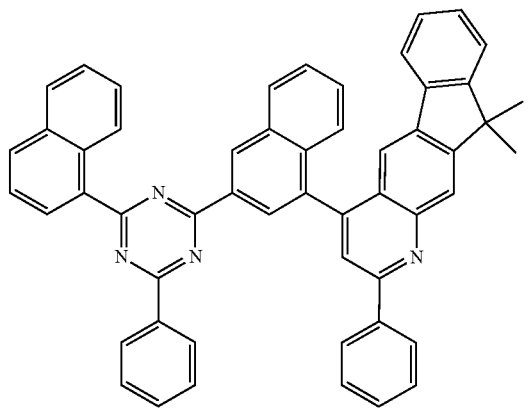
C-85
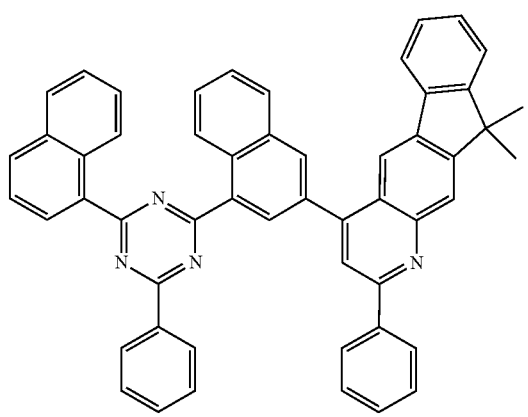
C-86
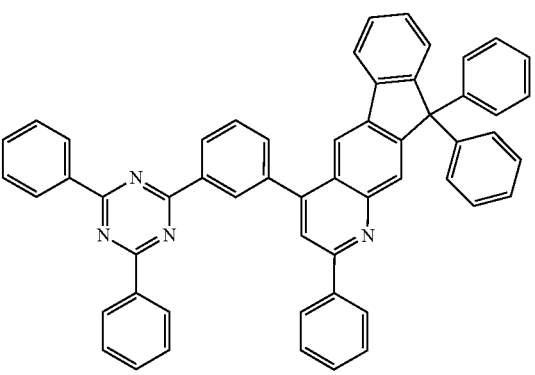
C-87
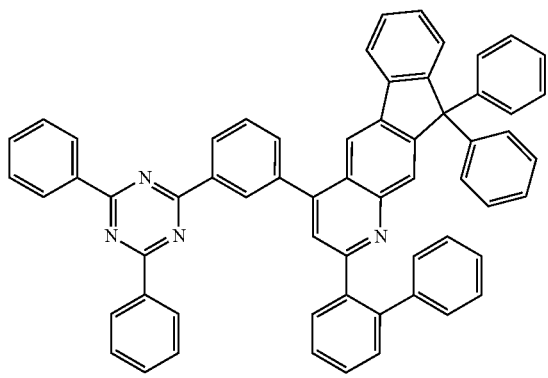
-continued
C-88
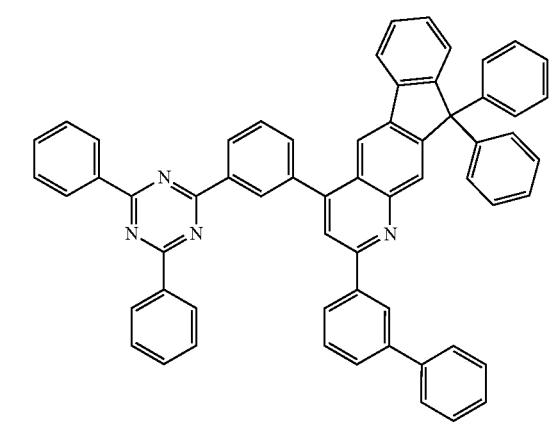
C-89
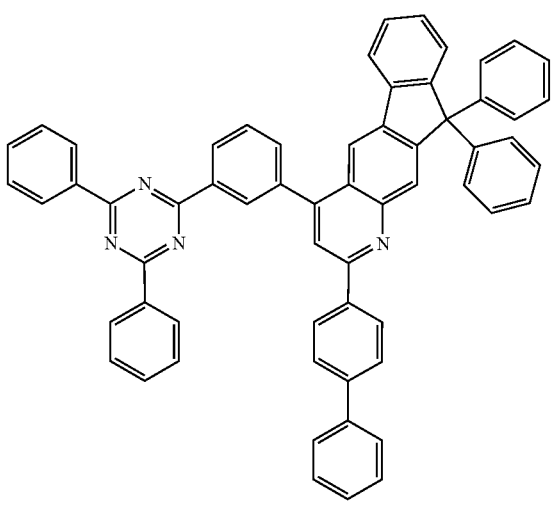
C-90
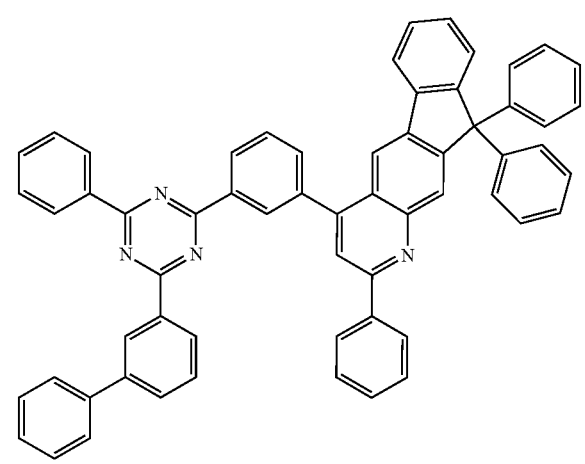

235
-continued
C-91
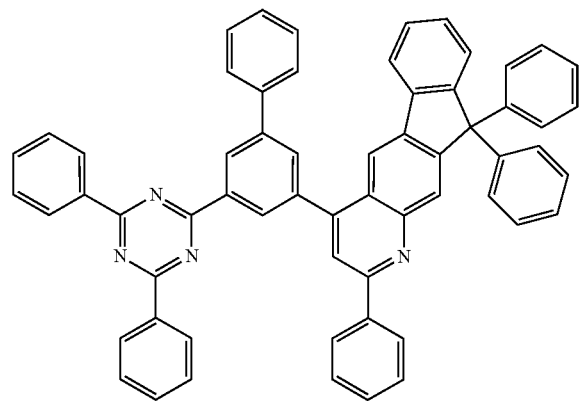
C-92
C-93
C-94
236
-continued
C-95
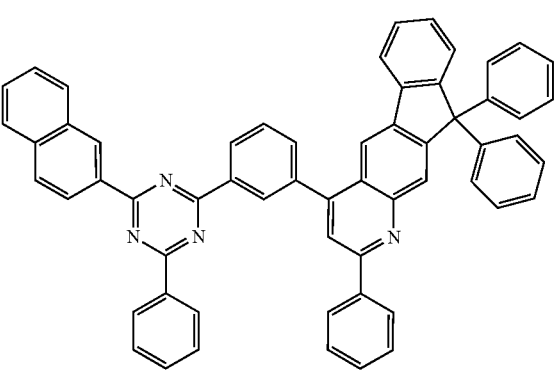
C-96
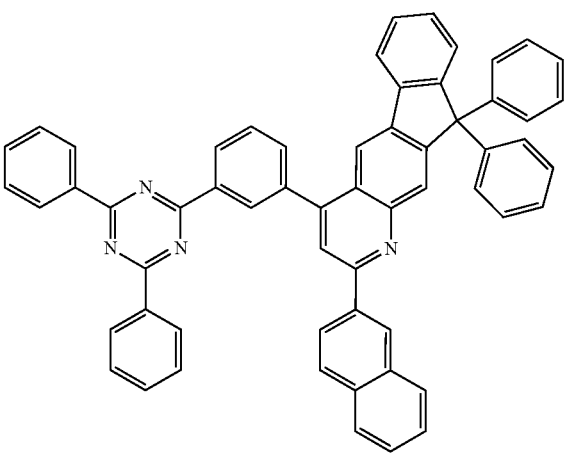
C-97
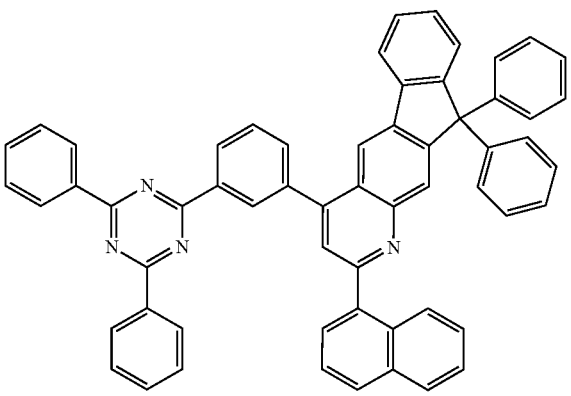

C-98
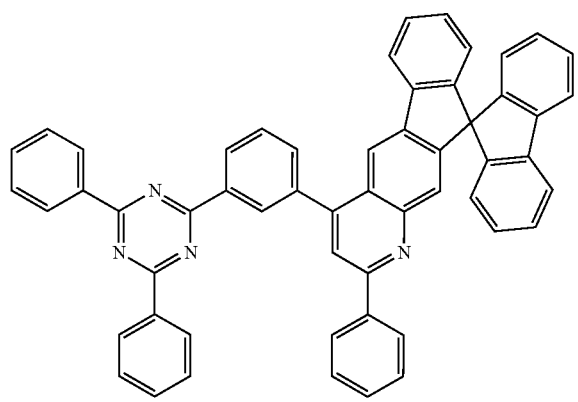
C-99
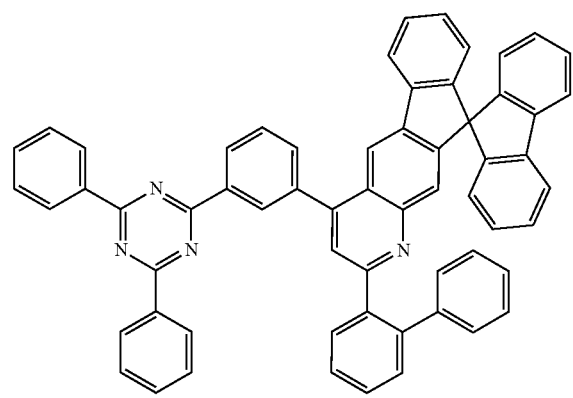
C-100
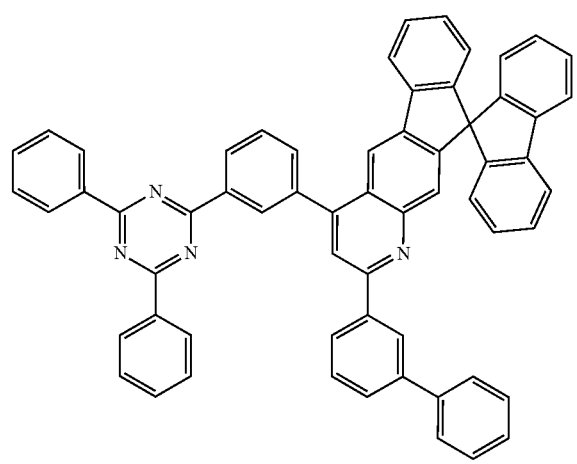
C-101
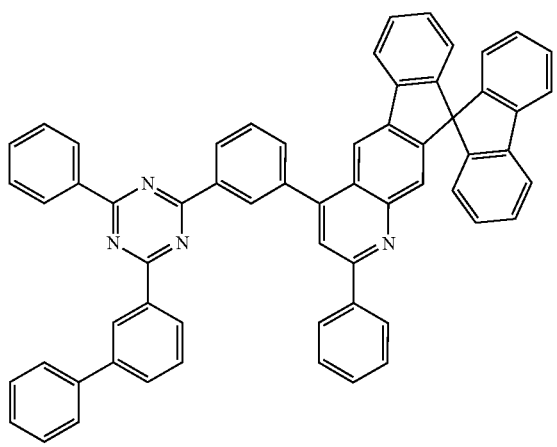
C-102
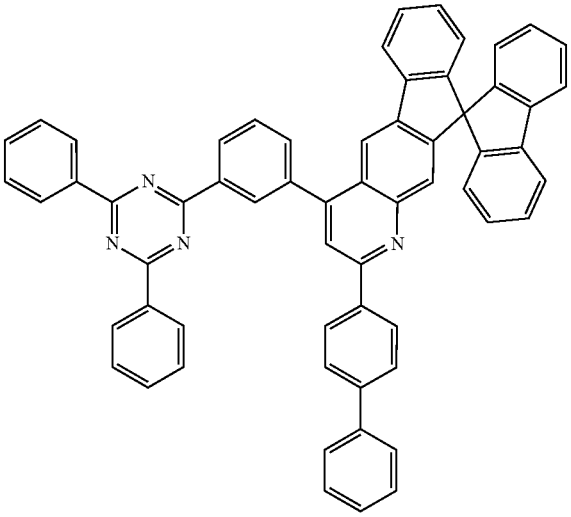
C-103
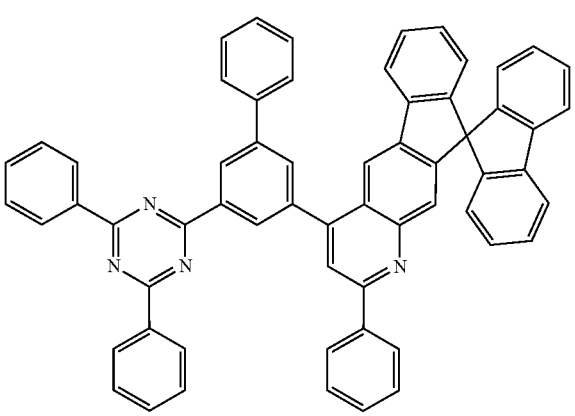

C-104
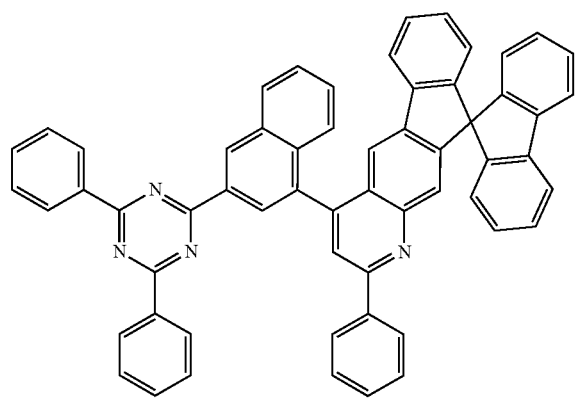
C-105
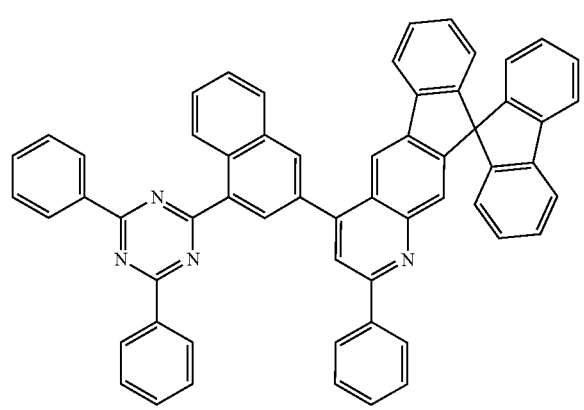
C-106
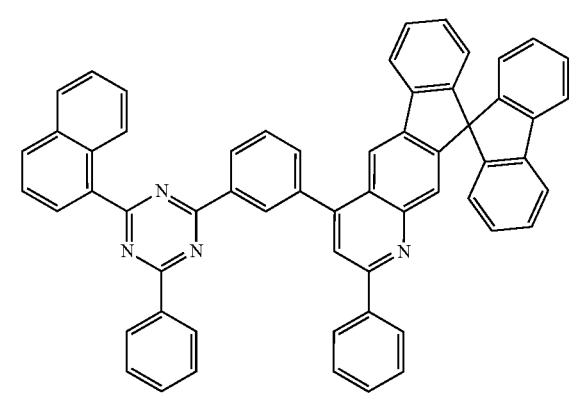
C-107
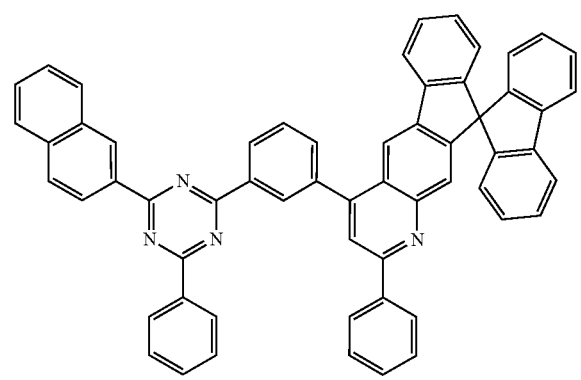
C-108
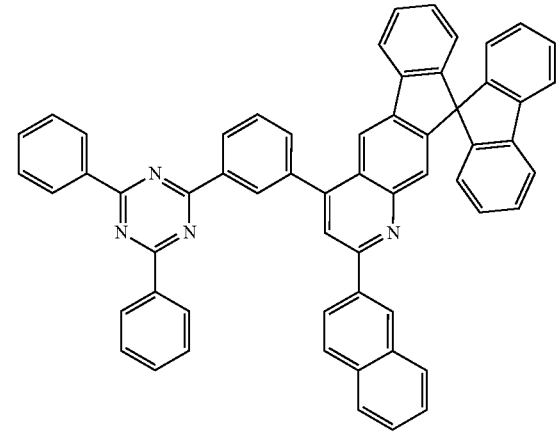
C-109
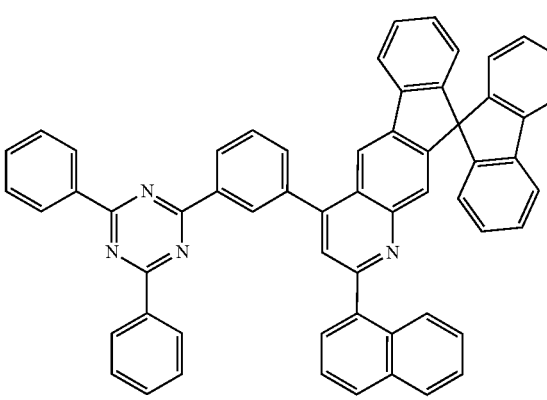
C-110
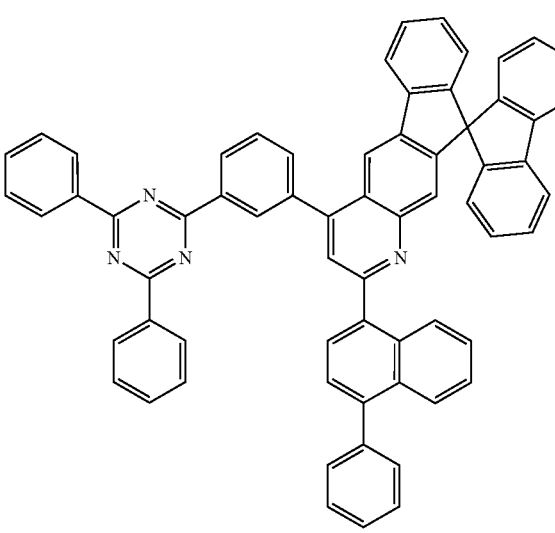

C-111
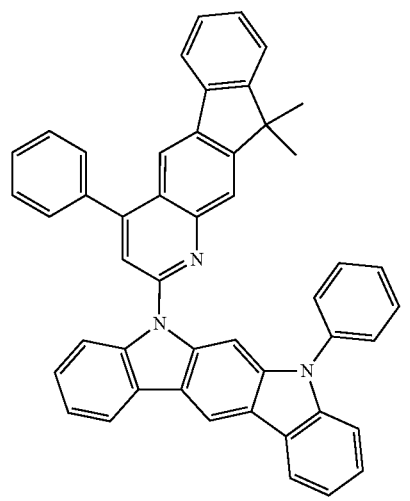
C-112
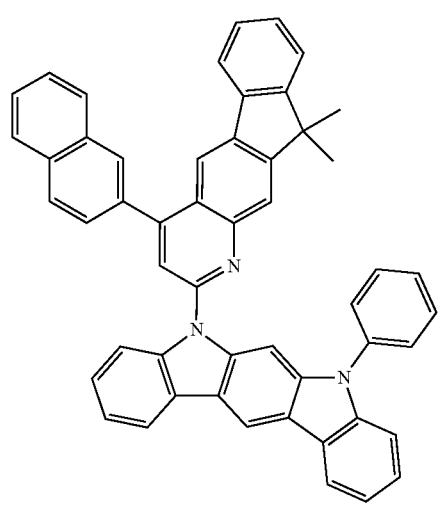
C-113
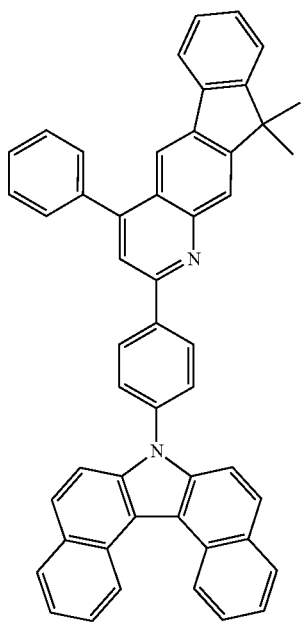
C-114
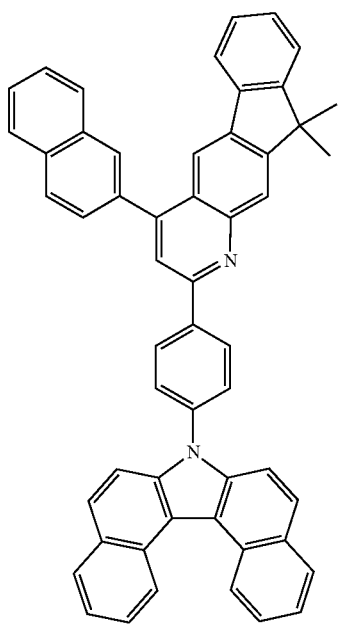
C-115
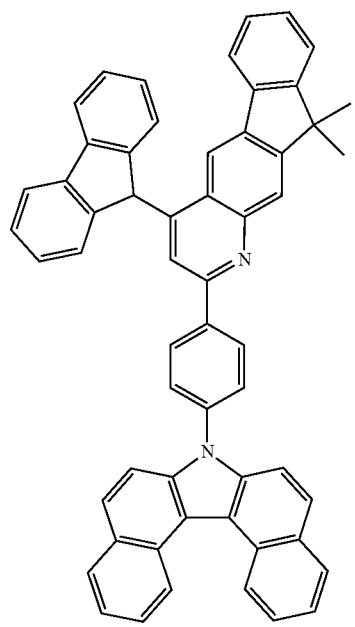

C-116
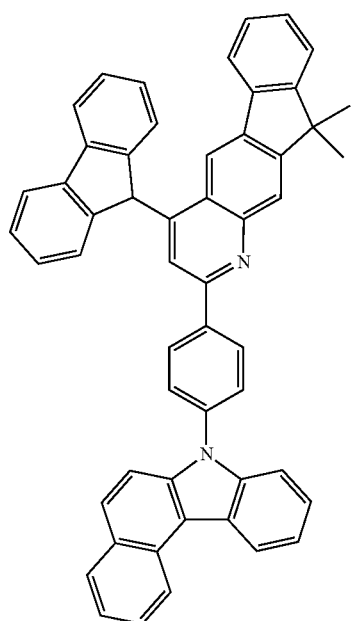
C-117
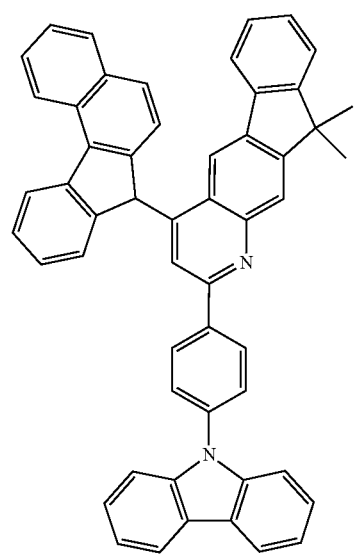
C-118
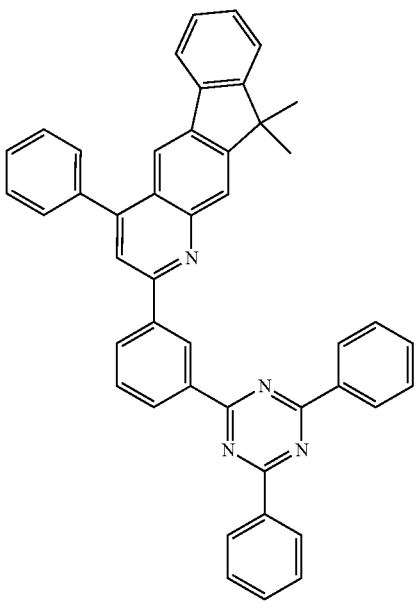
C-119
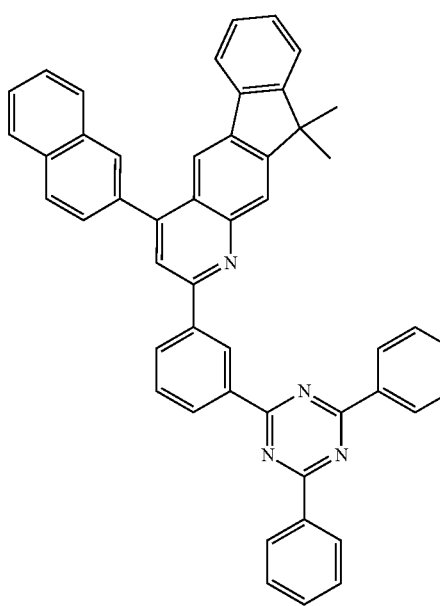

-continued
C-120
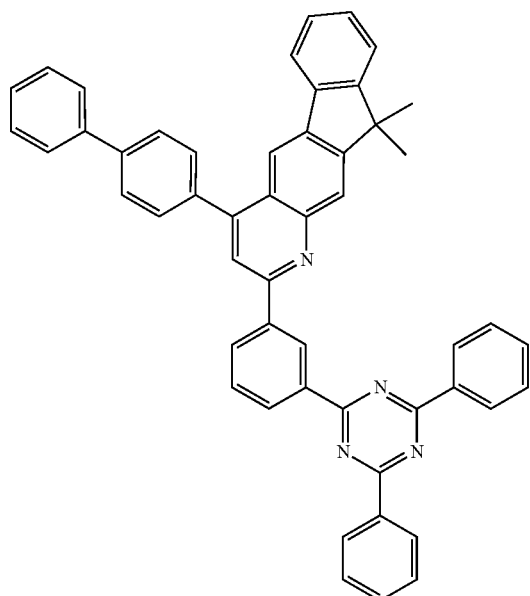
C-122
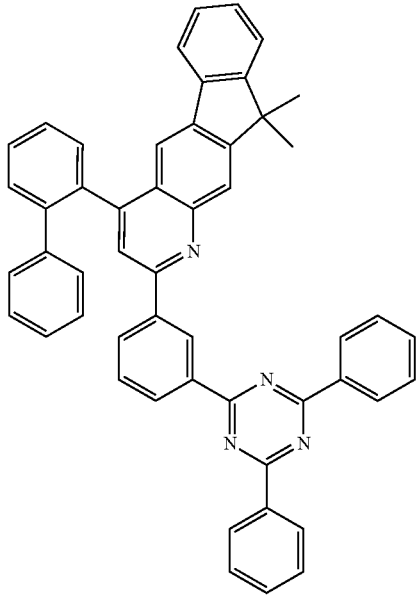
C-121
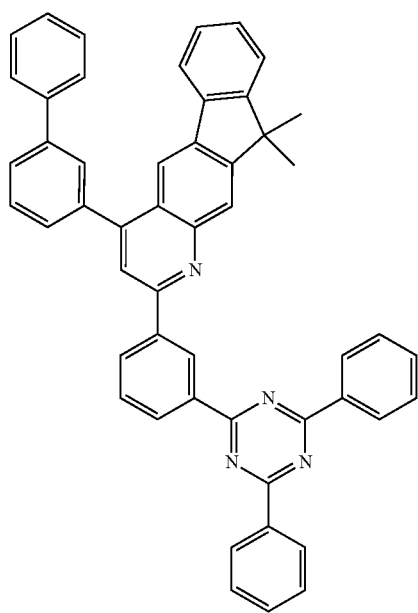
C-123
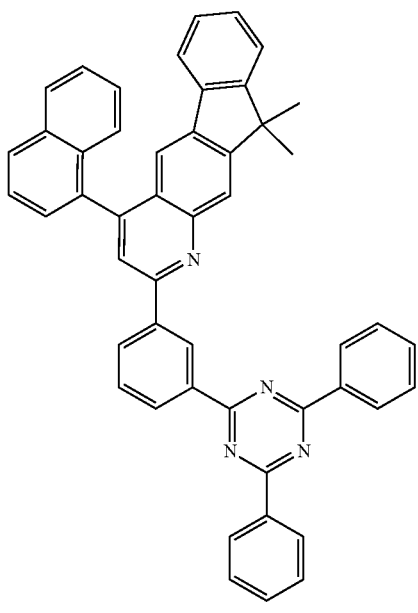

C-124
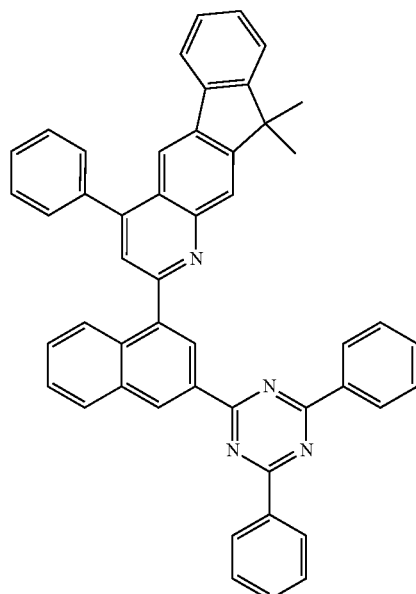
C-126
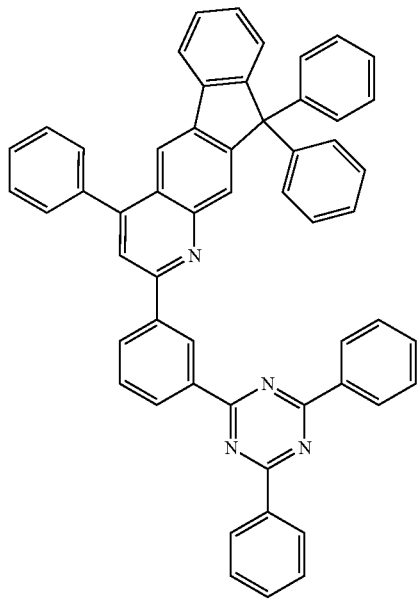
C-125
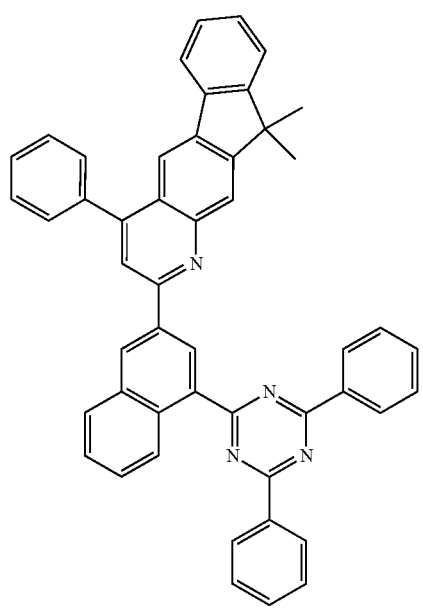
C-127
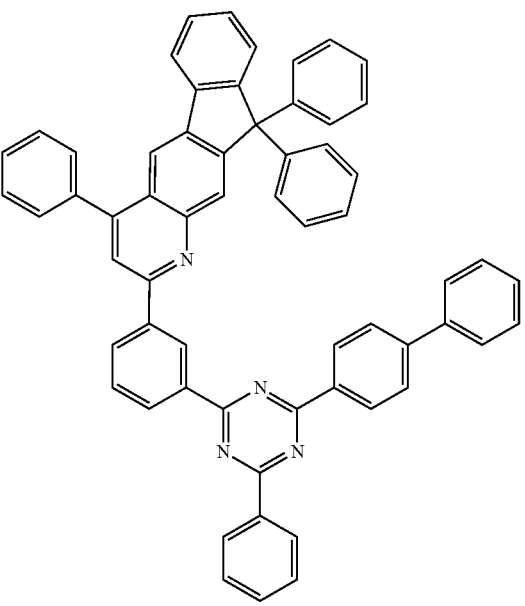

C-128
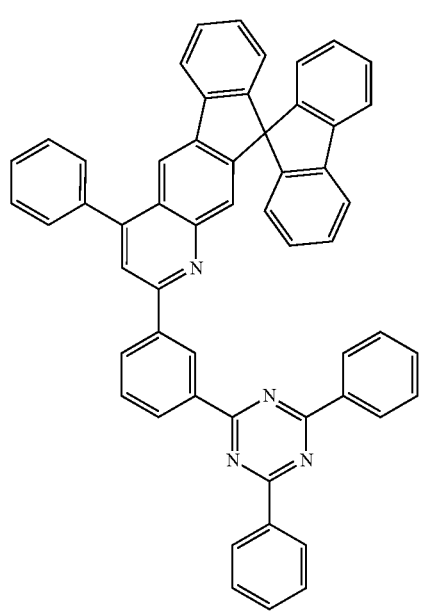
C-129
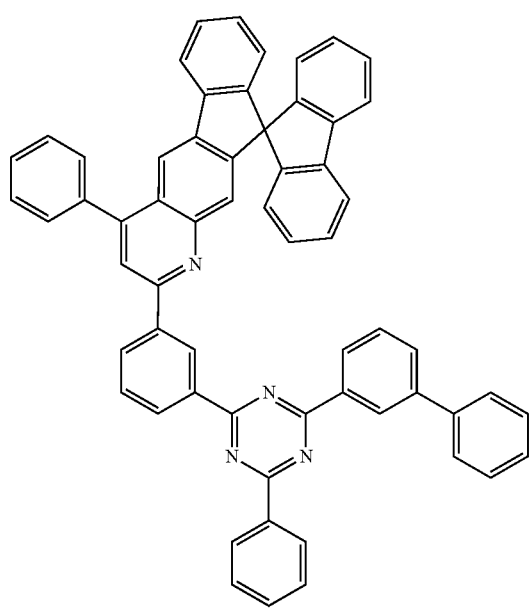
C-130
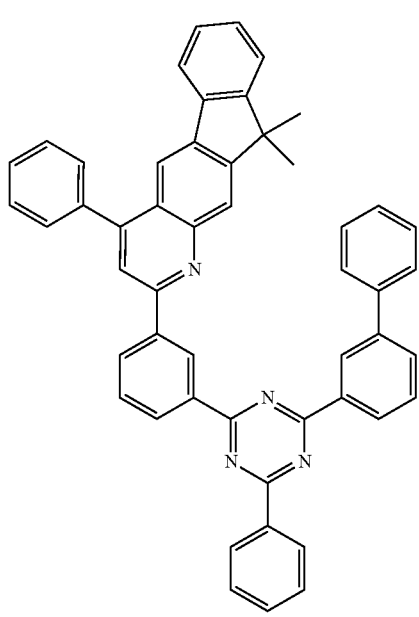
C-131
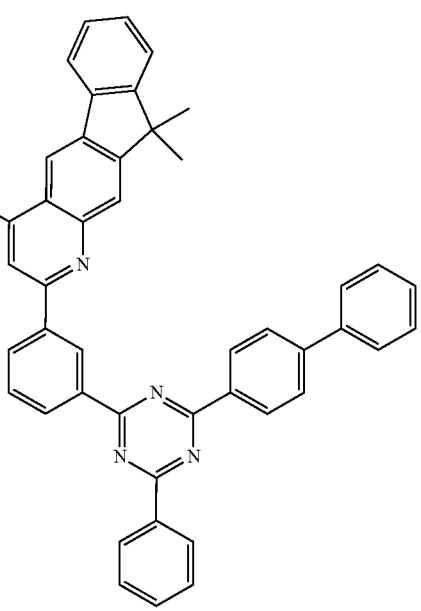

C-132
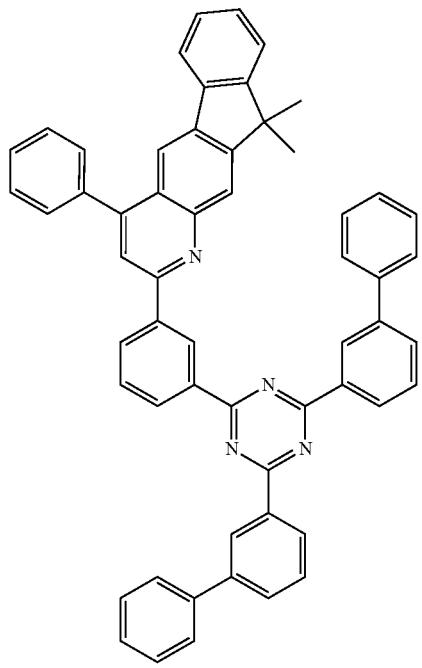
C-134
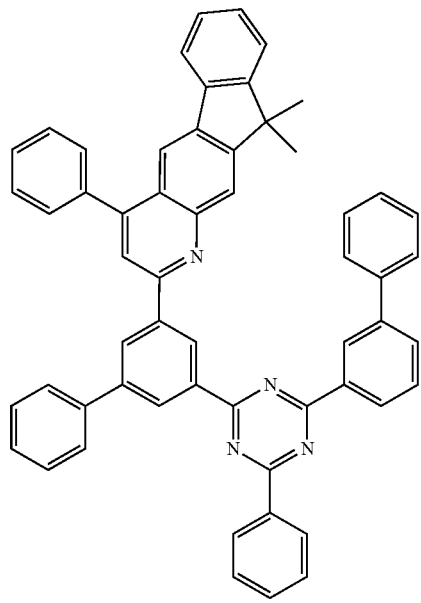
C-133
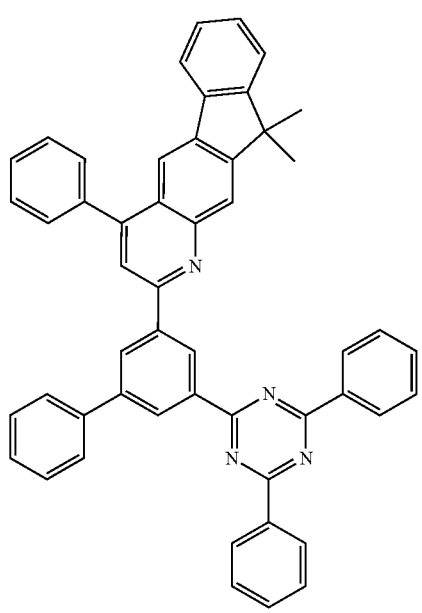
C-135
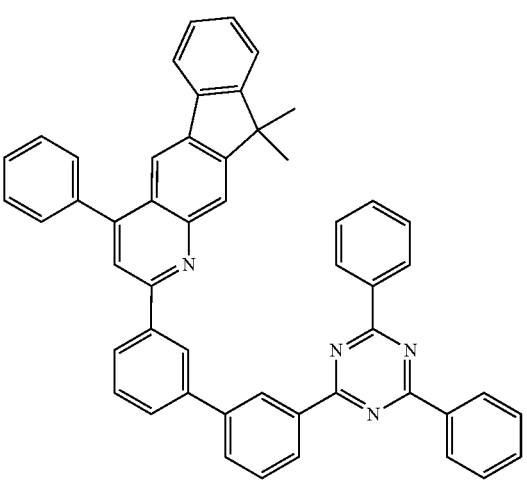

C-136
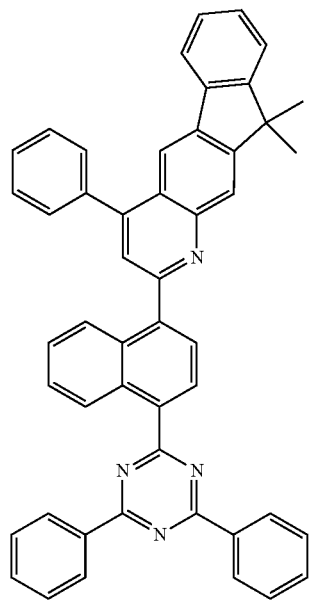
C-138
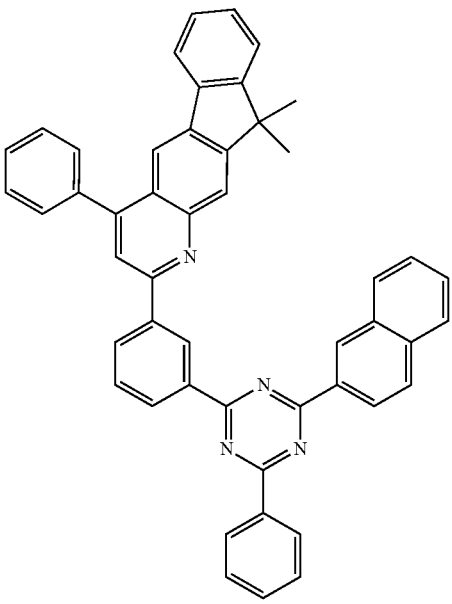
C-137
C-139
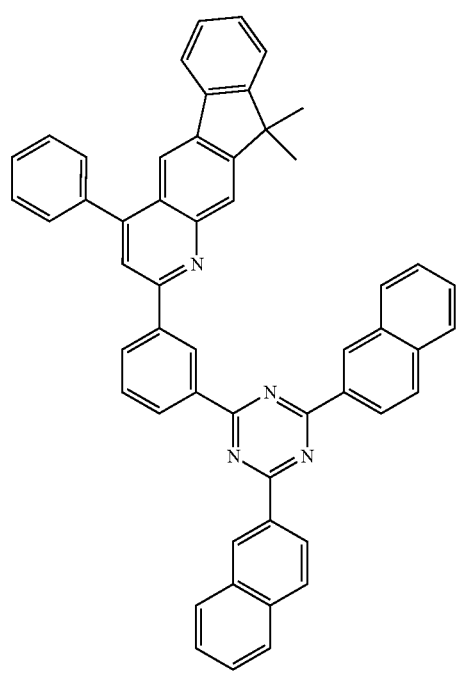

C-140
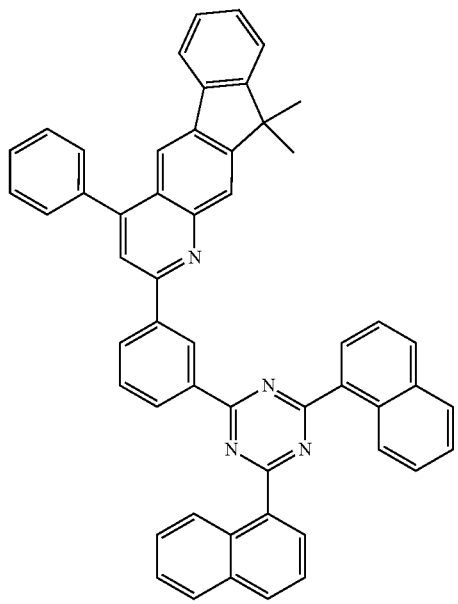
C-141
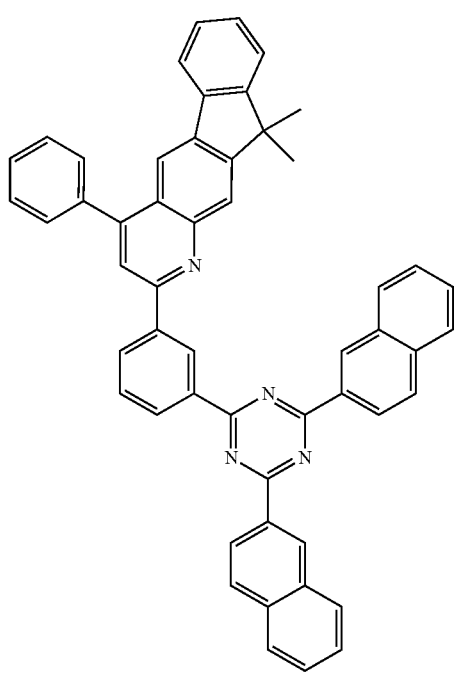
C-142
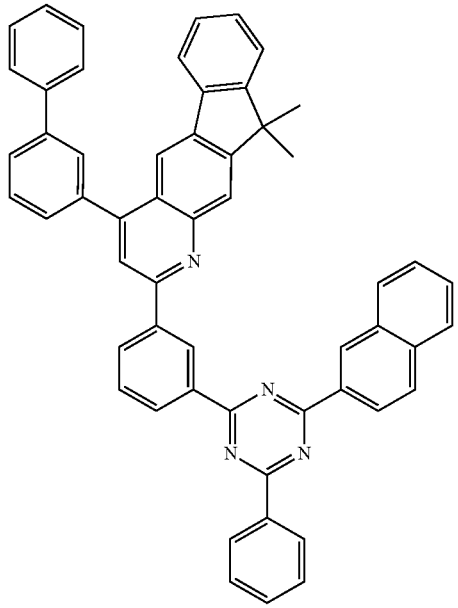
C-143
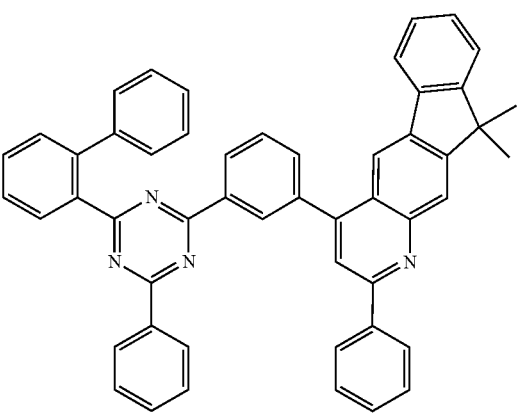
C-144
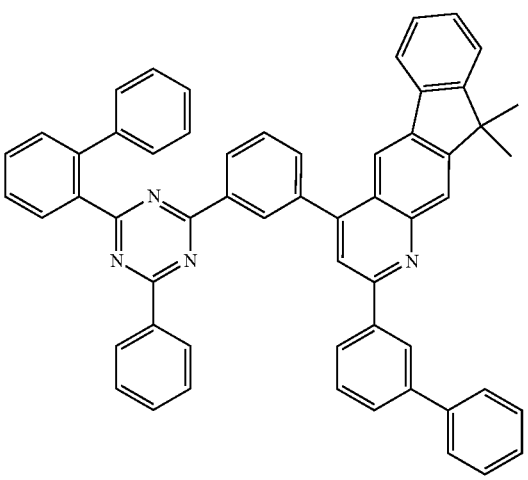

-continued
C-145
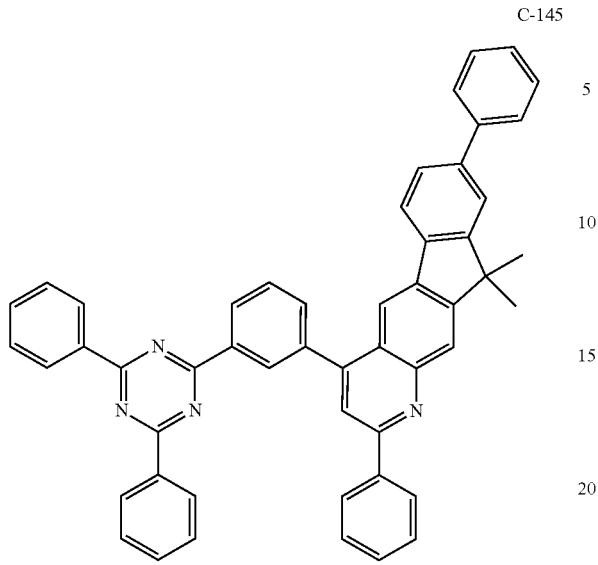
C-146
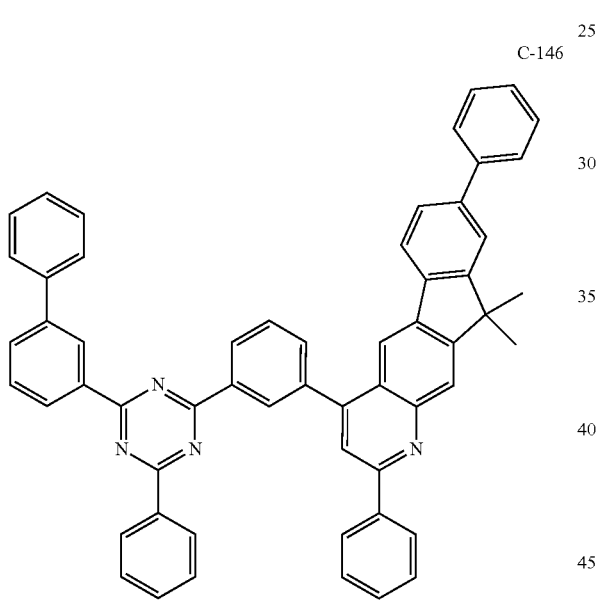
C-147
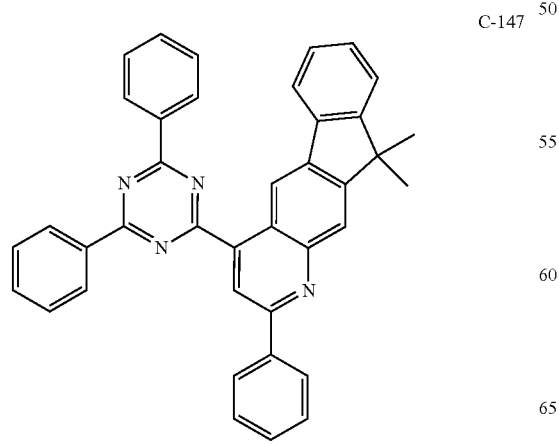
-continued
C-148
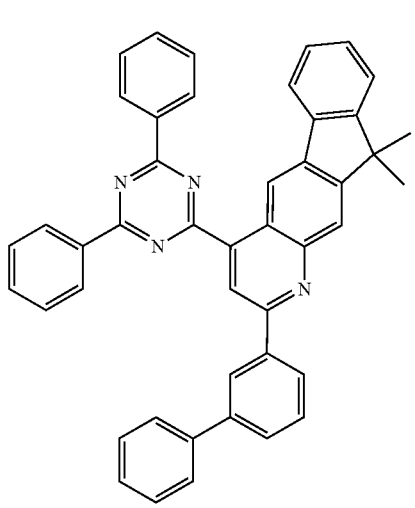
C-149
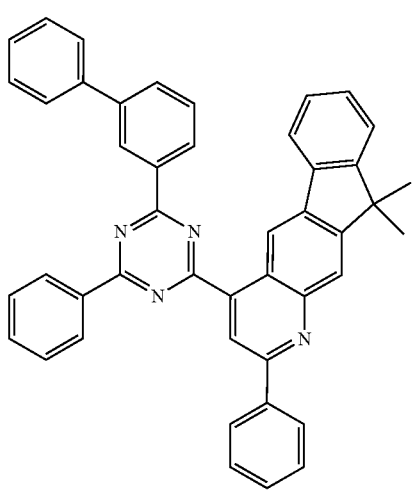
C-150
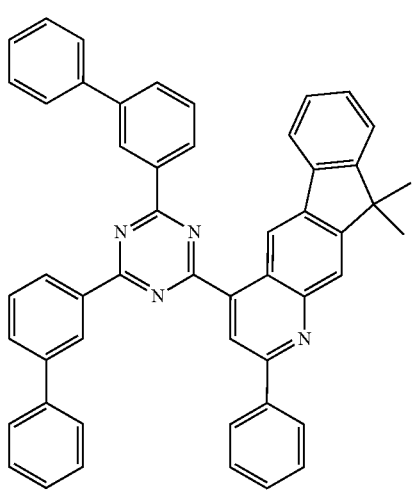

C-151
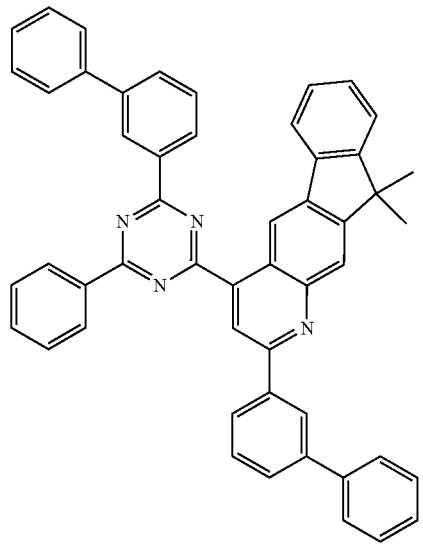
C-152
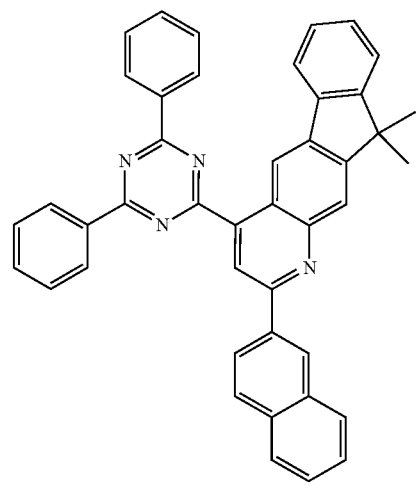
C-153
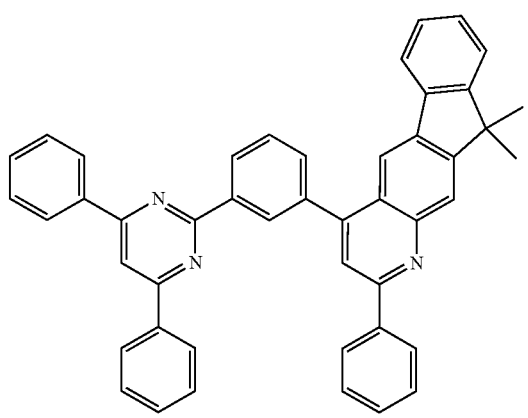
C-154
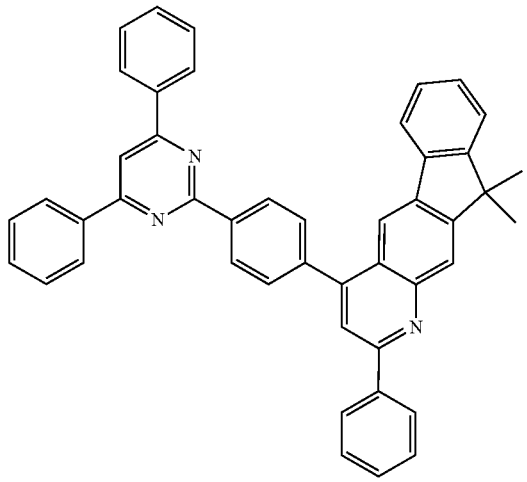
C-155
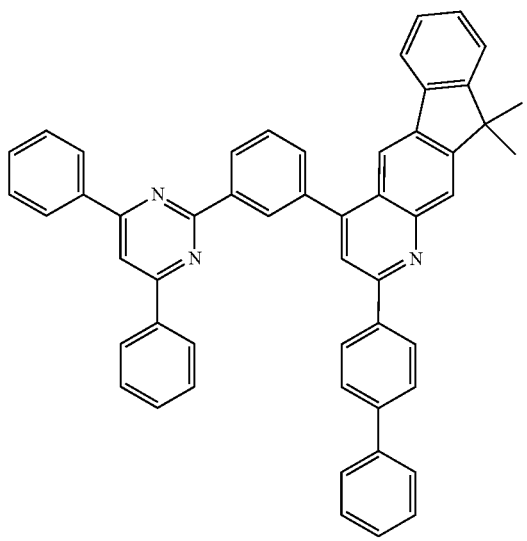
C-156
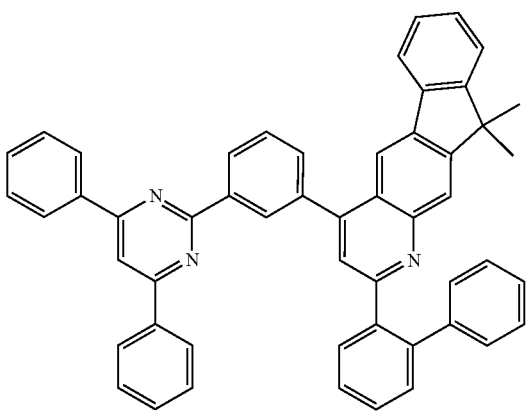

C-157
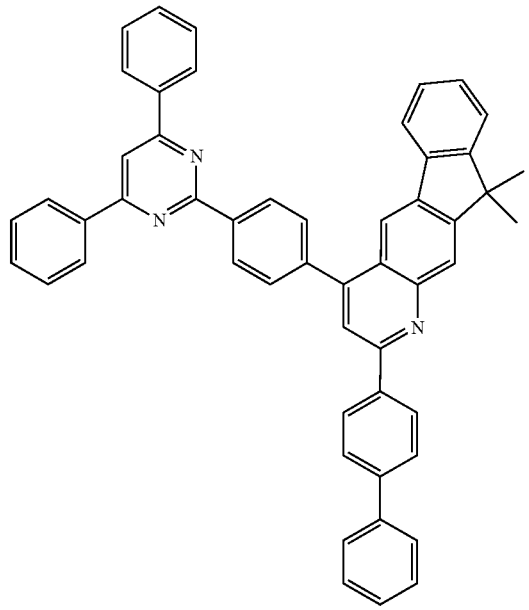
C-158
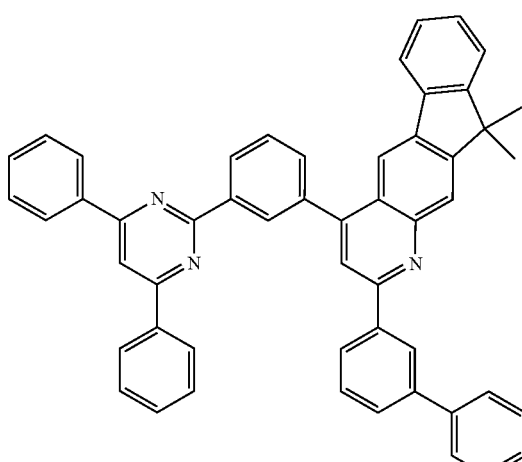
C-159
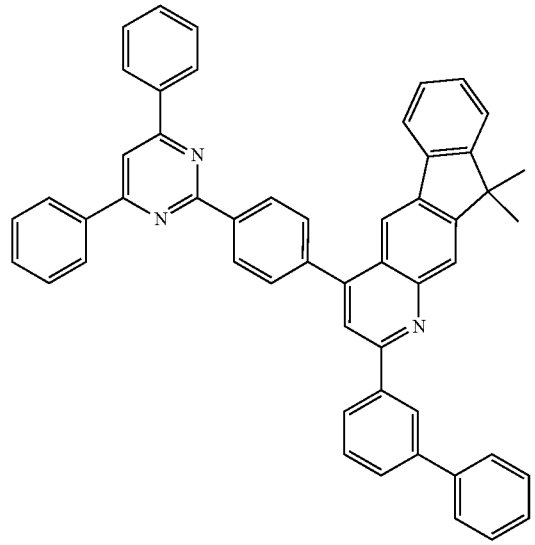
C-160
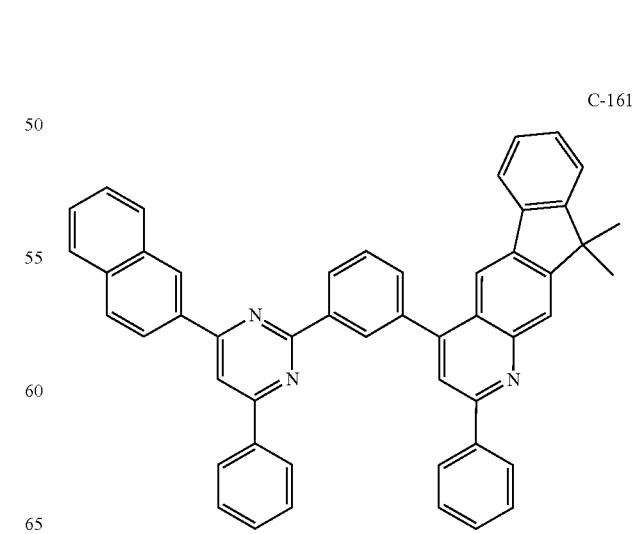
C-161

C-162
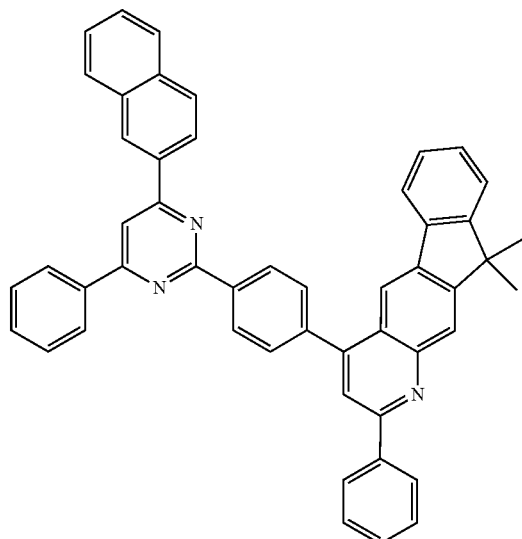
C-163
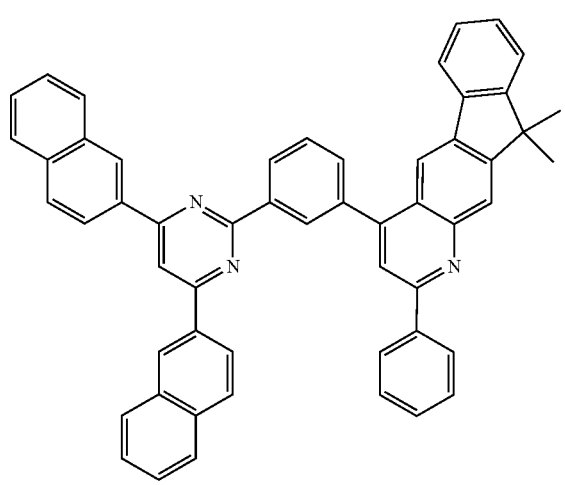
C-164
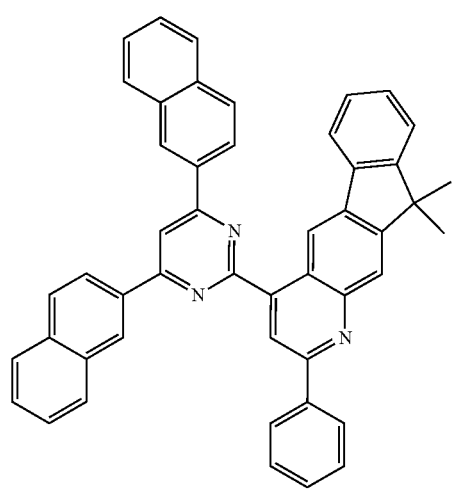
C-165
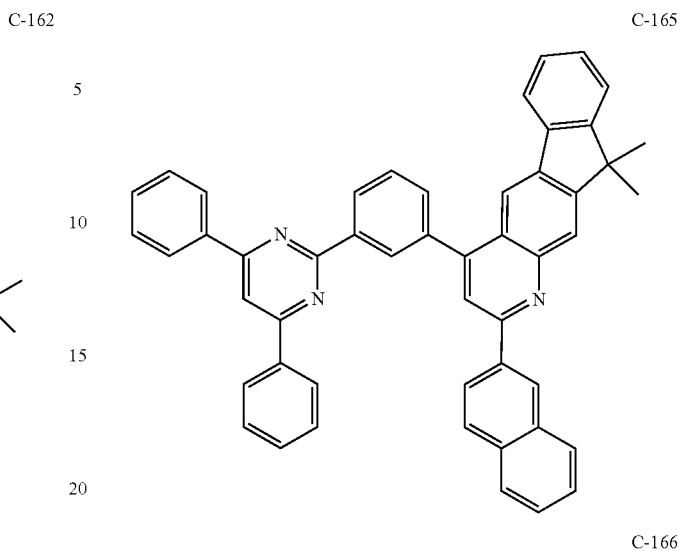
C-166
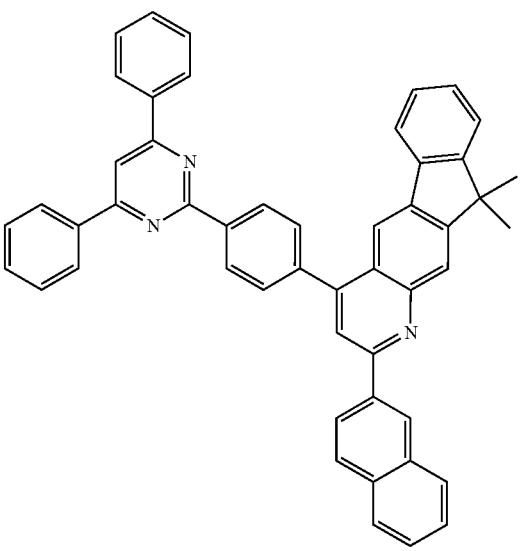
C-167
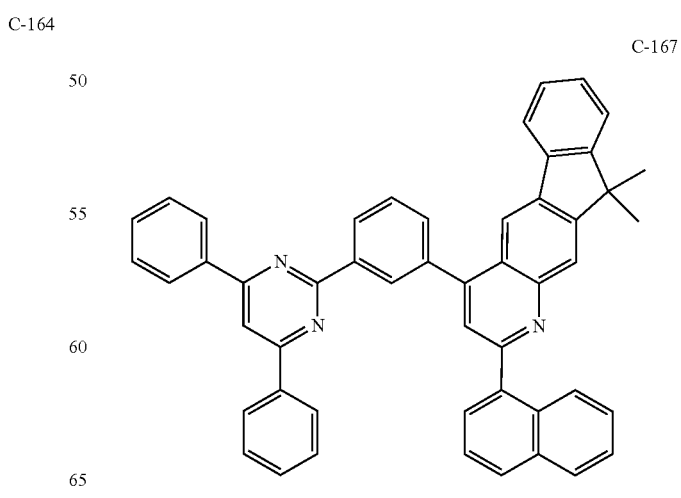

C-168
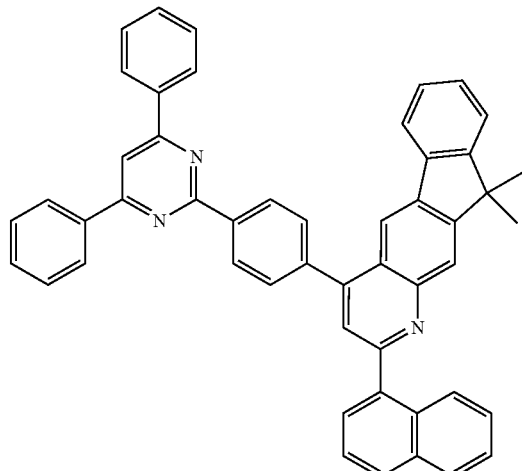
C-169
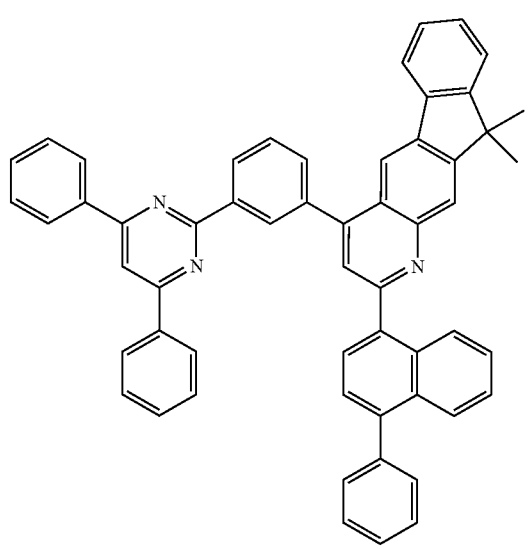
C-170
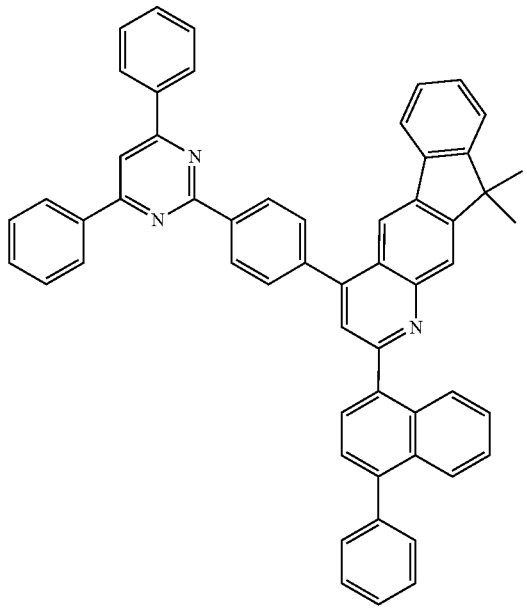
C-171
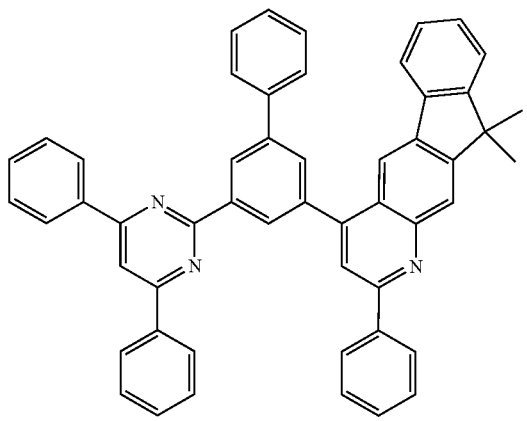
C-172
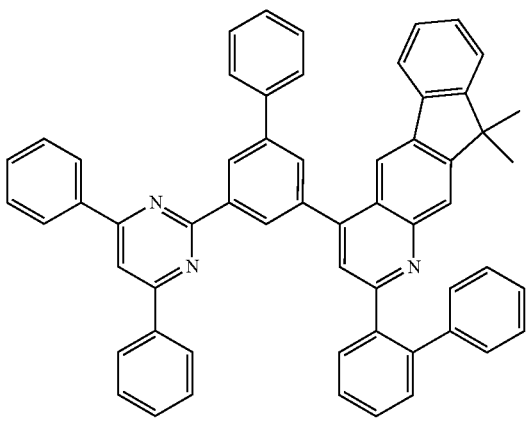

C-173
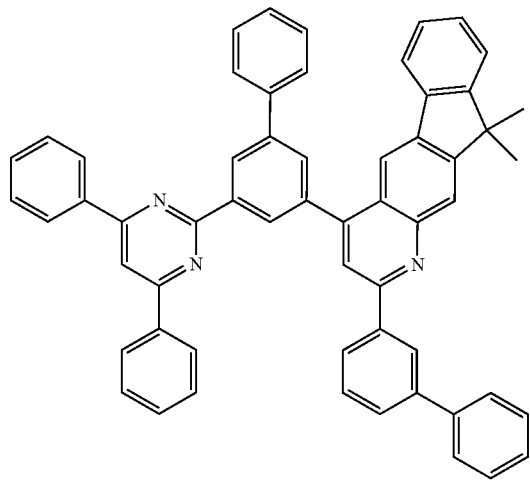
C-176
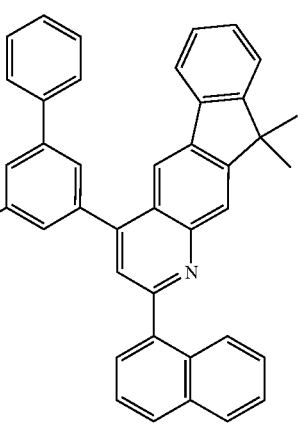
C-174
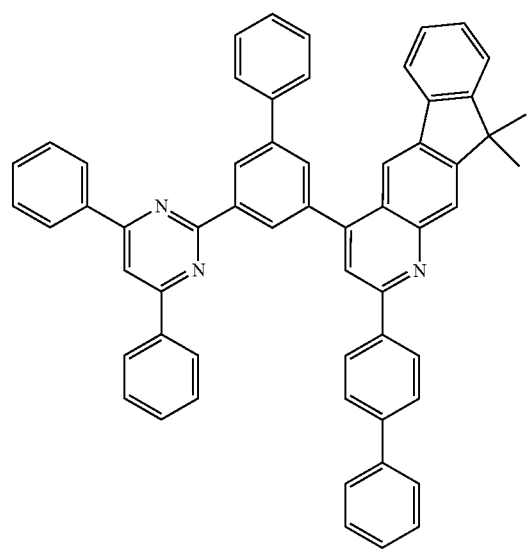
C-177
C-175
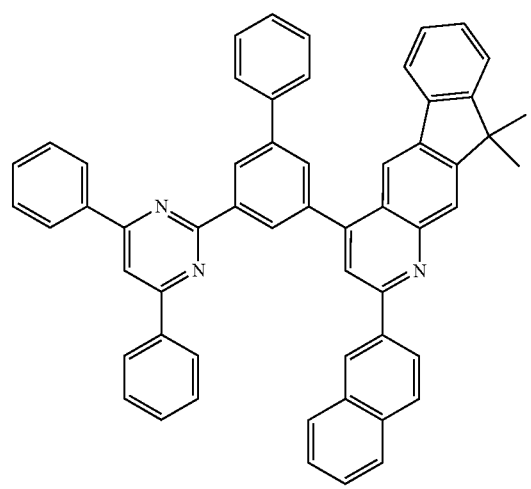
C-178
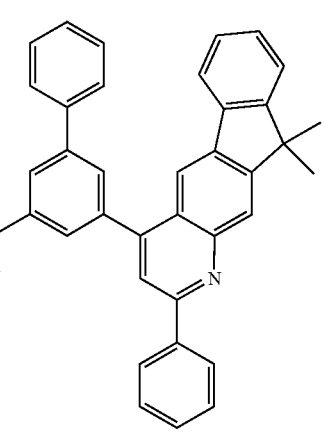

C-179
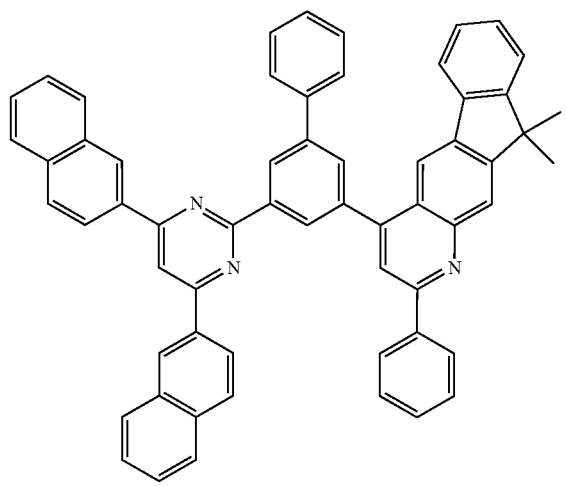
C-180
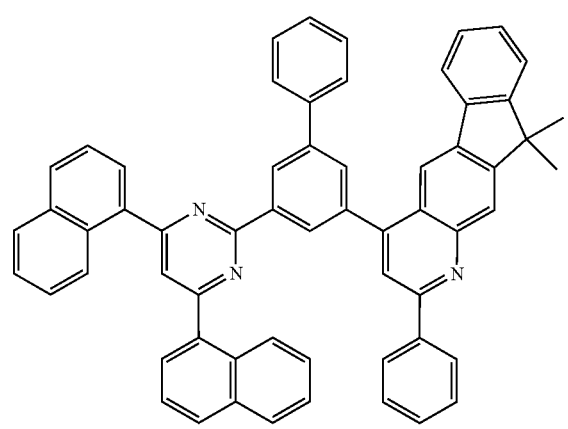
C-181
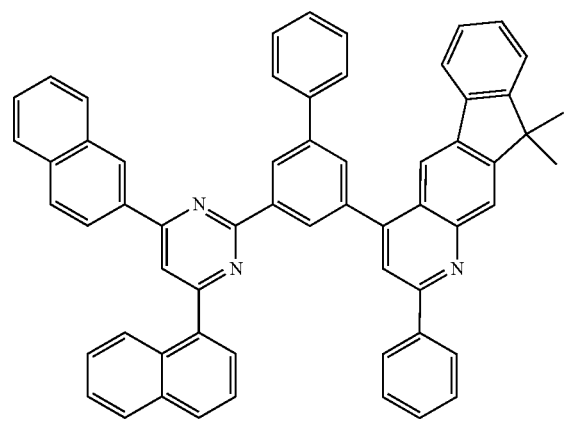
C-182
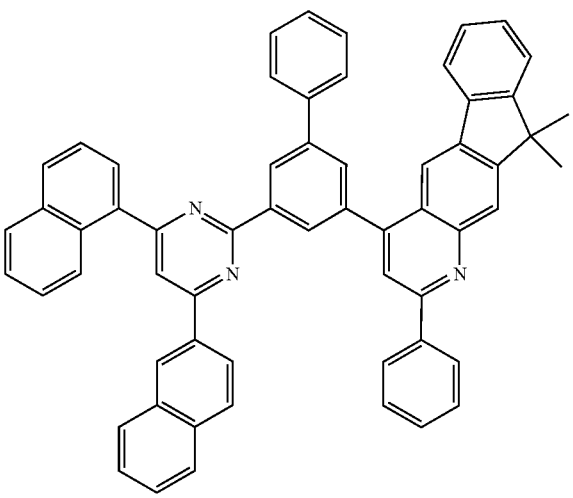
C-183
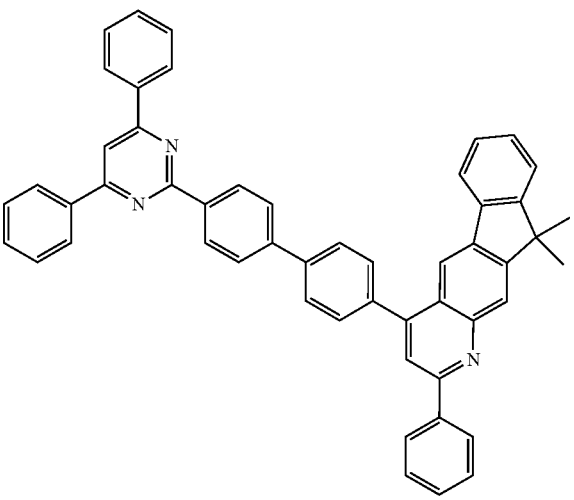
C-184
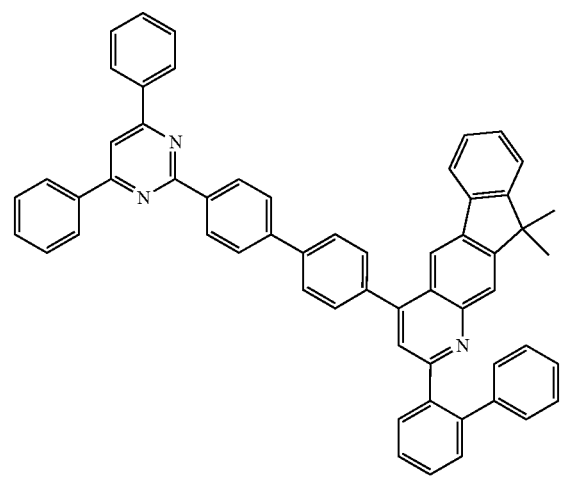

C-185
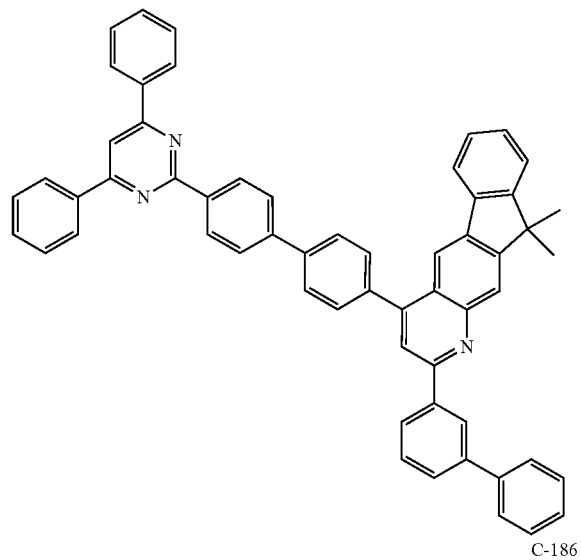
C-188
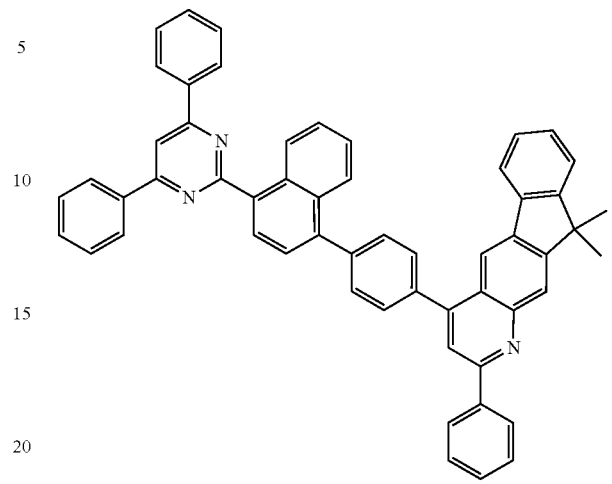
C-186
C-189
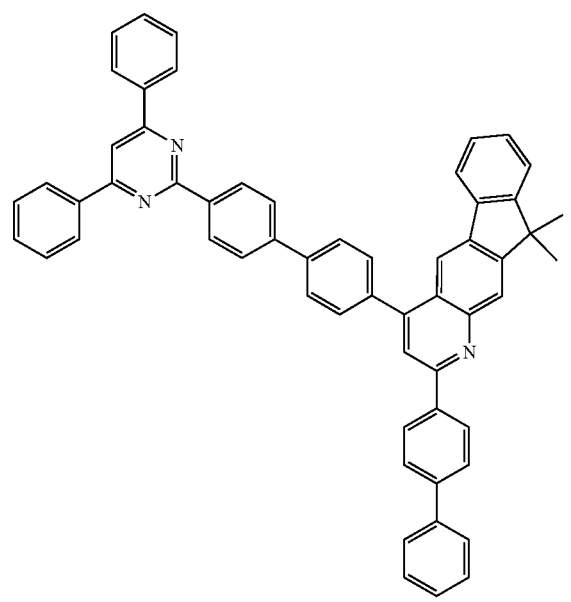
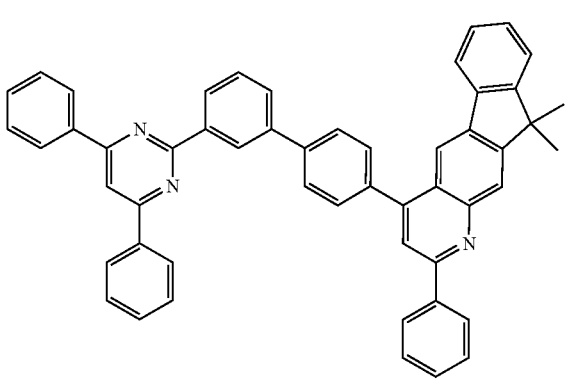
C-187
C-190
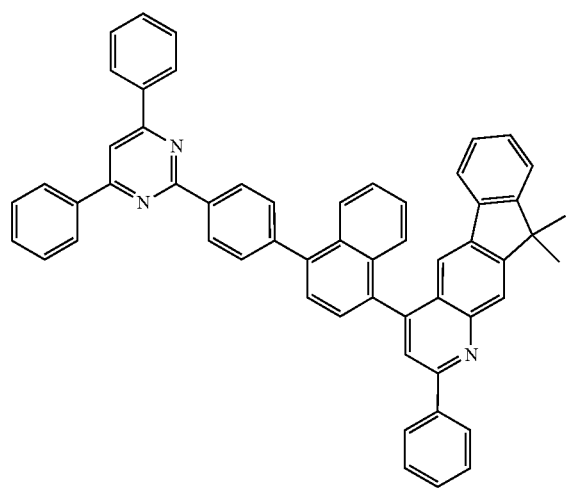

C-191
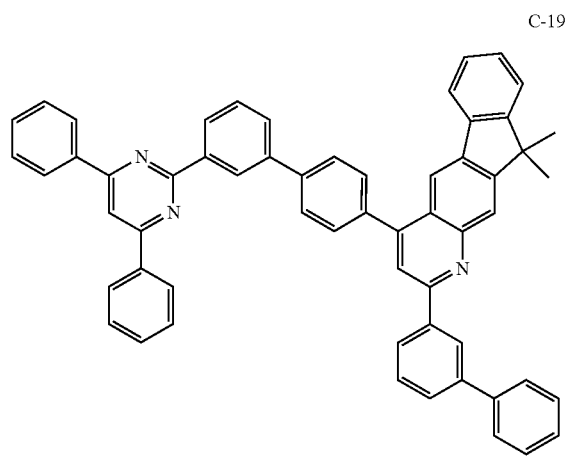
C-192
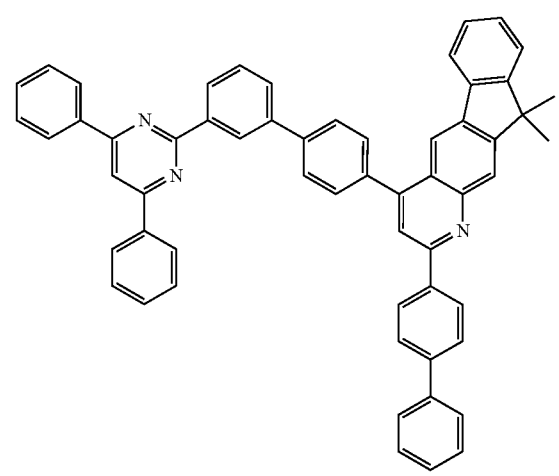
C-193
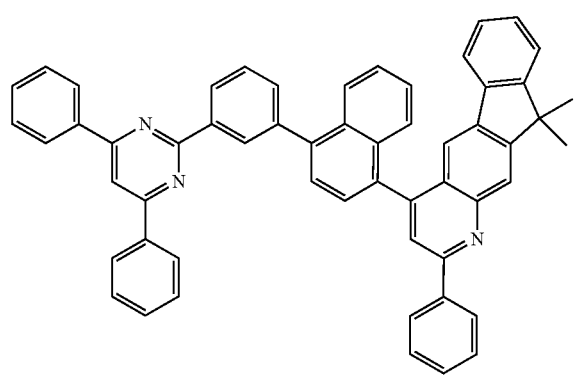
C-194
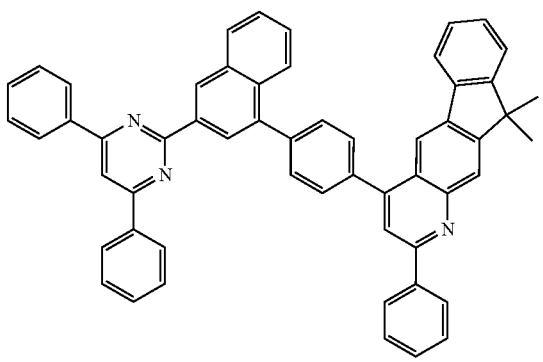
C-195
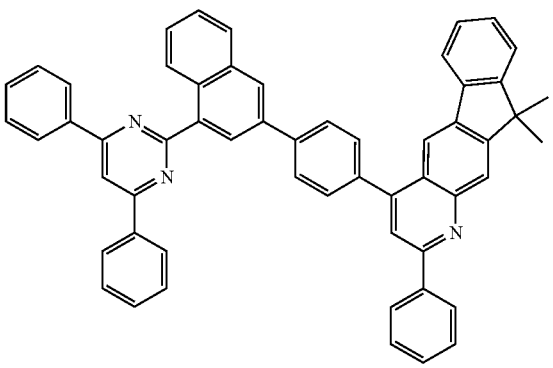
C-196
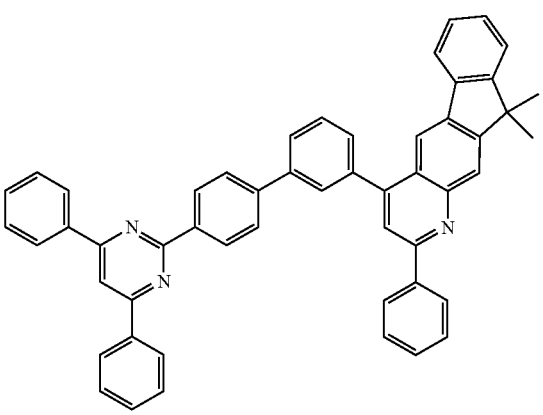
C-197
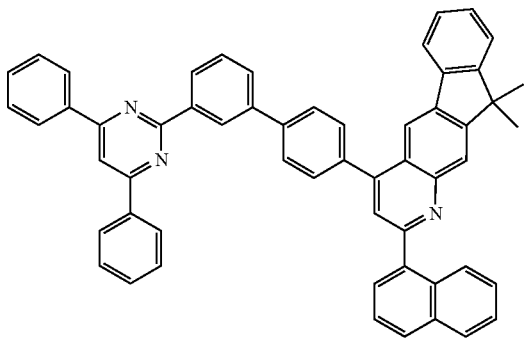

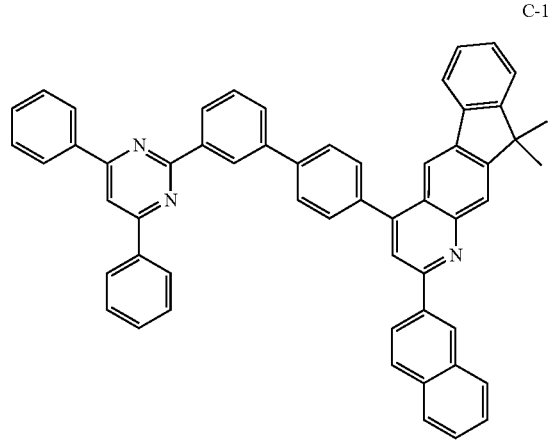
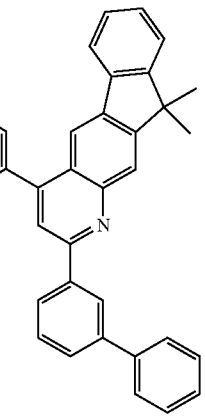
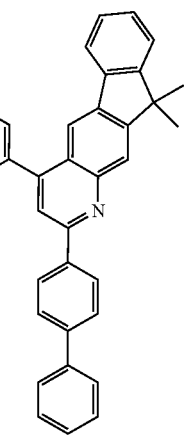
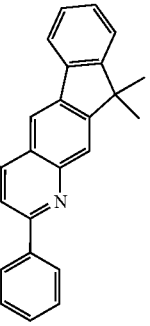
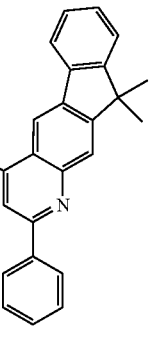

C-205
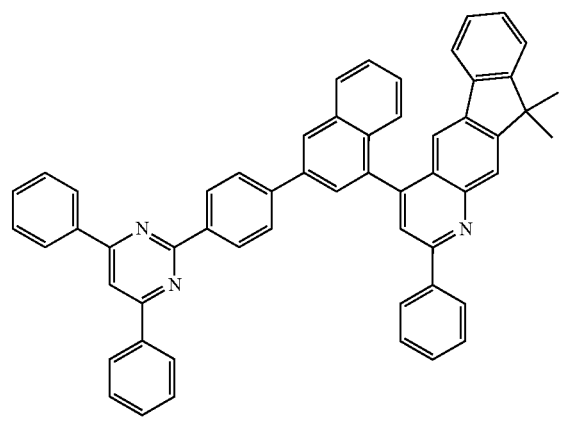
C-206
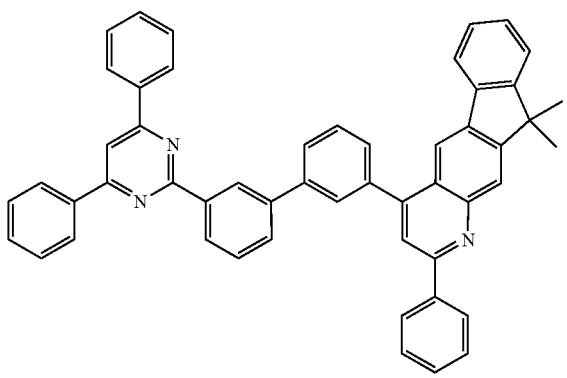
C-207
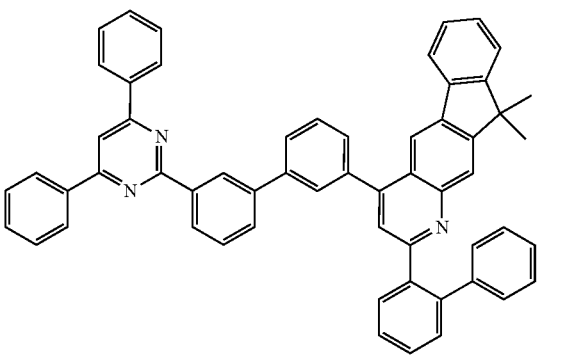
C-208
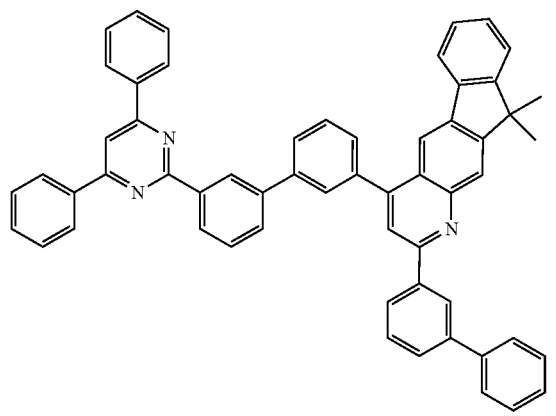
C-209
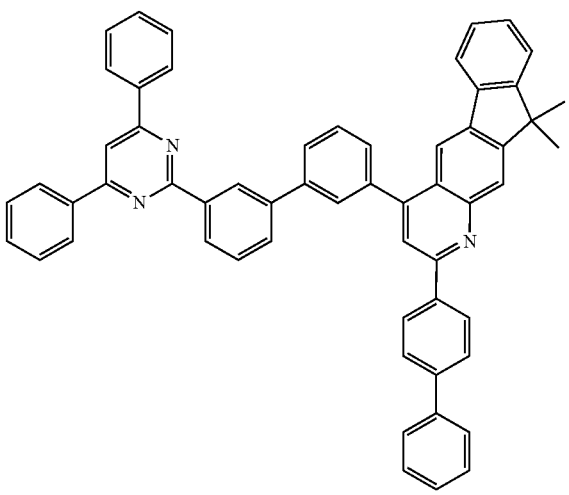
C-210
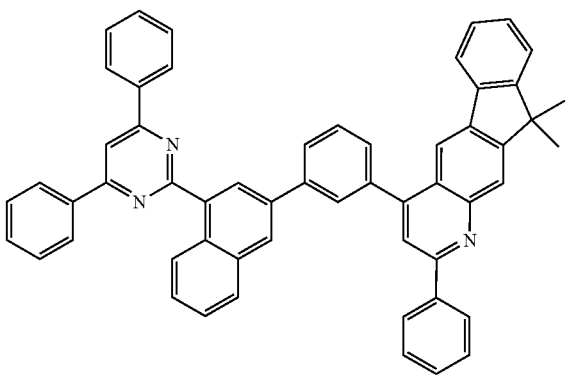
C-211
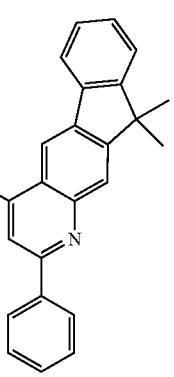

-continued
C-212
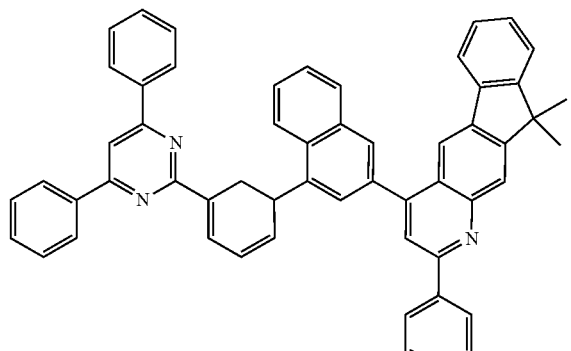
C-213
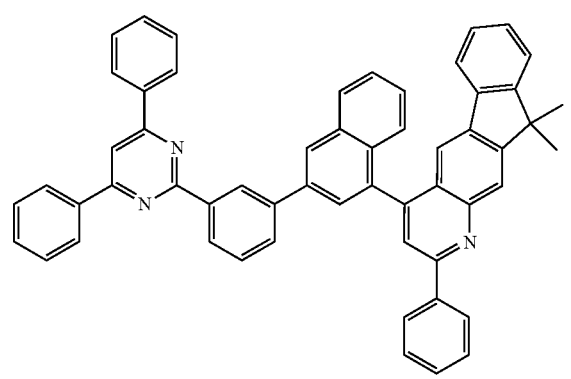
C-214
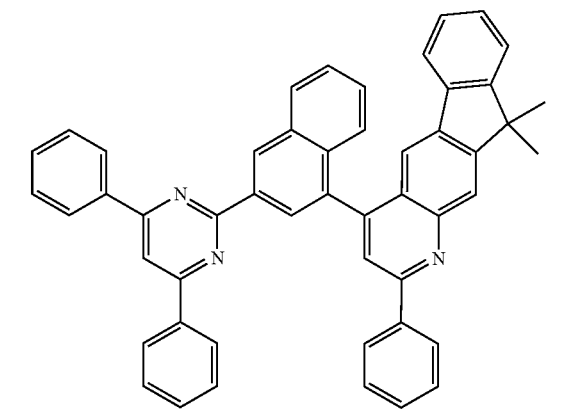
C-215
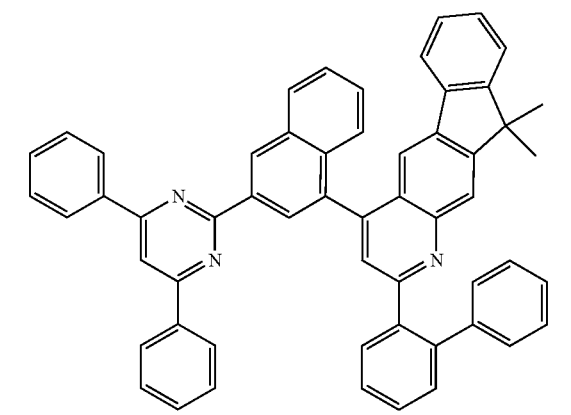
-continued
C-216
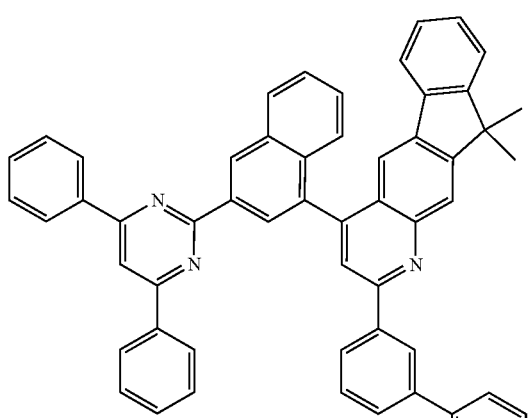
C-217
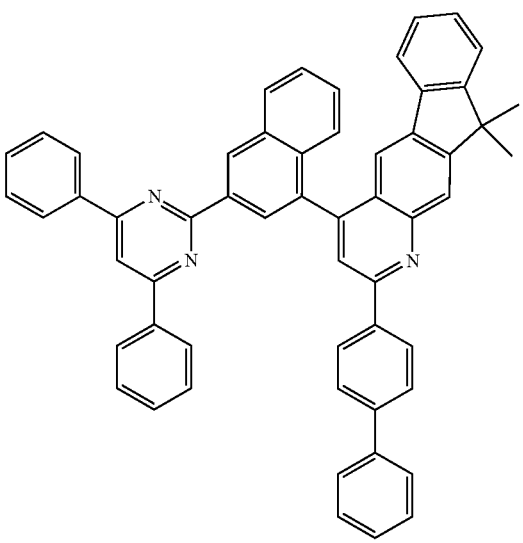
C-218
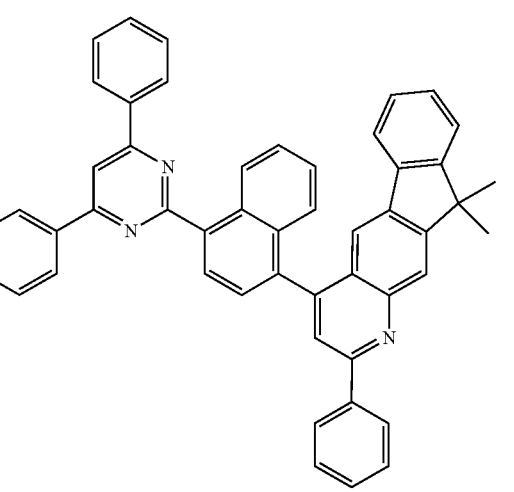

C-219
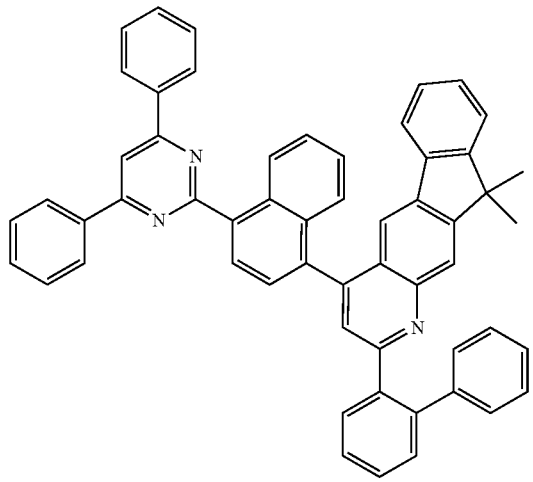
C-220
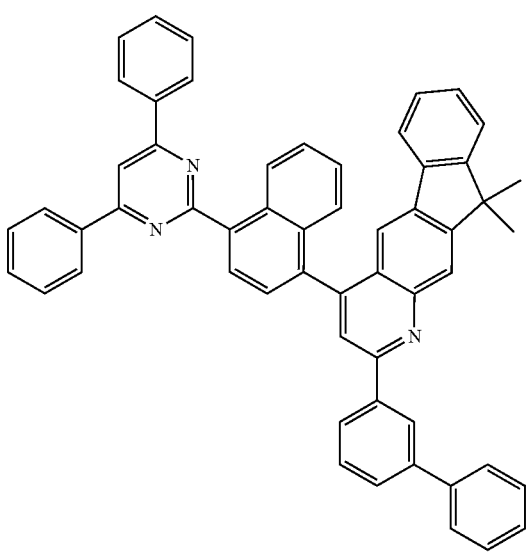
C-221
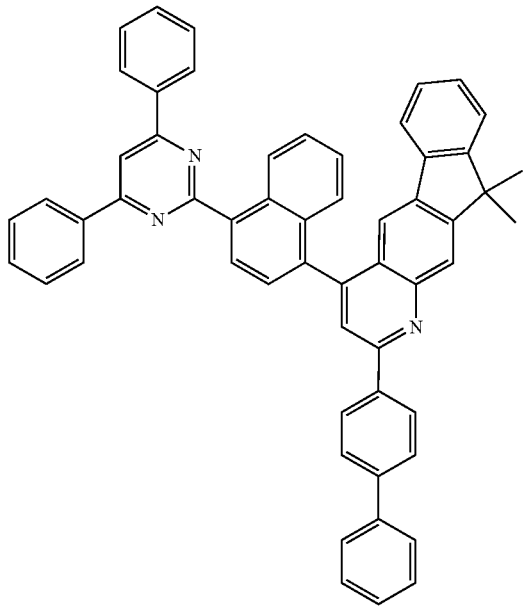
C-222
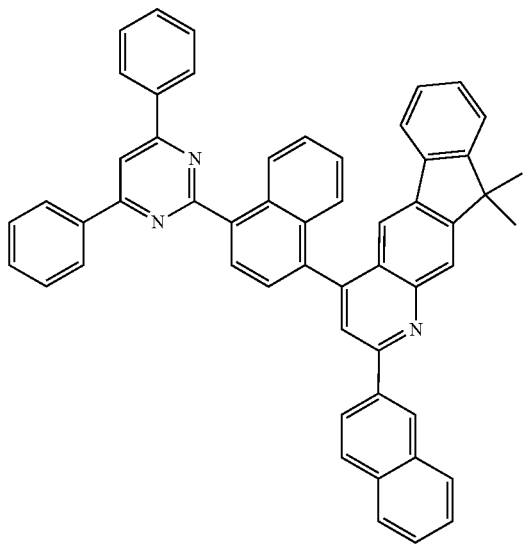
C-223
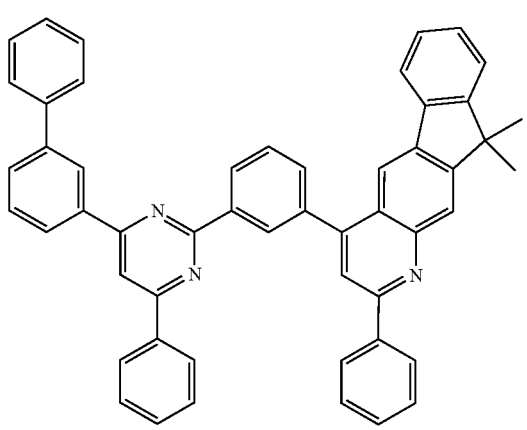

C-224
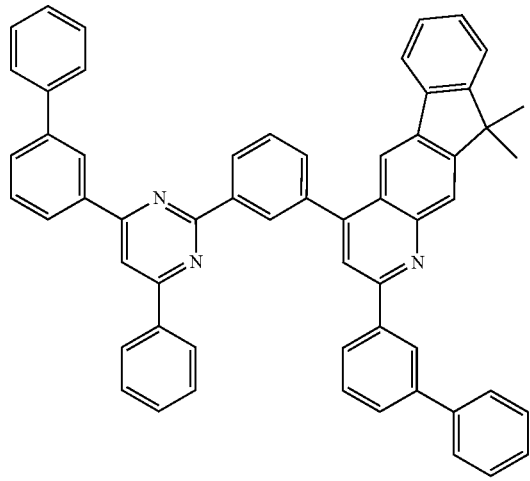
C-225
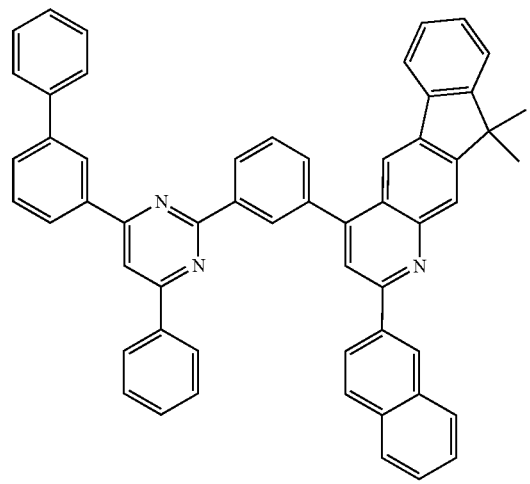
C-226
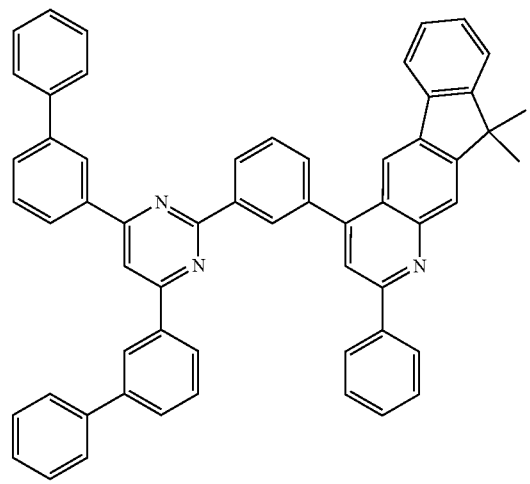
C-227
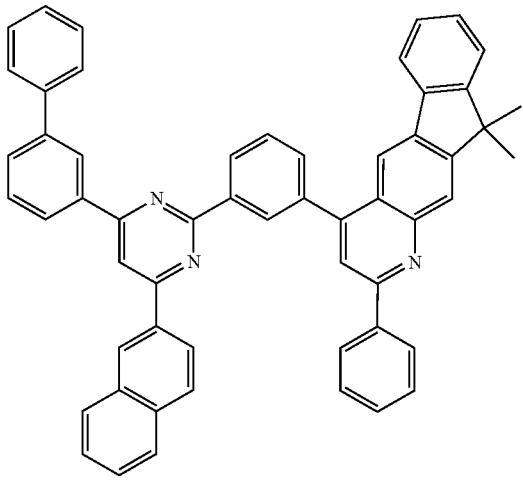
C-228
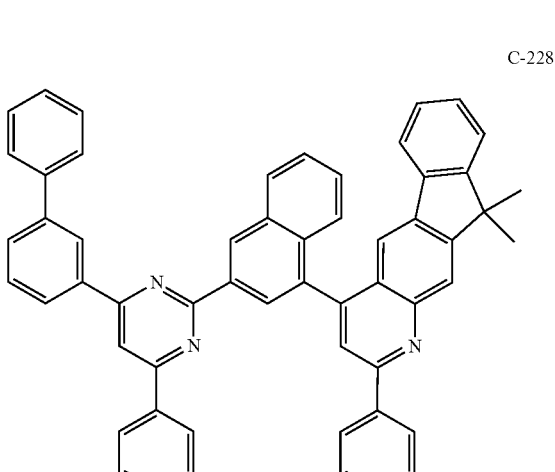
C-229
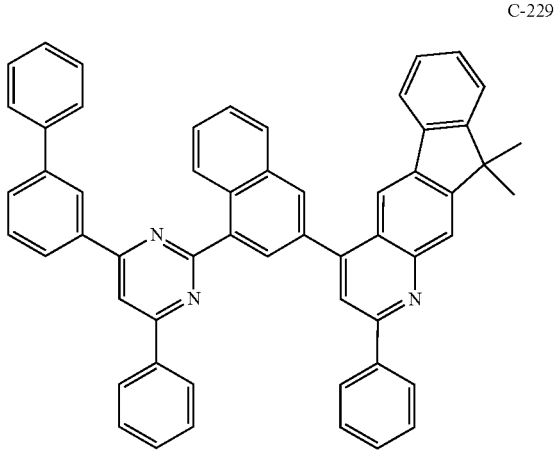

C-230
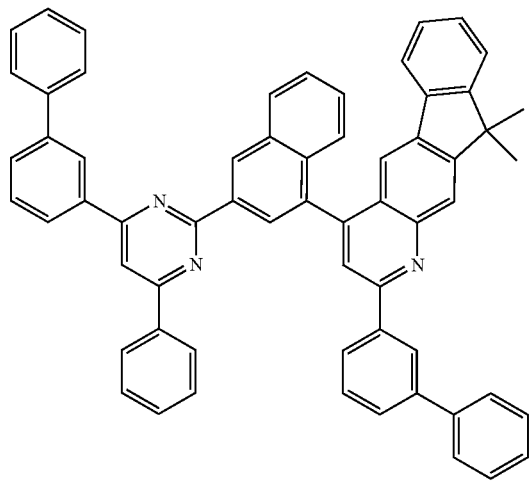
C-233
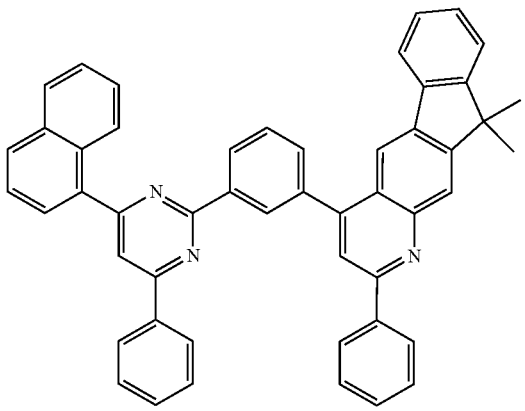
C-231
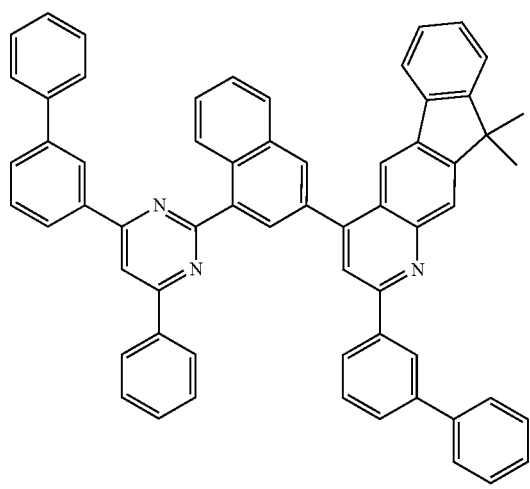
C-234
C-232
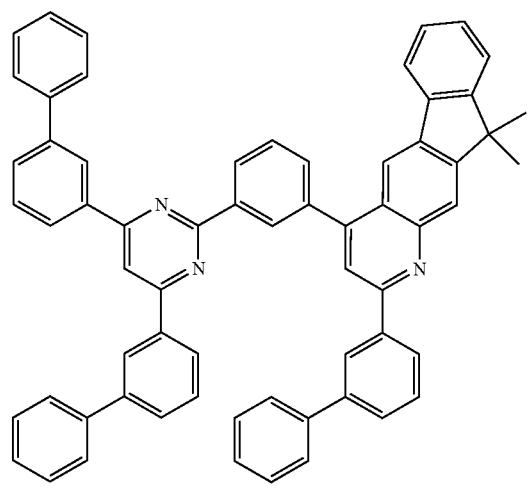
C-235
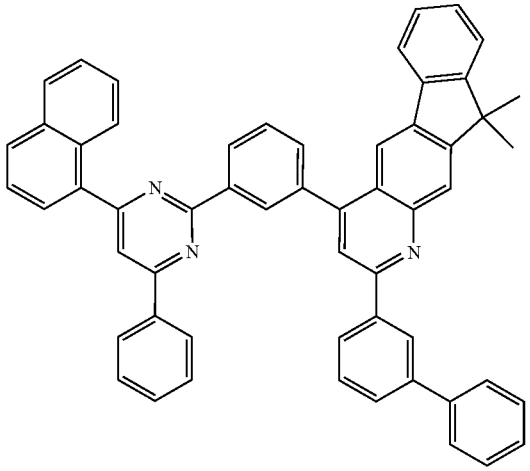

-continued
C-236
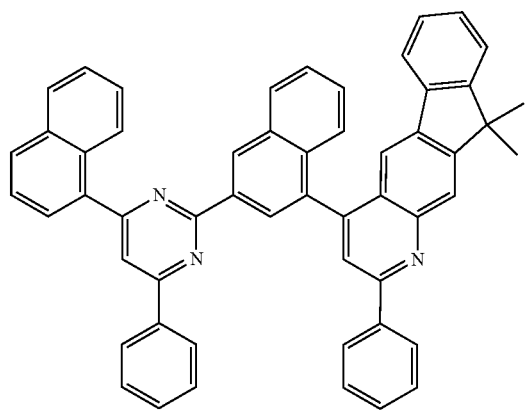
C-237
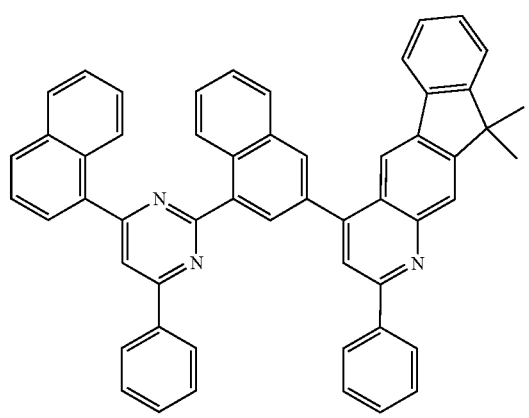
C-238
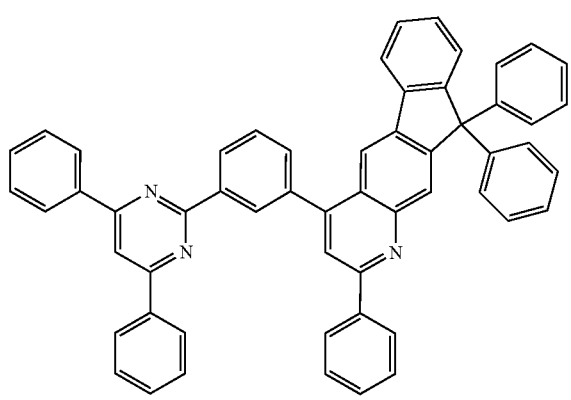
-continued
C-239
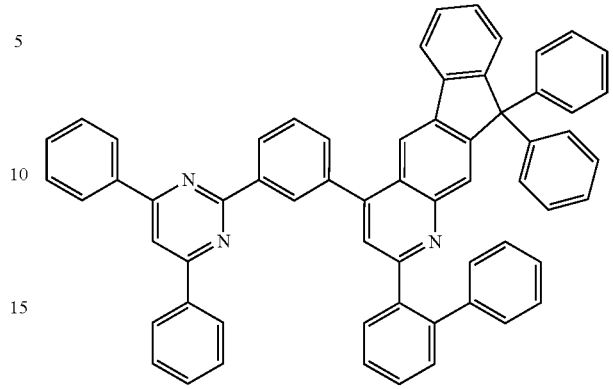
C-240
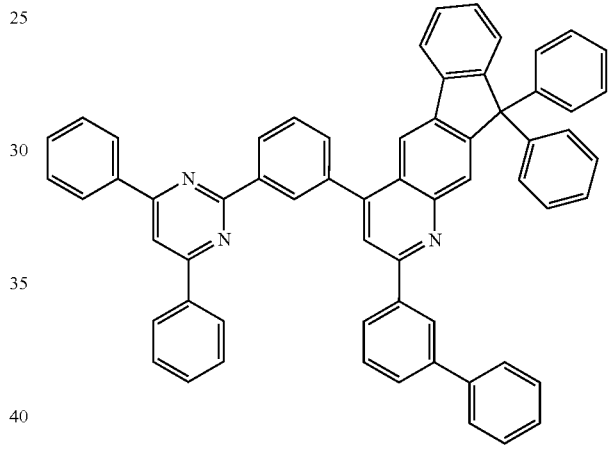
C-241
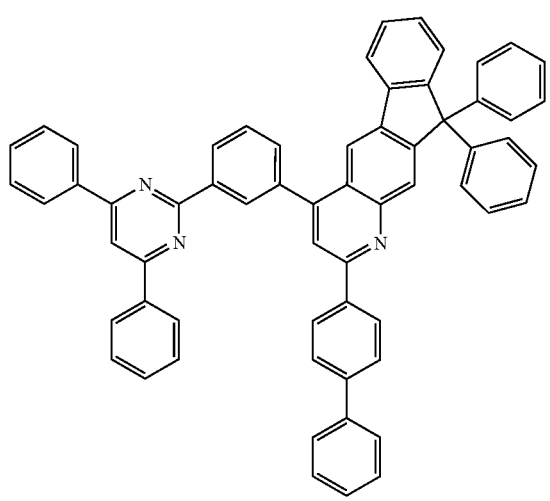

C-242
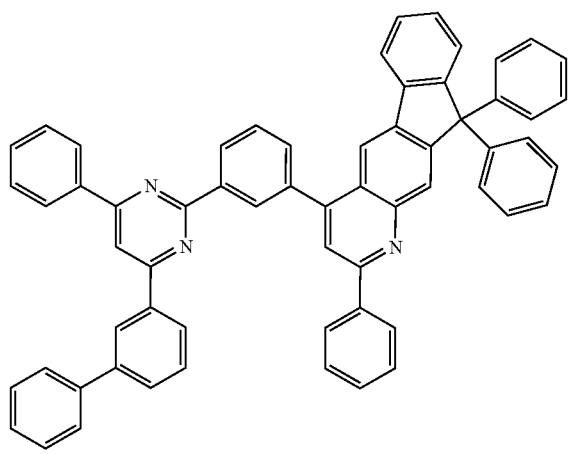
C-243
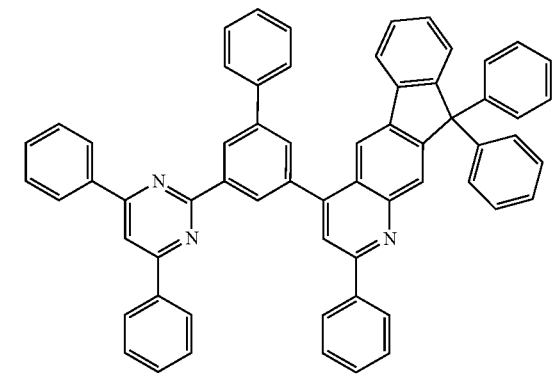
C-244
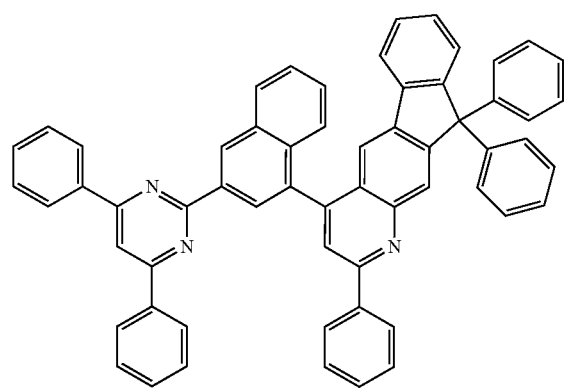
C-245
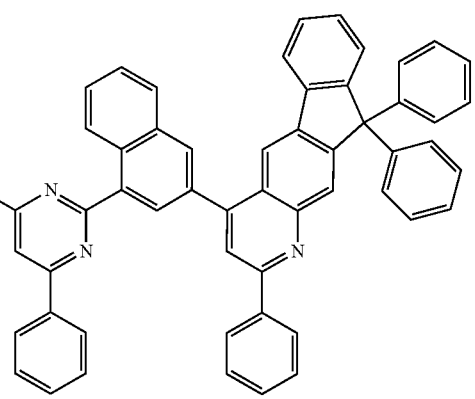
C-246
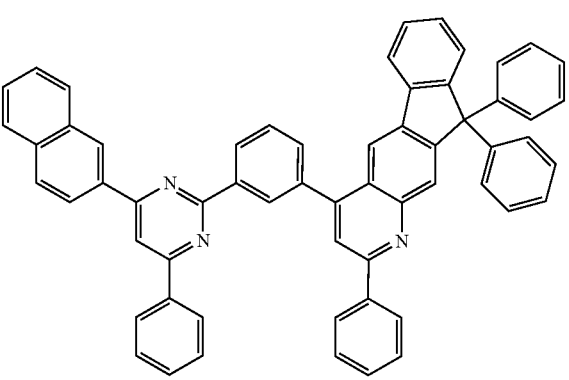
C-247

C-248
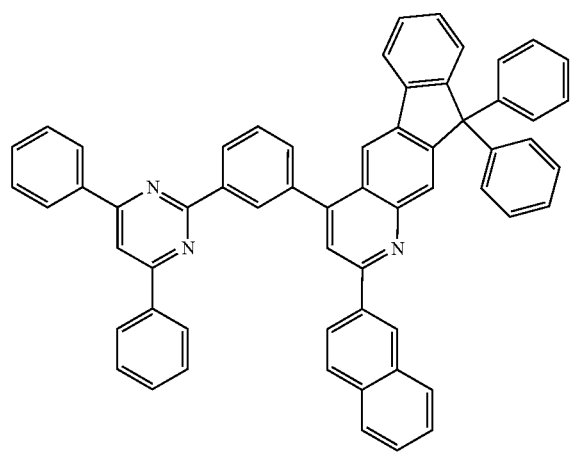
C-249
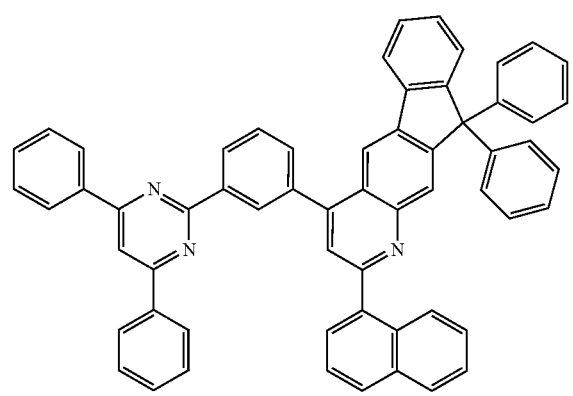
C-250
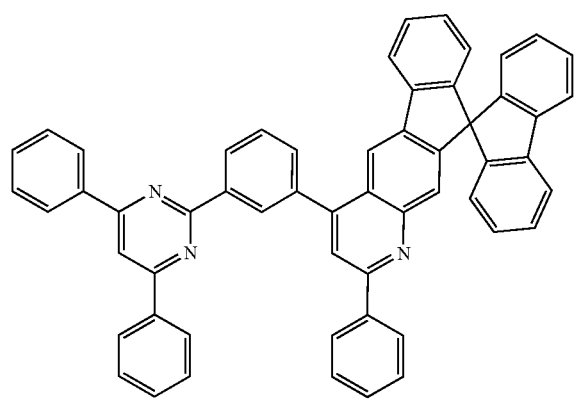
C-251
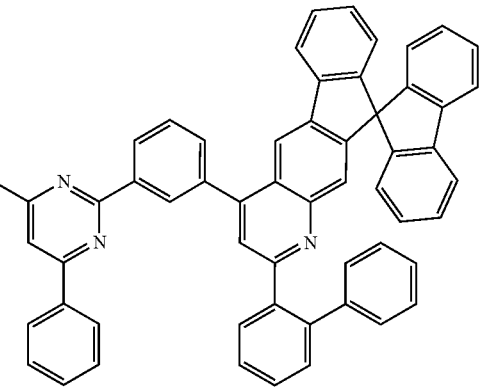
C-252
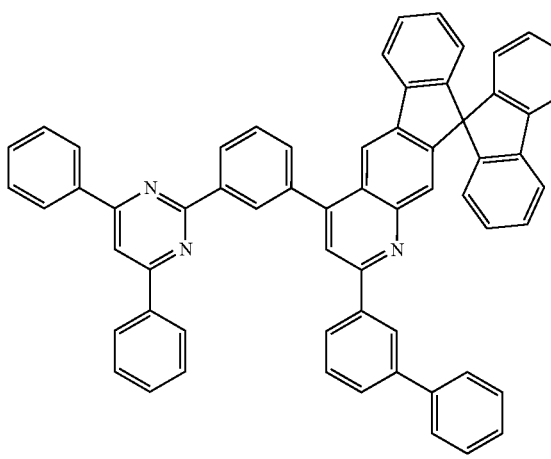
C-253
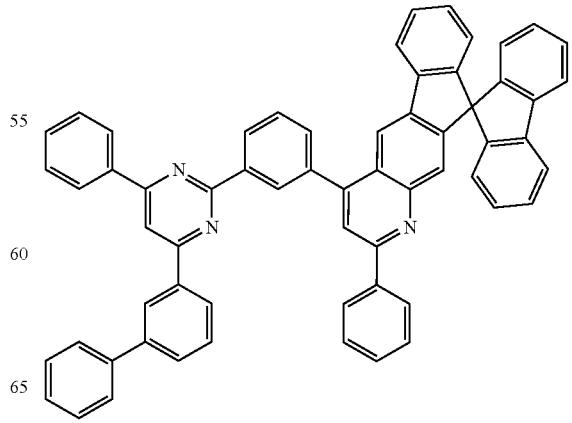

C-254
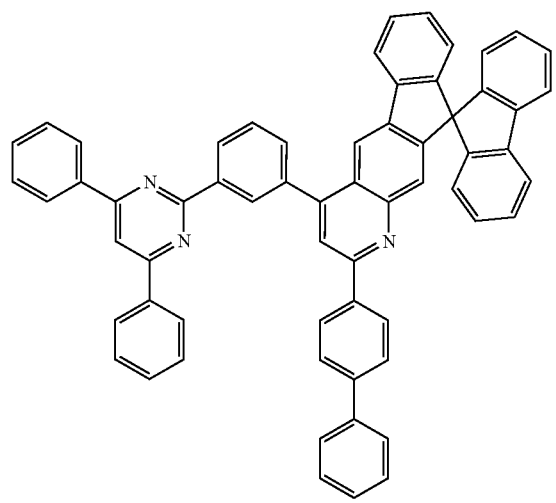
C-255
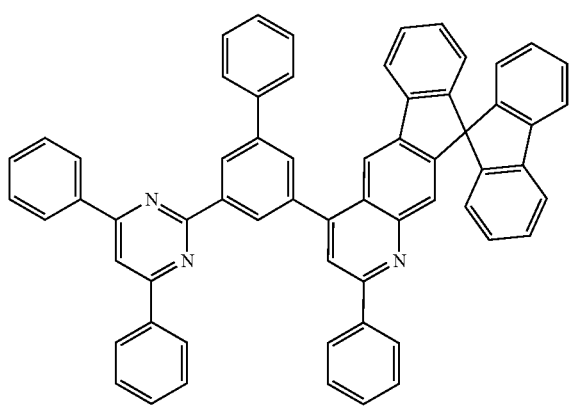
C-256
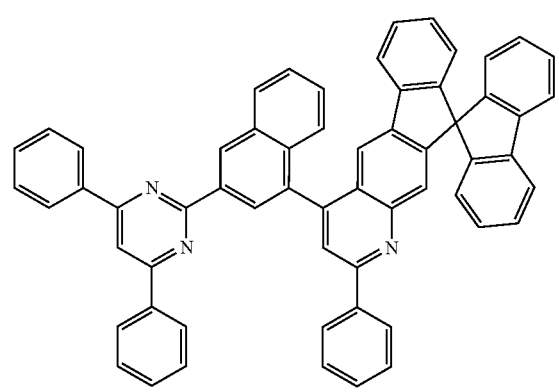
C-257
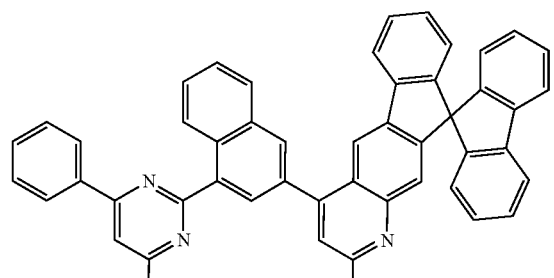
C-258
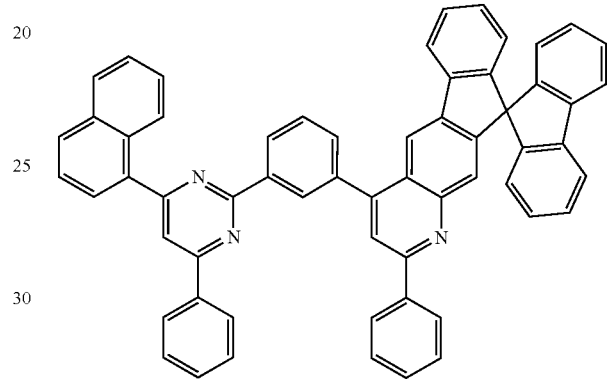
C-259
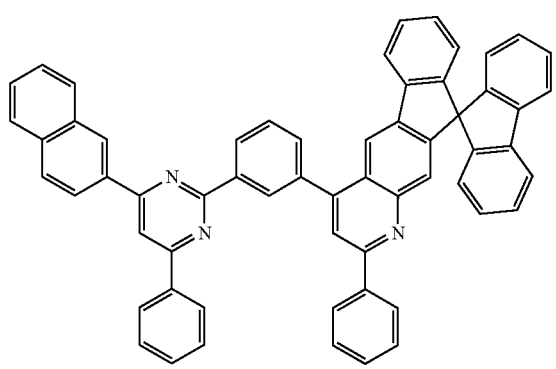
C-260
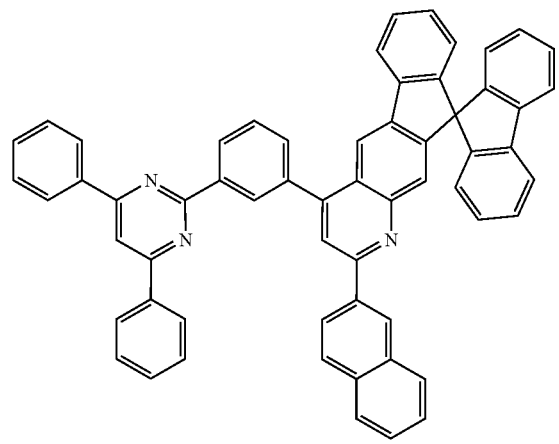

-continued
C-261
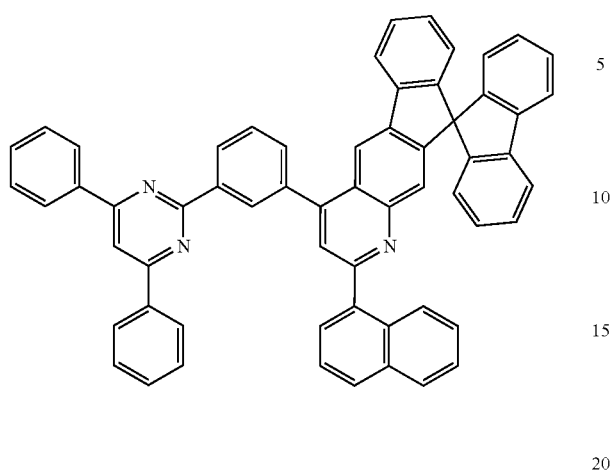
C-262
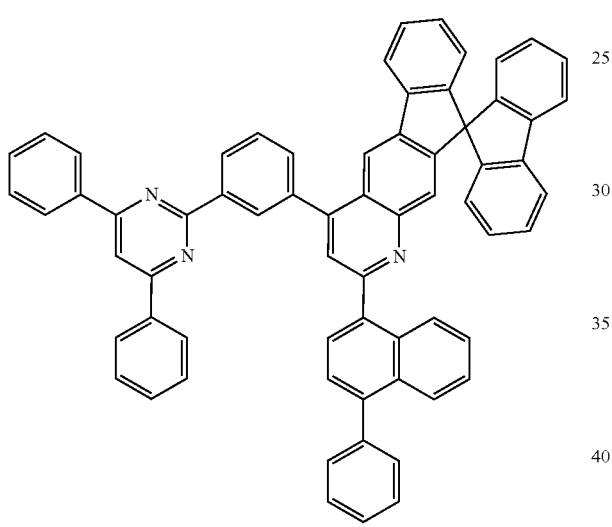
C-263
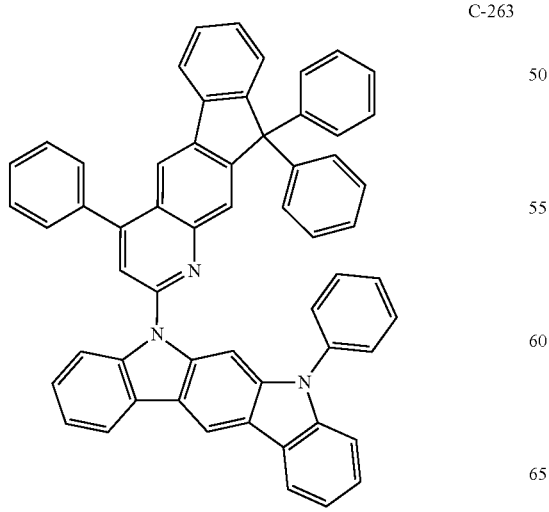
-continued
C-264
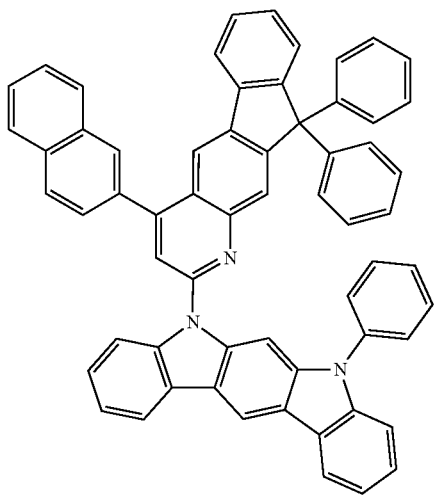
C-265
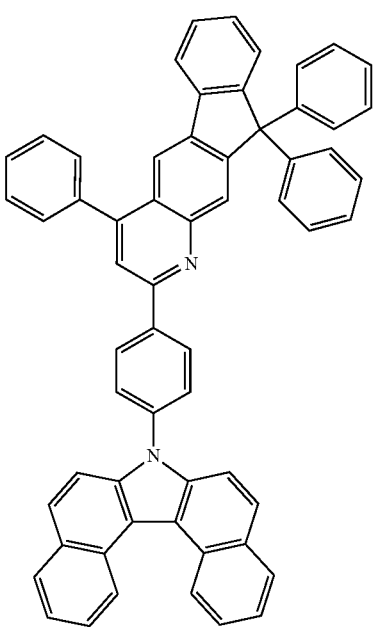

C-266
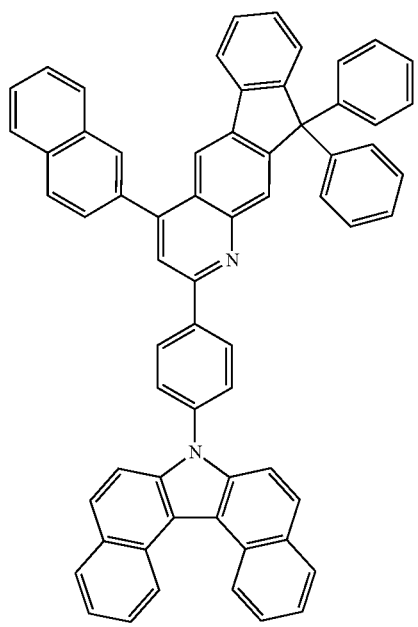
C-267
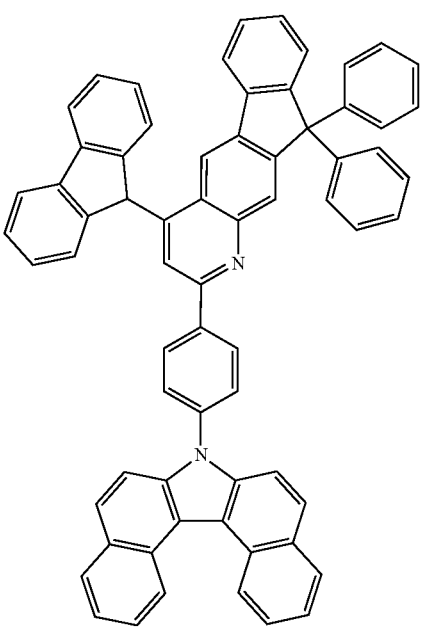
C-268
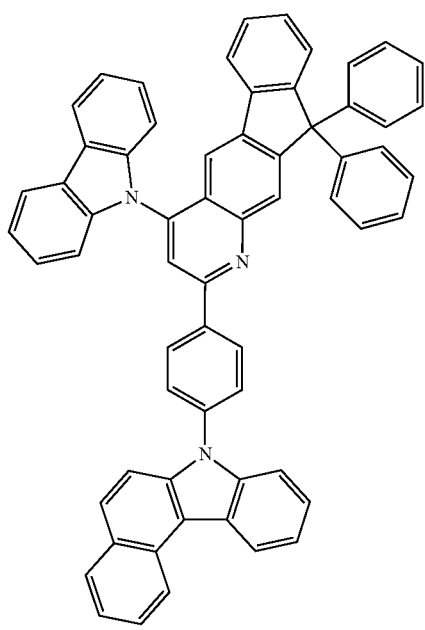
C-269
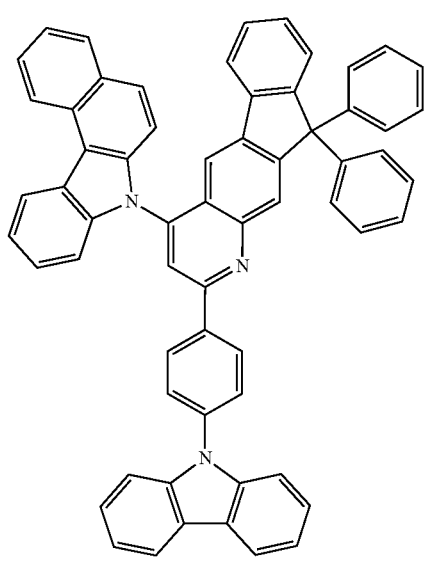

C-270
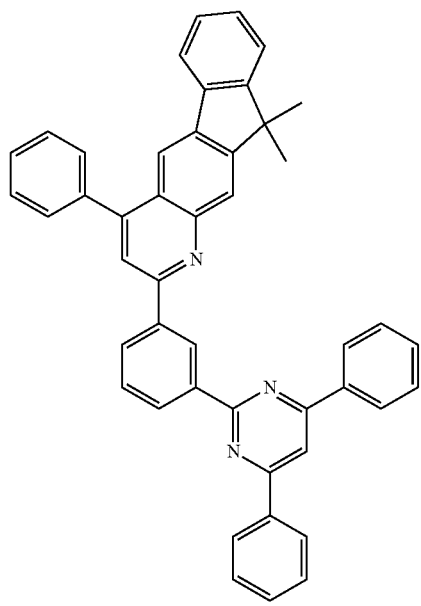
C-272
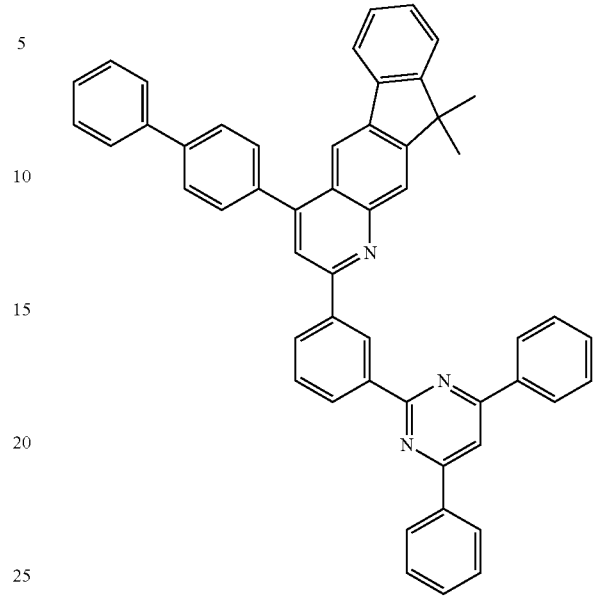
C-271
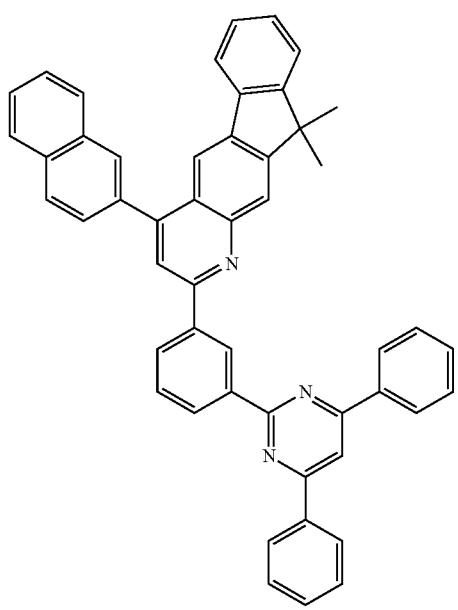
C-273

C-274
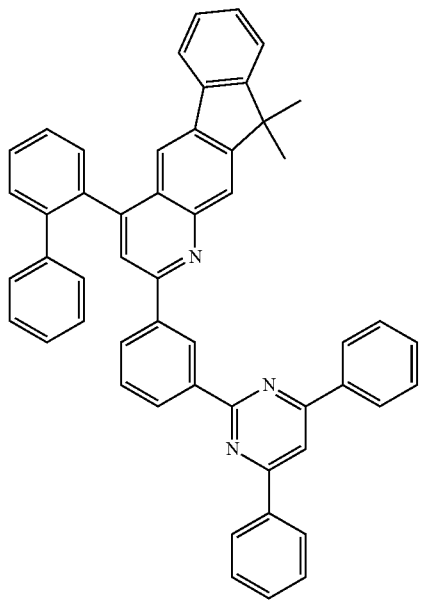
C-275
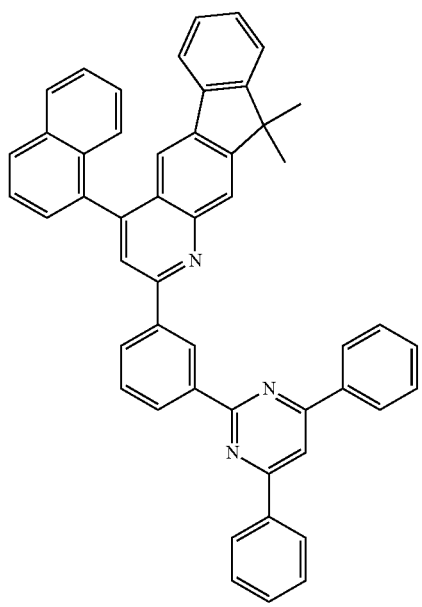
C-276
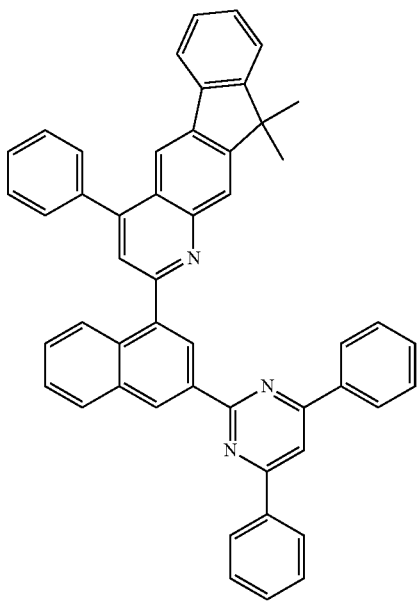
C-277
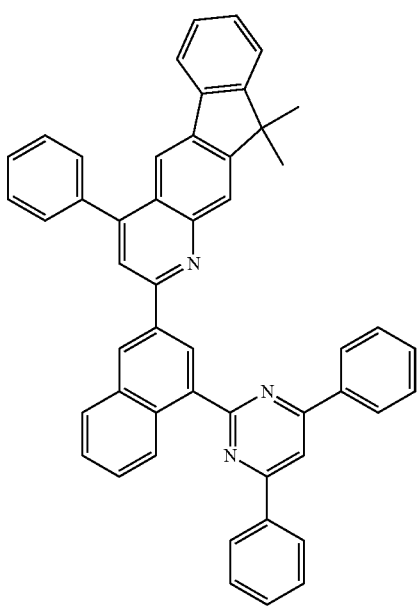

C-278
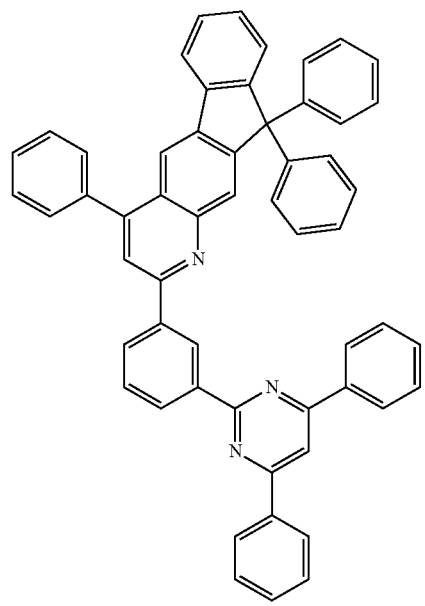
C-279
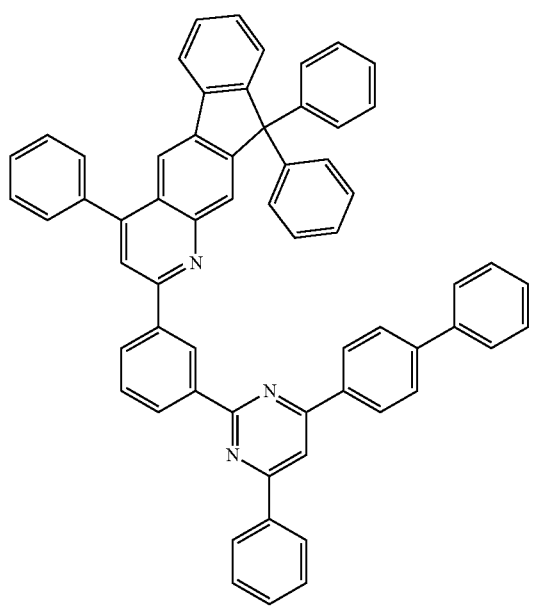
C-280
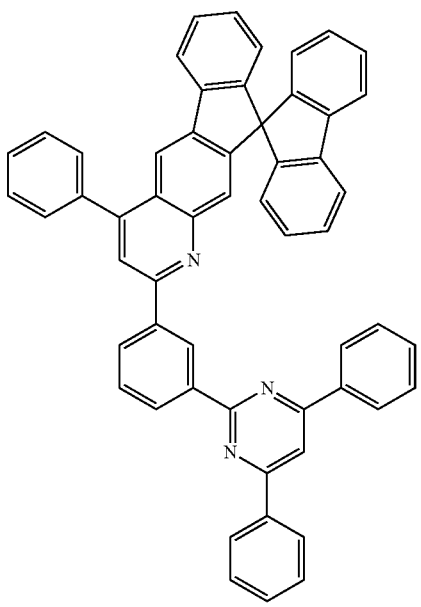
C-281
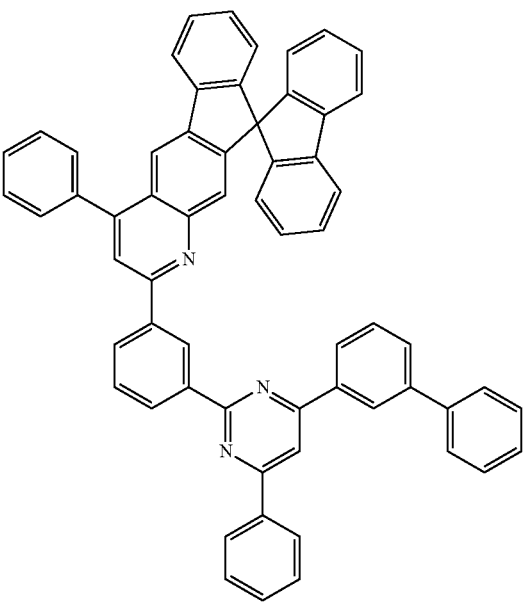

C-282
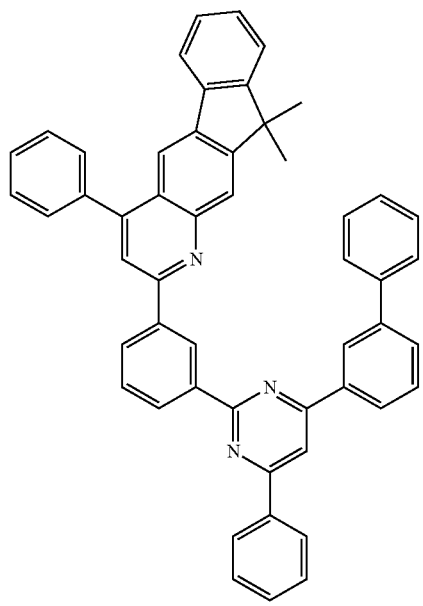
C-283
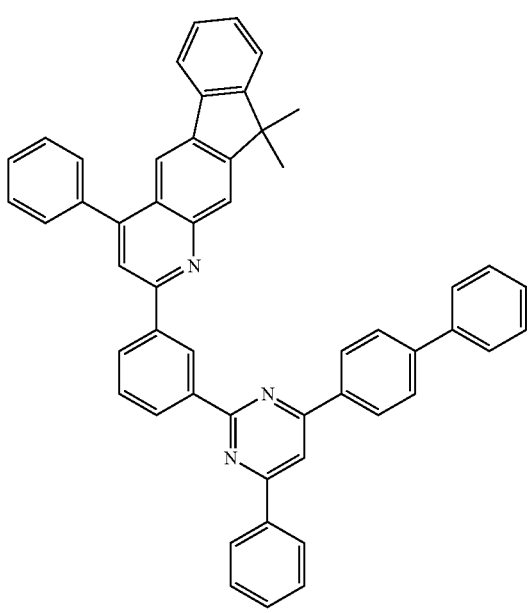
C-284
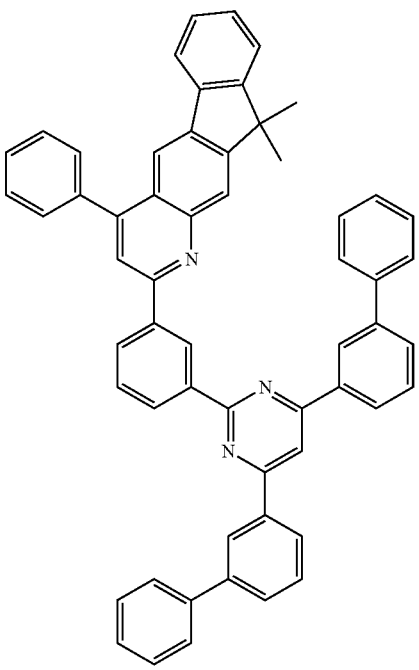
C-285
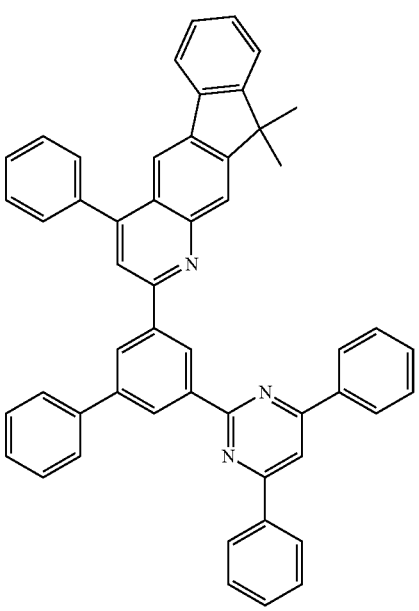

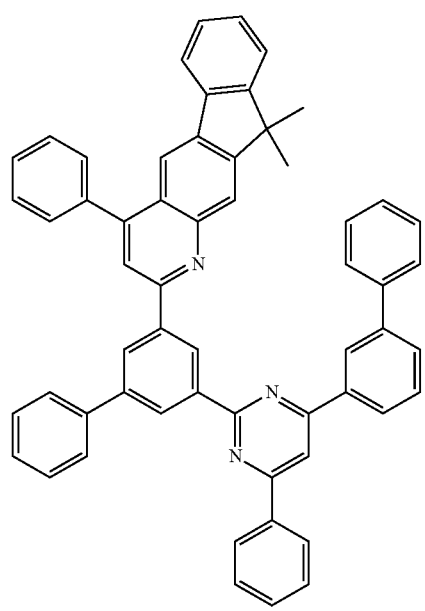
C-286
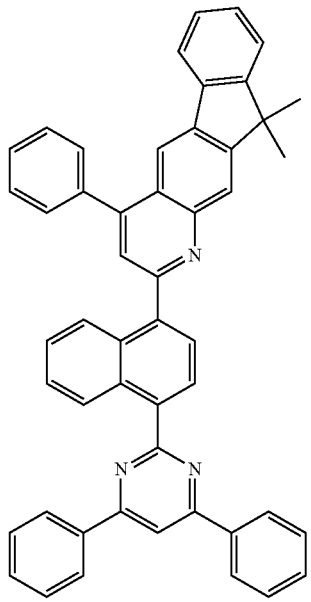
C-288
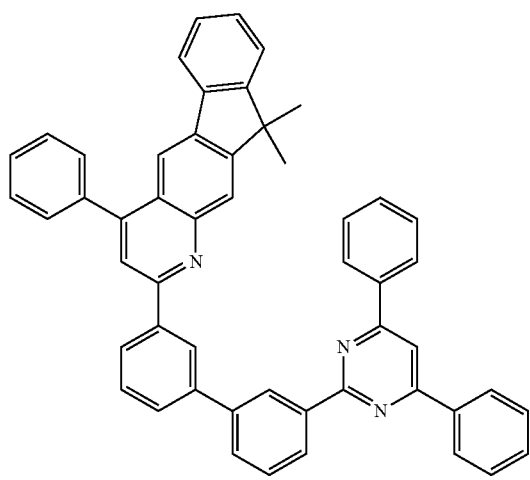
C-287
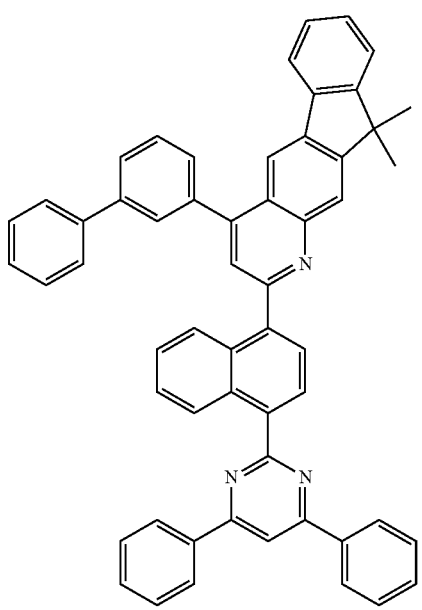
C-289

C-290
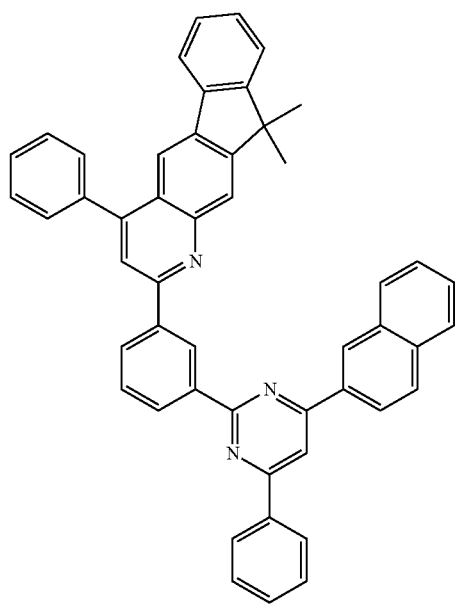
C-292
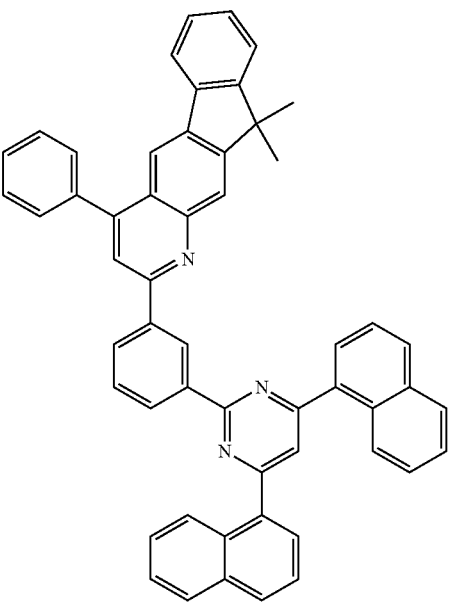
C-291
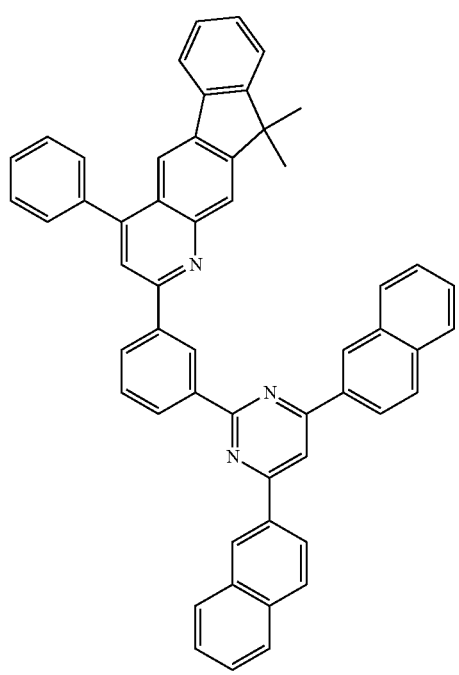
C-293
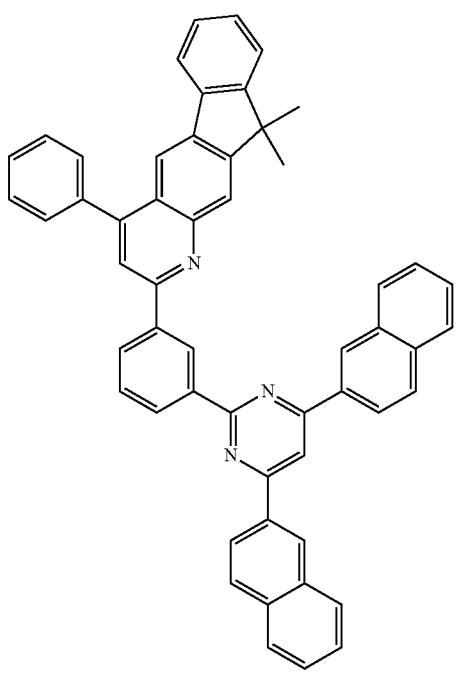

C-294
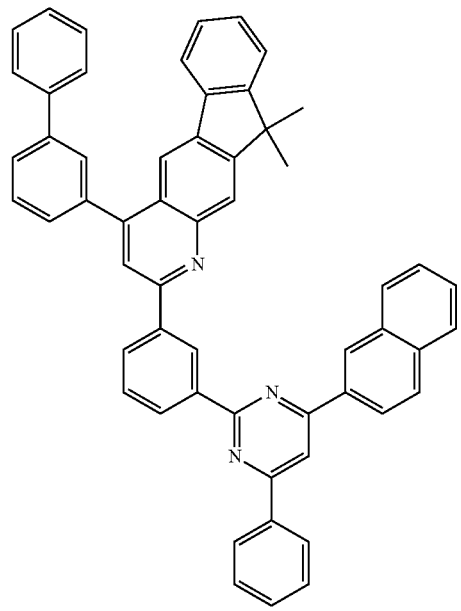
C-295
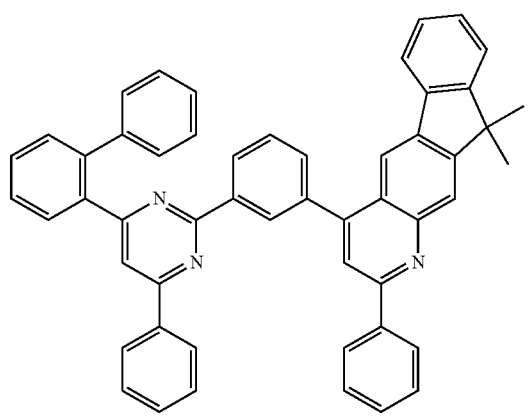
C-296
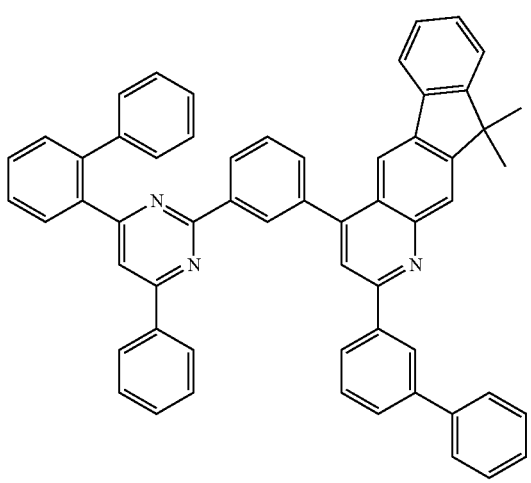
C-297
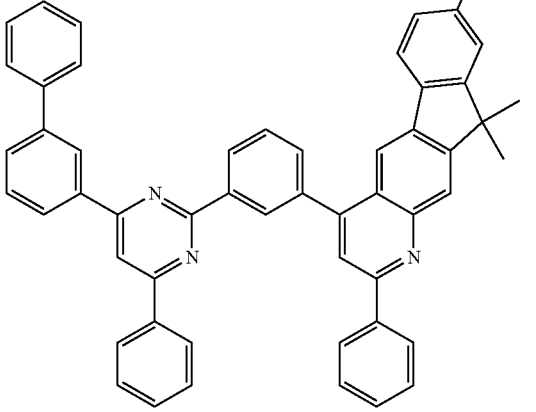
C-298
C-299
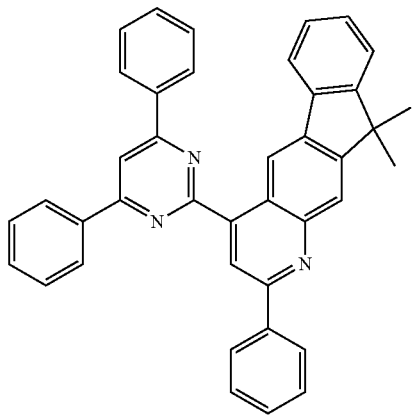

C-300
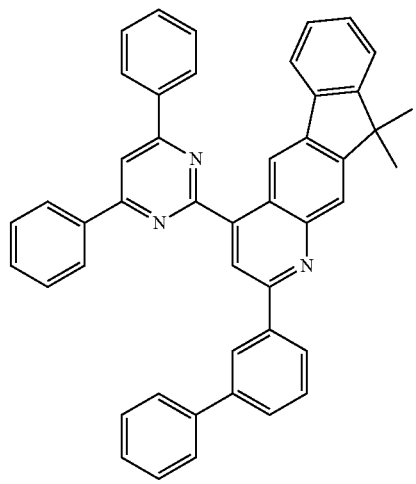
C-303
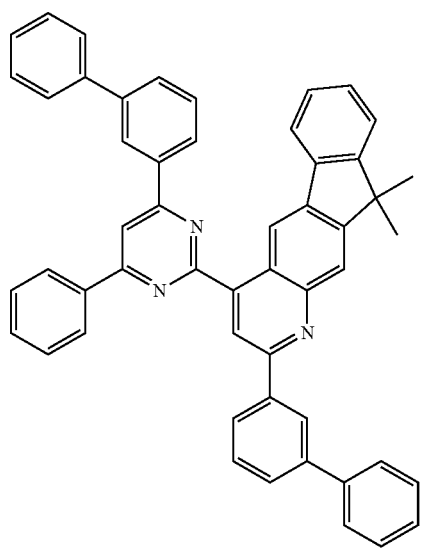
C-301
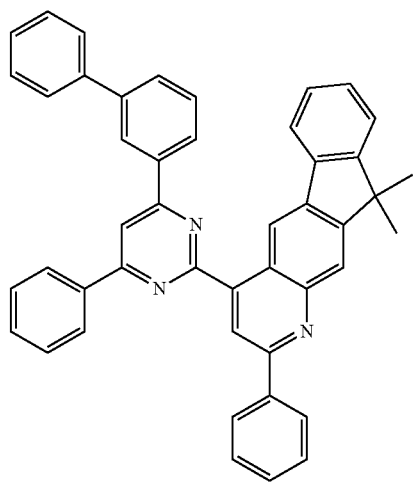
C-304
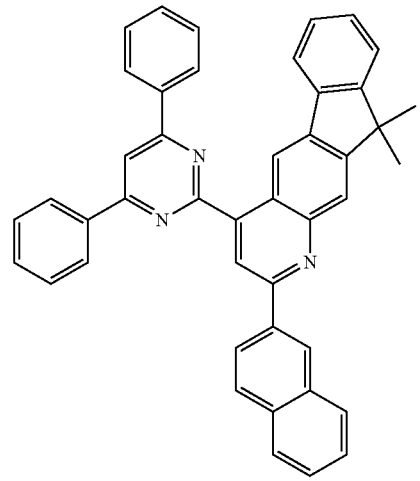
C-302
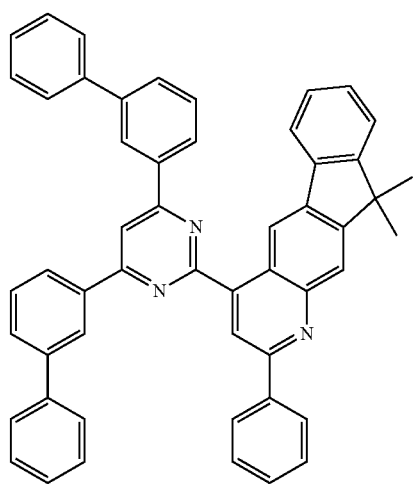

C-305
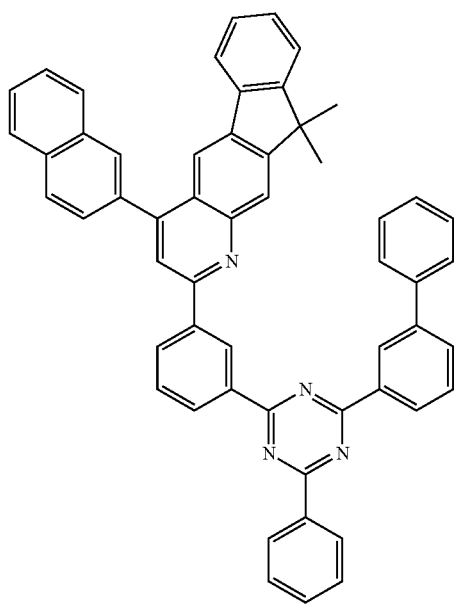
C-309
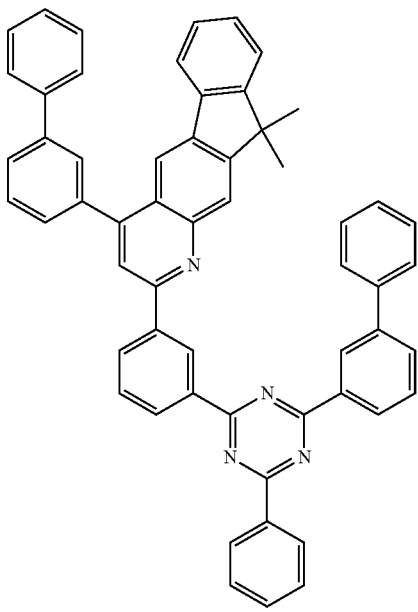
C-306
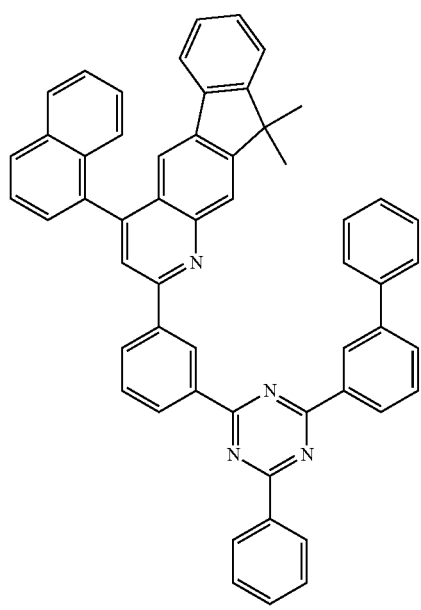
C-310
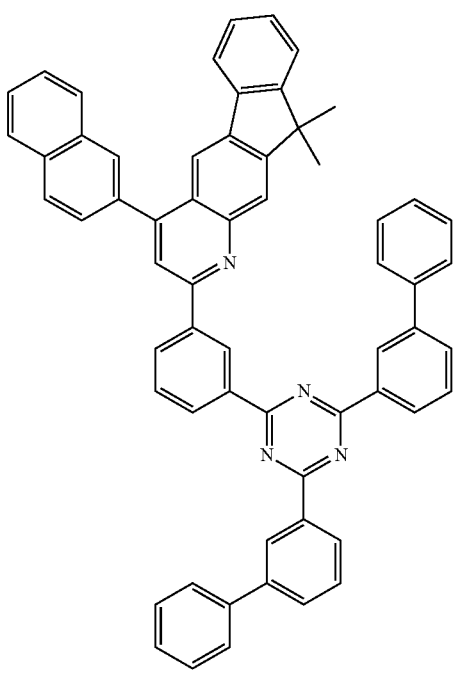

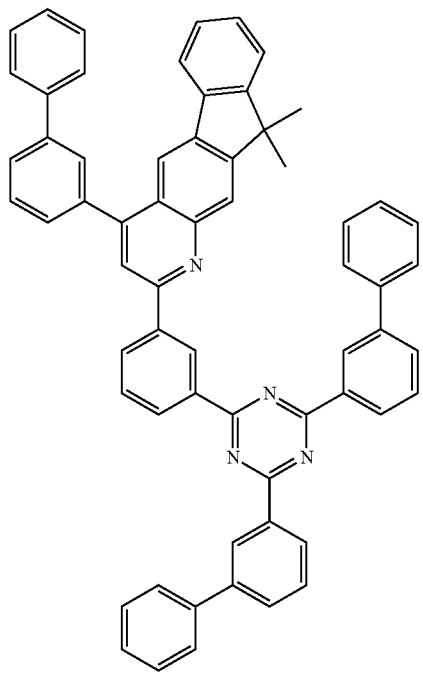

C-311 and

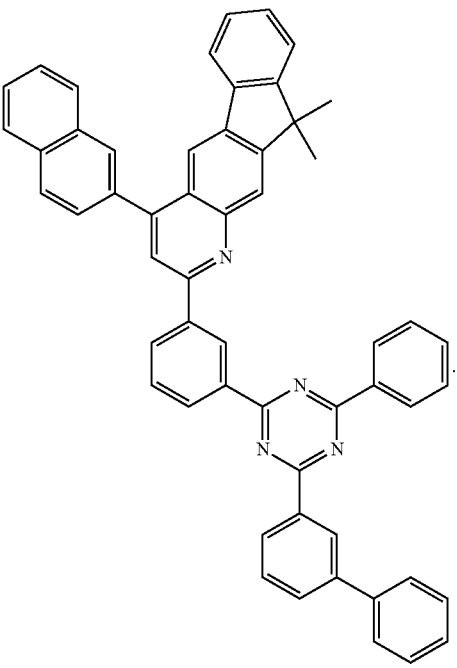

C-322

6. An organic electroluminescent material comprising the organic electroluminescent compound according to claim 1.

7. An organic electroluminescent device comprising the organic electroluminescent compound according to claim 1.

8. The organic electroluminescent device according to claim 7, wherein the organic electroluminescent compound is contained in at least one layer of an electron buffer layer and an electron transport layer.

9. A display device comprising the organic electroluminescent compound according to claim 1.

* * * * *